United States Patent
Ahmed et al.

(10) Patent No.: US 9,487,482 B2
(45) Date of Patent: Nov. 8, 2016

(54) 3,4,5-TRIMETHOXYSTYRYLARYLAMINO-PROPENONES AS POTENTIAL ANTICANCER AGENTS

(71) Applicant: Council of Scientific and Industrial Research, New Delhi (IN)

(72) Inventors: Kamal Ahmed, Hyderabad (IN); Bharath Kumar Gajjela, Hyderabad (IN); Basha Shaik Anver, Hyderabad (IN); Santhosh Reddy Vangala, Hyderabad (IN); Rasala Mahesh, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 20 days.

(21) Appl. No.: 14/689,742

(22) Filed: Apr. 17, 2015

(65) Prior Publication Data

US 2015/0322009 A1 Nov. 12, 2015

(30) Foreign Application Priority Data

May 9, 2014 (IN) .......................... 1255/DEL/2014

(51) Int. Cl.
| | | |
|---|---|---|
| *C07D 209/14* | (2006.01) | |
| *C07C 221/00* | (2006.01) | |
| *C07C 225/16* | (2006.01) | |
| *A61K 31/136* | (2006.01) | |
| *A61K 31/404* | (2006.01) | |
| *A61P 35/00* | (2006.01) | |
| *C07D 209/24* | (2006.01) | |
| *C07C 225/22* | (2006.01) | |

(52) U.S. Cl.
CPC ........... *C07D 209/14* (2013.01); *C07C 221/00* (2013.01); *C07C 225/16* (2013.01); *C07C 225/22* (2013.01); *C07D 209/24* (2013.01)

(58) Field of Classification Search
CPC C07D 209/14; C07D 209/24; C07C 225/22; C07C 221/00; C07C 225/16; A61K 31/36; A61K 31/044
See application file for complete search history.

(56) References Cited

PUBLICATIONS

Kamal et al. "Design and Synthesis of Aminostilbene—Arylpropenones as Tubulin Polymerization Inhibitors" ChemMedChem 2014, 9, 2565-2579.*
Tsai et al. "Manganese (III) Acetate Mediated Oxidative Radical Cyclizations of N-(2-Alkenylaryl)-Substituted Enamines" Synthesis 2014, 46, 175-182.*
Ducki, Sylvie, et al., "Potent antimitotic and cell growth inhibitory properties of substituted chalcones", Bioorg. Med. Chem. Lett., 8(9). (1998), 1051-1056.
Dumontet, Charles, et al., "Microtubule-binding agents: a dynamic of cancer therapeutics", Nat. Rev. Drug Discov., 9, (2010), 790-803.
Jordan, Mary Ann, et al., "Microtubules as a target for anticancer drugs", Nat. Rev. Cancer, 4(4), (2004), 253-265.
Kumar, A. Suresh, et al., "Design and synthesis of biaryl aryl stilbenes/ethylenes as antimicrotubule agents", European Journal of Medicinal Chemistry, 60, (2013), 305-324.
McGown, A. T., et al., "Structural and biochemical comparison of the anti-mitotic agents colchicine, combretastatin A4 and amphethinile", (Abstract), Anti-Cancer Drug Design, 3(4), 249-254, (1989), 1 pg.
Monk, Keith A., et al., "Design, synthesis, and biological evaluation of combretastatin nitrogen-containing derivatives as inhibitors of tubulin assembly and vascular disrupting agents", Bioorganic & Medicinal Chemistry, 14 (9), (2006), 3231-3244.
Pinney, Kevin G,, et al., "Synthesis and Biological Evaluation of Aryl Azide Derivative of Combretastatin A-4 as Molecular Probes for Tubulin", Bioorganic & Medicinal Chemistry, 8, (2000), 2417-2425.
Reddy, M. V, Ramana, et al,, "(Z)-1-Aryl-3-arylamino-2-propen-1-ones, Highly Active Stimulators of Tubulin Polymerization: Synthesis, Structure-Activity Relationship (SAR), Tubulin Polymerization, and Cell Growth Inhibition Studies", J Med Chem. 55(11), (2012), 5174-5187.
Simoni, Daniele, et al., "Novel A-Ring and B-Ring Modified Combretastatin A-4 (CA-4) Analogues Endowed with Interesting Cytotoxic Activity", J. Med. Chem. 51(19), (2008), 6211-6215.

* cited by examiner

*Primary Examiner* — Nyeemah A Grazier
*Assistant Examiner* — Amanda L Aguirre
(74) *Attorney, Agent, or Firm* — Schwegman Lundberg & Woessner, P.A.

(57) ABSTRACT

The present invention relate to compounds of general formula A. The invention also provides the synthesis of 3,4,5-trimethoxystyrylarylaminopropenones useful as potential antitumor agents against human cancer cell lines and a process for the preparation thereof.

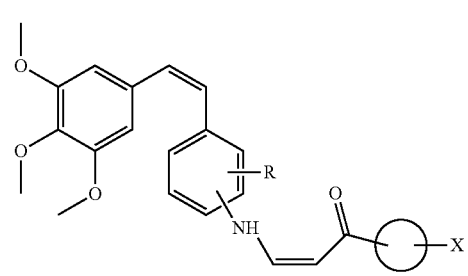

wherein:
R=H, OMe, Cl, F, OH, Me
X=aryl, heteroaryl.

7 Claims, No Drawings

3,4,5-TRIMETHOXYSTYRYLARYLAMINO-PROPENONES AS POTENTIAL ANTICANCER AGENTS

CLAIM OF PRIORITY

This application claims the benefit of priority of Indian Patent Application No. 1255/DEL/2014, filed on May 9, 2014, the benefit of priority of which is claimed hereby, and which is incorporated by reference herein in its entirety.

FIELD OF THE INVENTION

The present invention relates to a 3,4,5-trimethoxystyrylarylaminopropenones as potential anticancer agents.

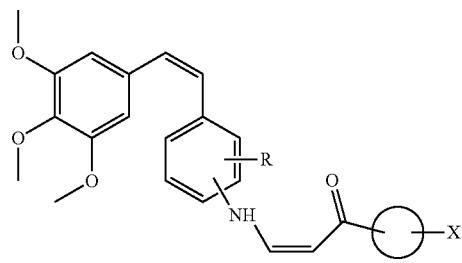

A wherein:
R=H, OMe, Cl, F, OH, Me
X=aryl, heteroaryl

The present invention relates to the synthesis and biological evaluation of a novel 3,4,5-trimethoxystyrylarylaminopropenones of general formula A as potential anticancer agents and a process for the preparation thereof.

BACKGROUND OF THE INVENTION

Microtubules compose of α and β-tubulin heterodimers, are major components in eukaryotic cells as they are highly conserved among the eukaryotic proteins (Jordan M A, Wilson L, Microtubules as a target for anticancer drugs, *Nat. Rev. Cancer,* 2004, (4), 253-265). Microtubules are pleiotropic in their function, particularly in organizing the spatial distribution of organelles in cells and chromosomes during cell division. The dynamic equilibrium between microtubule polymerization and depolymerization is central to most of microtubule mediated functions including cell division. Due to their essential functions in the cell, tubulin dynamics is a promising target for new chemotherapeutic agents. (Dumontet C, Jordan M A, Microtubule-binding agents: a dynamic field of cancer therapeutics, *Nat. Rev. Drug. Discov.* 2010, (10), 790-803).

Combretastatin (CA-4; S1) and colchicines (S2) are well known compounds that effectively inhibit the tubulin polymerization that leads to antiproliferation of cell. (McGown A. T, Fox B. W, Structural and biochemical comparison of the anti-mitotic agents colchicines, combretastatin A4 and amphethinile, *Anti-Cancer Drug Design,* 1989, 3, 249; and Ducki S, Forrest R, Hadfield J A, Kendall A, Lawrence N J, McGown A T, Rennison D, Potent antimitotic and cell growth inhibitory properties of substituted chalcones, *Bioorg. Med. Chem. Lett.* 1998, 8, (9), 1051-1056). Recently it has been reported that a new class of combretastatins such as (Z)-5-(3,5-dimethoxystyryl)-2-methoxyaniline (S4) exhibit potential cell growth inhibition against CA-4 resistant cell lines (BMEC and HT-29) and also explained that in these (Z)-5-(3,5-dimethoxystyryl)-2-methoxyaniline inhibited tubulin polymerization five times stronger than CA-4 by binding at colchicine binding site. (Simoni D, Romagnoli R, Baruchello R, Rondanin R, Grisolia G, Eleopra M, Rizzi M, Tolomeo M, Giannini G, Alloatti D, Castorina M, Marcellini M, Pisano C, Novel A-ring and B-ring modified combretastatin A-4 (CA-4) analogues endowed with interesting cytotoxic activity, *J. Med. Chem.* 2008, 51, (19), 6211-6215).

More recently a report revealed that a series of (Z)-1-aryl-3-arylamino-2-propen-1-ones (S3) exhibit profound activities against a number of tumor cell lines including multidrug resistant phenotype and the observations made in thus investigation demonstrate that these compounds represent a new class of microtubule-stabilizing agents (Reddy M V, Akula B, Cosenza S C, Lee C M, Mallireddigari M R, Pallela V R, Subbaiah D R, Udofa A, Reddy E P, (Z)-1-aryl-3-arylamino-2-propen-1-ones, highly active stimulators of tubulin polymerization: synthesis, structure-activity relationship (SAR), tubulin polymerization, and cell growth inhibition studies, *J Med Chem.* 2012, 55, (11), 5174-5187). In continuation of these efforts and our interest in the structural modifications of the combretastatin A4, we describe herein an efficient access to the construction of some new 3,4,5-trimethoxystyrylarylaminopropenones with improved cytotoxicity.

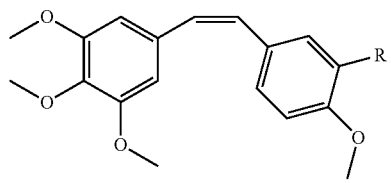

S1

R = OH (CA4)
R = OPO₃Na₂ (CA4P)
R = NHSer, NH₂•HCl (AVE8062)

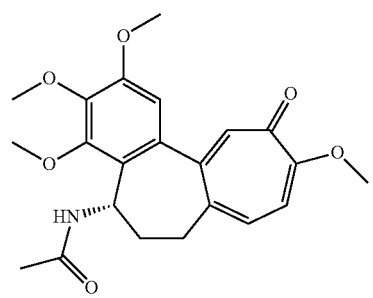

S2

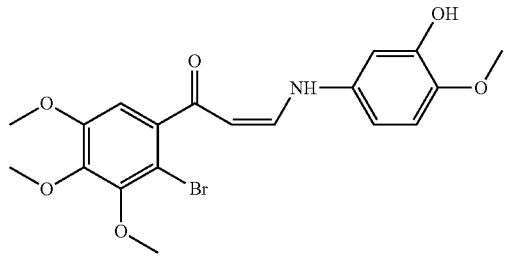

S3

-continued

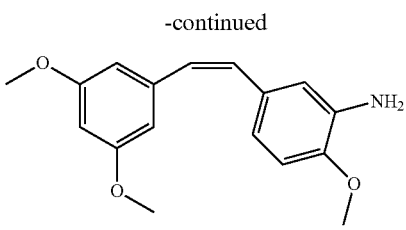

S4

OBJECTIVES OF THE INVENTION

The main objective of the present invention to provide 3,4,5-trimethoxystyrylarylaminopropenones useful as potential anticancer agents.

Yet another object of this invention is to provide a process for the preparation of novel 3,4,5-trimethoxystyrylarylaminopropenones.

Further object of the present invention is to provide novel 3,4,5-trimethoxystyrylarylaminopropenones of general formula A as promising tubulin polymerization inhibitors.

SUMMARY OF THE INVENTION

Accordingly, the present invention provides a novel 3,4,5-trimethoxystyrylaryl amino propenones of general formulae A

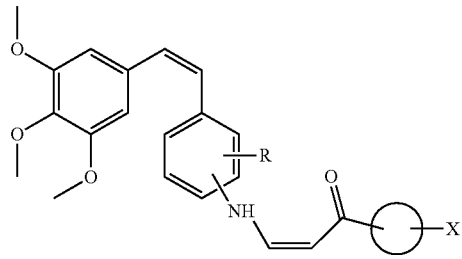

A wherein:
R=H, OMe, Cl, F, OH, Me
X=aryl, heteroaryl

In an embodiment of the invention wherein novel 3,4,5-trimethoxystyrylarylaminopropenones of general formulae A is comprising compounds of 7a-7y, 8a-8y, 9a-9y, 10a-10y, 11a-11y, 12a-12y, 13a-13y, 14a-14y, 15a-15y, 16a-16y, 17a-17y, 18a-18y, 19a-19y, 20a-20y, 21a-21y.

In another embodiment of the invention wherein novel 3,4,5-trimethoxystyrylarylaminopropenones of general formulae A comprising the group of the following compounds:
1. (Z)-1-phenyl-3-(3-(3,4,5-trimethoxystyryl)phenylamino)prop-2-en-1-one (7a)
2. (Z)-1-(4-methoxyphenyl)-3-(3-(3,4,5-trimethoxystyryl)phenylamino)prop-2-en-1-one (7b)
3. (Z)-1-(3-methoxyphenyl)-3-(3-(3,4,5-trimethoxystyryl)phenylamino)prop-2-en-1-one (7c)
4. (Z)-1-(2-methoxyphenyl)-3-(3-(3,4,5-trimethoxystyryl)phenylamino)prop-2-en-1-one (7d)
5. (Z)-1-(4-hydroxyphenyl)-3-(3-(3,4,5-trimethoxystyryl)phenylamino)prop-2-en-1-one (7e)
6. (Z)-1-(4-nitrophenyl)-3-(3-(3,4,5-trimethoxystyryl)phenylamino)prop-2-en-1-one (7f)
7. (Z)-1-(4-aminophenyl)-3-(3-(3,4,5-trimethoxystyryl)phenylamino)prop-2-en-1-one (7g)
8. (Z)-1-(2-nitrophenyl)-3-(3-(3,4,5-trimethoxystyryl)phenylamino)prop-2-en-1-one (7h)
9. (Z)-1-(2-aminophenyl)-3-(3-(3,4,5-trimethoxystyryl)phenylamino)prop-2-en-1-one (7i)
10. (Z)-1-(4-fluorophenyl)-3-(3-(3,4,5-trimethoxystyryl)phenylamino)prop-2-en-1-one (7J)
11. (Z)-1-(4-(trifluoromethyl)phenyl)-3-(3-(3,4,5-trimethoxystyryl)phenylamino)prop-2-en-1-one (7k)
12. (Z)-1-(3-fluorophenyl)-3-(3-(3,4,5-trimethoxystyryl)phenylamino)prop-2-en-1-one (7l)
13. (Z)-1-(3-chlorophenyl)-3-(3-(3,4,5-trimethoxystyryl)phenylamino)prop-2-en-1-one (7m)
14. (Z)-1-(4-chlorophenyl)-3-(3-(3,4,5-trimethoxystyryl)phenylamino)prop-2-en-1-one (7n)
15. (Z)-1-(4-(trifluoromethoxy)phenyl)-3-(3-(3,4,5-trimethoxystyryl)phenylamino)prop-2-en-1-one (7o)
16. (Z)-1-(3,4-dimethoxyphenyl)-3-(3-(3,4,5-trimethoxystyryl)phenylamino)prop-2-en-1-one (7p)
17. (Z)-1-(3-hydroxy-4-methoxyphenyl)-3-(3-(3,4,5-trimethoxystyryl)phenylamino)prop-2-en-1-one (7q)
18. (Z)-1-(3-fluoro-4-methoxyphenyl)-3-(3-(3,4,5-trimethoxystyryl)phenylamino)prop-2-en-1-one (7r)
19. (Z)-1-(3-chloro-4-methoxyphenyl)-3-(3-(3,4,5-trimethoxystyryl)phenylamino)prop-2-en-1-one (7s)
20. (Z)-1-(4-methoxy-3-nitrophenyl)-3-(3-(3,4,5-trimethoxystyryl)phenylamino)prop-2-en-1-one (7t)
21. (Z)-1-(3-amino-4-methoxyphenyl)-3-(3-(3,4,5-trimethoxystyryl)phenylamino)prop-2-en-1-one (7u)
22. (Z)-1-(1H-indol-3-yl)-3-(3-(3,4,5-trimethoxystyryl)phenylamino)prop-2-en-1-one (7v)
23. (Z)-1-(1-methyl-1H-indol-3-yl)-3-(3-(3,4,5-trimethoxystyryl)phenylamino)prop-2-en-1-one (7w)
24. (Z)-1-(3,4,5-trimethoxyphenyl)-3-(3-(3,4,5-trimethoxystyryl)phenylamino)prop-2-en-1-one (7x)
25. (Z)-1-(2-bromo-3,4,5-trimethoxyphenyl)-3-(3-(3,4,5-trimethoxystyryl)phenylamino)prop-2-en-1-one (7y)
26. (Z)-1-phenyl-3-((4-((Z)-3,4,5-trimethoxystyryl)phenyl)amino)prop-2-en-1-one (8a)
27. (Z)-1-(4-methoxyphenyl)-3-((4-((Z)-3,4,5-trimethoxystyryl)phenyl)amino)prop-2-en-1-one (8b)
28. (Z)-1-(3-methoxyphenyl)-3-((4-((Z)-3,4,5-trimethoxystyryl)phenyl)amino)prop-2-en-1-one (8c)
29. (Z)-1-(2-methoxyphenyl)-3-((4-((Z)-3,4,5-trimethoxystyryl)phenyl)amino)prop-2-en-1-one (8d)
30. (Z)-1-(4-hydroxyphenyl)-3-((4-((Z)-3,4,5-trimethoxystyryl)phenyl)amino)prop-2-en-1-one (8e)
31. (Z)-1-(4-nitrophenyl)-3-((4-((Z)-3,4,5-trimethoxystyryl)phenyl)amino)prop-2-en-1-one (8f)
32. (Z)-1-(4-aminophenyl)-3-((4-((Z)-3,4,5-trimethoxystyryl)phenyl)amino)prop-2-en-1-one (8g)
33. (Z)-1-(2-nitrophenyl)-3-((4-((Z)-3,4,5-trimethoxystyryl)phenyl)amino)prop-2-en-1-one (8h)
34. (Z)-1-(2-aminophenyl)-3-((4-((Z)-3,4,5-trimethoxystyryl)phenyl)amino)prop-2-en-1-one (8i)
35. (Z)-1-(4-fluorophenyl)-3-((4-((Z)-3,4,5-trimethoxystyryl)phenyl)amino)prop-2-en-1-one (8j)
36. (Z)-1-(4-(trifluoromethyl)phenyl)-3-((4-((Z)-3,4,5-trimethoxystyryl)phenyl)amino)prop-2-en-1-one (8k)
37. (Z)-1-(3-fluorophenyl)-3-((4-((Z)-3,4,5-trimethoxystyryl)phenyl)amino)prop-2-en-1-one (8l)
38. (Z)-1-(3-chlorophenyl)-3-((4-((Z)-3,4,5-trimethoxystyryl)phenyl)amino)prop-2-en-1-one (8m)
39. (Z)-1-(4-chlorophenyl)-3-((4-((Z)-3,4,5-trimethoxystyryl)phenyl)amino)prop-2-en-1-one (8n)
40. (Z)-1-(4-(trifluoromethoxy)phenyl)-3-((4-((Z)-3,4,5-trimethoxystyryl)phenyl)amino)prop-2-en-1-one (8o)

41. (Z)-1-(3,4-dimethoxyphenyl)-3-((4-((Z)-3,4,5-trimethoxystyryl)phenyl)amino)prop-2-en-1-one (8p)
42. (Z)-1-(3-hydroxy-4-methoxyphenyl)-3-((4-((Z)-3,4,5-trimethoxystyryl)phenyl)amino)prop-2-en-1-one (8q)
43. (Z)-1-(3-fluoro-4-methoxyphenyl)-3-((4-((Z)-3,4,5-trimethoxystyryl)phenyl)amino)prop-2-en-1-one (8r)
44. (Z)-1-(3-chloro-4-methoxyphenyl)-3-((4-((Z)-3,4,5-trimethoxystyryl)phenyl)amino)prop-2-en-1-one (8s)
45. (Z)-1-(4-methoxy-3-nitrophenyl)-3-((4-((Z)-3,4,5-trimethoxystyryl)phenyl)amino)prop-2-en-1-one (8t)
46. (Z)-1-(3-amino-4-methoxyphenyl)-3-((4-((Z)-3,4,5-trimethoxystyryl)phenyl)amino)prop-2-en-1-one (8u)
47. (Z)-1-(1H-indol-3-yl)-3-(4-(3,4,5-trimethoxystyryl)phenylamino)prop-2-en-1-one (8v)
48. (Z)-1-(1-methyl-1H-indol-3-yl)-3-(4-(3,4,5-trimethoxystyryl)phenylamino)prop-2-en-1-one (8w)
49. (Z)-1-(3,4,5-trimethoxyphenyl)-3-((4-((Z)-3,4,5-trimethoxystyryl)phenyl)amino)prop-2-en-1-one (8x)
50. (Z)-1-(2-bromo-3,4,5-trimethoxyphenyl)-3-((4-((Z)-3,4,5-trimethoxystyryl)phenyl)amino)prop-2-en-1-one (8y)
51. (Z)-1-phenyl-3-((2-((Z)-3,4,5-trimethoxystyryl)phenyl)amino)prop-2-en-1-one (9a)
52. (Z)-1-(4-methoxyphenyl)-3-((2-((Z)-3,4,5-trimethoxystyryl)phenyl)amino)prop-2-en-1-one (9b)
53. (Z)-1-(3-methoxyphenyl)-3-((2-((Z)-3,4,5-trimethoxystyryl)phenyl)amino)prop-2-en-1-one (9c)
54. (Z)-1-(2-methoxyphenyl)-3-((2-((Z)-3,4,5-trimethoxystyryl)phenyl)amino)prop-2-en-1-one (9d)
55. (Z)-1-(4-hydroxyphenyl)-3-((2-((Z)-3,4,5-trimethoxystyryl)phenyl)amino)prop-2-en-1-one (9e)
56. (Z)-1-(4-nitrophenyl)-3-((2-((Z)-3,4,5-trimethoxystyryl)phenyl)amino)prop-2-en-1-one (9f)
57. (Z)-1-(4-aminophenyl)-3-((2-((Z)-3,4,5-trimethoxystyryl)phenyl)amino)prop-2-en-1-one (9g)
58. (Z)-1-(2-nitrophenyl)-3-((2-((Z)-3,4,5-trimethoxystyryl)phenyl)amino)prop-2-en-1-one (9h)
59. (Z)-1-(2-aminophenyl)-3-((2-((Z)-3,4,5-trimethoxystyryl)phenyl)amino)prop-2-en-1-one (9i)
60. (Z)-1-(4-fluorophenyl)-3-((2-((Z)-3,4,5-trimethoxystyryl)phenyl)amino)prop-2-en-1-one (9j)
61. (Z)-1-(4-(trifluoromethyl)phenyl)-3-((2-((Z)-3,4,5-trimethoxystyryl)phenyl)amino)prop-2-en-1-one (9k)
62. (Z)-1-(3-fluorophenyl)-3-((2-((Z)-3,4,5-trimethoxystyryl)phenyl)amino)prop-2-en-1-one (9l)
63. (Z)-1-(3-chlorophenyl)-3-((2-((Z)-3,4,5-trimethoxystyryl)phenyl)amino)prop-2-en-1-one (9m)
64. (Z)-1-(4-chlorophenyl)-3-((2-((Z)-3,4,5-trimethoxystyryl)phenyl)amino)prop-2-en-1-one (9n)
65. (Z)-1-(4-(trifluoromethoxy)phenyl)-3-((2-((Z)-3,4,5-trimethoxystyryl)phenyl)amino)prop-2-en-1-one (9o)
66. (Z)-1-(3,4-dimethoxyphenyl)-3-((2-((Z)-3,4,5-trimethoxystyryl)phenyl)amino)prop-2-en-1-one (9p)
67. (Z)-1-(3-hydroxy-4-methoxyphenyl)-3-((2-((Z)-3,4,5-trimethoxystyryl)phenyl)amino)prop-2-en-1-one (9q)
68. (Z)-1-(3-fluoro-4-methoxyphenyl)-3-((2-((Z)-3,4,5-trimethoxystyryl)phenyl)amino)prop-2-en-1-one (9r)
69. (Z)-1-(3-chloro-4-methoxyphenyl)-3-((2-((Z)-3,4,5-trimethoxystyryl)phenyl)amino)prop-2-en-1-one (9s)
70. (Z)-1-(4-methoxy-3-nitrophenyl)-3-((2-((Z)-3,4,5-trimethoxystyryl)phenyl)amino)prop-2-en-1-one (9t)
71. (Z)-1-(3-amino-4-methoxyphenyl)-3-((2-((Z)-3,4,5-trimethoxystyryl)phenyl)amino)prop-2-en-1-one (9u)
72. (Z)-1-(1H-indol-3-yl)-3-(2-(3,4,5-trimethoxystyryl)phenylamino)prop-2-en-1-one (9v)
73. (Z)-1-(1-methyl-1H-indol-3-yl)-3-(2-(3,4,5-trimethoxystyryl)phenylamino)prop-2-en-1-one (9w)
74. (Z)-1-(3,4,5-trimethoxyphenyl)-3-((2-((Z)-3,4,5-trimethoxystyryl)phenyl)amino)prop-2-en-1-one (9x)
75. (Z)-1-(2-bromo-3,4,5-trimethoxyphenyl)-3-((2-((Z)-3,4,5-trimethoxystyryl)phenyl)amino)prop-2-en-1-one (9y)
76. (Z)-3-((2-methoxy-5-((Z)-3,4,5-trimethoxystyryl)phenyl)amino)-1-phenylprop-2-en-1-one (10a)
77. (Z)-3-((2-methoxy-5-((Z)-3,4,5-trimethoxystyryl)phenyl)amino)-1-(4-methoxyphenyl)prop-2-en-1-ne (10b)
78. (Z)-3-((2-methoxy-5-((Z)-3,4,5-trimethoxystyryl)phenyl)amino)-1-(3-methoxyphenyl)prop-2-en-1-ne (10c)
79. (Z)-3-((2-methoxy-5-((Z)-3,4,5-trimethoxystyryl)phenyl)amino)-1-(2-methoxyphenyl)prop-2-en-1-ne (10d)
80. (Z)-1-(4-hydroxyphenyl)-3-((2-methoxy-5-((Z)-3,4,5-trimethoxystyryl)phenyl)amino)prop-2-en-1-one (10e)
81. (Z)-3-((2-methoxy-5-((Z)-3,4,5-trimethoxystyryl)phenyl)amino)-1-(4-nitrophenyl)prop-2-en-1-one (10f)
82. (Z)-1-(4-aminophenyl)-3-((2-methoxy-5-((Z)-3,4,5-trimethoxystyryl)phenyl)amino)prop-2-en-1-one (10g)
83. (Z)-3-((2-methoxy-5-((Z)-3,4,5-trimethoxystyryl)phenyl)amino)-1-(2-nitrophenyl)prop-2-en-1-one (10h)
84. (Z)-1-(2-aminophenyl)-3-((2-methoxy-5-((Z)-3,4,5-trimethoxystyryl)phenyl)amino)prop-2-en-1-one (10i)
85. (Z)-1-(4-fluorophenyl)-3-((2-methoxy-5-((Z)-3,4,5-trimethoxystyryl)phenyl)amino)prop-2-en-1-one (10j)
86. (Z)-3-((2-methoxy-5-((Z)-3,4,5-trimethoxystyryl)phenyl)amino)-1-(4-(trifluoromethyl)phenyl)prop-2-en-1-one (10k)
87. (Z)-1-(3-fluorophenyl)-3-((2-methoxy-5-((Z)-3,4,5-trimethoxystyryl)phenyl)amino)prop-2-en-1-one (10l)
88. (Z)-1-(3-chlorophenyl)-3-((2-methoxy-5-((Z)-3,4,5-trimethoxystyryl)phenyl)amino)prop-2-en-1-one (10m)
89. (Z)-1-(4-chlorophenyl)-3-((2-methoxy-5-((Z)-3,4,5-trimethoxystyryl)phenyl)amino)prop-2-en-1-one (10n)
90. (Z)-3-((2-methoxy-5-((Z)-3,4,5-trimethoxystyryl)phenyl)amino)-1-(4-(trifluoromethoxy)phenyl)prop-2-en-1-one (10o)
91. (Z)-1-(3,4-dimethoxyphenyl)-3-((2-methoxy-5-((Z)-3,4,5-trimethoxystyryl)phenyl)amino)prop-2-en-1-one (10p)
92. (Z)-1-(3-hydroxy-4-methoxyphenyl)-3-((2-methoxy-5-((Z)-3,4,5-trimethoxystyryl)phenyl)amino)prop-2-en-1-one (10q)
93. (Z)-1-(3-fluoro-4-methoxyphenyl)-3-((2-methoxy-5-((Z)-3,4,5-trimethoxystyryl)phenyl)amino)prop-2-en-1-one (10r)
94. (Z)-1-(3-chloro-4-methoxyphenyl)-3-((2-methoxy-5-((Z)-3,4,5-trimethoxystyryl)phenyl)amino)prop-2-en-1-one (10s)
95. (Z)-1-(4-methoxy-3-nitrophenyl)-3-((2-methoxy-5-((Z)-3,4,5-trimethoxystyryl)phenyl)amino)prop-2-en-1-one (10t)
96. (Z)-1-(3-amino-4-methoxyphenyl)-3-((2-methoxy-5-((Z)-3,4,5-trimethoxystyryl)phenyl)amino)prop-2-en-1-one (10u)
97. (Z)-1-(1H-indol-3-yl)-3-(2-methoxy-5-(3,4,5-trimethoxystyryl)phenylamino)prop-2-en-1-one (10v)
98. (Z)-3-(2-methoxy-5-(3,4,5-trimethoxystyryl)phenylamino)-1-(1-methyl-1H-indol-3-yl)prop-2-en-1-one (10w)
99. (Z)-3-((2-methoxy-5-((Z)-3,4,5-trimethoxystyryl)phenyl)amino)-1-(3,4,5-trimethoxyphenyl)prop-2-en-1-one (10x)
100. (Z)-1-(2-bromo-3,4,5-trimethoxyphenyl)-3-((2-methoxy-5-((Z)-3,4,5-trimethoxystyryl)phenyl)amino)prop-2-en-1-one (10y)
101. (Z)-3-((2,3-dimethoxy-5-((Z)-3,4,5-trimethoxystyryl)phenyl)amino)-1-phenylprop-2-en-1-one (11a)

102. (Z)-3-((2,3-dimethoxy-5-((Z)-3,4,5-trimethoxystyryl) phenyl)amino)-1-(4-methoxyphenyl)prop-2-en-1-one (11b)
103. (Z)-3-((2,3-dimethoxy-5-((Z)-3,4,5-trimethoxystyryl) phenyl)amino)-1-(3-methoxyphenyl)prop-2-en-1-one (11c)
104. (Z)-3-((2,3-dimethoxy-5-((Z)-3,4,5-trimethoxystyryl) phenyl)amino)-1-(2-methoxyphenyl)prop-2-en-1-one (11d)
105. (Z)-3-((2,3-dimethoxy-5-((Z)-3,4,5-trimethoxystyryl) phenyl)amino)-1-(4-hydroxyphenyl)prop-2-en-1-one (11e)
106. (Z)-3-((2,3-dimethoxy-5-((Z)-3,4,5-trimethoxystyryl) phenyl)amino)-1-(4-nitrophenyl)prop-2-en-1-one (11f)
107. (Z)-1-(4-aminophenyl)-3-((2,3-dimethoxy-5-((Z)-3,4, 5-trimethoxystyryl)phenyl)amino)prop-2-en-1-one (11g)
108. (Z)-3-((2,3-dimethoxy-5-((Z)-3,4,5-trimethoxystyryl) phenyl)amino)-1-(2-nitrophenyl)prop-2-en-1-one (11h)
109. (Z)-1-(2-aminophenyl)-3-((2,3-dimethoxy-5-((Z)-3,4, 5-trimethoxystyryl)phenyl)amino)prop-2-en-1-one (11i)
110. (Z)-3-((2,3-dimethoxy-5-((Z)-3,4,5-trimethoxystyryl) phenyl)amino)-1-(4-fluorophenyl)prop-2-en-1-one (11j)
111. (Z)-3-((2,3-dimethoxy-5-((Z)-3,4,5-trimethoxystyryl) phenyl)amino)-1-(4-(trifluoromethyl)phenyl)prop-2-en-1-one (11k)
112. (Z)-3-((2,3-dimethoxy-5-((Z)-3,4,5-trimethoxystyryl) phenyl)amino)-1-(3-fluorophenyl)prop-2-en-1-one (11l)
113. (Z)-1-(3-chlorophenyl)-3-((2,3-dimethoxy-5-((Z)-3,4, 5-trimethoxystyryl)phenyl)amino)prop-2-en-1-one (11 n)
114. (Z)-1-(4-chlorophenyl)-3-((2,3-dimethoxy-5-((Z)-3,4, 5-trimethoxystyryl)phenyl)amino)prop-2-en-1-one (11n)
115. (Z)-3-((2,3-dimethoxy-5-((Z)-3,4,5-trimethoxystyryl) phenyl)amino)-1-(4-(trifluoromethoxy)phenyl)prop-2-en-1-one (11o)
116. (Z)-3-((2,3-dimethoxy-5-((Z)-3,4,5-trimethoxystyryl) phenyl)amino)-1-(3,4-dimethoxyphenyl)prop-2-en-1-one (11p)
117. (Z)-3-((2,3-dimethoxy-5-((Z)-3,4,5-trimethoxystyryl) phenyl)amino)-1-(3-hydroxy-4-methoxyphenyl)prop-2-en-1-one (11q)
118. (Z)-3-((2,3-dimethoxy-5-((Z)-3,4,5-trimethoxystyryl) phenyl)amino)-1-(3-fluoro-4-methoxyphenyl)prop-2-en-1-one (11r)
119. (Z)-1-(3-chloro-4-methoxyphenyl)-3-((2,3-dimethoxy-5-((Z)-3,4,5-trimethoxystyryl)phenyl)amino)prop-2-en-1-one (11s)
120. (Z)-3-((2,3-dimethoxy-5-((Z)-3,4,5-trimethoxystyryl) phenyl)amino)-1-(4-methoxy-3-nitrophenyl)prop-2-en-1-one (11t)
121. (Z)-1-(3-amino-4-methoxyphenyl)-3-((2,3-dimethoxy-5-((Z)-3,4,5-trimethoxystyryl)phenyl)amino)prop-2-en-1-one (11u)
122. (Z)-3-(2,3-dimethoxy-5-(3,4,5-trimethoxystyryl)phenylamino)-1-(1H-indol-3-yl)prop-2-en-1-one (11v)
123. (Z)-3-(2,3-dimethoxy-5-(3,4,5-trimethoxystyryl)phenylamino)-1-(1-methyl-1H-indol-3-yl)prop-2-en-1-one (11w)
124. (Z)-3-((2,3-dimethoxy-5-((Z)-3,4,5-trimethoxystyryl) phenyl)amino)-1-(3,4,5-trimethoxyphenyl)prop-2-en-1-one (11x)
125. (Z)-1-(2-bromo-3,4,5-trimethoxyphenyl)-3-((2,3-dimethoxy-5-((Z)-3,4,5-trimethoxystyryl)phenyl)amino) prop-2-en-1-one (11y)
126. (Z)-3-((3-fluoro-2-methoxy-5-((Z)-3,4,5-trimethoxystyryl)phenyl)amino)-1-phenylprop-2-en-1-one (12a)
127. (Z)-3-((3-fluoro-2-methoxy-5-((Z)-3,4,5-trimethoxystyryl)phenyl)amino)-1-(4-methoxyphenyl)prop-2-en-1-one (12b)
128. (Z)-3-((3-fluoro-2-methoxy-5-((Z)-3,4,5-trimethoxystyryl)phenyl)amino)-1-(3-methoxyphenyl)prop-2-en-1-one (12c)
129. (Z)-3-((3-fluoro-2-methoxy-5-((Z)-3,4,5-trimethoxystyryl)phenyl)amino)-1-(2-methoxyphenyl)prop-2-en-1-one (12d)
130. (Z)-3-((3-fluoro-2-methoxy-5-((Z)-3,4,5-trimethoxystyryl)phenyl)amino)-1-(4-hydroxyphenyl)prop-2-en-1-one (12e)
131. (Z)-3-((3-fluoro-2-methoxy-5-((Z)-3,4,5-trimethoxystyryl)phenyl)amino)-1-(4-nitrophenyl)prop-2-en-1-one (12f)
132. (Z)-1-(4-aminophenyl)-3-((3-fluoro-2-methoxy-5-((Z)-3,4,5-trimethoxystyryl)phenyl)amino)prop-2-en-1-one (12g)
133. (Z)-3-((3-fluoro-2-methoxy-5-((Z)-3,4,5-trimethoxystyryl)phenyl)amino)-1-(2-nitrophenyl)prop-2-en-1-one (12h)
134. (Z)-1-(2-aminophenyl)-3-((3-fluoro-2-methoxy-5-((Z)-3,4,5-trimethoxystyryl)phenyl)amino)prop-2-en-1-one (12i)
135. (Z)-3-((3-fluoro-2-methoxy-5-((Z)-3,4,5-trimethoxystyryl)phenyl)amino)-1-(4-fluorophenyl)prop-2-en-1-one (12j)
136. (Z)-3-((3-fluoro-2-methoxy-5-((Z)-3,4,5-trimethoxystyryl)phenyl)amino)-1-(4-(trifluoromethyl)phenyl) prop-2-en-1-one (12k)
137. (Z)-3-((3-fluoro-2-methoxy-5-((Z)-3,4,5-trimethoxystyryl)phenyl)amino)-1-(3-fluorophenyl)prop-2-en-1-one (12l)
138. (Z)-1-(3-chlorophenyl)-3-((3-fluoro-2-methoxy-5-((Z)-3,4,5-trimethoxystyryl)phenyl)amino)prop-2-en-1-one (12m)
139. (Z)-1-(4-chlorophenyl)-3-((3-fluoro-2-methoxy-5-((Z)-3,4,5-trimethoxystyryl)phenyl)amino)prop-2-en-1-one (12n)
140. (Z)-3-((3-fluoro-2-methoxy-5-((Z)-3,4,5-trimethoxystyryl)phenyl)amino)-1-(4-(trifluoromethoxy)phenyl) prop-2-en-1-one (12o)
141. (Z)-1-(3,4-dimethoxyphenyl)-3-((3-fluoro-2-methoxy-5-((Z)-3,4,5-trimethoxystyryl)phenyl)amino)prop-2-en-1-one (12p)
142. (Z)-3-((3-fluoro-2-methoxy-5-((Z)-3,4,5-trimethoxystyryl)phenyl)amino)-1-(3-hydroxy-4-methoxyphenyl) prop-2-en-1-one (12q)
143. (Z)-3-((3-fluoro-2-methoxy-5-((Z)-3,4,5-trimethoxystyryl)phenyl)amino)-1-(3-fluoro-4-methoxyphenyl) prop-2-en-1-one (12r)
144. (Z)-1-(3-chloro-4-methoxyphenyl)-3-((3-fluoro-2-methoxy-5-((Z)-3,4,5-trimethoxystyryl)phenyl)amino) prop-2-en-1-one (12s)
145. (Z)-3-((3-fluoro-2-methoxy-5-((Z)-3,4,5-trimethoxystyryl)phenyl)amino)-1-(4-methoxy-3-nitrophenyl) prop-2-en-1-one (12t)
146. (Z)-1-(3-amino-4-methoxyphenyl)-3-((3-fluoro-2-methoxy-5-((Z)-3,4,5-trimethoxystyryl)phenyl)amino) prop-2-en-1-one (12u)
147. (Z)-3-(3-fluoro-2-methoxy-5-(3,4,5-trimethoxystyryl) phenylamino)-1-(1H-indol-3-yl)prop-2-en-1-one (12v)
148. (Z)-3-(3-fluoro-2-methoxy-5-(3,4,5-trimethoxystyryl) phenylamino)-1-(1-methyl-1H-indol-3-yl)prop-2-en-1-one (12w)

149. (Z)-3-((3-fluoro-2-methoxy-5-((Z)-3,4,5-trimethoxystyryl)phenyl)amino)-1-(3,4,5-trimethoxyphenyl)prop-2-en-1-one (12x)
150. (Z)-1-(2-bromo-3,4,5-trimethoxyphenyl)-3-((3-fluoro-2-methoxy-5-((Z)-3,4,5-trimethoxystyryl)phenyl)amino)prop-2-en-1-one (12y)
151. (Z)-3-((3-chloro-2-methoxy-5-((Z)-3,4,5-trimethoxystyryl)phenyl)amino)-1-phenylprop-2-en-1-one (13a)
152. (Z)-3-((3-chloro-2-methoxy-5-((Z)-3,4,5-trimethoxystyryl)phenyl)amino)-1-(4-methoxyphenyl)prop-2-en-1-one (13b)
153. (Z)-3-((3-chloro-2-methoxy-5-((Z)-3,4,5-trimethoxystyryl)phenyl)amino)-1-(3-methoxyphenyl)prop-2-en-1-one (13c)
154. (Z)-3-((3-chloro-2-methoxy-5-((Z)-3,4,5-trimethoxystyryl)phenyl)amino)-1-(2-methoxyphenyl)prop-2-en-1-one (13d)
155. (Z)-3-((3-chloro-2-methoxy-5-((Z)-3,4,5-trimethoxystyryl)phenyl)amino)-1-(4-hydroxyphenyl)prop-2-en-1-one (13e)
156. (Z)-3-((3-chloro-2-methoxy-5-((Z)-3,4,5-trimethoxystyryl)phenyl)amino)-1-(4-nitrophenyl)prop-2-en-1-one (13f)
157. (Z)-1-(4-aminophenyl)-3-((3-chloro-2-methoxy-5-((Z)-3,4,5-trimethoxystyryl)phenyl)amino)prop-2-en-1-one (13g)
158. (Z)-3-((3-chloro-2-methoxy-5-((Z)-3,4,5-trimethoxystyryl)phenyl)amino)-1-(2-nitrophenyl)prop-2-en-1-one (13h)
159. (Z)-1-(2-aminophenyl)-3-((3-chloro-2-methoxy-5-((Z)-3,4,5-trimethoxystyryl)phenyl)amino)prop-2-en-1-one (13i)
160. (Z)-3-((3-chloro-2-methoxy-5-((Z)-3,4,5-trimethoxystyryl)phenyl)amino)-1-(4-fluorophenyl)prop-2-en-1-one (13j)
161. (Z)-3-((3-chloro-2-methoxy-5-((Z)-3,4,5-trimethoxystyryl)phenyl)amino)-1-(4-(trifluoromethyl)phenyl)prop-2-en-1-one (13k)
162. (Z)-3-((3-chloro-2-methoxy-5-((Z)-3,4,5-trimethoxystyryl)phenyl)amino)-1-(3-fluorophenyl)prop-2-en-1-one (13l)
163. (Z)-3-((3-chloro-2-methoxy-5-((Z)-3,4,5-trimethoxystyryl)phenyl)amino)-1-(3-chlorophenyl)prop-2-en-1-one (13m)
164. (Z)-3-((3-chloro-2-methoxy-5-((Z)-3,4,5-trimethoxystyryl)phenyl)amino)-1-(4-chlorophenyl)prop-2-en-1-one (13n)
165. (Z)-3-((3-chloro-2-methoxy-5-((Z)-3,4,5-trimethoxystyryl)phenyl)amino)-1-(4-(trifluoromethoxy)phenyl)prop-2-en-1-one (13o)
166. (Z)-3-((3-chloro-2-methoxy-5-((Z)-3,4,5-trimethoxystyryl)phenyl)amino)-1-((3,4-dimethoxyphenyl)prop-2-en-1-one (13p)
167. (Z)-3-((3-chloro-2-methoxy-5-((Z)-3,4,5-trimethoxystyryl)phenyl)amino)-1-(3-hydroxy-4-methoxyphenyl)prop-2-en-1-one (13q)
168. (Z)-3-((3-chloro-2-methoxy-5-((Z)-3,4,5-trimethoxystyryl)phenyl)amino)-1-(3-fluoro-4-methoxyphenyl)prop-2-en-1-one (13r)
169. (Z)-3-((3-chloro-2-methoxy-5-((Z)-3,4,5-trimethoxystyryl)phenyl)amino)-1-(3-chloro-4-methoxyphenyl)prop-2-en-1-one (13s)
170. (Z)-3-((3-chloro-2-methoxy-5-((Z)-3,4,5-trimethoxystyryl)phenyl)amino)-1-(4-methoxy-3-nitrophenyl)prop-2-en-1-one (13t)
171. (Z)-1-(3-amino-4-methoxyphenyl)-3-((3-chloro-2-methoxy-5-((Z)-3,4,5-trimethoxystyryl)phenyl)amino)prop-2-en-1-one (13u)
172. (Z)-3-(3-chloro-2-methoxy-5-(3,4,5-trimethoxystyryl)phenylamino)-1-(1H-indol-3-yl)prop-2-en-1-one (13v)
173. (Z)-3-(3-chloro-2-methoxy-5-(3,4,5-trimethoxystyryl)phenylamino)-1-(1-methyl-1H-indol-3-yl)prop-2-en-1-one (13w)
174. (Z)-3-((3-chloro-2-methoxy-5-((Z)-3,4,5-trimethoxystyryl)phenyl)amino)-1-(3,4,5-trimethoxyphenyl)prop-2-en-1-one (13x)
175. (Z)-1-(2-bromo-3,4,5-trimethoxyphenyl)-3-((3-chloro-2-methoxy-5-((Z)-3,4,5-trimethoxystyryl)phenyl)amino)prop-2-en-1-one (13y)
176. (Z)-3-((3-bromo-2-methoxy-5-((Z)-3,4,5-trimethoxystyryl)phenyl)amino)-1-phenylprop-2-en-1-one (14a)
177. (Z)-3-((3-bromo-2-methoxy-5-((Z)-3,4,5-trimethoxystyryl)phenyl)amino)-1-(4-methoxyphenyl)prop-2-en-1-one (14b)
178. (Z)-3-((3-bromo-2-methoxy-5-((Z)-3,4,5-trimethoxystyryl)phenyl)amino)-1-(3-methoxyphenyl)prop-2-en-1-one (14c)
179. (Z)-3-((3-bromo-2-methoxy-5-((Z)-3,4,5-trimethoxystyryl)phenyl)amino)-1-(2-methoxyphenyl)prop-2-en-1-one (14d)
180. (Z)-3-((3-bromo-2-methoxy-5-((Z)-3,4,5-trimethoxystyryl)phenyl)amino)-1-(4-hydroxyphenyl)prop-2-en-1-one (14e)
181. (Z)-3-((3-bromo-2-methoxy-5-((Z)-3,4,5-trimethoxystyryl)phenyl)amino)-1-(4-nitrophenyl)prop-2-en-1-one (14f)
182. (Z)-1-(4-aminophenyl)-3-((3-bromo-2-methoxy-5-((Z)-3,4,5-trimethoxystyryl)phenyl)amino)prop-2-en-1-one (14g)
183. (Z)-3-((3-bromo-2-methoxy-5-((Z)-3,4,5-trimethoxystyryl)phenyl)amino)-1-(2-nitrophenyl)prop-2-en-1-one (14h)
184. (Z)-1-(2-aminophenyl)-3-((3-bromo-2-methoxy-5-((Z)-3,4,5-trimethoxystyryl)phenyl)amino)prop-2-en-1-one (14i)
185. (Z)-3-((3-bromo-2-methoxy-5-((Z)-3,4,5-trimethoxystyryl)phenyl)amino)-1-(4-fluorophenyl)prop-2-en-1-one (14j)
186. (Z)-3-((3-bromo-2-methoxy-5-((Z)-3,4,5-trimethoxystyryl)phenyl)amino)-1-(4-(trifluoromethyl)phenyl)prop-2-en-1-one (14k)
187. (Z)-3-((3-bromo-2-methoxy-5-((Z)-3,4,5-trimethoxystyryl)phenyl)amino)-1-(3-fluorophenyl)prop-2-en-1-one (14l)
188. (Z)-3-((3-bromo-2-methoxy-5-((Z)-3,4,5-trimethoxystyryl)phenyl)amino)-1-(3-chlorophenyl)prop-2-en-1-one (14m)
189. (Z)-3-((3-bromo-2-methoxy-5-((Z)-3,4,5-trimethoxystyryl)phenyl)amino)-1-(4-chlorophenyl)prop-2-en-1-one (14n)
190. (Z)-3-((3-bromo-2-methoxy-5-((Z)-3,4,5-trimethoxystyryl)phenyl)amino)-1-(4-(trifluoromethoxy)phenyl)prop-2-en-1-one (14o)
191. (Z)-3-((3-bromo-2-methoxy-5-((Z)-3,4,5-trimethoxystyryl)phenyl)amino)-1-(3,4-dimethoxyphenyl)prop-2-en-1-one (14p)
192. (Z)-3-((3-bromo-2-methoxy-5-((Z)-3,4,5-trimethoxystyryl)phenyl)amino)-1-(3-hydroxy-4-methoxyphenyl)prop-2-en-1-one (14q)
193. (Z)-3-((3-bromo-2-methoxy-5-((Z)-3,4,5-trimethoxystyryl)phenyl)amino)-1-(3-fluoro-4-methoxyphenyl)prop-2-en-1-one (14r)

194. (Z)-3-((3-bromo-2-methoxy-5-((Z)-3,4,5-trimethoxystyryl)phenyl)amino)-1-(3-chloro-4-methoxyphenyl)prop-2-en-1-one (14s)
195. (Z)-3-((3-bromo-2-methoxy-5-((Z)-3,4,5-trimethoxystyryl)phenyl)amino)-1-(4-methoxy-3-nitrophenyl)prop-2-en-1-one (14t)
196. (Z)-1-(3-amino-4-methoxyphenyl)-3-((3-bromo-2-methoxy-5-((Z)-3,4,5-trimethoxystyryl)phenyl)amino)prop-2-en-1-one (14u)
197. (Z)-3-(3-bromo-2-methoxy-5-(3,4,5-trimethoxystyryl phenylamino)-1-(1H-indol-3-yl)prop-2-en-1-one (14v)
198. (Z)-3-(3-bromo-2-methoxy-5-(3,4,5-trimethoxystyryl phenylamino)-1-(1-methyl-1H-indol-3-yl)prop-2-en-1-one (14w)
199. (Z)-3-((3-bromo-2-methoxy-5-((Z)-3,4,5-trimethoxystyryl)phenyl)amino)-1-(3,4,5-trimethoxyphenyl)prop-2-en-1-one (14x)
200. (Z)-3-((3-bromo-2-methoxy-5-((Z)-3,4,5-trimethoxystyryl)phenyl)amino)-1-(2-bromo-3,4,5-trimethoxyphenyl)prop-2-en-1-one (14y)
201. (Z)-3-((3-hydr oxy-2-methoxy-5-((Z)-3,4,5-trimethoxystyryl)phenyl)amino)-1-phenylprop-2-en-1-one (15a)
202. (Z)-3-((3-hydroxy-2-methoxy-5-((Z)-3,4,5-trimethoxystyryl)phenyl)amino)-1-(4-methoxyphenyl)prop-2-en-1-one (15b)
203. (Z)-3-((3-hydroxy-2-methoxy-5-((Z)-3,4,5-trimethoxystyryl)phenyl)amino)-1-(3-methoxyphenyl)prop-2-en-1-one (15c)
204. (Z)-3-((3-hydroxy-2-methoxy-5-((Z)-3,4,5-trimethoxystyryl)phenyl)amino)-1-(2-methoxyphenyl)prop-2-en-1-one (15d)
205. (Z)-3-((3-hydroxy-2-methoxy-5-((Z)-3,4,5-trimethoxystyryl)phenyl)amino)-1-(4-hydroxyphenyl)prop-2-en-1-one (15e)
206. (Z)-3-((3-hydroxy-2-methoxy-5-((Z)-3,4,5-trimethoxystyryl)phenyl)amino)-1-(4-nitrophenyl)prop-2-en-1-one (15f)
207. (Z)-1-(4-aminophenyl)-3-((3-hydroxy-2-methoxy-5-((Z)-3,4,5-trimethoxystyryl)phenyl)amino)prop-2-en-1-one (15g)
208. (Z)-3-((3-hydroxy-2-methoxy-5-((Z)-3,4,5-trimethoxystyryl)phenyl)amino)-1-(2-nitrophenyl)prop-2-en-1-one (15h)
209. (Z)-1-(2-aminophenyl)-3-((3-hydroxy-2-methoxy-5-((Z)-3,4,5-trimethoxystyryl)phenyl)amino)prop-2-en-1-one (15i)
210. (Z)-1-(4-fluorophenyl)-3-((3-hydroxy-2-methoxy-5-((Z)-3,4,5-trimethoxystyryl)phenyl)amino)prop-2-en-1-one (15j)
211. (Z)-3-((3-hydroxy-2-methoxy-5-((Z)-3,4,5-trimethoxystyryl)phenyl)amino)-1-(4-(trifluoromethyl)phenyl)prop-2-en-1-one (15k)
212. (Z)-1-(3-fluorophenyl)-3-((3-hydroxy-2-methoxy-5-((Z)-3,4,5-trimethoxystyryl)phenyl)amino)prop-2-en-1-one (15l)
213. (Z)-1-(3-chlorophenyl)-3-((3-hydroxy-2-methoxy-5-((Z)-3,4,5-trimethoxystyryl)phenyl)amino)prop-2-en-1-one (15m)
214. (Z)-1-(4-chlorophenyl)-3-((3-hydroxy-2-methoxy-5-((Z)-3,4,5-trimethoxystyryl)phenyl)amino)prop-2-en-1-one (15n)
215. (Z)-3-((3-hydr oxy-2-methoxy-5-((Z)-3,4,5-trimethoxystyryl)phenyl)amino)-1-(4-(trifluoromethoxy)phenyl)prop-2-en-1-one (15o)
216. (Z)-1-(3,4-dimethoxyphenyl)-3-((3-hydroxy-2-methoxy-5-((Z)-3,4,5-trimethoxystyryl)phenyl)amino)prop-2-en-1-one (15p)
217. (Z)-3-((3-hydroxy-2-methoxy-5-((Z)-3,4,5-trimethoxystyryl)phenyl)amino)-1-(3-hydroxy-4-methoxyphenyl)prop-2-en-1-one (15q)
218. (Z)-1-(3-fluoro-4-methoxyphenyl)-3-((3-hydroxy-2-methoxy-5-((Z)-3,4,5-trimethoxystyryl)phenyl)amino)prop-2-en-1-one (15r)
219. (Z)-1-(3-chloro-4-methoxyphenyl)-3-((3-hydroxy-2-methoxy-5-((Z)-3,4,5-trimethoxystyryl)phenyl)amino)prop-2-en-1-one (15s)
220. (Z)-3-((3-hydroxy-2-methoxy-5-((Z)-3,4,5-trimethoxystyryl)phenyl)amino)-1-(4-methoxy-3-nitrophenyl)prop-2-en-1-one (15t)
221. (Z)-1-(3-amino-4-methoxyphenyl)-3-((3-hydroxy-2-methoxy-5-((Z)-3,4,5-trimethoxystyryl)phenyl)amino)prop-2-en-1-one (15u)
222. (Z)-3-(3-hydroxy-2-methoxy-5-(3,4,5-trimethoxystyryl)phenylamino)-1-(1H-indol-3-yl)prop-2-en-1-one (15v)
223. (Z)-3-(3-hydroxy-2-methoxy-5-(3,4,5-trimethoxystyryl)phenylamino)-1-(1-methyl-1H-indol-3-yl)prop-2-en-1-one (15w)
224. (Z)-3-((3-hydroxy-2-methoxy-5-((Z)-3,4,5-trimethoxystyryl)phenyl)amino)-1-(3,4,5-trimethoxyphenyl)prop-2-en-1-one (15x)
225. (Z)-1-(2-bromo-3,4,5-trimethoxyphenyl)-3-((3-hydroxy-2-methoxy-5-((Z)-3,4,5-trimethoxystyryl)phenyl)amino)prop-2-en-1-one (15y)
226. (Z)-3-((2-hydroxy-3-methoxy-6-((Z)-3,4,5-trimethoxystyryl)phenyl)amino)-1-phenylprop-2-en-1-one (16a)
227. (Z)-3-((2-hydroxy-3-methoxy-6-((Z)-3,4,5-trimethoxystyryl)phenyl)amino)-1-(4-methoxyphenyl)prop-2-en-1-one (16b)
228. (Z)-3-((2-hydroxy-3-methoxy-6-((Z)-3,4,5-trimethoxystyryl)phenyl)amino)-1-(3-methoxyphenyl)prop-2-en-1-one (16c)
229. (Z)-3-((2-hydroxy-3-methoxy-6-((Z)-3,4,5-trimethoxystyryl)phenyl)amino)-1-(2-methoxyphenyl)prop-2-en-1-one (16d)
230. (Z)-3-((2-hydroxy-3-methoxy-6-((Z)-3,4,5-trimethoxystyryl)phenyl)amino)-1-(4-hydroxyphenyl)prop-2-en-1-one (16e)
231. (Z)-3-((2-hydroxy-3-methoxy-6-((Z)-3,4,5-trimethoxystyryl)phenyl)amino)-1-(4-nitrophenyl)prop-2-en-1-one (16f)
232. (Z)-1-(4-aminophenyl)-3-((2-hydroxy-3-methoxy-6-((Z)-3,4,5-trimethoxystyryl)phenyl)amino)prop-2-en-1-one (16g)
233. (Z)-3-((2-hydroxy-3-methoxy-6-((Z)-3,4,5-trimethoxystyryl)phenyl)amino)-1-(2-nitrophenyl)prop-2-en-1-one (16h)
234. (Z)-1-(2-aminophenyl)-3-((2-hydroxy-3-methoxy-6-((Z)-3,4,5-trimethoxystyryl)phenyl)amino)prop-2-en-1-one (16i)
235. (Z)-1-(4-fluorophenyl)-3-((2-hydroxy-3-methoxy-6-((Z)-3,4,5-trimethoxystyryl)phenyl)amino)prop-2-en-1-one (16j)
236. (Z)-3-((2-hydroxy-3-methoxy-6-((Z)-3,4,5-trimethoxystyryl)phenyl)amino)-1-(4-(trifluoromethyl)phenyl)prop-2-en-1-one (16k)
237. (Z)-1-(3-fluorophenyl)-3-((2-hydroxy-3-methoxy-6-((Z)-3,4,5-trimethoxystyryl)phenyl)amino)prop-2-en-1-one (16l)
238. (Z)-1-(3-chlorophenyl)-3-((2-hydroxy-3-methoxy-6-((Z)-3,4,5-trimethoxystyryl)phenyl)amino)prop-2-en-1-one (16m)

239. (Z)-1-(4-chlorophenyl)-3-((2-hydroxy-3-methoxy-6-((Z)-3,4,5-trimethoxystyryl)phenyl)amino)prop-2-en-1-one (16n)
240. (Z)-3-((2-hydroxy-3-methoxy-6-((Z)-3,4,5-trimethoxystyryl)phenyl)amino)-1-(4-(trifluoromethoxy)phenyl)prop-2-en-1-one (16o)
241. (Z)-1-(3,4-dimethoxyphenyl)-3-((2-hydroxy-3-methoxy-6-((Z)-3,4,5-trimethoxystyryl)phenyl)amino)prop-2-en-1-one (16p)
242. (Z)-3-((2-hydroxy-3-methoxy-6-((Z)-3,4,5-trimethoxystyryl)phenyl)amino)-1-(3-hydroxy-4-methoxyphenyl)prop-2-en-1-one (16q)
243. (Z)-1-(3-fluoro-4-methoxyphenyl)-3-((2-hydroxy-3-methoxy-6-((Z)-3,4,5-trimethoxystyryl)phenyl)amino)prop-2-en-1-one (16r)
244. (Z)-1-(3-chloro-4-methoxyphenyl)-3-((2-hydroxy-3-methoxy-6-((Z)-3,4,5-trimethoxystyryl)phenyl)amino)prop-2-en-1-one (16s)
245. (Z)-3-((2-hydroxy-3-methoxy-6-((Z)-3,4,5-trimethoxystyryl)phenyl)amino)-1-(4-methoxy-3-nitrophenyl)prop-2-en-1-one (16t)
246. (Z)-3-(2-hydroxy-3-methoxy-6-(3,4,5-trimethoxystyryl)phenylamino)-1-(1H-indol-3-yl)prop-2-en-1-one (16v)
247. (Z)-3-(2-hydroxy-3-methoxy-6-(3,4,5-trimethoxystyryl)phenylamino)-1-(1-methyl-1H-indol-3-yl)prop-2-en-1-one (16w)
248. (Z)-3-((2-hydroxy-3-methoxy-6-((Z)-3,4,5-trimethoxystyryl)phenyl)amino)-1-(3,4,5-trimethoxyphenyl)prop-2-en-1-one (16x)
249. (Z)-1-(2-bromo-3,4,5-trimethoxyphenyl)-3-((2-hydroxy-3-methoxy-6-((Z)-3,4,5-trimethoxystyryl)phenyl)amino)prop-2-en-1-one (16y)
250. (Z)-3-((4,5-dimethoxy-2-((Z)-3,4,5-trimethoxystyryl)phenyl)amino)-1-phenylprop-2-en-1-one (17a)
251. (Z)-3-((4,5-dimethoxy-2-((Z)-3,4,5-trimethoxystyryl)phenyl)amino)-1-(4-methoxyphenyl)prop-2-en-1-one (17b)
252. (Z)-3-((4,5-dimethoxy-2-((Z)-3,4,5-trimethoxystyryl)phenyl)amino)-1-(3-methoxyphenyl)prop-2-en-1-one (17c)
253. (Z)-3-((4,5-dimethoxy-2-((Z)-3,4,5-trimethoxystyryl)phenyl)amino)-1-(2-methoxyphenyl)prop-2-en-1-one (17d)
254. (Z)-3-((4,5-dimethoxy-2-((Z)-3,4,5-trimethoxystyryl)phenyl)amino)-1-(4-hydroxyphenyl)prop-2-en-1-one (17e)
255. (Z)-3-((4,5-dimethoxy-2-((Z)-3,4,5-trimethoxystyryl)phenyl)amino)-1-(4-nitrophenyl)prop-2-en-1-one (17f)
256. (Z)-1-(4-aminophenyl)-3-((4,5-dimethoxy-2-((Z)-3,4,5-trimethoxystyryl)phenyl)amino)prop-2-en-1-one (17g)
257. (Z)-3-((4,5-dimethoxy-2-((Z)-3,4,5-trimethoxystyryl)phenyl)amino)-1-(2-nitrophenyl)prop-2-en-1-one (17h)
258. (Z)-1-(2-aminophenyl)-3-((4,5-dimethoxy-2-((Z)-3,4,5-trimethoxystyryl)phenyl)amino)prop-2-en-1-one (17i)
259. (Z)-3-((4,5-dimethoxy-2-((Z)-3,4,5-trimethoxystyryl)phenyl)amino)-1-(4-fluorophenyl)prop-2-en-1-one (17j)
260. (Z)-3-((4,5-dimethoxy-2-((Z)-3,4,5-trimethoxystyryl)phenyl)amino)-1-(4-(trifluoromethyl)phenyl)prop-2-en-1-one (17k)
261. (Z)-3-((4,5-dimethoxy-2-((Z)-3,4,5-trimethoxystyryl)phenyl)amino)-1-(3-fluorophenyl)prop-2-en-1-one (17l)
262. (Z)-1-(3-chlorophenyl)-3-((4,5-dimethoxy-2-((Z)-3,4,5-trimethoxystyryl)phenyl)amino)prop-2-en-1-one (17m)
263. (Z)-1-(4-chlorophenyl)-3-((4,5-dimethoxy-2-((Z)-3,4,5-trimethoxystyryl)phenyl)amino)prop-2-en-1-one (17n)
264. (Z)-3-((4,5-dimethoxy-2-((Z)-3,4,5-trimethoxystyryl)phenyl)amino)-1-(4-(trifluoromethoxy)phenyl)prop-2-en-1-one (17o)
265. (Z)-3-((4,5-dimethoxy-2-((Z)-3,4,5-trimethoxystyryl)phenyl)amino)-1-(3,4-dimethoxyphenyl)prop-2-en-1-one (17p)
266. (Z)-3-((4,5-dimethoxy-2-((Z)-3,4,5-trimethoxystyryl)phenyl)amino)-1-(3-hydroxy-4-methoxyphenyl)prop-2-en-1-one (17q)
267. (Z)-3-((4,5-dimethoxy-2-((Z)-3,4,5-trimethoxystyryl)phenyl)amino)-1-(3-fluoro-4-methoxyphenyl)prop-2-en-1-one (17r)
268. (Z)-1-(3-chloro-4-methoxyphenyl)-3-((4,5-dimethoxy-2-((Z)-3,4,5-trimethoxystyryl)phenyl)amino)prop-2-en-1-one (17s)
269. (Z)-3-((4,5-dimethoxy-2-((Z)-3,4,5-trimethoxystyryl)phenyl)amino)-1-(4-methoxy-3-nitrophenyl)prop-2-en-1-one (17t)
270. (Z)-1-(3-amino-4-methoxyphenyl)-3-((4,5-dimethoxy-2-((Z)-3,4,5-trimethoxystyryl)phenyl)amino)prop-2-en-1-one (17u)
271. (Z)-3-(4,5-dimethoxy-2-(3,4,5-trimethoxystyryl)phenylamino)-1-(1H-indol-3-yl)prop-2-en-1-one (17v)
272. (Z)-3-(4,5-dimethoxy-2-(3,4,5-trimethoxystyryl)phenylamino)-1-(1-methyl-1H-indol-3-yl)prop-2-en-1-one (17w)
273. (Z)-1-(3-amino-4,5-dimethoxyphenyl)-3-((4,5-dimethoxy-2-((Z)-3,4,5-trimethoxystyryl)phenyl)amino)prop-2-en-1-one (17x)
274. (Z)-1-(2-bromo-3,4,5-trimethoxyphenyl)-3-((4,5-dimethoxy-2-((Z)-3,4,5-trimethoxystyryl)phenyl)amino)prop-2-en-1-one (17y)
275. (Z)-3-((4-hydroxy-5-methoxy-2-((Z)-3,4,5-trimethoxystyryl)phenyl)amino)-1-phenylprop-2-en-1-one (18a)
276. (Z)-3-((4-hydroxy-5-methoxy-2-((Z)-3,4,5-trimethoxystyryl)phenyl)amino)-1-(4-methoxyphenyl)prop-2-en-1-one (18b)
277. (Z)-3-((4-hydroxy-5-methoxy-2-((Z)-3,4,5-trimethoxystyryl)phenyl)amino)-1-(3-methoxyphenyl)prop-2-en-1-one (18c)
278. (Z)-3-((4-hydroxy-5-methoxy-2-((Z)-3,4,5-trimethoxystyryl)phenyl)amino)-1-(2-methoxyphenyl)prop-2-en-1-one (18d)
279. (Z)-3-((4-hydroxy-5-methoxy-2-((Z)-3,4,5-trimethoxystyryl)phenyl)amino)-1-(4-hydroxyphenyl)prop-2-en-1-one (18e)
280. (Z)-3-((4-hydroxy-5-methoxy-2-((Z)-3,4,5-trimethoxystyryl)phenyl)amino)-1-(4-nitrophenyl)prop-2-en-1-one (18f)
281. (Z)-1-(4-aminophenyl)-3-((4-hydroxy-5-methoxy-2-((Z)-3,4,5-trimethoxystyryl)phenyl)amino)prop-2-en-1-one (18g)
282. (Z)-3-((4-hydroxy-5-methoxy-2-((Z)-3,4,5-trimethoxystyryl)phenyl)amino)-1-(2-nitrophenyl)prop-2-en-1-one (18h)
283. (Z)-1-(2-aminophenyl)-3-((4-hydroxy-5-methoxy-2-((Z)-3,4,5-trimethoxystyryl)phenyl)amino)prop-2-en-1-one (18i)
284. (Z)-1-(4-fluorophenyl)-3-((4-hydroxy-5-methoxy-2-((Z)-3,4,5-trimethoxystyryl)phenyl)amino)prop-2-en-1-one (18j)
285. (Z)-3-((4-hydroxy-5-methoxy-2-((Z)-3,4,5-trimethoxystyryl)phenyl)amino)-1-(4-(trifluoromethyl)phenyl)prop-2-en-1-one (18k)
286. (Z)-1-(3-fluorophenyl)-3-((4-hydroxy-5-methoxy-2-((Z)-3,4,5-trimethoxystyryl)phenyl)amino)prop-2-en-1-one (18l)

287. (Z)-1-(3-chlorophenyl)-3-((4-hydroxy-5-methoxy-2-((Z)-3,4,5-trimethoxystyryl)phenyl)amino)prop-2-en-1-one (18m)
288. (Z)-1-(4-chlorophenyl)-3-((4-hydroxy-5-methoxy-2-((Z)-3,4,5-trimethoxystyryl)phenyl)amino)prop-2-en-1-one (18n)
289. (Z)-3-((4-hydroxy-5-methoxy-2-((Z)-3,4,5-trimethoxystyryl)phenyl)amino)-1-(4-(trifluoromethoxy)phenyl)prop-2-en-1-one (18o)
290. (Z)-1-(3,4-dimethoxyphenyl)-3-((4-hydroxy-5-methoxy-2-((Z)-3,4,5-trimethoxystyryl)phenyl)amino)prop-2-en-1-one (18p)
291. (Z)-1-(3-hydroxy-4-methoxyphenyl)-3-((4-hydroxy-5-methoxy-2-((Z)-3,4,5-trimethoxystyryl)phenyl)amino)prop-2-en-1-one (18q)
292. (Z)-1-(3-fluoro-4-methoxyphenyl)-3-((4-hydroxy-5-methoxy-2-((Z)-3,4,5-trimethoxystyryl)phenyl)amino)prop-2-en-1-one (18r)
293. (Z)-1-(3-chloro-4-methoxyphenyl)-3-((4-hydroxy-5-methoxy-2-((Z)-3,4,5-trimethoxystyryl)phenyl)amino)prop-2-en-1-one (18s)
294. (Z)-3-((4-hydroxy-5-methoxy-2-((Z)-3,4,5-trimethoxystyryl)phenyl)amino)-1-(4-methoxy-3-nitrophenyl)prop-2-en-1-one (18t)
295. (Z)-1-(3-amino-4-methoxyphenyl)-3-((4-hydroxy-5-methoxy-2-((Z)-3,4,5-trimethoxystyryl)phenyl)amino)prop-2-en-1-one (18u)
296. (Z)-3-(4-hydroxy-5-methoxy-2-(3,4,5-trimethoxystyryl)phenylamino)-1-(1H-indol-3-yl)prop-2-en-1-one (18v)
297. (Z)-3-(4-hydroxy-5-methoxy-2-(3,4,5-trimethoxystyryl)phenylamino)-1-(1-methyl-1H-indol-3-yl)prop-2-en-1-one (18w)
298. (Z)-3-((4-hydroxy-5-methoxy-2-((Z)-3,4,5-trimethoxystyryl)phenyl)amino)-1-(3,4,5-trimethoxyphenyl)prop-2-en-1-one (18x)
299. (Z)-1-(2-bromo-3,4,5-trimethoxyphenyl)-3-((4-hydroxy-5-methoxy-2-((Z)-3,4,5-trimethoxystyryl)phenyl)amino)prop-2-en-1-one (18y)
300. (Z)-3-((4-fluoro-5-methoxy-2-((Z)-3,4,5-trimethoxystyryl)phenyl)amino)-1-phenylprop-2-en-1-one (19a)
301. (Z)-3-((4-fluoro-5-methoxy-2-((Z)-3,4,5-trimethoxystyryl)phenyl)amino)-1-(4-methoxyphenyl)prop-2-en-1-one (19b)
302. (Z)-3-((4-fluoro-5-methoxy-2-((Z)-3,4,5-trimethoxystyryl)phenyl)amino)-1-(3-methoxyphenyl)prop-2-en-1-one (19c)
303. (Z)-3-((4-fluoro-5-methoxy-2-((Z)-3,4,5-trimethoxystyryl)phenyl)amino)-1-(2-methoxyphenyl)prop-2-en-1-one (19d)
304. (Z)-3-((4-fluoro-5-methoxy-2-((Z)-3,4,5-trimethoxystyryl)phenyl)amino)-1-(4-hydroxyphenyl)prop-2-en-1-one (19e)
305. (Z)-3-((4-fluoro-5-methoxy-2-((Z)-3,4,5-trimethoxystyryl)phenyl)amino)-1-(4-nitrophenyl)prop-2-en-1-one (19f)
306. (Z)-1-(4-aminophenyl)-3-((4-fluoro-5-methoxy-2-((Z)-3,4,5-trimethoxystyryl)phenyl)amino)prop-2-en-1-one (19g)
307. (Z)-3-((4-fluoro-5-methoxy-2-((Z)-3,4,5-trimethoxystyryl)phenyl)amino)-1-(2-nitrophenyl)prop-2-en-1-one (19h)
308. (Z)-1-(2-aminophenyl)-3-((4-fluoro-5-methoxy-2-((Z)-3,4,5-trimethoxystyryl)phenyl)amino)prop-2-en-1-one (19i)
309. (Z)-3-((4-fluoro-5-methoxy-2-((Z)-3,4,5-trimethoxystyryl)phenyl)amino)-1-(4-fluorophenyl)prop-2-en-1-one (19j)
310. (Z)-3-((4-fluoro-5-methoxy-2-((Z)-3,4,5-trimethoxystyryl)phenyl)amino)-1-(4-(trifluoromethyl)phenyl)prop-2-en-1-one (19k)
311. (Z)-3-((4-fluoro-5-methoxy-2-((Z)-3,4,5-trimethoxystyryl)phenyl)amino)-1-(3-fluorophenyl)prop-2-en-1-one (19l)
312. (Z)-1-(3-chlorophenyl)-3-((4-fluoro-5-methoxy-2-((Z)-3,4,5-trimethoxystyryl)phenyl)amino)prop-2-en-1-one (19m)
313. (Z)-1-(4-chlorophenyl)-3-((4-fluoro-5-methoxy-2-((Z)-3,4,5-trimethoxystyryl)phenyl)amino)prop-2-en-1-one (19n)
314. (Z)-3-((4-fluoro-5-methoxy-2-((Z)-3,4,5-trimethoxystyryl)phenyl)amino)-1-(4-(trifluoromethoxy)phenyl)prop-2-en-1-one (19o)
315. (Z)-1-(3,4-dimethoxyphenyl)-3-((4-fluoro-5-methoxy-2-((Z)-3,4,5-trimethoxystyryl)phenyl)amino)prop-2-en-1-one (19p)
316. (Z)-3-((4-fluoro-5-methoxy-2-((Z)-3,4,5-trimethoxystyryl)phenyl)amino)-1-(3-hydroxy-4-methoxyphenyl)prop-2-en-1-one (19q)
317. (Z)-1-(3-fluoro-4-methoxyphenyl)-3-((4-fluoro-5-methoxy-2-((Z)-3,4,5-trimethoxystyryl)phenyl)amino)prop-2-en-1-one (19r)
318. (Z)-1-(3-chloro-4-methoxyphenyl)-3-((4-fluoro-5-methoxy-2-((Z)-3,4,5-trimethoxystyryl)phenyl)amino)prop-2-en-1-one (19s)
319. (Z)-3-((4-fluoro-5-methoxy-2-((Z)-3,4,5-trimethoxystyryl)phenyl)amino)-1-(4-methoxy-3-nitrophenyl)prop-2-en-1-one (19t)
320. (Z)-1-(3-amino-4-methoxyphenyl)-3-((4-fluoro-5-methoxy-2-((Z)-3,4,5-trimethoxystyryl)phenyl)amino)prop-2-en-1-one (19u)
321. (Z)-3-(4-fluoro-5-methoxy-2-(3,4,5-trimethoxystyryl)phenylamino)-1-(1H-indol-3-yl)prop-2-en-1-one (19v)
322. (Z)-3-(4-fluoro-5-methoxy-2-(3,4,5-trimethoxystyryl)phenylamino)-1-(1-methyl-1H-indol-3-yl)prop-2-en-1-one (19w)
323. (Z)-3-((4-fluoro-5-methoxy-2-((Z)-3,4,5-trimethoxystyryl)phenyl)amino)-1-(3,4,5-trimethoxyphenyl)prop-2-en-1-one (19x)
324. (Z)-1-(2-bromo-3,4,5-trimethoxyphenyl)-3-((4-fluoro-5-methoxy-2-((Z)-3,4,5-trimethoxystyryl)phenyl)amino)prop-2-en-1-one (19y)
325. (Z)-3-((4-chloro-5-methoxy-2-((Z)-3,4,5-trimethoxystyryl)phenyl)amino)-1-phenylprop-2-en-1-one (20a)
326. (Z)-3-((4-chloro-5-methoxy-2-((Z)-3,4,5-trimethoxystyryl)phenyl)amino)-1-(4-methoxyphenyl)prop-2-en-1-one (20b)
327. (Z)-3-((4-chloro-5-methoxy-2-((Z)-3,4,5-trimethoxystyryl)phenyl)amino)-1-(3-methoxyphenyl)prop-2-en-1-one (20c)
328. (Z)-3-((4-chloro-5-methoxy-2-((Z)-3,4,5-trimethoxystyryl)phenyl)amino)-1-(2-methoxyphenyl)prop-2-en-1-one (20d)
329. (Z)-3-((4-chloro-5-methoxy-2-((Z)-3,4,5-trimethoxystyryl)phenyl)amino)-1-(4-hydroxyphenyl)prop-2-en-1-one (20e)
330. (Z)-3-((4-chloro-5-methoxy-2-((Z)-3,4,5-trimethoxystyryl)phenyl)amino)-1-(4-nitrophenyl)prop-2-en-1-one (20f)
331. (Z)-1-(4-aminophenyl)-3-((4-chloro-5-methoxy-2-((Z)-3,4,5-trimethoxystyryl)phenyl)amino)prop-2-en-1-one (20g)

332. (Z)-3-((4-chloro-5-methoxy-2-((Z)-3,4,5-trimethoxystyryl)phenyl)amino)-1-(2-nitrophenyl)prop-2-en-1-one (20h)
333. (Z)-1-(2-aminophenyl)-3-((4-chloro-5-methoxy-2-((Z)-3,4,5-trimethoxystyryl)phenyl)amino)prop-2-en-1-one (20i)
334. (Z)-3-((4-chloro-5-methoxy-2-((Z)-3,4,5-trimethoxystyryl)phenyl)amino)-1-(4-fluorophenyl)prop-2-en-1-one (20j)
335. (Z)-3-((4-chloro-5-methoxy-2-((Z)-3,4,5-trimethoxystyryl)phenyl)amino)-1-(4-(trifluoromethyl)phenyl)prop-2-en-1-one (20k)
336. (Z)-3-((4-chloro-5-methoxy-2-((Z)-3,4,5-trimethoxystyryl)phenyl)amino)-1-(3-fluorophenyl)prop-2-en-1-one (20l)
337. (Z)-3-((4-chloro-5-methoxy-2-((Z)-3,4,5-trimethoxystyryl)phenyl)amino)-1-(3-chlorophenyl)prop-2-en-1-one (20m)
338. (Z)-3-((4-chloro-5-methoxy-2-((Z)-3,4,5-trimethoxystyryl)phenyl)amino)-1-(4-chlorophenyl)prop-2-en-1-one (20n)
339. (Z)-3-((4-chloro-5-methoxy-2-((Z)-3,4,5-trimethoxystyryl)phenyl)amino)-1-(4-(trifluoromethoxy)phenyl)prop-2-en-1-one (20o)
340. (Z)-3-((4-chloro-5-methoxy-2-((Z)-3,4,5-trimethoxystyryl)phenyl)amino)-1-(3,4-dimethoxyphenyl)prop-2-en-1-one (20p)
341. (Z)-3-((4-chloro-5-methoxy-2-((Z)-3,4,5-trimethoxystyryl)phenyl)amino)-1-(3-hydroxy-4-methoxyphenyl)prop-2-en-1-one (20q)
342. (Z)-3-((4-chloro-5-methoxy-2-((Z)-3,4,5-trimethoxystyryl)phenyl)amino)-1-(3-fluoro-4-methoxyphenyl)prop-2-en-1-one (20r)
343. (Z)-1-(3-chloro-4-methoxyphenyl)-3-((4-chloro-5-methoxy-2-((Z)-3,4,5-trimethoxystyryl)phenyl)amino)prop-2-en-1-one (20s)
344. (Z)-3-((4-chloro-5-methoxy-2-((Z)-3,4,5-trimethoxystyryl)phenyl)amino)-1-(4-methoxy-3-nitrophenyl)prop-2-en-1-one (20t)
345. (Z)-1-(3-amino-4-methoxyphenyl)-3-((4-chloro-5-methoxy-2-((Z)-3,4,5-trimethoxystyryl)phenyl)amino)prop-2-en-1-one (20u)
346. (Z)-3-(4-chloro-5-methoxy-2-(3,4,5-trimethoxystyryl)phenylamino)-1-(1H-indol-3-yl)prop-2-en-1-one (20v)
347. (Z)-3-(4-chloro-5-methoxy-2-(3,4,5-trimethoxystyryl)phenylamino)-1-(1-methyl-1H-indol-3-yl)prop-2-en-1-one (20w)
348. (Z)-3-((4-chloro-5-methoxy-2-((Z)-3,4,5-trimethoxystyryl)phenyl)amino)-1-(3,4,5-trimethoxyphenyl)prop-2-en-1-one (20x)
349. (Z)-1-(2-bromo-3,4,5-trimethoxyphenyl)-3-((4-chloro-5-methoxy-2-((Z)-3,4,5-trimethoxystyryl)phenyl)amino)prop-2-en-1-one (20y)
350. (Z)-3-((2,3-dimethoxy-6-((Z)-3,4,5-trimethoxystyryl)phenyl)amino)-1-phenylprop-2-en-1-one (21a)
351. (Z)-3-((2,3-dimethoxy-6-((Z)-3,4,5-trimethoxystyryl)phenyl)amino)-1-(4-methoxyphenyl)prop-2-en-1-one (21b)
352. (Z)-3-((2,3-dimethoxy-6-((Z)-3,4,5-trimethoxystyryl)phenyl)amino)-1-(3-methoxyphenyl)prop-2-en-1-one (21c)
353. (Z)-3-((2,3-dimethoxy-6-((Z)-3,4,5-trimethoxystyryl)phenyl)amino)-1-(2-methoxyphenyl)prop-2-en-1-one (21d)
354. (Z)-3-((2,3-dimethoxy-6-((Z)-3,4,5-trimethoxystyryl)phenyl)amino)-1-(4-hydroxyphenyl)prop-2-en-1-one (21e)
355. (Z)-3-((2,3-dimethoxy-6-((Z)-3,4,5-trimethoxystyryl)phenyl)amino)-1-(4-nitrophenyl)prop-2-en-1-one (21f)
356. (Z)-1-(4-aminophenyl)-3-((2,3-dimethoxy-6-((Z)-3,4,5-trimethoxystyryl)phenyl)amino)prop-2-en-1-one (21g)
357. (Z)-3-((2,3-dimethoxy-6-((Z)-3,4,5-trimethoxystyryl)phenyl)amino)-1-(2-nitrophenyl)prop-2-en-1-one (21h)
358. (Z)-1-(2-aminophenyl)-3-((2,3-dimethoxy-6-((Z)-3,4,5-trimethoxystyryl)phenyl)amino)prop-2-en-1-one (21i)
359. (Z)-3-((2,3-dimethoxy-6-((Z)-3,4,5-trimethoxystyryl)phenyl)amino)-1-(4-fluorophenyl)prop-2-en-1-one (21j)
360. (Z)-3-((2,3-dimethoxy-6-((Z)-3,4,5-trimethoxystyryl)phenyl)amino)-1-(4-(trifluoromethyl)phenyl)prop-2-en-1-one (21k)
361. (Z)-3-((2,3-dimethoxy-6-((Z)-3,4,5-trimethoxystyryl)phenyl)amino)-1-(3-fluorophenyl)prop-2-en-1-one (21l)
362. (Z)-1-(3-chlorophenyl)-3-((2,3-dimethoxy-6-((Z)-3,4,5-trimethoxystyryl)phenyl)amino)prop-2-en-1-one (21m)
363. (Z)-1-(4-chlorophenyl)-3-((2,3-dimethoxy-6-((Z)-3,4,5-trimethoxystyryl)phenyl)amino)prop-2-en-1-one (21n)
364. (Z)-3-((2,3-dimethoxy-6-((Z)-3,4,5-trimethoxystyryl)phenyl)amino)-1-(4-(trifluoromethoxy)phenyl)prop-2-en-1-one (21o)
365. (Z)-3-((2,3-dimethoxy-6-((Z)-3,4,5-trimethoxystyryl)phenyl)amino)-1-(3,4-dimethoxyphenyl)prop-2-en-1-one (21p)
366. (Z)-3-((2,3-dimethoxy-6-((Z)-3,4,5-trimethoxystyryl)phenyl)amino)-1-(3-hydroxy-4-methoxyphenyl)prop-2-en-1-one (21q)
367. (Z)-3-((2,3-dimethoxy-6-((Z)-3,4,5-trimethoxystyryl)phenyl)amino)-1-(3-fluoro-4-methoxyphenyl)prop-2-en-1-one (21r)
368. (Z)-1-(3-chloro-4-methoxyphenyl)-3-((2,3-dimethoxy-6-((Z)-3,4,5-trimethoxystyryl)phenyl)amino)prop-2-en-1-one (21s)
369. (Z)-3-((2,3-dimethoxy-6-((Z)-3,4,5-trimethoxystyryl)phenyl)amino)-1-(4-methoxy-3-nitrophenyl)prop-2-en-1-one (21t)
370. (Z)-1-(3-amino-4-methoxyphenyl)-3-((2,3-dimethoxy-6-((Z)-3,4,5-trimethoxystyryl)phenyl)amino)prop-2-en-1-one (21u)
371. (Z)-3-(2,3-dimethoxy-6-(3,4,5-trimethoxystyryl)phenylamino)-1-(1H-indol-3-yl)prop-2-en-1-one (21v)
372. (Z)-3-(2,3-dimethoxy-6-(3,4,5-trimethoxystyryl)phenylamino)-1-(1-methyl-1H-indol-3-yl)prop-2-en-1-one (21w)
373. (Z)-3-((2,3-dimethoxy-6-((Z)-3,4,5-trimethoxystyryl)phenyl)amino)-1-(3,4,5-trimethoxyphenyl)prop-2-en-1-one (21x)
374. (Z)-1-(2-bromo-3,4,5-trimethoxyphenyl)-3-((2,3-dimethoxy-6-((Z)-3,4,5-trimethoxystyryl)phenyl)amino)prop-2-en-1-one (21y)

In a further embodiment of the invention wherein novel 3,4,5-trimethoxystyrylarylaminopropenones of general formulae A are useful as antitumor agents.

In one of the embodiment of the invention wherein novel 3,4,5-trimethoxy styrylarylaminopropenones of general formulae A have antitumor activity against cell lines selected from the group consisting of (non-small cell lung cancer, colon cancer, cervical carcinoma and breast cancer).

The present invention also provides a process for the preparation of compounds of general formulae A
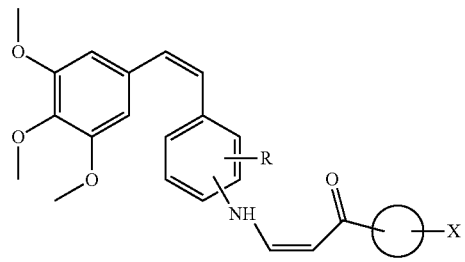
A
wherein:
R=H, OMe, Cl, F, OH, Me
X=aryl, heteroaryl
wherein, said process comprising reacting (Z)-3-(3,4,5-trimethoxystyryl)aniline of formula 5(a-o)
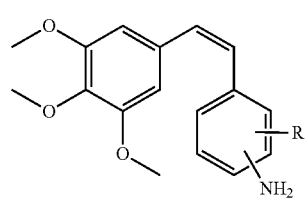
5(a-o)
wherein R=H, OMe, OH, Cl, F, Me
with the compounds of formulae 6a, 6b, 6c, 6d, 6f, 6g, 6h, 6i, 6j, 6k, 6l, 6m, 6n, 6o, 6p, 6q, 6r, 6s, 6t, 6u, 6v, 6w, 6x and 6y,
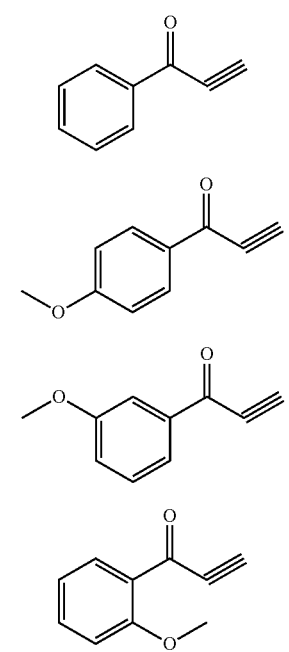
6a
6b
6c
6d
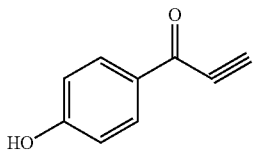
6e
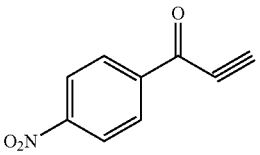
6f
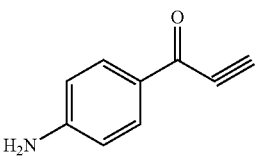
6g
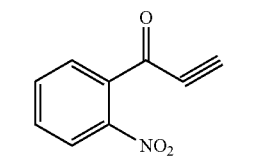
6h
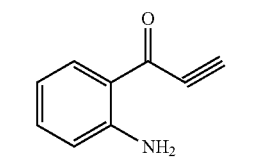
6i
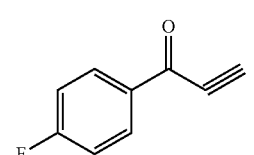
6j
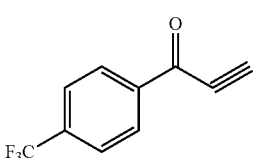
6k
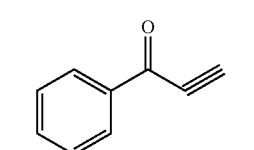
6l
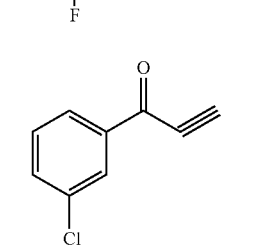
6m

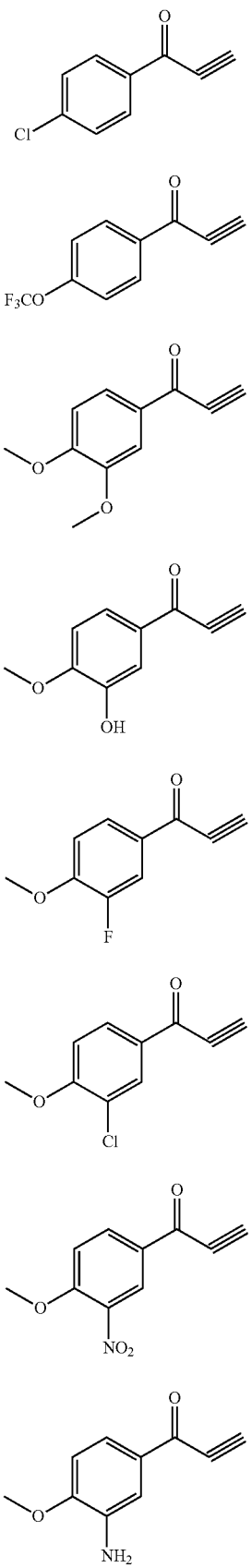
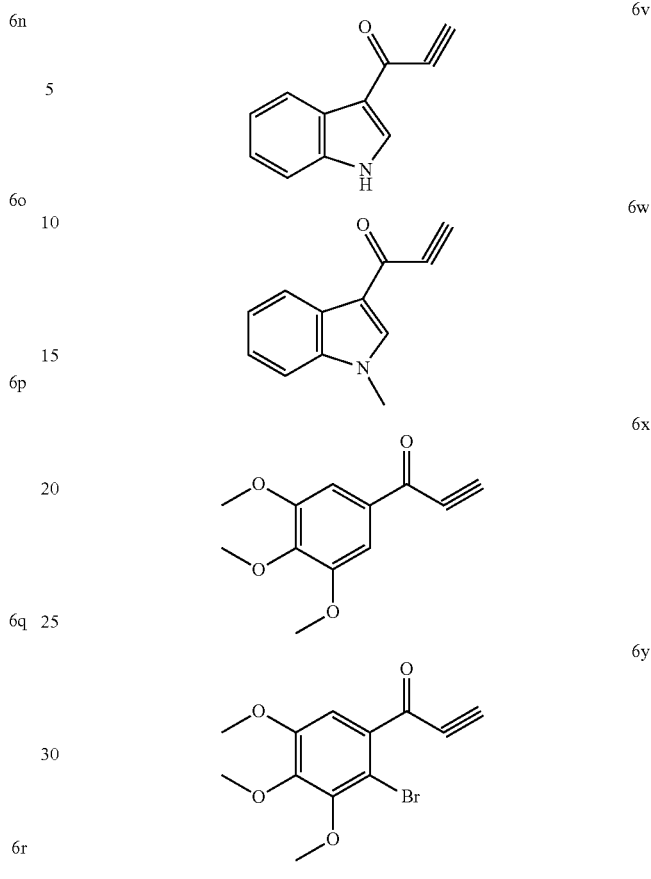

in ethanol/methanol at a temperature ranging between 25-35° C. for a period ranging between 3-4 h to obtain the desired products of formulae 7a-7y, 8a-8y, 9a-9y, 10a-10y, 11a-11y, 12a-12y, 13a-13y, 14a-14y, 15a-15y, 16a-16y, 17a-17y, 18a-18y, 19a-19y, 20a-20y, 21a-21y, respectively.

DETAILED DESCRIPTION OF THE INVENTION

The precursors (Z)-3-(3,4,5-trimethoxystyryl)aniline of formula 5(a-o) have been prepared
using literature method (Keith A. Monk, a Rogelio Siles, a Mallinath B. Hadimani, a Benon E. ugabe, a J. Freeland Ackley, a Scott W. Studerus, a Klaus Edvardsen, b Mary Lynn Trawick, a Charles M. Garner, a Monte R. Rhodes, c George R. Pettitc and Kevin G. Pinneya,*, Bioorganic & Medicinal Chemistry 14 (2006) 3231-3244) The crucial intermediates for the preparation of precursors (Z)-3-(3,4, 5-trimethoxystyryl)aniline formula 5(a-o) are (Z)-1,2,3-trimethoxy-5-(3-nitrostyryl)benzene 4(a-o) have been prepared using literature methods (Kevin G. Pinney, a,*Maria P. Mejia, a Victor M. Villalobos, a Brent E. Rosenquist, a George R. Pettit, b Pascal Verdier-Pinardc and Ernest Hamelc, Bioorganic & Medicinal Chemistry 8 (2000) 2417±2425)

These new 3,4,5-trimethoxystyrylarylaminopropenone derivatives have shown promising anticancer activity in various cell lines. The molecules synthesized are of immense biological significance. This resulted in design and synthesis of new congeners as illustrated in scheme1 which comprise: The Michael condensation between (Z)-3-(3,4,5- trimethoxystyryl)aniline of formula 5(a-o) and the 1-aryl-prop-2-yn-1-one compounds of formulae 6a to 6y for the compounds (7a-7y to 21a-21y)

Stirring the reaction mixtures at room temperature for 3-4 h. to obtain the compounds (7a-7y to 21a-21y) respectively.

Synthesis of 3,4,5-trimethoxystyrylarylaminopropenones.

Purified by the column chromatography using different solvents like ethyl acetate and hexane.

The Synthesis of 3,4,5-trimethoxystyrylarylaminopropenone described in the present invention are outlined in Scheme 1. The final step has been carried out by the application of Michael condensation between (Z)-3-(3,4,5-trimethoxystyryl)aniline of formula 5(a-o) and substituted phenylprop-2-yn-1-one in ethanol the compounds of formulae 6a to 6y for the compounds (7a-7y to 21a-21y). The key intermediates 3-substituted (Z)-3-(3,4,5-trimethoxystyryl) aniline 5(a-o) are prepared in five sequential steps. Trimethoxy benzaldehyde (1a) reduces with sodium borohydride in methanol gives (3,4,5-trimethoxyphenyl)methanol (1b). This was further reacted with PBr$_3$ in CH$_2$Cl$_2$ to produce 5-(bromomethyl)-1,2,3-trimethoxybenzene (1c), then this was further reacted with triphenyl phosphine in toluene to give 3,4,5-tri-methoxybenzyltriphenylphosphonium bromide (2) in good yields. The obtained witting salt was reacted with substituted benzaldehyde 3(a-o) in presence of NaH in CH$_2$Cl$_2$ to produce (Z)-1,2,3-trimethoxy-5-(substituted-nitrostyryl)benzene 4(a-o) and (E)-1,2,3-trimethoxy-5-(substituted-nitrostyryl)benzene in (1:1)% of yield. (Z)-1,2,3-trimethoxy-5-(substituted nitrostyryl)benzene reduced with Zn in acetic acid produced (Z)-3-(3,4,5-trimethoxystyryl)aniline 5(a-o).

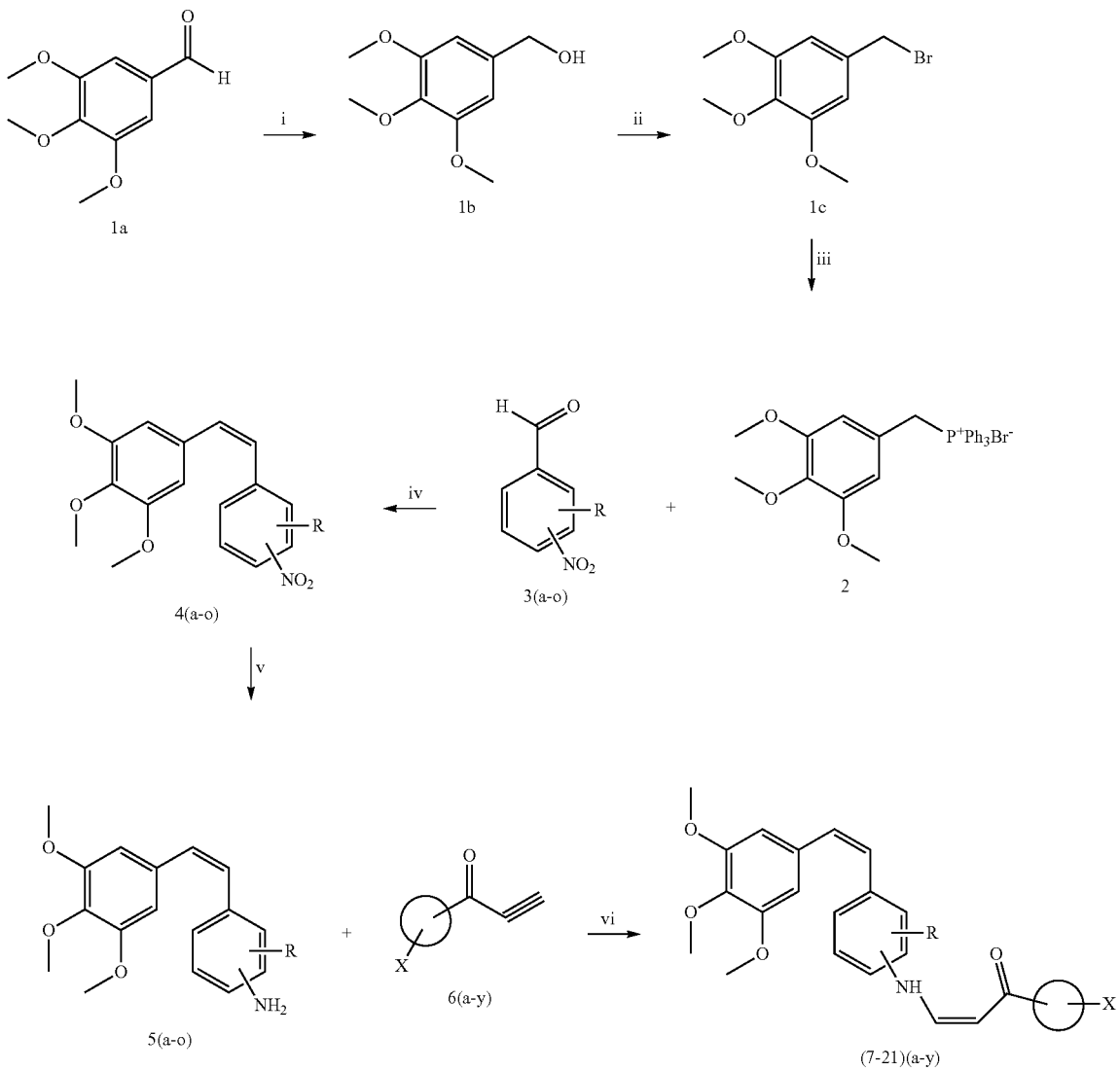

Scheme 1

Reagents & conditions:
(i) NaBH$_4$, MeOH, 3 h, 15-20° C. (85%)
(ii) PBr$_3$, CH$_2$Cl$_2$ 2 h, 15-20° C. (90%)
(iii) PPh$_3$, toluene, 12 h, 80° C. (75%)
(iv) NaH, CH$_2$Cl$_2$, 18 h, 15-20 °C (65%)
(v) Zn AcOH, 4 h, RT (70%)
(vi) EtOH, 24-30° C., 4h (85%)

The present invention relates to compounds synthesis and biological evaluation of novel 3,4,5-trimethoxystyrylarylaminopropenone derivatives of general formula A as potential anticancer agents and a process for the preparation thereof,

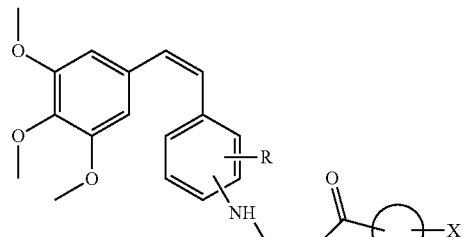

A wherein:
R=H, OMe, Cl, F, OH, Me
X=aryl, heteroaryl

More particularly the present invention relates to
(Z)-1-phenyl-3-(3-(3,4,5-trimethoxystyryl)phenylamino)
  prop-2-en-1-one (7a-7y)
(Z)-1-phenyl-3-(4-(3,4,5-trimethoxystyryl)phenylamino)
  prop-2-en-1-one (8a-8y)
(Z)-1-phenyl-3-(2-(3,4,5-trimethoxystyryl)phenylamino)
  prop-2-en-1-one (9a-9y)
(Z)-3-(2-methoxy-5-(3,4,5-trimethoxystyryl)phenylamino)-
  1-phenylprop-2-en-1-one (10a10y)
(Z)-3-(2,3-dimethoxy-5-(3,4,5-trimethoxystyryl)phenylamino)-1-phenylprop-2-en-1-one (11a-11y)
(Z)-3-(3-fluoro-2-methoxy-5-(3,4,5-trimethoxystyryl)phenylamino)-1-phenylprop-2-en-1-one (12a-12y)
(Z)-3-(3-bromo-2-methoxy-5-(3,4,5-trimethoxystyryl)phenylamino)-1-phenylprop-2-en-1-one (13a-13y)
(Z)-3-(3-chloro-2-methoxy-5-(3,4,5-trimethoxystyryl)phenylamino)-1-phenylprop-2-en-1-one (14a-14y)
(Z)-3-(3-hydroxy-2-methoxy-5-(3,4,5-trimethoxystyryl)phenylamino)-1-phenylprop-2-en-1-one (15a-15y)
(Z)-3-(2-hydroxy-3-methoxy-6-(3,4,5-trimethoxystyryl)phenylamino)-1-phenylprop-2-en-1-one (16a-16y)
(Z)-3-(4,5-dimethoxy-2-(3,4,5-trimethoxystyryl)phenylamino)-1-phenylprop-2-en-1-one (17a-17y)
(Z)-3-(4-hydroxy-5-methoxy-2-(3,4,5-trimethoxystyryl)phenylamino)-1-phenylprop-2-en-1-one (18a-18y)
(Z)-3-(4-fluoro-5-methoxy-2-(3,4,5-trimethoxystyryl)phenylamino)-1-phenylprop-2-en-1-one (19a-19y)
(Z)-3-(2,3-dimethoxy-6-(3,4,5-trimethoxystyryl)phenylamino)-1-phenylprop-2-en-1-one (20a-20y)
(Z)-3-(4-chloro-5-methoxy-2-(3,4,5-trimethoxystyryl)phenylamino)-1-phenylprop-2-en-1-one (21a-21y)
compounds useful as anticancer (antitumour) agents.

The structural formulae of these compounds are given below.

(7a-7y)

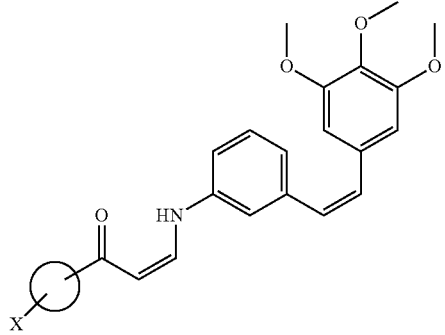

(8a-8y)

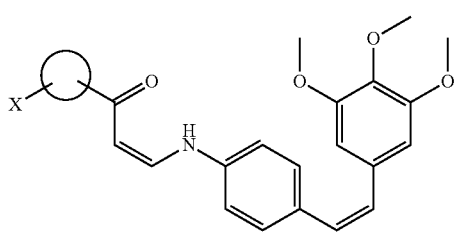

(9a-9y)

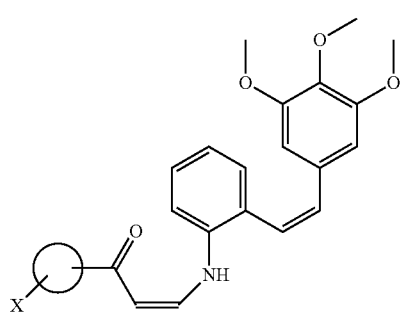

(10a-10y)

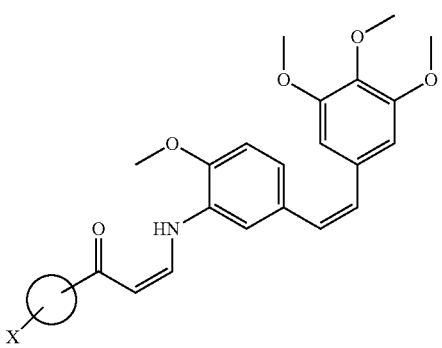

(11a-11y)
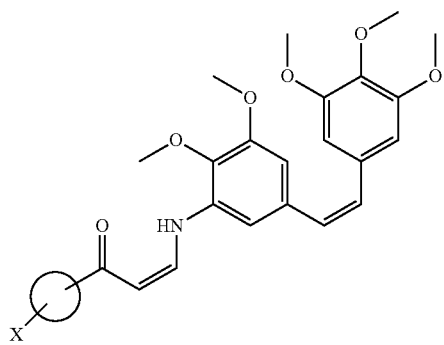
(12a-12y)
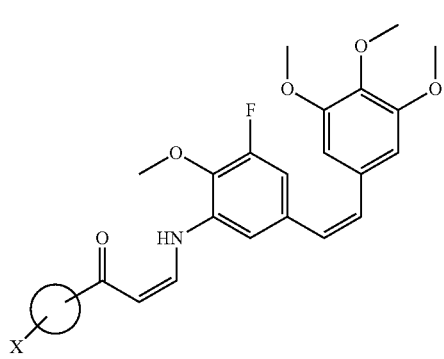
(13a-13y)
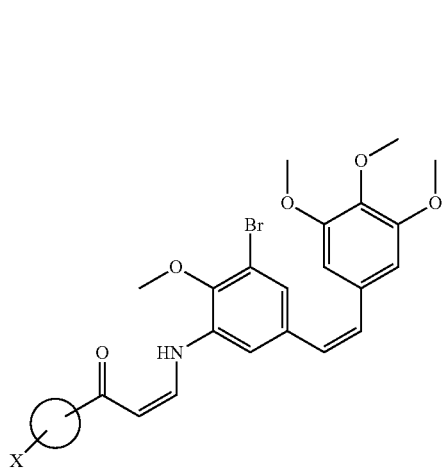
(14a-14y)
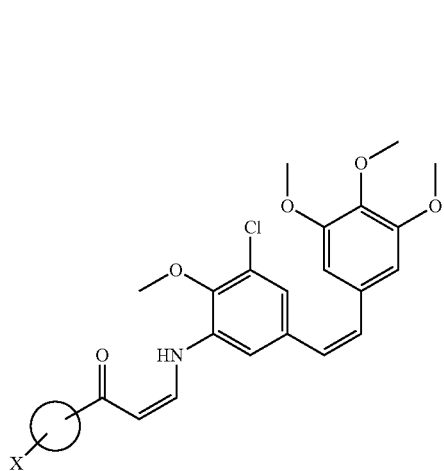
(15a-15y)
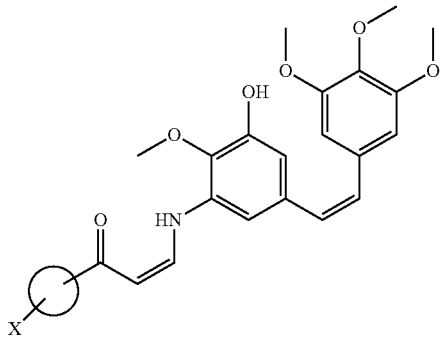
(16a-16y)
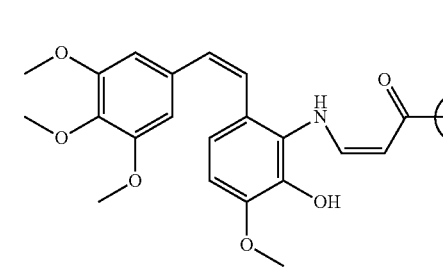
(17a-17y)
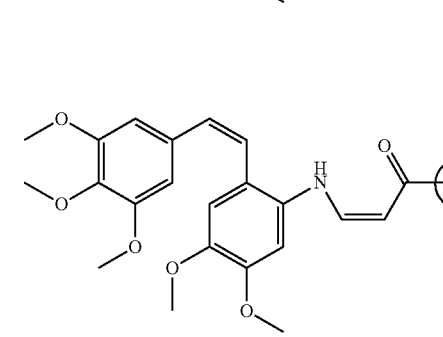
(18a-18y)
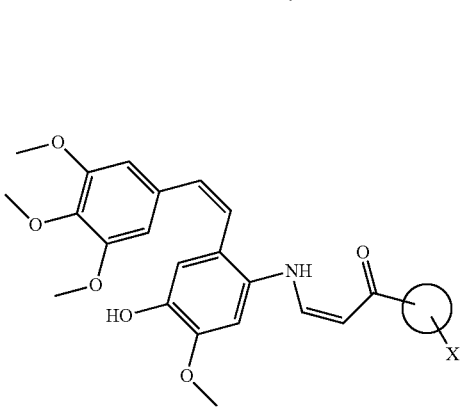
(19a-19y)
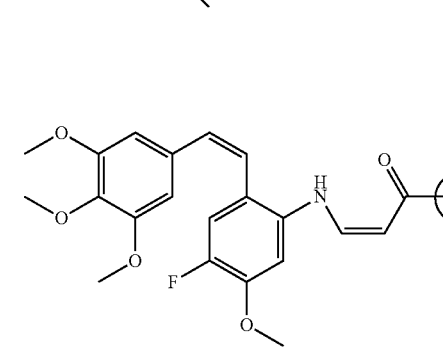

-continued

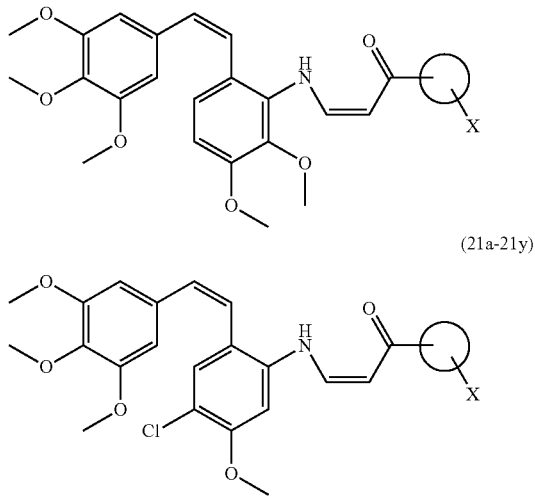

X=aryl, heteroaryl;

The following examples are given by way of illustration and therefore should not be construed to the present limit of the scope of invention.

Example 1

(Z)-3-((2-methoxy-5-((Z)-3,4,5-trimethoxystyryl) phenyl)amino)-1-(4-(trifluoromethoxy)phenyl) prop-2-en-1-one (10o)

To a stirred solution of (Z)-2-methoxy-5-(3,4,5-trimethoxystyryl)aniline (5d) (100 mg, 0.317 mmol) in ethanol (5 ml) 1-(4-(trifluoromethoxy)phenyl)prop-2-yn-1-one (6o) (67.9 mg, 0.317 mmol) was added. The reaction mixture was stirred at a temperature of 28° C. for 4 h and the reaction was monitored by TLC using ethyl acetate/hexane (1:1) as a solvent system. Then water (10 ml) was added to reaction mixture. A yellow colour solid appears which was filtered and washed with ethanol. (yield: 120 mg, 71%), mp: 112-115° C.; $^1$H NMR (CDCl$_3$, 300 MHz) δδ (ppm): 3.96 (s, 3H), 3.85 (s, 3H), 3.71 (s, 6H), 5.95 (d, J=7.55 Hz, 1H), 6.50 (d, J=10.09 Hz, 4H), 6.82 (d, J=8.49 Hz, 1H), 6.97 (d, J=8.49 Hz, 1H), 7.14 (s, 1H), 7.26 (s, 3H), 7.99 (d, J=7.17 Hz, 2H), 12.15 (d, J=13.4 Hz, 1H); FABMAS:(M+H)=530.

Example 2

(Z)-1-(2-bromo-3,4,5-trimethoxyphenyl)-3-((2-methoxy-5-((Z)-3,4,5-trimethoxystyryl)phenyl) amino)prop-2-en-1-one (10y)

To a stirred solution of (Z)-2-methoxy-5-(3,4,5-trimethoxystyryl)aniline (5d) (100 mg, 0.317 mmol) in ethanol (5 ml) 1-(2-bromo-3,4,5-trimethoxyphenyl)prop-2-yn-1-one (6y) (94.9 mg, 0.317 mmol) was added. The reaction mixture was stirred at a temperature of 27° C. for 4 h and the reaction was monitored by TLC using ethyl acetate/hexane (1:1) as a solvent system. Then water (10 ml) was added to reaction mixture. A yellow colour solid appears which was filtered and washed with ethanol. (yield: 150 mg, 76%); mp: 108-110° C.; $^1$H NMR (CDCl$_3$, 300 MHz) δδ (ppm): 3.94 (s, 3H), 3.91 (s, 3H), 3.90 (s, 3H), 3.87 (s, 3H), 3.84 (s, 3H), 3.70 (s, 6H), 5.64 (d, J=8.30 Hz, 1H), 6.49 (d, J=9.06 Hz, 4H), 6.81 (d, J=8.3 Hz, 1H), 6.87 (s, 1H) 6.97 (d, J=8.3 Hz, 1H), 7.14 (s, 1H), 7.28-7.19 (m, 1H), 11.92 (d, J=12.8 Hz, NH); FABMAS: (M+H)=614.

Example 3

(Z)-3-((2-methoxy-5-((Z)-3,4,5-trimethoxystyryl) phenyl)amino)-1-(1-methyl-1H-indol-3-yl)prop-2-en-1-one (10w)

To a stirred solution of (Z)-2-methoxy-5-(3,4,5-trimethoxystyryl)aniline (5d) (100 mg, 0.317 mmol) in ethanol (5 ml) 1-(1-methyl-1H-indol-3-yl)prop-2-yn-1-one (6v) (58.1 mg, 0.317 mmol) was added. The reaction mixture was stirred at a temperature of 28° C. for 4 h and the reaction was monitored by TLC using hexane/ethyl acetate (4:6) as a solvent system. Then water (10 ml) was added to reaction mixture. A light brown colour solid appears which was filtered and washed with ethanol. (yield: 110 mg, 70%); mp: 120-122° C.; $^1$H NMR (CDCl$_3$, 300 MHz) δδ (ppm): 3.96 (s, 3H), 3.83 (d, 6H), 3.70 (s, 6H), 5.79 (d, J=7.55 Hz, 1H), 6.49 (qt, J=12.1 Hz, 5.3 Hz, 2H), 6.58 (s, 2H), 6.78 (d, J=8.3 Hz, 1H), 6.92 (d, J=8.3 Hz, 1H), 7.11-7.03 (s, 2H), 7.35-7.23 (m, 3H), 7.67 (s, 1H), 8.45-8.41 (m, 1H), 11.87 (d, J=12.1 Hz, NH); FABMAS:(M+H)=499

Example 4

(Z)-3-((2,3-dimethoxy-5-((Z)-3,4,5-trimethoxystyryl)phenyl)amino)-1-(1-methyl-1H-indol-3-yl) prop-2-en-1-one. (11w)

To a stirred solution of (Z)-2,3-dimethoxy-5-(3,4,5-trimethoxystyryl)aniline (5e) (100 mg, 0.289 mmol) in ethanol (5 ml) 1-(1-methyl-1H-indol-3-yl)prop-2-yn-1-one (6v) (94.7 mg, 0.289 mmol) was added. The reaction mixture was stirred at a temperature of 29° C. for 4 h and the reaction was monitored by TLC using hexane/ethyl acetate (1:1) as a solvent system. Then appropriate water was added to reaction mixture. A light yellow colour solid appears which was filtered and washed with ethanol. (yield: 120 mg, 78%); mp: 130-132° C.; $^1$H NMR (CDCl$_3$, 300 MHz) δδ (ppm): 3.72 (s, 9H), 3.87 (s, 3H), 3.92 (s, 3H), 4.05 (s, 3H), 5.90 (d, J=7.55 Hz, 1H), 6.59 (d, J=12.1 Hz, 5H) 6.8 (s, 1H), 7.24-7.17 (m, 1H) 7.37 (s, 3H), 7.73 (s, 1H), 8.50 (s, 1H), 12.01 (d, J=12.1 Hz, NH); FABMAS:(M+H)=529.

Example 5

(Z)-3-((2,3-dimethoxy-5-((Z)-3,4,5-trimethoxystyryl)phenyl)amino)-1-(3,4,5-trimethoxyphenyl) prop-2-en-1-one (11x)

To a stirred solution of (Z)-2,3-dimethoxy-5-(3,4,5-trimethoxystyryl)aniline (5e) (100 mg, 0.289 mmol) in ethanol (5 ml) 1-(3,4,5-trimethoxyphenyl)prop-2-yn-1-one (6x) (63.7 mg, 0.289 mmol) was added. The reaction mixture was stirred at a temperature of 25° C. for 4 hrs and the reaction was monitored by TLC using hexane/ethyl acetate (6:4) as a solvent system. Then appropriate water was added to reaction mixture. A yellow colour solid appears which was filtered and washed with ethanol. (yield: 140 mg, 85%); mp: 101-103° C.; $^1$H NMR (CDCl$_3$, 300 MHz) δδ (ppm): δ 3.72 (s, 6H), 3.82 (s, 3H), 3.84 (s, 3H), 3.90 (s, 3H), 3.94 (s, 6H), 3.96 (s, 3H), 5.93 (d, J=8.3 Hz, 1H), 6.58-6.49 (m, 5H) 6.79 (s, 1H), 7.19 (s, 2H) 7.30-7.23 (m, 1H), 12.12 (d, J=12.1 Hz, NH); FABMAS:(M+H)=566.

Example 6

(Z)-3-((2,3-dimethoxy-5-((Z)-3,4,5-trimethoxystyryl)phenyl)amino)-1-(4-(trifluoromethoxy)phenyl)prop-2-en-1-one (11o)

To a stirred solution of (Z)-2,3-dimethoxy-5-(3,4,5-trimethoxystyryl)aniline (5e) (100 mg, 0.289 mmol) in ethanol (5 ml) 1-(4-(trifluoromethoxy)phenyl)prop-2-yn-1-one (6o) (61.8 mg, 0.289 mmol) was added. The reaction mixture was stirred at a temperature of 26° C. for 4 h and the reaction was monitored by TLC using ethyl acetate/hexane (1:1) as a solvent system. Then water (10 ml) was added to reaction mixture. A yellow colour solid appears which was filtered and washed with ethanol. (yield: 120 mg, 83%), mp: 120-123° C.; $^1$H NMR (CDCl$_3$, 300 MHz) δ (ppm): 12.21 (d, J=12.8 Hz, NH), 7.98 (d, J=8.3 Hz, 2H), 7.35-7.31 (m, 1H), 7.27-7.25 (m, 3H), 6.77 (s, 1H), 6.57-6.46 (m, 4H), 5.93 (d, J=8.3 Hz), 3.96 (s, 3H), 3.83 (s, 3H), 3.71 (s, 9H); FABMAS:(M+H)=560

Example 7

(Z)-1-(2-bromo-3,4,5-trimethoxyphenyl)-3-((2,3-dimethoxy-5-((Z)-3,4,5-trimethoxystyryl)phenyl)amino) prop-2-en-1-one (11y)

To a stirred solution of (Z)-2,3-dimethoxy-5-(3,4,5-trimethoxystyryl)aniline (5e) (100 mg, 0.289 mmol) in ethanol (5 ml) 1-(2-bromo-3,4,5-trimethoxyphenyl)prop-2-yn-1-one (6y) (86.6 mg, 0.289 mmol) was added. The reaction mixture was stirred at a temperature of 27° C. for 4 h and the reaction was monitored by TLC using hexane/ethyl acetate (1:1) as a solvent system. Then appropriate water was added to reaction mixture. A yellow colour solid appears which was filtered and washed with ethanol. (yield: 150 mg, 80%); mp: 102-105° C.; $^1$H NMR (CDCl$_3$, 300 MHz) δδ (ppm): 3.71 (s, 9H), 3.87 (s, 3H), 3.90 (d, J=3.02 Hz, 9H), 3.96 (s, 3H), 5.67 (d, J=7.55 Hz, 1H), 6.52-6.47 (m, 4H), 6.57 (s, 1H) 6.76 (d, J=6.7 Hz, 1H), 6.87 (s, 1H) 7.31-7.24 (m, 1H), 12.04 (d, J=12.8 Hz, NH); FABMAS:(M+H)=644.

Example 8

(Z)-1-(3-hydroxy-4-methoxyphenyl)-3-((2-methoxy-5-((Z)-3,4,5-trimethoxystyryl)phenyl)amino) prop-2-en-1-one (10q)

To a stirred solution of (Z)-2-methoxy-5-(3,4,5-trimethoxystyryl)aniline (5d) (100 mg, 0.317 mmol) in ethanol (5 ml) 1-(3-hydroxy-4-methoxyphenyl)prop-2-yn-1-one (6q) (55.85 mg, 0.317 mmol) was added. The reaction mixture was stirred at a temperature of 24° C. for 4 h and the reaction was monitored by TLC using hexane/ethyl acetate (6:4) as a solvent system. Then appropriate water was added to reaction mixture. A yellow colour solid appears which was filtered and washed with ethanol. (yield: 110 mg, 70%); mp: 88-91° C.; $^1$H NMR (CDCl$_3$, 300 MHz) δδ (ppm): 3.71 (s, 6H), 3.85 (s, 3H), 3.94 (s, 6H), 5.68 (s, 1H), 5.91 (d, J=8.3 Hz, 1H), 6.49 (d, J=13.6 Hz, 4H), 6.79 (d, J=8.3 Hz, 1H), 6.96-6.87 (m, 2H), 7.12 (s, 1H), 7.24-7.18 (m, 1H), 7.50 (d, J=6.7 Hz, 2H), 12.06 (d, J=12.1 Hz, NH); FABMAS:(M+H)=478.

Example 9

(Z)-3-((2,3-dimethoxy-5-((Z)-3,4,5-trimethoxystyryl)phenyl)amino)-1-(3-hydroxy-4-methoxyphenyl)prop-2-en-1-one (11q)

To a stirred solution of (Z)-2,3-dimethoxy-5-(3,4,5-trimethoxystyryl)aniline (5e) (100 mg, 0.289 mmol) in ethanol (5 ml) 1-(3-hydroxy-4-methoxyphenyl)prop-2-yn-1-one (6q) (51.02 mg, 0.289 mmol) was added. The reaction mixture was stirred at a temperature of 25° C. for 4 h and the reaction was monitored by TLC using hexane/ethyl acetate (1:1) as a solvent system. Then appropriate water was added to reaction mixture. A yellow colour solid appears which was filtered and washed with ethanol. (yield: 115 mg, 76%); mp: 99-101° C.; $^1$H NMR (CDCl$_3$, 300 MHz) δ (ppm): 3.71 (s, 9H), 3.83 (s, 3H), 3.94 (s, 3H), 3.95 (s, 3H), 5.78 (s, 1H), 5.94 (d, J=8.3 Hz, 1H), 6.53-6.51 (m, 5H), 6.75 (s, 1H), 6.89 (d, J=9.06 Hz, 1H), 7.29-7.22 (m, 1H), 7.53 (d, J=6.7 Hz, 2H), 12.09 (d, J=12.8 Hz, NH); FABMAS:(M+H)=508.

Example 10

(Z)-3-(2-hydroxy-3-methoxy-6-(3,4,5-trimethoxystyryl)phenylamino)-1-(3-hydroxy-4-methoxyphenyl)prop-2-en-1-one (16q)

To a stirred solution of (Z)-2-amino-6-methoxy-3-(3,4,5-trimethoxystyryl)phenol (5j) (100 mg, 0.301 mmol) in ethanol (5 ml) 1-(3-hydroxy-4-methoxyphenyl)prop-2-yn-1-one (6q) (53.17 mg, 0.301 mmol) was added. The reaction mixture was stirred at a temperature of 25° C. for 4 h and the reaction was monitored by TLC using hexane/ethyl acetate (8:2) as a solvent system. Then appropriate water was added to reaction mixture. A yellow colour solid appears which was filtered and washed with ethanol (yield: 112 mg, 73%); mp: 98-100° C.; $^1$H NMR (CDCl$_3$, 300 MHz) δ (ppm): 3.59 (s, 6H), 3.81 (s, 3H), 3.90 (s, 3H), 3.94 (s, 3H), 3.95 (s, 3H), 5.64 (s, 1H), 5.84-5.81 (m, 2H), 6.44 (s, 1H), 6.56-6.54 (m, 1H) 6.59 (s, 1H), 6.67 (d, J=12.08 Hz, 1H), 6.79 (d, J=8.3 Hz, 1H), 6.86 (d, J=8.3 Hz, 1H), 7.52-7.48 (m, 2H), 7.82-7.73 (m, 1H), 11.95 (d, J=12.08 Hz, NH); FABMAS:(M+H)=508.

Example 11

(Z)-3-((2-methoxy-5-((Z)-3,4,5-trimethoxystyryl)phenyl)amino)-1-(3,4,5-trimethoxyphenyl) prop-2-en-1-one (10x)

To a stirred solution of (Z)-2-methoxy-5-(3,4,5-trimethoxystyryl)aniline (5d) (100 mg, 0.317 mmol) in ethanol (5 ml) 1-(3,4,5-trimethoxyphenyl)prop-2-yn-1-one (6x) (69.7 mg, 0.317 mmol) was added. The reaction mixture was stirred at a temperature of 30° C. for 4 h and the reaction was monitored by TLC using ethyl acetate/hexane (1:1) as a solvent system. Then water (10 ml) was added to reaction mixture. A yellow colour solid appears which was filtered and washed with ethanol. (yield: 120 mg, 70%); mp: 120-122° C.; $^1$H NMR (CDCl$_3$, 500 MHz) δ (ppm): 12.09 (d, J=12.5 Hz, NH), 7.23-7.21 (m, 1H), 7.2 (s, 2H), 7.15 (d, J=1.8 Hz, 1H), 6.96 (dd, J=6.56 Hz, 1.8 Hz, 1H), 6.82 (d, J=8.3 Hz, 1H), 6.54 (s, 2H), 6.49 (q, J=12.2 Hz, 2.44 Hz, 2H), 5.92 (d, J=7.9 Hz, 1H), 3.96 (s, 3H), 3.93 (s, 6H), 3.9 (s, 3H), 3.85 (s, 3H), 3.71 (s, 3H); FABMAS:(M+H)=536.

Example 12

(Z)-1-(4-methoxy-3-nitrophenyl)-3-((2-methoxy-5-((Z)-3,4,5-trimethoxystyryl)phenyl)amino)prop-2-en-1-one (10t)

To a stirred solution of (Z)-2-methoxy-5-(3,4,5-trimethoxystyryl)aniline (5d) (100 mg, 0.317 mmol) in ethanol (5 ml) 1-(4-methoxy-3-nitrophenyl)prop-2-yn-1-one (6t) (64.9 mg, 0.317 mmol) was added. The reaction mixture was stirred at a temperature of 28° C. for 4 h and the reaction was monitored by TLC using ethyl acetate/hexane (1:1) as a solvent system. Then water (10 ml) was added to reaction mixture. A yellow colour solid appears which was filtered and washed with ethanol. (yield: 130 mg, 79%); mp: 130-132° C.; $^1$H NMR (CDCl$_3$, 300 MHz) δδ (ppm): 12.15 (d, J=12.8 Hz, NH), 8.44 (s, 1H), 8.14 (d, J=9.06 Hz, 2H), 7.32-7.26 (m, 1H), 7.12 (d, J=8.13 Hz, 2H), 6.98 (d, J=8.3 Hz, 1H), 6.81 (d, J=9.06 Hz, 1H), 6.50 (d, J=8.3 Hz, 4H), 5.91 (d, J=7.55 Hz, 1H), 4.02 (s, 3H), 3.96 (s, 3H), 3.85 (s, 3H), 3.7 (s, 6H); FABMAS:(M+H)=521.

Example 13

(Z)-3-((2,3-dimethoxy-5-((Z)-3,4,5-trimethoxystyryl)phenyl)amino)-1-(4-methoxy-3-nitrophenyl)prop-2-en-1-one (11t)

To a stirred solution of (Z)-2,3-dimethoxy-5-(3,4,5-trimethoxystyryl)aniline (5e) (100 mg, 0.289 mmol) in ethanol (5 ml) 1-(4-methoxy-3-nitrophenyl)prop-2-yn-1-one (6t) (59.2 mg, 0.289 mmol) was added. The reaction mixture was stirred at a temperature of 25° C. for 4 hrs and the reaction was monitored by TLC using hexane/ethyl acetate (6:4) as a solvent system. Then appropriate water was added to reaction mixture. A yellow colour solid appears which was filtered and washed with ethanol. (yield: 115 mg, 72%); mp: 110-112° C.; $^1$H NMR (CDCl$_3$, 300 MHz) δ (ppm): 12.21 (d, J=12.8 Hz, NH), 8.43 (s, 1H), 8.14 (d, J=9.06 Hz, 1H), 7.37-7.30 (m, 1H), 7.12 (d, J=9.06 Hz, 1H), 6.77 (s, 1H), 6.57-6.47 (m, 5H), 5.92 (d, J=7.5 Hz, 1H), 4.03 (s, 3H), 3.97 (s, 3H), 3.84 (s, 3H), 3.74 (s, 9H); FABMAS:(M+H)=551.

Example 14

(Z)-3-((2-hydroxy-3-methoxy-6-((Z)-3,4,5-trimethoxystyryl)phenyl)amino)-1-(3,4,5-trimethoxyphenyl)prop-2-en-1-one (16x)

To a stirred solution of (Z)-2-amino-6-methoxy-3-(3,4,5-trimethoxystyryl)phenol (5j) (100 mg, 0.301 mmol) in ethanol (5 ml) 1-(3,4,5-trimethoxyphenyl)prop-2-yn-1-one (6x) (66.2 mg, 0.301 mmol) was added. The reaction mixture was stirred at a temperature of 25° C. for 4 h and the reaction was monitored by TLC using hexane/ethyl acetate (8:2) as a solvent system. Then appropriate water was added to reaction mixture. A yellow colour solid appears which was filtered and washed with ethanol. (yield: 125 mg, 75%); mp: 98-99° C.; $^1$H NMR (CDCl$_3$, 300 MHz) δ (ppm): 11.93 (d, J=12.2 Hz, NH), 7.84-7.75 (m, 1H), 7.18 (s, 2H), 6.80 (d, J=8.12 Hz, 1H), 6.67 (d, J=11.8 Hz, 1H), 6.61-6.55 (m, 2H), 6.44 (s, 2H), 5.85-5.81 (m, 2H), 3.92 (s, 6H), 3.91 (s, 3H), 3.90 (s, 3H), 3.81 (s, 3H), 3.58 (s, 6H); FABMAS:(M+H)=552.

Example 15

(Z)-1-(2-bromo-3,4,5-trimethoxyphenyl)-3-((2-hydroxy-3-methoxy-6-((Z)-3,4,5-trimethoxystyryl)phenyl)amino)prop-2-en-1-one (16y)

To a stirred solution of (Z)-2-amino-6-methoxy-3-(3,4,5-trimethoxystyryl)phenol (5j) (100 mg, 0.301 mmol) in ethanol (5 ml) 1-(2-bromo-3,4,5-trimethoxyphenyl)prop-2-yn-1-one (6y) (89.4 mg, 0.301 mmol) was added. The reaction mixture was stirred at a temperature of 25° C. for 4 h and the reaction was monitored by TLC using hexane/ethyl acetate (8:2) as a solvent system. Then appropriate water was added to reaction mixture. A yellow colour solid appears which was filtered and washed with ethanol. (yield: 150 mg, 79%); mp: 98-99° C.; $^1$H NMR (CDCl$_3$, 300 MHz) d (ppm): 11.86 (d, J=12.6 Hz, NH), 7.93-7.84 (m, 1H), 6.85-6.80 (m, 2H), 6.68 (d, J=11.89 Hz, 1H), 6.61-6.55 (m, 2H), 6.46 (s, 2H), 5.89 (s, 1H), 5.54 (d, J=7.55 Hz, 1H), 3.96 (s, 6H), 3.89 (s, 3H), 3.87 (s, 3H), 3.63 (s, 6H); FABMAS:(M+2H)=631.

Biological Activity:

All cell lines used in this study were purchased from the American Type Culture Collection (ATCC, United States). A549, MCF-7, and HeLa were grown in Dulbecco's modified Eagle's medium (containing 10% FBS in a humidified atmosphere of 5% CO2 at 37° C.). HCT116 cells were cultured in Eagle's minimal essential medium (MEM) containing non-essential amino acids, 1 mM sodium pyruvate, 10 mg/mL bovine insulin, and 10% FBS. Cells were trypsinized when sub-confluent from T25 flasks/60 mm dishes and seeded in 96-well plates. The synthesized test compounds were evaluated for their in vitro antiproliferative in four different human cancer cell lines. A protocol of 48 h continuous drug exposure was used, and a MTT cell proliferation assay was used to estimate cell viability or growth. The cell lines were grown in their respective media containing 10% fetal bovine serum and were seeded into 96-well microtiter plates in 200 μL, aliquots at plating densities depending on the doubling time of individual cell lines. The microtiter plates were incubated at 37° C., 5% CO2, 95% air, and 100% relative humidity for 24 h prior to addition of experimental drugs. Aliquots of 2 μL, of the test compounds were added to the wells already containing 198 μL, of cells, resulting in the required final drug concentrations. For each compound, four concentrations (1, 10, 100, and 1000 μM) were evaluated, and each was done in triplicate wells. Plates were incubated further for 48 h, and the assay was terminated by the addition of 10 μL, of 5% MTT and incubated for 60 min at 37° C. Later, the plates were air-dried. Bound stain was subsequently eluted with 100 μL, of DMSO, and the absorbance was read on an multimode plate reader (Tecan M200) at a wavelength of 560 nm. Percent growth was calculated on a plate by plate basis for test wells relative to control wells. The above determinations were repeated thrice. The growth inhibitory effects of the compounds were analyzed by generating dose response curves as a plot of the percentage surviving cells versus compound concentration. The sensitivity of the cancer cells to the test compound was expressed in terms of IC$_{50}$, a value defined as the concentration of compound that produced 50% reduction as compared to the control absorbance. (A. S. Kumar, M. A. Reddy, N. Jain, C. Kishor, T. R. Murthy, D. Ramesh, B. Supriya, A. Addlagatta, S. V. Kalivendi, B. Sreedhar. Eur. J. Med. Chem. 60 (2013) 305-24).

TABLE 1

In vitro cytotoxicity of 3,4,5-trimethoxystyrylarylaminopropenones on the A549, HeLa, MCF-7 and HCT116cells determined by MTT assay

| Compound | IC$_{50}$ (μM) | | | |
| --- | --- | --- | --- | --- |
| | A549 | HeLa | MCF-7 | HCT116 |
| 10x | 1.68 | 0.26 | 0.27 | 1.51 |
| 10y | 3.51 | 0.25 | 2.95 | 3.98 |
| 10q | 3.89 | 0.23 | 4.68 | 0.83 |

TABLE 1-continued

In vitro cytotoxicity of 3,4,5-trimethoxystyrylarylaminopropenones on the A549, HeLa, MCF-7 and HCT116cells determined by MTT assay

| Compound | IC$_{50}$ (μM) | | | |
|---|---|---|---|---|
| | A549 | HeLa | MCF-7 | HCT116 |
| 10u | 2.40 | 0.52 | 0.25 | 0.77 |
| 10o | 2.69 | 0.26 | 1.32 | 2.95 |
| 10t | 0.77 | 0.21 | 2.0 | 1.29 |
| 10v | 0.17 | 0.53 | 0.11 | 0.33 |
| 10w | 0.67 | 0.46 | 1.07 | 0.37 |
| 11x | 3.33 | 3.72 | 7.08 | 0.28 |
| 11y | 0.28 | 1.58 | 5.37 | 0.3 |
| 11q | 0.32 | 1.91 | 2.09 | 3.24 |
| 11u | 0.12 | 4.27 | 5.25 | 7.59 |
| 11o | 0.21 | 1.86 | 5.75 | 7.08 |
| 11t | 0.15 | 1.2 | 1.55 | 4.79 |
| 11v | 0.56 | 0.67 | 3.02 | 1.48 |
| 11w | 0.14 | 5.89 | 3.39 | 1.95 |
| 16x | 0.25 | 0.56 | 0.23 | 3.63 |
| 16y | 7.08 | 1.78 | 0.19 | 2.69 |
| 16q | 1.58 | 4.17 | 0.2 | 6.76 |
| 16u | 1.32 | 2.51 | 0.18 | 1.74 |
| 16o | 1.318 | 7.08 | 2.24 | 1.95 |
| 16t | 7.33 | 1.66 | 0.6 | 3.98 |
| Ca-4 | 0.31 | 0.58 | 0.58 | 3.98 |
| S4 (Ca-4 amine) | 1.78 | 0.58 | 4.07 | 1.62 |

Some of the 3,4,5-trimethoxystyrylarylaminopropenones have been tested against human cancer cell lines such as HeLa (cervical carcinoma), A549 (non-small cell lung cancer), MCF-7 (breast cancer) and HCT116 (colon carcinoma) and the results are shown in Table 1. Interestingly all the tested compounds exhibited wide spectrum of anticancer effect towards all the cancer cell lines with IC$_{50}$ value range of 0.11-7.59 μM. The compounds like 10x, 10y, 10q, 10u, 10o, 10t, 10v and 10w are composed of one methoxy substituent in CA-4 amine ring (R=p-OMe) showed tremendous anticancer activity than rest of the tested compounds with IC$_{50}$ value range of 0.11-4.68 μM. Particularly the compound 10v which contain indole moiety inhibited breast cancer cells with IC$_{50}$ value 0.11 μM where as 10q showed deletious effect in which indole is replaced with isovaniline against same cell line with IC$_{50}$ value 4.68 μM. All the cell lines were inhibited by the compounds 11x, 11y, 11q, 11u, 11o, 11t, 11v and 11w with IC$_{50}$ value range of 0.12-5.75 μM in which two methoxy substituents present in CA-4 amine ring (R=m, p(-OMe)$_2$). Especially the compound 11u inhibited the growth of non-small cell lung cancer cells with IC$_{50}$ value 0.12 μM that contain amine and methoxy phenyl ring (X=p-OMe m-NH$_2$) but the compound 11o showed lower activity with IC$_{50}$ value 5.7 μM against MCF 7 cell line in which trifluoromethoxy group present (X=p-OCF$_3$). The compounds such as 16x, 16y, 16q, 16u, 16o and 16t also displayed potential anticancer activities with IC$_{50}$ value range of 0.18-7.33 μM as these compounds consist hydroxy and methoxy substituents (R=m-OH, p-OMe). The breast cancer cells affected by the compound 16u with IC$_{50}$ value 0.18 μM in which amino and methoxy groups present on phenyl ring (X=m-NH$_2$, p-OMe) where as the compound 16t showed less inhibitory activity towards lung cancer cells with IC$_{50}$ value 7.33 μM that contain nitro and methoxy groups present (X=m-NO$_2$, p-OMe). Overall the compounds those contain methoxy and amino groups on phenyl ring exhibited better cytotoxic effect against all the cell lines than the compounds in which nitro and methoxy groups pres

Significance of the Work Carried Out

Some new 3,4,5-trimethoxystyrylarylaminopropenones that have been synthesized exhibited significant cytotoxic activity against four human cancer cell lines.

Advantages of the Invention

1. The present invention provides new 3,4,5-trimethoxystyrylarylaminopropenones that may be useful as antitumor agents.
2. It also provides a process for the preparation of 3,4,5-trimethoxystyrylarylaminopropenones

We claim:

1. A novel 3,4,5-trimethoxystyrylarylaminopropenone of general formulae A

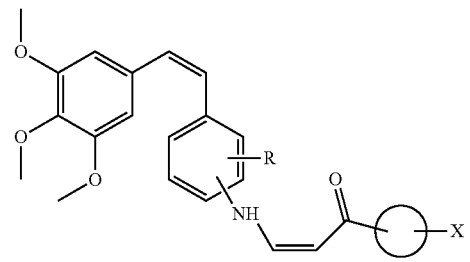

A wherein:
R=H, OMe, Cl, F, OH, Me
X=aryl, heteroaryl.

2. A novel 3,4,5-trimethoxystyrylarylaminopropenone of general formulae A as claimed in claim 1 selected from the compounds of 7a-7y, 8a-8y, 9a-9y, 10a-10y, 11a-11y, 12a-12y, 13a-13y, 14a-14y, 15a-15y, 16a-16y, 17a-17y, 18a-18y, 19a-19y, 20a-20y, and 21a-21y,

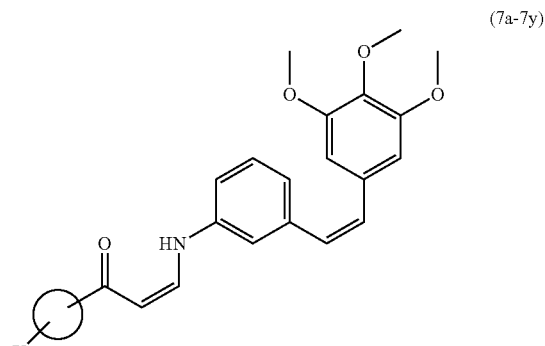

(7a-7y)

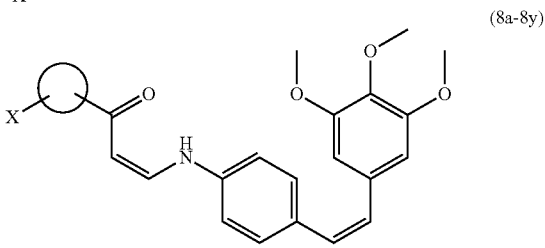

(8a-8y)

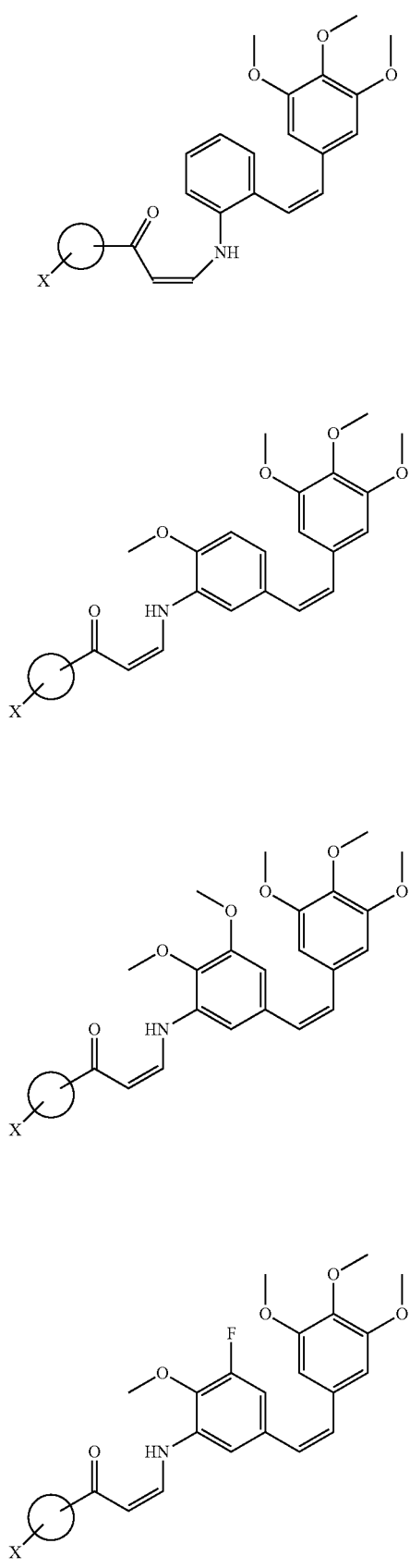
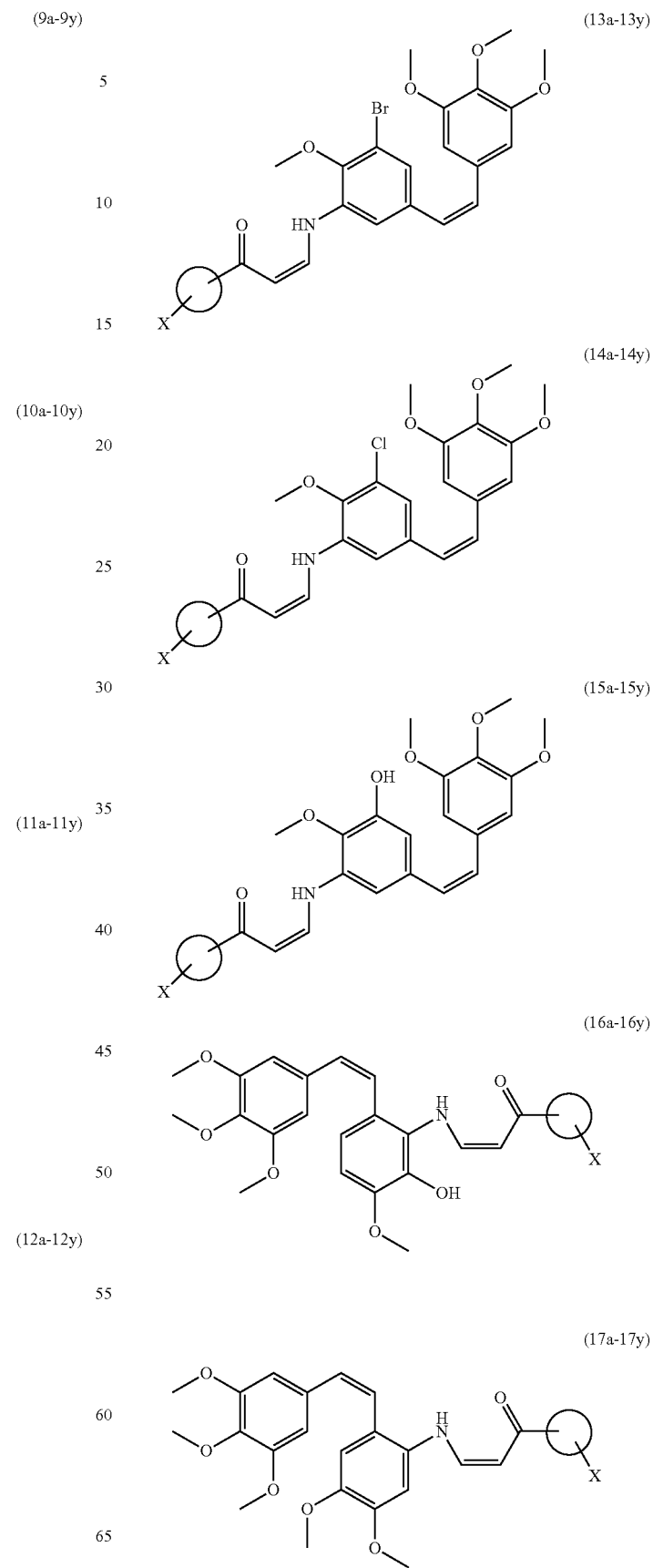

-continued

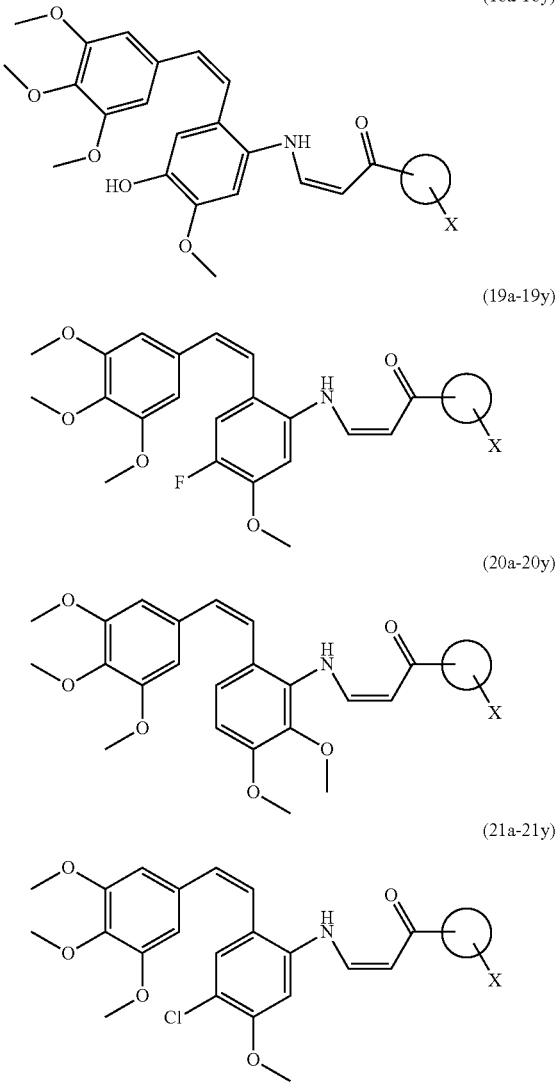

X=aryl, heteroaryl.

3. A novel 3,4,5-trimethoxystyrylarylaminopropenone of general formulae A as claimed in claim 1 selected from the following compounds:

(Z)-1-phenyl-3-(3-(3,4,5-trimethoxystyryl)phenylamino)prop-2-en-1-one (7a)
(Z)-1-(4-methoxyphenyl)-3-(3-(3,4,5-trimethoxystyryl)phenylamino)prop-2-en-1-one (7b)
(Z)-1-(3-methoxyphenyl)-3-(3-(3,4,5-trimethoxystyryl)phenylamino)prop-2-en-1-one (7c)
(Z)-1-(2-methoxyphenyl)-3-(3-(3,4,5-trimethoxystyryl)phenylamino)prop-2-en-1-one (7d)
(Z)-1-(4-hydroxyphenyl)-3-(3-(3,4,5-trimethoxystyryl)phenylamino)prop-2-en-1-one (7e)
(Z)-1-(4-nitrophenyl)-3-(3-(3,4,5-trimethoxystyryl)phenylamino)prop-2-en-1-one (7f)
(Z)-1-(4-aminophenyl)-3-(3-(3,4,5-trimethoxystyryl)phenylamino)prop-2-en-1-one (7g)
(Z)-1-(2-nitrophenyl)-3-(3-(3,4,5-trimethoxystyryl)phenylamino)prop-2-en-1-one (7h)
(Z)-1-(2-aminophenyl)-3-(3-(3,4,5-trimethoxystyryl)phenylamino)prop-2-en-1-one (7i)
(Z)-1-(4-fluorophenyl)-3-(3-(3,4,5-trimethoxystyryl)phenylamino)prop-2-en-1-one (7J)
(Z)-1-(4-(trifluoromethyl)phenyl)-3-(3-((3,4,5-trimethoxystyryl)phenylamino)prop-2-en-1-one (7k)
(Z)-1-(3-fluorophenyl)-3-(3-(3,4,5-trimethoxystyryl)phenylamino)prop-2-en-1-one (7l)
(Z)-1-(3-chlorophenyl)-3-(3-(3,4,5-trimethoxystyryl)phenylamino)prop-2-en-1-one (7m)
(Z)-1-(4-chlorophenyl)-3-(3-(3,4,5-trimethoxystyryl)phenylamino)prop-2-en-1-one (7n)
(Z)-1-(4-(trifluoromethoxy)phenyl)-3-(3-((3,4,5-trimethoxystyryl)phenylamino)prop-2-en-1-one (7o)
(Z)-1-(3,4-dimethoxyphenyl)-3-(3-(3,4,5-trimethoxystyryl)phenylamino)prop-2-en-1-one (7p)
(Z)-1-(3-hydroxy-4-methoxyphenyl)-3-(3-(3,4,5-trimethoxystyryl)phenylamino)prop-2-en-1-one (7q)
(Z)-1-(3-fluoro-4-methoxyphenyl)-3-(3-((3,4,5-trimethoxystyryl)phenylamino)prop-2-en-1-one (7r)
(Z)-1-(3-chloro-4-methoxyphenyl)-3-(3-(3,4,5-trimethoxystyryl)phenylamino)prop-2-en-1-one (7s)
(Z)-1-(4-methoxy-3-nitrophenyl)-3-(3-(3,4,5-trimethoxystyryl)phenylamino)prop-2-en-1-one (7t)
(Z)-1-(3-amino-4-methoxyphenyl)-3-(3-((3,4,5-trimethoxystyryl)phenylamino)prop-2-en-1-one (7u)
(Z)-1-(1H-indol-3-yl)-3-(3-(3,4,5-trimethoxystyryl)phenylamino)prop-2-en-1-one (7v)
(Z)-1-(1-methyl-1H-indol-3-yl)-3-(3-(3,4,5-trimethoxystyryl)phenylamino)prop-2-en-1-one (7w)
(Z)-1-(3,4,5-trimethoxyphenyl)-3-(3-(3,4,5-trimethoxystyryl)phenylamino)prop-2-en-1-one (7x)
(Z)-1-(2-bromo-3,4,5-trimethoxyphenyl)-3-(3-(3,4,5-trimethoxystyryl)phenylamino)prop-2-en-1-one (7y)
(Z)-1-phenyl-3-((4-((Z)-3,4,5-trimethoxystyryl)phenyl)amino)prop-2-en-1-one (8a)
(Z)-1-(4-methoxyphenyl)-3-((4-((Z)-3,4,5-trimethoxystyryl)phenyl)amino)prop-2-en-1-one (8b)
(Z)-1-(3-methoxyphenyl)-3-((4-((Z)-3,4,5-trimethoxystyryl)phenyl)amino)prop-2-en-1-one (8c)
(Z)-1-(2-methoxyphenyl)-3-((4-((Z)-3,4,5-trimethoxystyryl)phenyl)amino)prop-2-en-1-one (8d)
(Z)-1-(4-hydroxyphenyl)-3-((4-((Z)-3,4,5-trimethoxystyryl)phenyl)amino)prop-2-en-1-one (8e)
(Z)-1-(4-nitrophenyl)-3-((4-((Z)-3,4,5-trimethoxystyryl)phenyl)amino)prop-2-en-1-one (8f)
(Z)-1-(4-aminophenyl)-3-((4-((Z)-3,4,5-trimethoxystyryl)phenyl)amino)prop-2-en-1-one (8g)
(Z)-1-(2-nitrophenyl)-3-((4-((Z)-3,4,5-trimethoxystyryl)phenyl)amino)prop-2-en-1-one (8h)
(Z)-1-(2-aminophenyl)-3-((4-((Z)-3,4,5-trimethoxystyryl)phenyl)amino)prop-2-en-1-one (8i)
(Z)-1-(4-fluorophenyl)-3-((4-((Z)-3,4,5-trimethoxystyryl)phenyl)amino)prop-2-en-1-one (8j)
(Z)-1-(4-(trifluoromethyl)phenyl)-3-((4-((Z)-3,4,5-trimethoxystyryl)phenyl)amino)prop-2-en-1-one (8k)
(Z)-1-(3-fluorophenyl)-3-((4-((Z)-3,4,5-trimethoxystyryl)phenyl)amino)prop-2-en-1-one (8l)
(Z)-1-(3-chlorophenyl)-3-((4-((Z)-3,4,5-trimethoxystyryl)phenyl)amino)prop-2-en-1-one (8m)
(Z)-1-(4-chlorophenyl)-3-((4-((Z)-3,4,5-trimethoxystyryl)phenyl)amino)prop-2-en-1-one (8n)
(Z)-1-(4-(trifluoromethoxy)phenyl)-3-((4-((Z)-3,4,5-trimethoxystyryl)phenyl)amino)prop-2-en-1-one (8o)
(Z)-1-(3,4-dimethoxyphenyl)-3-((4-((Z)-3,4,5-trimethoxystyryl)phenyl)amino)prop-2-en-1-one (8p)
(Z)-1-(3-hydroxy-4-methoxyphenyl)-3-((4-((Z)-3,4,5-trimethoxystyryl)phenyl)amino)prop-2-en-1-one (8q)

(Z)-1-(3-fluoro-4-methoxyphenyl)-3-((4-((Z)-3,4,5-trimethoxystyryl)phenyl)amino)prop-2-en-1-one (8r)

(Z)-1-(3-chloro-4-methoxyphenyl)-3-((4-((Z)-3,4,5-trimethoxystyryl)phenyl)amino)prop-2-en-1-one (8s)

(Z)-1-(4-methoxy-3-nitrophenyl)-3-((4-((Z)-3,4,5-trimethoxystyryl)phenyl)amino)prop-2-en-1-one (8t)

(Z)-1-(3-amino-4-methoxyphenyl)-3-((4-((Z)-3,4,5-trimethoxystyryl)phenyl)amino)prop-2-en-1-one (8u)

(Z)-1-(1H-indol-3-yl)-3-(4-((3,4,5-trimethoxystyryl)phenylamino)prop-2-en-1-one (8v)

(Z)-1-(1-methyl-1H-indol-3-yl)-3-(4-(3,4,5-trimethoxystyryl)phenylamino)prop-2-en-1-one (8w)

(Z)-1-(3,4,5-trimethoxyphenyl)-3-((4-((Z)-3,4,5-trimethoxystyryl)phenyl)amino)prop-2-en-1-one (8x)

(Z)-1-(2-bromo-3,4,5-trimethoxyphenyl)-3-((4-((Z)-3,4,5-trimethoxystyryl)phenyl)amino)prop-2-en-1-one (8y)

(Z)-1-phenyl-3-((2-((Z)-3,4,5-trimethoxystyryl)phenyl)amino)prop-2-en-1-one (9a)

(Z)-1-(4-methoxyphenyl)-3-((2-((Z)-3,4,5-trimethoxystyryl)phenyl)amino)prop-2-en-1-one (9b)

(Z)-1-(3-methoxyphenyl)-3-((2-((Z)-3,4,5-trimethoxystyryl)phenyl)amino)prop-2-en-1-one (9c)

(Z)-1-(2-methoxyphenyl)-3-((2-((Z)-3,4,5-trimethoxystyryl)phenyl)amino)prop-2-en-1-one (9d)

(Z)-1-(4-hydroxyphenyl)-3-((2-((Z)-3,4,5-trimethoxystyryl)phenyl)amino)prop-2-en-1-one (9e)

(Z)-1-(4-nitrophenyl)-3-((2-((Z)-3,4,5-trimethoxystyryl)phenyl)amino)prop-2-en-1-one (9f)

(Z)-1-(4-aminophenyl)-3-((2-((Z)-3,4,5-trimethoxystyryl)phenyl)amino)prop-2-en-1-one (9g)

(Z)-1-(2-nitrophenyl)-3-((2-((Z)-3,4,5-trimethoxystyryl)phenyl)amino)prop-2-en-1-one (9h)

(Z)-1-(2-aminophenyl)-3-((2-((Z)-3,4,5-trimethoxystyryl)phenyl)amino)prop-2-en-1-one (9i)

(Z)-1-(4-fluorophenyl)-3-((2-((Z)-3,4,5-trimethoxystyryl)phenyl)amino)prop-2-en-1-one (9j)

(Z)-1-(4-(trifluoromethyl)phenyl)-3-((2-((Z)-3,4,5-trimethoxystyryl)phenyl)amino)prop-2-en-1-one (9k)

(Z)-1-(3-fluorophenyl)-3-((2-((Z)-3,4,5-trimethoxystyryl)phenyl)amino)prop-2-en-1-one (9l)

(Z)-1-(3-chlorophenyl)-3-((2-((Z)-3,4,5-trimethoxystyryl)phenyl)amino)prop-2-en-1-one (9m)

(Z)-1-(4-chlorophenyl)-3-((2-((Z)-3,4,5-trimethoxystyryl)phenyl)amino)prop-2-en-1-one (9n)

(Z)-1-(4-(trifluoromethoxy)phenyl)-3-((2-((Z)-3,4,5-trimethoxystyryl)phenyl)amino)prop-2-en-1-one (9o)

(Z)-1-(3,4-dimethoxyphenyl)-3-((2-((Z)-3,4,5-trimethoxystyryl)phenyl)amino)prop-2-en-1-one (9p)

(Z)-1-(3-hydroxy-4-methoxyphenyl)-3-((2-((Z)-3,4,5-trimethoxystyryl)phenyl)amino)prop-2-en-1-one (9q)

(Z)-1-(3-fluoro-4-methoxyphenyl)-3-((2-((Z)-3,4,5-trimethoxystyryl)phenyl)amino)prop-2-en-1-one (9r)

(Z)-1-(3-chloro-4-methoxyphenyl)-3-((2-((Z)-3,4,5-trimethoxystyryl)phenyl)amino)prop-2-en-1-one (9s)

(Z)-1-(4-methoxy-3-nitrophenyl)-3-((2-((Z)-3,4,5-trimethoxystyryl)phenyl)amino)prop-2-en-1-one (9t)

(Z)-1-(3-amino-4-methoxyphenyl)-3-((2-((Z)-3,4,5-trimethoxystyryl)phenyl)amino)prop-2-en-1-one (9u)

(Z)-1-(1H-indol-3-yl)-3-(2-(3,4,5-trimethoxystyryl)phenylamino)prop-2-en-1-one (9v)

(Z)-1-(1-methyl-1H-indol-3-yl)-3-(2-(3,4,5-trimethoxystyryl)phenylamino)prop-2-en-1-one (9w)

(Z)-1-(3,4,5-trimethoxyphenyl)-3-((2-((Z)-3,4,5-trimethoxystyryl)phenyl)amino)prop-2-en-1-one (9x)

(Z)-1-(2-bromo-3,4,5-trimethoxyphenyl)-3-((2-((Z)-3,4,5-trimethoxystyryl)phenyl)amino)prop-2-en-1-one (9y)

(Z)-3-((2-methoxy-5-((Z)-3,4,5-trimethoxystyryl)phenyl)amino)-1-phenylprop-2-en-1-one (10a)

(Z)-3-((2-methoxy-5-((Z)-3,4,5-trimethoxystyryl)phenyl)amino)-1-(4-methoxyphenyl)prop-2-en-1-ne (10b)

(Z)-3-((2-methoxy-5-((Z)-3,4,5-trimethoxystyryl)phenyl)amino)-1-(3-methoxyphenyl)prop-2-en-1-ne (10c)

(Z)-3-((2-methoxy-5-((Z)-3,4,5-trimethoxystyryl)phenyl)amino)-1-(2-methoxyphenyl)prop-2-en-1-ne (10d)

(Z)-1-(4-hydroxyphenyl)-3-((2-methoxy-5-((Z)-3,4,5-trimethoxystyryl)phenyl)amino)prop-2-en-1-one (10e)

(Z)-3-((2-methoxy-5-((Z)-3,4,5-trimethoxystyryl)phenyl)amino)-1-(4-nitrophenyl)prop-2-en-1-one (10f)

(Z)-1-(4-aminophenyl)-3-((2-methoxy-5-((Z)-3,4,5-trimethoxystyryl)phenyl)amino)prop-2-en-1-one (10g)

(Z)-3-((2-methoxy-5-((Z)-3,4,5-trimethoxystyryl)phenyl)amino)-1-(2-nitrophenyl)prop-2-en-1-one (10h)

(Z)-1-(2-aminophenyl)-3-((2-methoxy-5-((Z)-3,4,5-trimethoxystyryl)phenyl)amino)prop-2-en-1-one (10i)

(Z)-1-(4-fluorophenyl)-3-((2-methoxy-5-((Z)-3,4,5-trimethoxystyryl)phenyl)amino)prop-2-en-1-one (10j)

(Z)-3-((2-methoxy-5-((Z)-3,4,5-trimethoxystyryl)phenyl)amino)-1-(4-(trifluoromethyl)phenyl)prop-2-en-1-one (10k)

(Z)-1-(3-fluorophenyl)-3-((2-methoxy-5-((Z)-3,4,5-trimethoxystyryl)phenyl)amino)prop-2-en-1-one (10l)

(Z)-1-(3-chlorophenyl)-3-((2-methoxy-5-((Z)-3,4,5-trimethoxystyryl)phenyl)amino)prop-2-en-1-one (10m)

(Z)-1-(4-chlorophenyl)-3-((2-methoxy-5-((Z)-3,4,5-trimethoxystyryl)phenyl)amino)prop-2-en-1-one (10n)

(Z)-3-((2-methoxy-5-((Z)-3,4,5-trimethoxystyryl)phenyl)amino)-1-(4-(trifluoromethoxy)phenyl)prop-2-en-1-one (10o)

(Z)-1-(3,4-dimethoxyphenyl)-3-((2-methoxy-5-((Z)-3,4,5-trimethoxystyryl)phenyl)amino)prop-2-en-1-one (10p)

(Z)-1-(3-hydroxy-4-methoxyphenyl)-3-((2-methoxy-5-((Z)-3,4,5-trimethoxystyryl)phenyl)amino)prop-2-en-1-one (10q)

(Z)-1-(3-fluoro-4-methoxyphenyl)-3-((2-methoxy-5-((Z)-3,4,5-trimethoxystyryl)phenyl)amino)prop-2-en-1-one (10r)

(Z)-1-(3-chloro-4-methoxyphenyl)-3-((2-methoxy-5-((Z)-3,4,5-trimethoxystyryl)phenyl)amino)prop-2-en-1-one (10s)

(Z)-1-(4-methoxy-3-nitrophenyl)-3-((2-methoxy-5-((Z)-3,4,5-trimethoxystyryl)phenyl)amino)prop-2-en-1-one (10t)

(Z)-1-(3-amino-4-methoxyphenyl)-3-((2-methoxy-5-((Z)-3,4,5-trimethoxystyryl)phenyl)amino)prop-2-en-1-one (10u)

(Z)-1-(1H-indol-3-yl)-3-(2-methoxy-5-(3,4,5-trimethoxystyryl)phenylamino)prop-2-en-1-one (10v)

(Z)-3-(2-methoxy-5-(3,4,5-trimethoxystyryl)phenylamino)-1-(1-methyl-1H-indol-3-yl)prop-2-en-1-one (10w)

(Z)-3-((2-methoxy-5-((Z)-3,4,5-trimethoxystyryl)phenyl)amino)-1-(3,4,5-trimethoxyphenyl)prop-2-en-1-one (10x)

(Z)-1-(2-bromo-3,4,5-trimethoxyphenyl)-3-((2-methoxy-5-((Z)-3,4,5-trimethoxystyryl)phenyl)amino)prop-2-en-1-one (10y)

(Z)-3-((2,3-dimethoxy-5-((Z)-3,4,5-trimethoxystyryl)phenyl)amino)-1-phenylprop-2-en-1-one (11a)

(Z)-3-((2,3-dimethoxy-5-((Z)-3,4,5-trimethoxystyryl)
phenyl)amino)-1-(4-methoxyphenyl)prop-2-en-1-one
(11b)
(Z)-3-((2,3-dimethoxy-5-((Z)-3,4,5-trimethoxystyryl)
phenyl)amino)-1-(3-methoxyphenyl)prop-2-en-1-one
(11c)
(Z)-3-((2,3-dimethoxy-5-((Z)-3,4,5-trimethoxystyryl)
phenyl)amino)-1-(2-methoxyphenyl)prop-2-en-1-one
(11d)
(Z)-3-((2,3-dimethoxy-5-((Z)-3,4,5-trimethoxystyryl)
phenyl)amino)-1-(4-hydroxyphenyl)prop-2-en-1-one
(11e)
(Z)-3-((2,3-dimethoxy-5-((Z)-3,4,5-trimethoxystyryl)
phenyl)amino)-1-(4-nitrophenyl)prop-2-en-1-one (11f)
(Z)-1-(4-aminophenyl)-3-((2,3-dimethoxy-5-((Z)-3,4,5-
trimethoxystyryl)phenyl)amino)prop-2-en-1-one (11g)
(Z)-3-((2,3-dimethoxy-5-((Z)-3,4,5-trimethoxystyryl)
phenyl)amino)-1-(2-nitrophenyl)prop-2-en-1-one
(11h)
(Z)-1-(2-aminophenyl)-3-((2,3-dimethoxy-5-((Z)-3,4,5-
trimethoxystyryl)phenyl)amino)prop-2-en-1-one (11i)
(Z)-3-((2,3-dimethoxy-5-((Z)-3,4,5-trimethoxystyryl)
phenyl)amino)-1-(4-fluorophenyl)prop-2-en-1-one
(11j)
(Z)-3-((2,3-dimethoxy-5-((Z)-3,4,5-trimethoxystyryl)
phenyl)amino)-1-(4-(trifluoromethyl)phenyl)prop-2-
en-1-one (11k)
(Z)-3-((2,3-dimethoxy-5-((Z)-3,4,5-trimethoxystyryl)
phenyl)amino)-1-(3-fluorophenyl)prop-2-en-1-one
(11l)
(Z)-1-(3-chlorophenyl)-3-((2,3-dimethoxy-5-((Z)-3,4,5-
trimethoxystyryl)phenyl)amino)prop-2-en-1-one
(11m)
(Z)-1-(4-chlorophenyl)-3-((2,3-dimethoxy-5-((Z)-3,4,5-
trimethoxystyryl)phenyl)amino)prop-2-en-1-one (11n)
(Z)-3-((2,3-dimethoxy-5-((Z)-3,4,5-trimethoxystyryl)
phenyl)amino)-1-(4-(trifluoromethoxy)phenyl)prop-2-
en-1-one (11o)
(Z)-3-((2,3-dimethoxy-5-((Z)-3,4,5-trimethoxystyryl)
phenyl)amino)-1-(3,4-dimethoxyphenyl)prop-2-en-1-
one (11p)
(Z)-3-((2,3-dimethoxy-5-((Z)-3,4,5-trimethoxystyryl)
phenyl)amino)-1-(3-hydroxy-4-methoxyphenyl)prop-
2-en-1-one (11q)
(Z)-3-((2,3-dimethoxy-5-((Z)-3,4,5-trimethoxystyryl)
phenyl)amino)-1-(3-fluoro-4-methoxyphenyl)prop-2-
en-1-one (11r)
(Z)-1-(3-chloro-4-methoxyphenyl)-3-((2,3-dimethoxy-5-
((Z)-3,4,5-trimethoxystyryl)phenyl)amino)prop-2-en-
1-one (11s)
(Z)-3-((2,3-dimethoxy-5-((Z)-3,4,5-trimethoxystyryl)
phenyl)amino)-1-(4-methoxy-3-nitrophenyl)prop-2-
en-1-one (11t)
(Z)-1-(3-amino-4-methoxyphenyl)-3-((2,3-dimethoxy-5-
((Z)-3,4,5-trimethoxystyryl)phenyl)amino)prop-2-en-
1-one (11u)
(Z)-3-(2,3-dimethoxy-5-(3,4,5-trimethoxystyryl)phe-
nylamino)-1-(1H-indol-3-yl)prop-2-en-1-one (11v)
(Z)-3-(2,3-dimethoxy-5-(3,4,5-trimethoxystyryl)phe-
nylamino)-1-(1-methyl-1H-indol-3-yl)prop-2-en-1-one
(11w)
(Z)-3-((2,3-dimethoxy-5-((Z)-3,4,5-trimethoxystyryl)
phenyl)amino)-1-(3,4,5-trimethoxyphenyl)prop-2-en-
1-one (11x)
(Z)-1-(2-bromo-3,4,5-trimethoxyphenyl)-3-((2,3-dime-
thoxy-5-((Z)-3,4,5-trimethoxystyryl)phenyl)amino)
prop-2-en-1-one (11y)
(Z)-3-((3-fluoro-2-methoxy-5-((Z)-3,4,5-trimethox-
ystyryl)phenyl)amino)-1-phenylprop-2-en-1-one (12a)
(Z)-3-((3-fluoro-2-methoxy-5-((Z)-3,4,5-trimethox-
ystyryl)phenyl)amino)-1-(4-methoxyphenyl)prop-2-
en-1-one (12b)
(Z)-3-((3-fluoro-2-methoxy-5-((Z)-3,4,5-trimethox-
ystyryl)phenyl)amino)-1-(3-methoxyphenyl)prop-2-
en-1-one (12c)
(Z)-3-((3-fluoro-2-methoxy-5-((Z)-3,4,5-trimethox-
ystyryl)phenyl)amino)-1-(2-methoxyphenyl)prop-2-
en-1-one (12d)
(Z)-3-((3-fluoro-2-methoxy-5-((Z)-3,4,5-trimethox-
ystyryl)phenyl)amino)-1-(4-hydroxyphenyl)prop-2-en-
1-one (12e)
(Z)-3-((3-fluoro-2-methoxy-5-((Z)-3,4,5-trimethox-
ystyryl)phenyl)amino)-1-(4-nitrophenyl)prop-2-en-1-
one (12f)
(Z)-1-(4-aminophenyl)-3-((3-fluoro-2-methoxy-5-((Z)-3,
4,5-trimethoxystyryl)phenyl)amino)prop-2-en-1-one
(12g)
(Z)-3-((3-fluoro-2-methoxy-5-((Z)-3,4,5-trimethox-
ystyryl)phenyl)amino)-1-(2-nitrophenyl)prop-2-en-1-
one (12h)
(Z)-1-(2-aminophenyl)-3-((3-fluoro-2-methoxy-5-((Z)-3,
4,5-trimethoxystyryl)phenyl)amino)prop-2-en-1-one
(12i)
(Z)-3-((3-fluoro-2-methoxy-5-((Z)-3,4,5-trimethox-
ystyryl)phenyl)amino)-1-(4-fluorophenyl)prop-2-en-1-
one (12j)
(Z)-3-((3-fluoro-2-methoxy-5-((Z)-3,4,5-trimethox-
ystyryl)phenyl)amino)-1-(4-(trifluoromethyl)phenyl)
prop-2-en-1-one (12k)
(Z)-3-((3-fluoro-2-methoxy-5-((Z)-3,4,5-trimethox-
ystyryl)phenyl)amino)-1-(3-fluorophenyl)prop-2-en-1-
one (12l)
(Z)-1-(3-chlorophenyl)-3-((3-fluoro-2-methoxy-5-((Z)-3,
4,5-trimethoxystyryl)phenyl)amino)prop-2-en-1-one
(12m)
(Z)-1-(4-chlorophenyl)-3-((3-fluoro-2-methoxy-5-((Z)-3,
4,5-trimethoxystyryl)phenyl)amino)prop-2-en-1-one
(12n)
(Z)-3-((3-fluoro-2-methoxy-5-((Z)-3,4,5-trimethox-
ystyryl)phenyl)amino)-1-(4-(trifluoromethoxy)phenyl)
prop-2-en-1-one (12o)
(Z)-1-(3,4-dimethoxyphenyl)-3-((3-fluoro-2-methoxy-5-
((Z)-3,4,5-trimethoxystyryl)phenyl)amino)prop-2-en-
1-one (12p)
(Z)-3-((3-fluoro-2-methoxy-5-((Z)-3,4,5-trimethox-
ystyryl)phenyl)amino)-1-(3-hydroxy-4-methoxyphe-
nyl)prop-2-en-1-one (12q)
(Z)-3-((3-fluoro-2-methoxy-5-((Z)-3,4,5-trimethox-
ystyryl)phenyl)amino)-1-(3-fluoro-4-methoxyphenyl)
prop-2-en-1-one (12r)
(Z)-1-(3-chloro-4-methoxyphenyl)-3-((3-fluoro-2-
methoxy-5-((Z)-3,4,5-trimethoxystyryl)phenyl)amino)
prop-2-en-1-one (12s)
(Z)-3-((3-fluoro-2-methoxy-5-((Z)-3,4,5-trimethox-
ystyryl)phenyl)amino)-1-(4-methoxy-3-nitrophenyl)
prop-2-en-1-one (12t)
(Z)-1-(3-amino-4-methoxyphenyl)-3-((3-fluoro-2-
methoxy-5-((Z)-3,4,5-trimethoxystyryl)phenyl)amino)
prop-2-en-1-one (12u)
(Z)-3-(3-fluoro-2-methoxy-5-(3,4,5-trimethoxystyryl)
phenylamino)-1-(1H-indol-3-yl)prop-2-en-1-one (12v)
(Z)-3-(3-fluoro-2-methoxy-5-(3,4,5-trimethoxystyryl)
phenylamino)-1-(1-methyl-1H-indol-3-yl)prop-2-en-1-
one (12w)

(Z)-3-((3-fluoro-2-methoxy-5-((Z)-3,4,5-trimethoxystyryl)phenyl)amino)-1-((3,4,5-trimethoxyphenyl)prop-2-en-1-one (12x)

(Z)-1-(2-bromo-3,4,5-trimethoxyphenyl)-3-((3-fluoro-2-methoxy-5-((Z)-3,4,5-trimethoxystyryl)phenyl)amino)prop-2-en-1-one (12y)

(Z)-3-((3-chloro-2-methoxy-5-((Z)-3,4,5-trimethoxystyryl)phenyl)amino)-1-phenylprop-2-en-1-one (13a)

(Z)-3-((3-chloro-2-methoxy-5-((Z)-3,4,5-trimethoxystyryl)phenyl)amino)-1-(4-methoxyphenyl)prop-2-en-1-one (13b)

(Z)-3-((3-chloro-2-methoxy-5-((Z)-3,4,5-trimethoxystyryl)phenyl)amino)-1-(3-methoxyphenyl)prop-2-en-1-one (13c)

(Z)-3-((3-chloro-2-methoxy-5-((Z)-3,4,5-trimethoxystyryl)phenyl)amino)-1-(2-methoxyphenyl)prop-2-en-1-one (13d)

(Z)-3-((3-chloro-2-methoxy-5-((Z)-3,4,5-trimethoxystyryl)phenyl)amino)-1-(4-hydroxyphenyl)prop-2-en-1-one (13e)

(Z)-3-((3-chloro-2-methoxy-5-((Z)-3,4,5-trimethoxystyryl)phenyl)amino)-1-(4-nitrophenyl)prop-2-en-1-one (13f)

(Z)-1-(4-aminophenyl)-3-((3-chloro-2-methoxy-5-((Z)-3,4,5-trimethoxystyryl)phenyl)amino)prop-2-en-1-one (13g)

(Z)-3-((3-chloro-2-methoxy-5-((Z)-3,4,5-trimethoxystyryl)phenyl)amino)-1-(2-nitrophenyl)prop-2-en-1-one (13h)

(Z)-1-(2-aminophenyl)-3-((3-chloro-2-methoxy-5-((Z)-3,4,5-trimethoxystyryl)phenyl)amino)prop-2-en-1-one (13i)

(Z)-3-((3-chloro-2-methoxy-5-((Z)-3,4,5-trimethoxystyryl)phenyl)amino)-1-(4-fluorophenyl)prop-2-en-1-one (13j)

(Z)-3-((3-chloro-2-methoxy-5-((Z)-3,4,5-trimethoxystyryl)phenyl)amino)-1-(4-(trifluoromethyl)phenyl)prop-2-en-1-one (13k)

(Z)-3-((3-chloro-2-methoxy-5-((Z)-3,4,5-trimethoxystyryl)phenyl)amino)-1-(3-fluorophenyl)prop-2-en-1-one (13l)

(Z)-3-((3-chloro-2-methoxy-5-((Z)-3,4,5-trimethoxystyryl)phenyl)amino)-1-(3-chlorophenyl)prop-2-en-1-one (13m)

(Z)-3-((3-chloro-2-methoxy-5-((Z)-3,4,5-trimethoxystyryl)phenyl)amino)-1-(4-chlorophenyl)prop-2-en-1-one (13n)

(Z)-3-((3-chloro-2-methoxy-5-((Z)-3,4,5-trimethoxystyryl)phenyl)amino)-1-(4-(trifluoromethoxy)phenyl)prop-2-en-1-one (13o)

(Z)-3-((3-chloro-2-methoxy-5-((Z)-3,4,5-trimethoxystyryl)phenyl)amino)-1-(3,4-dimethoxyphenyl)prop-2-en-1-one (13p)

(Z)-3-((3-chloro-2-methoxy-5-((Z)-3,4,5-trimethoxystyryl)phenyl)amino)-1-(3-hydroxy-4-methoxyphenyl)prop-2-en-1-one (13q)

(Z)-3-((3-chloro-2-methoxy-5-((Z)-3,4,5-trimethoxystyryl)phenyl)amino)-1-(3-fluoro-4-methoxyphenyl)prop-2-en-1-one (13r)

(Z)-3-((3-chloro-2-methoxy-5-((Z)-3,4,5-trimethoxystyryl)phenyl)amino)-1-(3-chloro-4-methoxyphenyl)prop-2-en-1-one (13s)

(Z)-3-((3-chloro-2-methoxy-5-((Z)-3,4,5-trimethoxystyryl)phenyl)amino)-1-(4-methoxy-3-nitrophenyl)prop-2-en-1-one (13t)

(Z)-1-(3-amino-4-methoxyphenyl)-3-((3-chloro-2-methoxy-5-((Z)-3,4,5-trimethoxystyryl)phenyl)amino)prop-2-en-1-one (13u)

(Z)-3-(3-chloro-2-methoxy-5-(3,4,5-trimethoxystyryl)phenylamino)-1-(1H-indol-3-yl)prop-2-en-1-one (13v)

(Z)-3-(3-chloro-2-methoxy-5-(3,4,5-trimethoxystyryl)phenylamino)-1-(1-methyl-1H-indol-3-yl)prop-2-en-1-one (13w)

(Z)-3-((3-chloro-2-methoxy-5-((Z)-3,4,5-trimethoxystyryl)phenyl)amino)-1-(3,4,5-trimethoxyphenyl)prop-2-en-1-one (13x)

(Z)-1-(2-bromo-3,4,5-trimethoxyphenyl)-3-((3-chloro-2-methoxy-5-((Z)-3,4,5-trimethoxystyryl)phenyl)amino)prop-2-en-1-one (13y)

(Z)-3-((3-bromo-2-methoxy-5-((Z)-3,4,5-trimethoxystyryl)phenyl)amino)-1-phenylprop-2-en-1-one (14a)

(Z)-3-((3-bromo-2-methoxy-5-((Z)-3,4,5-trimethoxystyryl)phenyl)amino)-1-(4-methoxyphenyl)prop-2-en-1-one (14b)

(Z)-3-((3-bromo-2-methoxy-5-((Z)-3,4,5-trimethoxystyryl)phenyl)amino)-1-(3-methoxyphenyl)prop-2-en-1-one (14c)

(Z)-3-((3-bromo-2-methoxy-5-((Z)-3,4,5-trimethoxystyryl)phenyl)amino)-1-(2-methoxyphenyl)prop-2-en-1-one (14d)

(Z)-3-((3-bromo-2-methoxy-5-((Z)-3,4,5-trimethoxystyryl)phenyl)amino)-1-(4-hydroxyphenyl)prop-2-en-1-one (14e)

(Z)-3-((3-bromo-2-methoxy-5-((Z)-3,4,5-trimethoxystyryl)phenyl)amino)-1-(4-nitrophenyl)prop-2-en-1-one (14f)

(Z)-1-(4-aminophenyl)-3-((3-bromo-2-methoxy-5-((Z)-3,4,5-trimethoxystyryl)phenyl)amino)prop-2-en-1-one (14g)

(Z)-3-((3-bromo-2-methoxy-5-((Z)-3,4,5-trimethoxystyryl)phenyl)amino)-1-(2-nitrophenyl)prop-2-en-1-one (14h)

(Z)-1-(2-aminophenyl)-3-((3-bromo-2-methoxy-5-((Z)-3,4,5-trimethoxystyryl)phenyl)amino)prop-2-en-1-one (14i)

(Z)-3-((3-bromo-2-methoxy-5-((Z)-3,4,5-trimethoxystyryl)phenyl)amino)-1-(4-fluorophenyl)prop-2-en-1-one (14j)

(Z)-3-((3-bromo-2-methoxy-5-((Z)-3,4,5-trimethoxystyryl)phenyl)amino)-1-(4-(trifluoromethyl)phenyl)prop-2-en-1-one (14k)

(Z)-3-((3-bromo-2-methoxy-5-((Z)-3,4,5-trimethoxystyryl)phenyl)amino)-1-(3-fluorophenyl)prop-2-en-1-one (14l)

(Z)-3-((3-bromo-2-methoxy-5-((Z)-3,4,5-trimethoxystyryl)phenyl)amino)-1-(3-chlorophenyl)prop-2-en-1-one (14m)

(Z)-3-((3-bromo-2-methoxy-5-((Z)-3,4,5-trimethoxystyryl)phenyl)amino)-1-(4-chlorophenyl)prop-2-en-1-one (14n)

(Z)-3-((3-bromo-2-methoxy-5-((Z)-3,4,5-trimethoxystyryl)phenyl)amino)-1-(4-(trifluoromethoxy)phenyl)prop-2-en-1-one (14o)

(Z)-3-((3-bromo-2-methoxy-5-((Z)-3,4,5-trimethoxystyryl)phenyl)amino)-1-(3,4-dimethoxyphenyl)prop-2-en-1-one (14p)

(Z)-3-((3-bromo-2-methoxy-5-((Z)-3,4,5-trimethoxystyryl)phenyl)amino)-1-(3-hydroxy-4-methoxyphenyl)prop-2-en-1-one (14q)

(Z)-3-((3-bromo-2-methoxy-5-((Z)-3,4,5-trimethoxystyryl)phenyl)amino)-1-(3-fluoro-4-methoxyphenyl)prop-2-en-1-one (14r)

(Z)-3-((3-bromo-2-methoxy-5-((Z)-3,4,5-trimethoxystyryl)phenyl)amino)-1-(3-chloro-4-methoxyphenyl)prop-2-en-1-one (14s)

(Z)-3-((3-bromo-2-methoxy-5-((Z)-3,4,5-trimethoxystyryl)phenyl)amino)-1-(4-methoxy-3-nitrophenyl)prop-2-en-1-one (14t)

(Z)-1-(3-amino-4-methoxyphenyl)-3-((3-bromo-2-methoxy-5-((Z)-3,4,5-trimethoxystyryl)phenyl)amino)prop-2-en-1-one (14u)

(Z)-3-(3-bromo-2-methoxy-5-(3,4,5-trimethoxystyryl)phenylamino)-1-(1H-indol-3-yl)prop-2-en-1-one (14v)

(Z)-3-(3-bromo-2-methoxy-5-(3,4,5-trimethoxystyryl)phenylamino)-1-(1-methyl-1H-indol-3-yl)prop-2-en-1-one (14w)

(Z)-3-((3-bromo-2-methoxy-5-((Z)-3,4,5-trimethoxystyryl)phenyl)amino)-1-(3,4,5-trimethoxyphenyl)prop-2-en-1-one (14x)

(Z)-3-((3-bromo-2-methoxy-5-((Z)-3,4,5-trimethoxystyryl)phenyl)amino)-1-(2-bromo-3,4,5-trimethoxyphenyl)prop-2-en-1-one (14y)

(Z)-3-((3-hydroxy-2-methoxy-5-((Z)-3,4,5-trimethoxystyryl)phenyl)amino)-1-phenylprop-2-en-1-one (15a)

(Z)-3-((3-hydroxy-2-methoxy-5-((Z)-3,4,5-trimethoxystyryl)phenyl)amino)-1-(4-methoxyphenyl)prop-2-en-1-one (15b)

(Z)-3-((3-hydroxy-2-methoxy-5-((Z)-3,4,5-trimethoxystyryl)phenyl)amino)-1-(3-methoxyphenyl)prop-2-en-1-one (15c)

(Z)-3-((3-hydroxy-2-methoxy-5-((Z)-3,4,5-trimethoxystyryl)phenyl)amino)-1-(2-methoxyphenyl)prop-2-en-1-one (15d)

(Z)-3-((3-hydroxy-2-methoxy-5-((Z)-3,4,5-trimethoxystyryl)phenyl)amino)-1-(4-hydroxyphenyl)prop-2-en-1-one (15e)

(Z)-3-((3-hydroxy-2-methoxy-5-((Z)-3,4,5-trimethoxystyryl)phenyl)amino)-1-(4-nitrophenyl)prop-2-en-1-one (15f)

(Z)-1-(4-aminophenyl)-3-((3-hydroxy-2-methoxy-5-((Z)-3,4,5-trimethoxystyryl)phenyl)amino)prop-2-en-1-one (15g)

(Z)-3-((3-hydroxy-2-methoxy-5-((Z)-3,4,5-trimethoxystyryl)phenyl)amino)-1-(2-nitrophenyl)prop-2-en-1-one (15h)

(Z)-1-(2-aminophenyl)-3-((3-hydroxy-2-methoxy-5-((Z)-3,4,5-trimethoxystyryl)phenyl)amino)prop-2-en-1-one (15i)

(Z)-1-(4-fluorophenyl)-3-((3-hydroxy-2-methoxy-5-((Z)-3,4,5-trimethoxystyryl)phenyl)amino)prop-2-en-1-one (15j)

(Z)-3-((3-hydroxy-2-methoxy-5-((Z)-3,4,5-trimethoxystyryl)phenyl)amino)-1-(4-(trifluoromethyl)phenyl)prop-2-en-1-one (15k)

(Z)-1-(3-fluorophenyl)-3-((3-hydroxy-2-methoxy-5-((Z)-3,4,5-trimethoxystyryl)phenyl)amino)prop-2-en-1-one (15l)

(Z)-1-(3-chlorophenyl)-3-((3-hydroxy-2-methoxy-5-((Z)-3,4,5-trimethoxystyryl)phenyl)amino)prop-2-en-1-one (15m)

(Z)-1-(4-chlorophenyl)-3-((3-hydroxy-2-methoxy-5-((Z)-3,4,5-trimethoxystyryl)phenyl)amino)prop-2-en-1-one (15n)

(Z)-3-((3-hydroxy-2-methoxy-5-((Z)-3,4,5-trimethoxystyryl)phenyl)amino)-1-(4-(trifluoromethoxy)phenyl)prop-2-en-1-one (15o)

(Z)-1-(3,4-dimethoxyphenyl)-3-((3-hydroxy-2-methoxy-5-((Z)-3,4,5-trimethoxystyryl)phenyl)amino)prop-2-en-1-one (15p)

(Z)-3-((3-hydroxy-2-methoxy-5-((Z)-3,4,5-trimethoxystyryl)phenyl)amino)-1-(3-hydroxy-4-methoxyphenyl)prop-2-en-1-one (15q)

(Z)-1-(3-fluoro-4-methoxyphenyl)-3-((3-hydroxy-2-methoxy-5-((Z)-3,4,5-trimethoxystyryl)phenyl)amino)prop-2-en-1-one (15r)

(Z)-1-(3-chloro-4-methoxyphenyl)-3-((3-hydroxy-2-methoxy-5-((Z)-3,4,5-trimethoxystyryl)phenyl)amino)prop-2-en-1-one (15s)

(Z)-3-((3-hydroxy-2-methoxy-5-((Z)-3,4,5-trimethoxystyryl)phenyl)amino)-1-(4-methoxy-3-nitrophenyl)prop-2-en-1-one (15t)

(Z)-1-(3-amino-4-methoxyphenyl)-3-((3-hydroxy-2-methoxy-5-((Z)-3,4,5-trimethoxystyryl)phenyl)amino)prop-2-en-1-one (15u)

(Z)-3-(3-hydroxy-2-methoxy-5-(3,4,5-trimethoxystyryl)phenylamino)-1-(1H-indol-3-yl)prop-2-en-1-one (15v)

(Z)-3-(3-hydroxy-2-methoxy-5-(3,4,5-trimethoxystyryl)phenylamino)-1-(1-methyl-1H-indol-3-yl)prop-2-en-1-one (15w)

(Z)-3-((3-hydroxy-2-methoxy-5-((Z)-3,4,5-trimethoxystyryl)phenyl)amino)-1-(3,4,5-trimethoxyphenyl)prop-2-en-1-one (15x)

(Z)-1-(2-bromo-3,4,5-trimethoxyphenyl)-3-((3-hydroxy-2-methoxy-5-((Z)-3,4,5-trimethoxystyryl)phenyl)amino)prop-2-en-1-one (15y)

(Z)-3-((2-hydroxy-3-methoxy-6-((Z)-3,4,5-trimethoxystyryl)phenyl)amino)-1-phenylprop-2-en-1-one (16a)

(Z)-3-((2-hydroxy-3-methoxy-6-((Z)-3,4,5-trimethoxystyryl)phenyl)amino)-1-(4-methoxyphenyl)prop-2-en-1-one (16b)

(Z)-3-((2-hydroxy-3-methoxy-6-((Z)-3,4,5-trimethoxystyryl)phenyl)amino)-1-(3-methoxyphenyl)prop-2-en-1-one (16c)

(Z)-3-((2-hydroxy-3-methoxy-6-((Z)-3,4,5-trimethoxystyryl)phenyl)amino)-1-(2-methoxyphenyl)prop-2-en-1-one (16d)

(Z)-3-((2-hydroxy-3-methoxy-6-((Z)-3,4,5-trimethoxystyryl)phenyl)amino)-1-(4-hydroxyphenyl)prop-2-en-1-one (16e)

(Z)-3-((2-hydroxy-3-methoxy-6-((Z)-3,4,5-trimethoxystyryl)phenyl)amino)-1-(4-nitrophenyl)prop-2-en-1-one (16f)

(Z)-1-(4-aminophenyl)-3-((2-hydroxy-3-methoxy-6-((Z)-3,4,5-trimethoxystyryl)phenyl)amino)prop-2-en-1-one (16g)

(Z)-3-((2-hydroxy-3-methoxy-6-((Z)-3,4,5-trimethoxystyryl)phenyl)amino)-1-(2-nitrophenyl)prop-2-en-1-one (16h)

(Z)-1-(2-aminophenyl)-3-((2-hydroxy-3-methoxy-6-((Z)-3,4,5-trimethoxystyryl)phenyl)amino)prop-2-en-1-one (16i)

(Z)-1-(4-fluorophenyl)-3-((2-hydroxy-3-methoxy-6-((Z)-3,4,5-trimethoxystyryl)phenyl)amino)prop-2-en-1-one (16j)

(Z)-3-((2-hydroxy-3-methoxy-6-((Z)-3,4,5-trimethoxystyryl)phenyl)amino)-1-(4-(trifluoromethyl)phenyl)prop-2-en-1-one (16k)

(Z)-1-(3-fluorophenyl)-3-((2-hydroxy-3-methoxy-6-((Z)-3,4,5-trimethoxystyryl)phenyl)amino)prop-2-en-1-one (16l)

(Z)-1-(3-chlorophenyl)-3-((2-hydroxy-3-methoxy-6-((Z)-3,4,5-trimethoxystyryl)phenyl)amino)prop-2-en-1-one (16m)

(Z)-1-(4-chlorophenyl)-3-((2-hydroxy-3-methoxy-6-((Z)-3,4,5-trimethoxystyryl)phenyl)amino)prop-2-en-1-one (16n)

(Z)-3-((2-hydroxy-3-methoxy-6-((Z)-3,4,5-trimethoxystyryl)phenyl)amino)-1-(4-(trifluoromethoxy)phenyl)prop-2-en-1-one (16o)
(Z)-1-(3,4-dimethoxyphenyl)-3-((2-hydroxy-3-methoxy-6-((Z)-3,4,5-trimethoxystyryl)phenyl)amino)prop-2-en-1-one (16p)
(Z)-3-((2-hydroxy-3-methoxy-6-((Z)-3,4,5-trimethoxystyryl)phenyl)amino)-1-(3-hydroxy-4-methoxyphenyl)prop-2-en-1-one (16q)
(Z)-1-(3-fluoro-4-methoxyphenyl)-3-((2-hydroxy-3-methoxy-6-((Z)-3,4,5-trimethoxystyryl)phenyl)amino)prop-2-en-1-one (16r)
(Z)-1-(3-chloro-4-methoxyphenyl)-3-((2-hydroxy-3-methoxy-6-((Z)-3,4,5-trimethoxystyryl)phenyl)amino)prop-2-en-1-one (16s)
(Z)-3-((2-hydroxy-3-methoxy-6-((Z)-3,4,5-trimethoxystyryl)phenyl)amino)-1-(4-methoxy-3-nitrophenyl)prop-2-en-1-one (16t)
(Z)-3-(2-hydroxy-3-methoxy-6-(3,4,5-trimethoxystyryl)phenylamino)-1-(1H-indol-3-yl)prop-2-en-1-one (16v)
(Z)-3-(2-hydroxy-3-methoxy-6-(3,4,5-trimethoxystyryl)phenylamino)-1-(1-methyl-1H-indol-3-yl)prop-2-en-1-one (16w)
(Z)-3-((2-hydroxy-3-methoxy-6-((Z)-3,4,5-trimethoxystyryl)phenyl)amino)-1-(3,4,5-trimethoxyphenyl)prop-2-en-1-one (16x)
(Z)-1-(2-bromo-3,4,5-trimethoxyphenyl)-3-((2-hydroxy-3-methoxy-6-((Z)-3,4,5-trimethoxystyryl)phenyl)amino)prop-2-en-1-one (16y)
(Z)-3-((4,5-dimethoxy-2-((Z)-3,4,5-trimethoxystyryl)phenyl)amino)-1-phenylprop-2-en-1-one (17a)
(Z)-3-((4,5-dimethoxy-2-((Z)-3,4,5-trimethoxystyryl)phenyl)amino)-1-(4-methoxyphenyl)prop-2-en-1-one (17b)
(Z)-3-((4,5-dimethoxy-2-((Z)-3,4,5-trimethoxystyryl)phenyl)amino)-1-(3-methoxyphenyl)prop-2-en-1-one (17c)
(Z)-3-((4,5-dimethoxy-2-((Z)-3,4,5-trimethoxystyryl)phenyl)amino)-1-(2-methoxyphenyl)prop-2-en-1-one (17d)
(Z)-3-((4,5-dimethoxy-2-((Z)-3,4,5-trimethoxystyryl)phenyl)amino)-1-(4-hydroxyphenyl)prop-2-en-1-one (17e)
(Z)-3-((4,5-dimethoxy-2-((Z)-3,4,5-trimethoxystyryl)phenyl)amino)-1-(4-nitrophenyl)prop-2-en-1-one (17f)
(Z)-1-(4-aminophenyl)-3-((4,5-dimethoxy-2-((Z)-3,4,5-trimethoxystyryl)phenyl)amino)prop-2-en-1-one (17g)
(Z)-3-((4,5-dimethoxy-2-((Z)-3,4,5-trimethoxystyryl)phenyl)amino)-1-(2-nitrophenyl)prop-2-en-1-one (17h)
(Z)-1-(2-aminophenyl)-3-((4,5-dimethoxy-2-((Z)-3,4,5-trimethoxystyryl)phenyl)amino)prop-2-en-1-one (17i)
(Z)-3-((4,5-dimethoxy-2-((Z)-3,4,5-trimethoxystyryl)phenyl)amino)-1-(4-fluorophenyl)prop-2-en-1-one (17j)
(Z)-3-((4,5-dimethoxy-2-((Z)-3,4,5-trimethoxystyryl)phenyl)amino)-1-(4-(trifluoromethyl)phenyl)prop-2-en-1-one (17k)
(Z)-3-((4,5-dimethoxy-2-((Z)-3,4,5-trimethoxystyryl)phenyl)amino)-1-(3-fluorophenyl)prop-2-en-1-one (17l)
(Z)-1-(3-chlorophenyl)-3-((4,5-dimethoxy-2-((Z)-3,4,5-trimethoxystyryl)phenyl)amino)prop-2-en-1-one (17m)
(Z)-1-(4-chlorophenyl)-3-((4,5-dimethoxy-2-((Z)-3,4,5-trimethoxystyryl)phenyl)amino)prop-2-en-1-one (17n)
(Z)-3-((4,5-dimethoxy-2-((Z)-3,4,5-trimethoxystyryl)phenyl)amino)-1-(4-(trifluoromethoxy)phenyl)prop-2-en-1-one (17o)
(Z)-3-((4,5-dimethoxy-2-((Z)-3,4,5-trimethoxystyryl)phenyl)amino)-1-(3,4-dimethoxyphenyl)prop-2-en-1-one (17p)
(Z)-3-((4,5-dimethoxy-2-((Z)-3,4,5-trimethoxystyryl)phenyl)amino)-1-(3-hydroxy-4-methoxyphenyl)prop-2-en-1-one (17q)
(Z)-3-((4,5-dimethoxy-2-((Z)-3,4,5-trimethoxystyryl)phenyl)amino)-1-(3-fluoro-4-methoxyphenyl)prop-2-en-1-one (17r)
(Z)-1-(3-chloro-4-methoxyphenyl)-3-((4,5-dimethoxy-2-((Z)-3,4,5-trimethoxystyryl)phenyl)amino)prop-2-en-1-one (17s)
(Z)-3-((4,5-dimethoxy-2-((Z)-3,4,5-trimethoxystyryl)phenyl)amino)-1-(4-methoxy-3-nitrophenyl)prop-2-en-1-one (17t)
(Z)-1-(3-amino-4-methoxyphenyl)-3-((4,5-dimethoxy-2-((Z)-3,4,5-trimethoxystyryl)phenyl)amino)prop-2-en-1-one (17u)
(Z)-3-(4,5-dimethoxy-2-(3,4,5-trimethoxystyryl)phenylamino)-1-(1H-indol-3-yl)prop-2-en-1-one (17v)
(Z)-3-(4,5-dimethoxy-2-(3,4,5-trimethoxystyryl)phenylamino)-1-(1-methyl-1H-indol-3-yl)prop-2-en-1-one (17w)
(Z)-1-(3-amino-4,5-dimethoxyphenyl)-3-((4,5-dimethoxy-2-((Z)-3,4,5-trimethoxystyryl)phenyl)amino)prop-2-en-1-one (17x)
(Z)-1-(2-bromo-3,4,5-trimethoxyphenyl)-3-((4,5-dimethoxy-2-((Z)-3,4,5-trimethoxystyryl)phenyl)amino)prop-2-en-1-one (17y)
(Z)-3-((4-hydroxy-5-methoxy-2-((Z)-3,4,5-trimethoxystyryl)phenyl)amino)-1-phenylprop-2-en-1-one (18a)
(Z)-3-((4-hydroxy-5-methoxy-2-((Z)-3,4,5-trimethoxystyryl)phenyl)amino)-1-(4-methoxyphenyl)prop-2-en-1-one (18b)
(Z)-3-((4-hydroxy-5-methoxy-2-((Z)-3,4,5-trimethoxystyryl)phenyl)amino)-1-(3-methoxyphenyl)prop-2-en-1-one (18c)
(Z)-3-((4-hydroxy-5-methoxy-2-((Z)-3,4,5-trimethoxystyryl)phenyl)amino)-1-(2-methoxyphenyl)prop-2-en-1-one (18d)
(Z)-3-((4-hydroxy-5-methoxy-2-((Z)-3,4,5-trimethoxystyryl)phenyl)amino)-1-(4-hydroxyphenyl)prop-2-en-1-one (18e)
(Z)-3-((4-hydroxy-5-methoxy-2-((Z)-3,4,5-trimethoxystyryl)phenyl)amino)-1-(4-nitrophenyl)prop-2-en-1-one (18f)
(Z)-1-(4-aminophenyl)-3-((4-hydroxy-5-methoxy-2-((Z)-3,4,5-trimethoxystyryl)phenyl)amino)prop-2-en-1-one (18g)
(Z)-3-((4-hydroxy-5-methoxy-2-((Z)-3,4,5-trimethoxystyryl)phenyl)amino)-1-(2-nitrophenyl)prop-2-en-1-one (18h)
(Z)-1-(2-aminophenyl)-3-((4-hydroxy-5-methoxy-2-((Z)-3,4,5-trimethoxystyryl)phenyl)amino)prop-2-en-1-one (18i)
(Z)-1-(4-fluorophenyl)-3-((4-hydroxy-5-methoxy-2-((Z)-3,4,5-trimethoxystyryl)phenyl)amino)prop-2-en-1-one (18j)
(Z)-3-((4-hydroxy-5-methoxy-2-((Z)-3,4,5-trimethoxystyryl)phenyl)amino)-1-(4-(trifluoromethyl)phenyl)prop-2-en-1-one (18k)
(Z)-1-(3-fluorophenyl)-3-((4-hydroxy-5-methoxy-2-((Z)-3,4,5-trimethoxystyryl)phenyl)amino)prop-2-en-1-one (18l)

(Z)-1-(3-chlorophenyl)-3-((4-hydroxy-5-methoxy-2-((Z)-3,4,5-trimethoxystyryl)phenyl)amino)prop-2-en-1-one (18m)

(Z)-1-(4-chlorophenyl)-3-((4-hydroxy-5-methoxy-2-((Z)-3,4,5-trimethoxystyryl)phenyl)amino)prop-2-en-1-one (18n)

(Z)-3-((4-hydroxy-5-methoxy-2-((Z)-3,4,5-trimethoxystyryl)phenyl)amino)-1-(4-(trifluoromethoxy)phenyl)prop-2-en-1-one (18o)

(Z)-1-(3,4-dimethoxyphenyl)-3-((4-hydroxy-5-methoxy-2-((Z)-3,4,5-trimethoxystyryl)phenyl)amino)prop-2-en-1-one (18p)

(Z)-1-(3-hydroxy-4-methoxyphenyl)-3-((4-hydroxy-5-methoxy-2-((Z)-3,4,5-trimethoxystyryl)phenyl)amino)prop-2-en-1-one (18q)

(Z)-1-(3-fluoro-4-methoxyphenyl)-3-((4-hydroxy-5-methoxy-2-((Z)-3,4,5-trimethoxystyryl)phenyl)amino)prop-2-en-1-one (18r)

(Z)-1-(3-chloro-4-methoxyphenyl)-3-((4-hydroxy-5-methoxy-2-((Z)-3,4,5-trimethoxystyryl)phenyl)amino)prop-2-en-1-one (18s)

(Z)-3-((4-hydroxy-5-methoxy-2-((Z)-3,4,5-trimethoxystyryl)phenyl)amino)-1-(4-methoxy-3-nitrophenyl)prop-2-en-1-one (18t)

(Z)-1-(3-amino-4-methoxyphenyl)-3-((4-hydroxy-5-methoxy-2-((Z)-3,4,5-trimethoxystyryl)phenyl)amino)prop-2-en-1-one (18u)

(Z)-3-(4-hydroxy-5-methoxy-2-(3,4,5-trimethoxystyryl)phenylamino)-1-(1H-indol-3-yl)prop-2-en-1-one (18v)

(Z)-3-(4-hydroxy-5-methoxy-2-(3,4,5-trimethoxystyryl)phenylamino)-1-(1-methyl-1H-indol-3-yl)prop-2-en-1-one (18w)

(Z)-3-((4-hydroxy-5-methoxy-2-((Z)-3,4,5-trimethoxystyryl)phenyl)amino)-1-(3,4,5-trimethoxyphenyl)prop-2-en-1-one (18x)

(Z)-1-(2-bromo-3,4,5-trimethoxyphenyl)-3-((4-hydroxy-5-methoxy-2-((Z)-3,4,5-trimethoxystyryl)phenyl)amino)prop-2-en-1-one (18y)

(Z)-3-((4-fluoro-5-methoxy-2-((Z)-3,4,5-trimethoxystyryl)phenyl)amino)-1-phenylprop-2-en-1-one (19a)

(Z)-3-((4-fluoro-5-methoxy-2-((Z)-3,4,5-trimethoxystyryl)phenyl)amino)-1-(4-methoxyphenyl)prop-2-en-1-one (19b)

(Z)-3-((4-fluoro-5-methoxy-2-((Z)-3,4,5-trimethoxystyryl)phenyl)amino)-1-(3-methoxyphenyl)prop-2-en-1-one (19c)

(Z)-3-((4-fluoro-5-methoxy-2-((Z)-3,4,5-trimethoxystyryl)phenyl)amino)-1-(2-methoxyphenyl)prop-2-en-1-one (19d)

(Z)-3-((4-fluoro-5-methoxy-2-((Z)-3,4,5-trimethoxystyryl)phenyl)amino)-1-(4-hydroxyphenyl)prop-2-en-1-one (19e)

(Z)-3-((4-fluoro-5-methoxy-2-((Z)-3,4,5-trimethoxystyryl)phenyl)amino)-1-(4-nitrophenyl)prop-2-en-1-one (19f)

(Z)-1-(4-aminophenyl)-3-((4-fluoro-5-methoxy-2-((Z)-3,4,5-trimethoxystyryl)phenyl)amino)prop-2-en-1-one (19g)

(Z)-3-((4-fluoro-5-methoxy-2-((Z)-3,4,5-trimethoxystyryl)phenyl)amino)-1-(2-nitrophenyl)prop-2-en-1-one (19h)

(Z)-1-(2-aminophenyl)-3-((4-fluoro-5-methoxy-2-((Z)-3,4,5-trimethoxystyryl)phenyl)amino)prop-2-en-1-one (19i)

(Z)-3-((4-fluoro-5-methoxy-2-((Z)-3,4,5-trimethoxystyryl)phenyl)amino)-1-(4-fluorophenyl)prop-2-en-1-one (19j)

(Z)-3-((4-fluoro-5-methoxy-2-((Z)-3,4,5-trimethoxystyryl)phenyl)amino)-1-(4-(trifluoromethyl)phenyl)prop-2-en-1-one (19k)

(Z)-3-((4-fluoro-5-methoxy-2-((Z)-3,4,5-trimethoxystyryl)phenyl)amino)-1-(3-fluorophenyl)prop-2-en-1-one (19l)

(Z)-1-(3-chlorophenyl)-3-((4-fluoro-5-methoxy-2-((Z)-3,4,5-trimethoxystyryl)phenyl)amino)prop-2-en-1-one (19m)

(Z)-1-(4-chlorophenyl)-3-((4-fluoro-5-methoxy-2-((Z)-3,4,5-trimethoxystyryl)phenyl)amino)prop-2-en-1-one (19n)

(Z)-3-((4-fluoro-5-methoxy-2-((Z)-3,4,5-trimethoxystyryl)phenyl)amino)-1-(4-(trifluoromethoxy)phenyl)prop-2-en-1-one (19o)

(Z)-1-(3,4-dimethoxyphenyl)-3-((4-fluoro-5-methoxy-2-((Z)-3,4,5-trimethoxystyryl)phenyl)amino)prop-2-en-1-one (19p)

(Z)-3-((4-fluoro-5-methoxy-2-((Z)-3,4,5-trimethoxystyryl)phenyl)amino)-1-(3-hydroxy-4-methoxyphenyl)prop-2-en-1-one (19q)

(Z)-1-(3-fluoro-4-methoxyphenyl)-3-((4-fluoro-5-methoxy-2-((Z)-3,4,5-trimethoxystyryl)phenyl)amino)prop-2-en-1-one (19r)

(Z)-1-(3-chloro-4-methoxyphenyl)-3-((4-fluoro-5-methoxy-2-((Z)-3,4,5-trimethoxystyryl)phenyl)amino)prop-2-en-1-one (19s)

(Z)-3-((4-fluoro-5-methoxy-2-((Z)-3,4,5-trimethoxystyryl)phenyl)amino)-1-(4-methoxy-3-nitrophenyl)prop-2-en-1-one (19t)

(Z)-1-(3-amino-4-methoxyphenyl)-3-((4-fluoro-5-methoxy-2-((Z)-3,4,5-trimethoxystyryl)phenyl)amino)prop-2-en-1-one (19u)

(Z)-3-(4-fluoro-5-methoxy-2-(3,4,5-trimethoxystyryl)phenylamino)-1-(1H-indol-3-yl)prop-2-en-1-one (19v)

(Z)-3-(4-fluoro-5-methoxy-2-(3,4,5-trimethoxystyryl)phenylamino)-1-(1-methyl-1H-indol-3-yl)prop-2-en-1-one (19w)

(Z)-3-((4-fluoro-5-methoxy-2-((Z)-3,4,5-trimethoxystyryl)phenyl)amino)-1-(3,4,5-trimethoxyphenyl)prop-2-en-1-one (19x)

(Z)-1-(2-bromo-3,4,5-trimethoxyphenyl)-3-((4-fluoro-5-methoxy-2-((Z)-3,4,5-trimethoxystyryl)phenyl)amino)prop-2-en-1-one (19y)

(Z)-3-((4-chloro-5-methoxy-2-((Z)-3,4,5-trimethoxystyryl)phenyl)amino)-1-phenylprop-2-en-1-one (20a)

(Z)-3-((4-chloro-5-methoxy-2-((Z)-3,4,5-trimethoxystyryl)phenyl)amino)-1-(4-methoxyphenyl)prop-2-en-1-one (20b)

(Z)-3-((4-chloro-5-methoxy-2-((Z)-3,4,5-trimethoxystyryl)phenyl)amino)-1-(3-methoxyphenyl)prop-2-en-1-one (20c)

(Z)-3-((4-chloro-5-methoxy-2-((Z)-3,4,5-trimethoxystyryl)phenyl)amino)-1-(2-methoxyphenyl)prop-2-en-1-one (20d)

(Z)-3-((4-chloro-5-methoxy-2-((Z)-3,4,5-trimethoxystyryl)phenyl)amino)-1-(4-hydroxyphenyl)prop-2-en-1-one (20e)

(Z)-3-((4-chloro-5-methoxy-2-((Z)-3,4,5-trimethoxystyryl)phenyl)amino)-1-(4-nitrophenyl)prop-2-en-1-one (20f)

(Z)-1-(4-aminophenyl)-3-((4-chloro-5-methoxy-2-((Z)-3,4,5-trimethoxystyryl)phenyl)amino)prop-2-en-1-one (20g)

(Z)-3-((4-chloro-5-methoxy-2-((Z)-3,4,5-trimethoxystyryl)phenyl)amino)-1-(2-nitrophenyl)prop-2-en-1-one (20h)

(Z)-1-(2-aminophenyl)-3-((4-chloro-5-methoxy-2-((Z)-3,4,5-trimethoxystyryl)phenyl)amino)prop-2-en-1-one (20i)

(Z)-3-((4-chloro-5-methoxy-2-((Z)-3,4,5-trimethoxystyryl)phenyl)amino)-1-(4-fluorophenyl)prop-2-en-1-one (20j)

(Z)-3-((4-chloro-5-methoxy-2-((Z)-3,4,5-trimethoxystyryl)phenyl)amino)-1-(4-(trifluoromethyl)phenyl)prop-2-en-1-one (20k)

(Z)-3-((4-chloro-5-methoxy-2-((Z)-3,4,5-trimethoxystyryl)phenyl)amino)-1-(3-fluorophenyl)prop-2-en-1-one (20l)

(Z)-3-((4-chloro-5-methoxy-2-((Z)-3,4,5-trimethoxystyryl)phenyl)amino)-1-(3-chlorophenyl)prop-2-en-1-one (20m)

(Z)-3-((4-chloro-5-methoxy-2-((Z)-3,4,5-trimethoxystyryl)phenyl)amino)-1-(4-chlorophenyl)prop-2-en-1-one (20n)

(Z)-3-((4-chloro-5-methoxy-2-((Z)-3,4,5-trimethoxystyryl)phenyl)amino)-1-(4-(trifluoromethoxy)phenyl)prop-2-en-1-one (20o)

(Z)-3-((4-chloro-5-methoxy-2-((Z)-3,4,5-trimethoxystyryl)phenyl)amino)-1-(3,4-dimethoxyphenyl)prop-2-en-1-one (20p)

(Z)-3-((4-chloro-5-methoxy-2-((Z)-3,4,5-trimethoxystyryl)phenyl)amino)-1-(3-hydroxy-4-methoxyphenyl)prop-2-en-1-one (20q)

(Z)-3-((4-chloro-5-methoxy-2-((Z)-3,4,5-trimethoxystyryl)phenyl)amino)-1-(3-fluoro-4-methoxyphenyl)prop-2-en-1-one (20r)

(Z)-1-(3-chloro-4-methoxyphenyl)-3-((4-chloro-5-methoxy-2-((Z)-3,4,5-trimethoxystyryl)phenyl)amino)prop-2-en-1-one (20s)

(Z)-3-((4-chloro-5-methoxy-2-((Z)-3,4,5-trimethoxystyryl)phenyl)amino)-1-(4-methoxy-3-nitrophenyl)prop-2-en-1-one (20t)

(Z)-1-(3-amino-4-methoxyphenyl)-3-((4-chloro-5-methoxy-2-((Z)-3,4,5-trimethoxystyryl)phenyl)amino)prop-2-en-1-one (20u)

(Z)-3-(4-chloro-5-methoxy-2-(3,4,5-trimethoxystyryl)phenylamino)-1-(1H-indol-3-yl)prop-2-en-1-one (20v)

(Z)-3-(4-chloro-5-methoxy-2-(3,4,5-trimethoxystyryl)phenylamino)-1-(1-methyl-1H-indol-3-yl)prop-2-en-1-one (20w)

(Z)-3-((4-chloro-5-methoxy-2-((Z)-3,4,5-trimethoxystyryl)phenyl)amino)-1-(3,4,5-trimethoxyphenyl)prop-2-en-1-one (20x)

(Z)-1-(2-bromo-3,4,5-trimethoxyphenyl)-3-((4-chloro-5-methoxy-2-((Z)-3,4,5-trimethoxystyryl)phenyl)amino)prop-2-en-1-one (20y)

(Z)-3-((2,3-dimethoxy-6-((Z)-3,4,5-trimethoxystyryl)phenyl)amino)-1-phenylprop-2-en-1-one (21a)

(Z)-3-((2,3-dimethoxy-6-((Z)-3,4,5-trimethoxystyryl)phenyl)amino)-1-(4-methoxyphenyl)prop-2-en-1-one (21b)

(Z)-3-((2,3-dimethoxy-6-((Z)-3,4,5-trimethoxystyryl)phenyl)amino)-1-(3-methoxyphenyl)prop-2-en-1-one (21c)

(Z)-3-((2,3-dimethoxy-6-((Z)-3,4,5-trimethoxystyryl)phenyl)amino)-1-(2-methoxyphenyl)prop-2-en-1-one (21d)

(Z)-3-((2,3-dimethoxy-6-((Z)-3,4,5-trimethoxystyryl)phenyl)amino)-1-(4-hydroxyphenyl)prop-2-en-1-one (21e)

(Z)-3-((2,3-dimethoxy-6-((Z)-3,4,5-trimethoxystyryl)phenyl)amino)-1-(4-nitrophenyl)prop-2-en-1-one (21f)

(Z)-1-(4-aminophenyl)-3-((2,3-dimethoxy-6-((Z)-3,4,5-trimethoxystyryl)phenyl)amino)prop-2-en-1-one (21g)

(Z)-3-((2,3-dimethoxy-6-((Z)-3,4,5-trimethoxystyryl)phenyl)amino)-1-(2-nitrophenyl)prop-2-en-1-one (21h)

(Z)-1-(2-aminophenyl)-3-((2,3-dimethoxy-6-((Z)-3,4,5-trimethoxystyryl)phenyl)amino)prop-2-en-1-one (21i)

(Z)-3-((2,3-dimethoxy-6-((Z)-3,4,5-trimethoxystyryl)phenyl)amino)-1-(4-fluorophenyl)prop-2-en-1-one (21j)

(Z)-3-((2,3-dimethoxy-6-((Z)-3,4,5-trimethoxystyryl)phenyl)amino)-1-(4-(trifluoromethyl)phenyl)prop-2-en-1-one (21k)

(Z)-3-((2,3-dimethoxy-6-((Z)-3,4,5-trimethoxystyryl)phenyl)amino)-1-(3-fluorophenyl)prop-2-en-1-one (21l)

(Z)-1-(3-chlorophenyl)-3-((2,3-dimethoxy-6-((Z)-3,4,5-trimethoxystyryl)phenyl)amino)prop-2-en-1-one (21m)

(Z)-1-(4-chlorophenyl)-3-((2,3-dimethoxy-6-((Z)-3,4,5-trimethoxystyryl)phenyl)amino)prop-2-en-1-one (21n)

(Z)-3-((2,3-dimethoxy-6-((Z)-3,4,5-trimethoxystyryl)phenyl)amino)-1-(4-(trifluoromethoxy)phenyl)prop-2-en-1-one (21o)

(Z)-3-((2,3-dimethoxy-6-((Z)-3,4,5-trimethoxystyryl)phenyl)amino)-1-(3,4-dimethoxyphenyl)prop-2-en-1-one (21p)

(Z)-3-((2,3-dimethoxy-6-((Z)-3,4,5-trimethoxystyryl)phenyl)amino)-1-(3-hydroxy-4-methoxyphenyl)prop-2-en-1-one (21q)

(Z)-3-((2,3-dimethoxy-6-((Z)-3,4,5-trimethoxystyryl)phenyl)amino)-1-(3-fluoro-4-methoxyphenyl)prop-2-en-1-one (21r)

(Z)-1-(3-chloro-4-methoxyphenyl)-3-((2,3-dimethoxy-6-((Z)-3,4,5-trimethoxystyryl)phenyl)amino)prop-2-en-1-one (21s)

(Z)-3-((2,3-dimethoxy-6-((Z)-3,4,5-trimethoxystyryl)phenyl)amino)-1-(4-methoxy-3-nitrophenyl)prop-2-en-1-one (21t)

(Z)-1-(3-amino-4-methoxyphenyl)-3-((2,3-dimethoxy-6-((Z)-3,4,5-trimethoxystyryl)phenyl)amino)prop-2-en-1-one (21u)

(Z)-3-(2,3-dimethoxy-6-(3,4,5-trimethoxystyryl)phenylamino)-1-(1H-indol-3-yl)prop-2-en-1-one (21v)

(Z)-3-(2,3-dimethoxy-6-(3,4,5-trimethoxystyryl)phenylamino)-1-(1-methyl-1H-indol-3-yl)prop-2-en-1-one (21w)

(Z)-3-((2,3-dimethoxy-6-((Z)-3,4,5-trimethoxystyryl)phenyl)amino)-1-(3,4,5-trimethoxyphenyl)prop-2-en-1-one (21x)

(Z)-1-(2-bromo-3,4,5-trimethoxyphenyl)-3-((2,3-dimethoxy-6-((Z)-3,4,5-trimethoxystyryl)phenyl)amino)prop-2-en-1-one (21y).

4. A novel 3,4,5-trimethoxystyrylarylaminopropenone of general formulae A as claimed in claim 1 selected from the following compounds:

(7a) 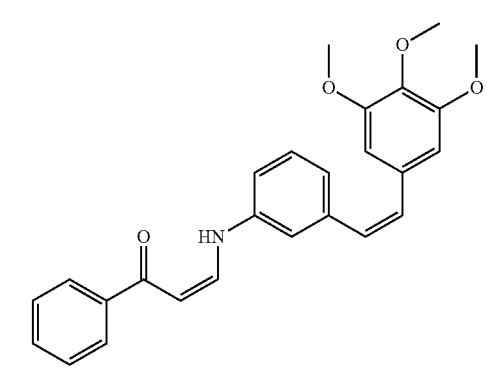
(7b) 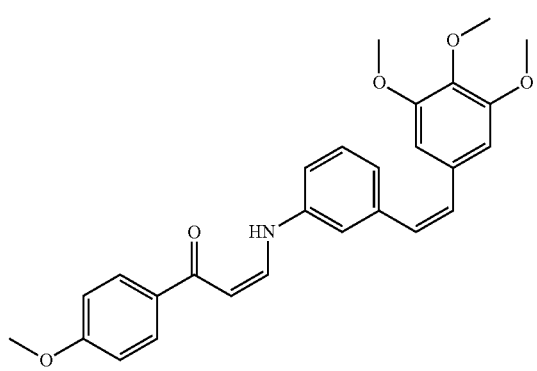
(7c) 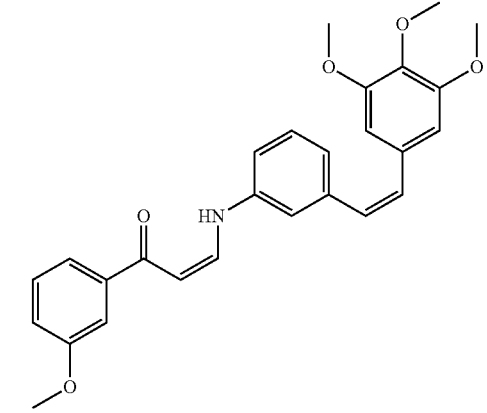
(7d) 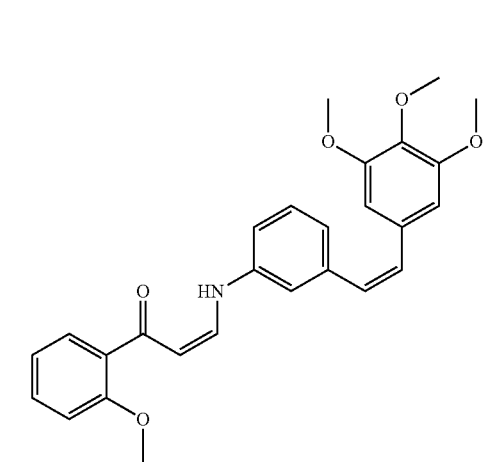
(7e) 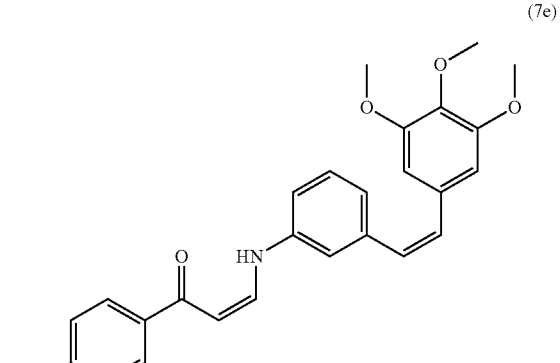
(7f) 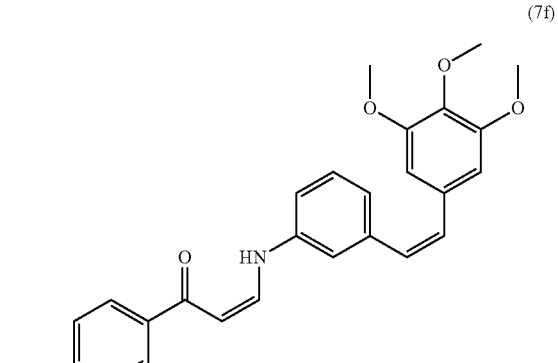
(7g) 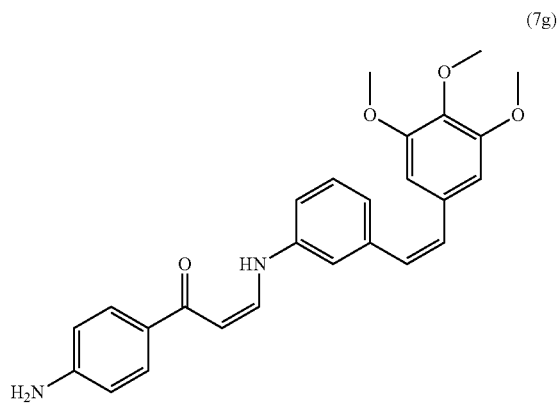
(7h) 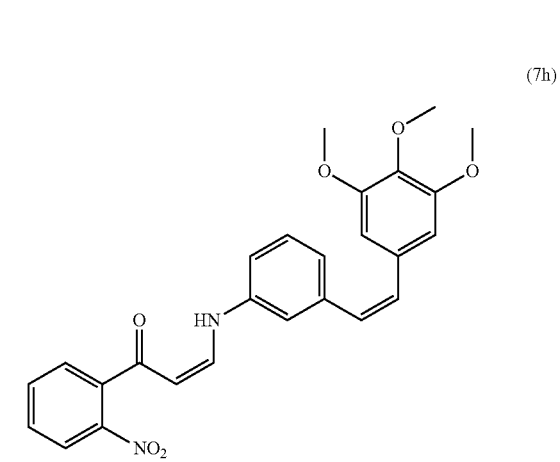

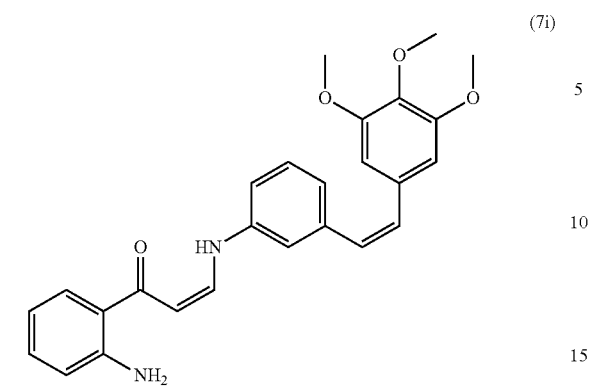
(7i)
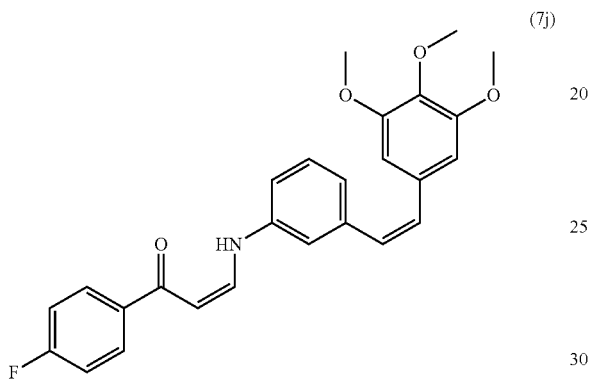
(7j)
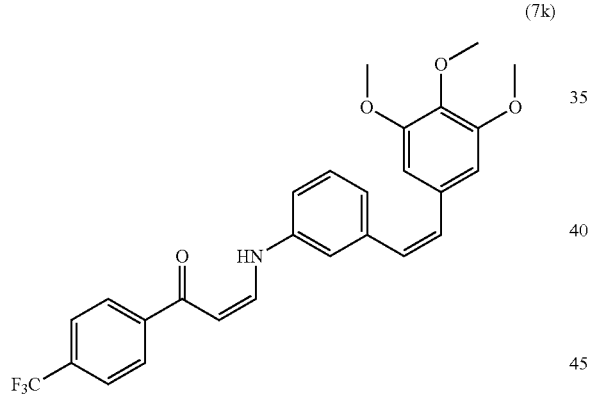
(7k)
(7l)
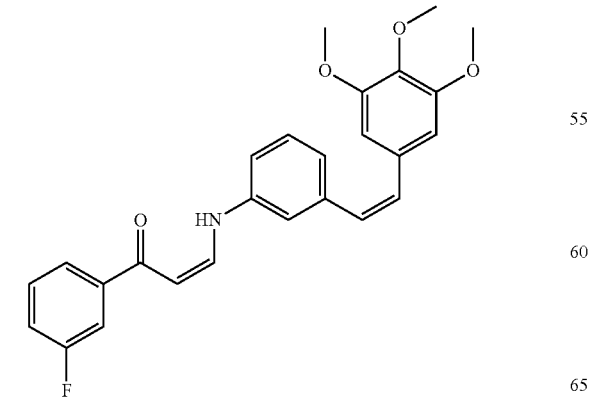
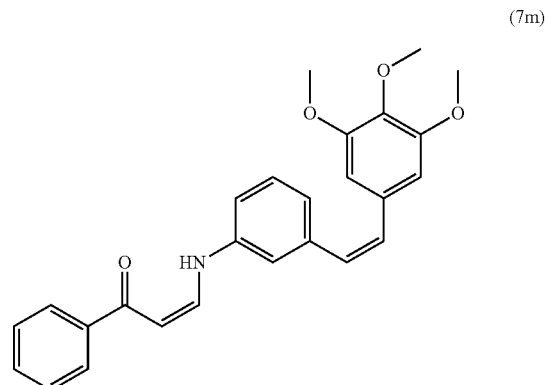
(7m)
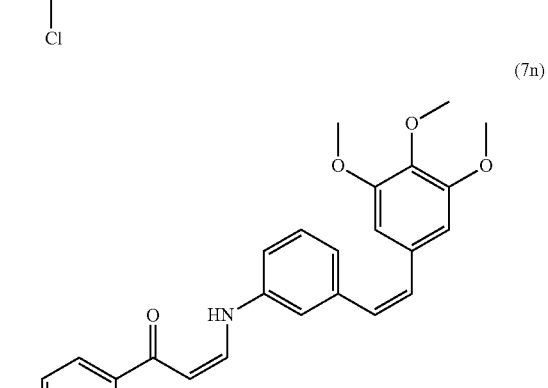
(7n)
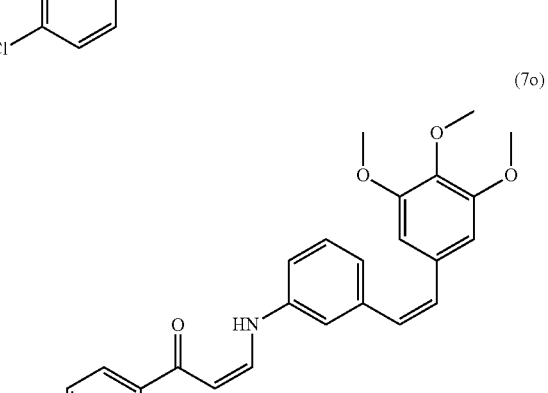
(7o)
(7p)
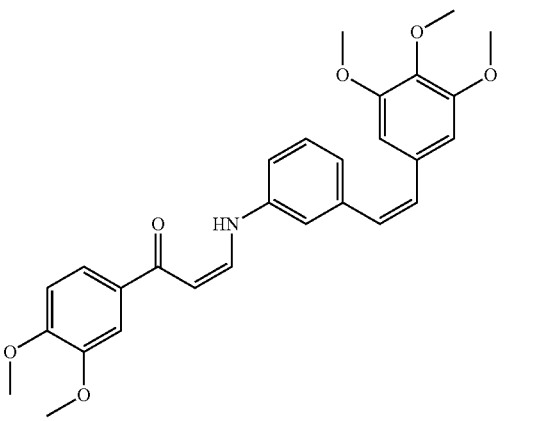

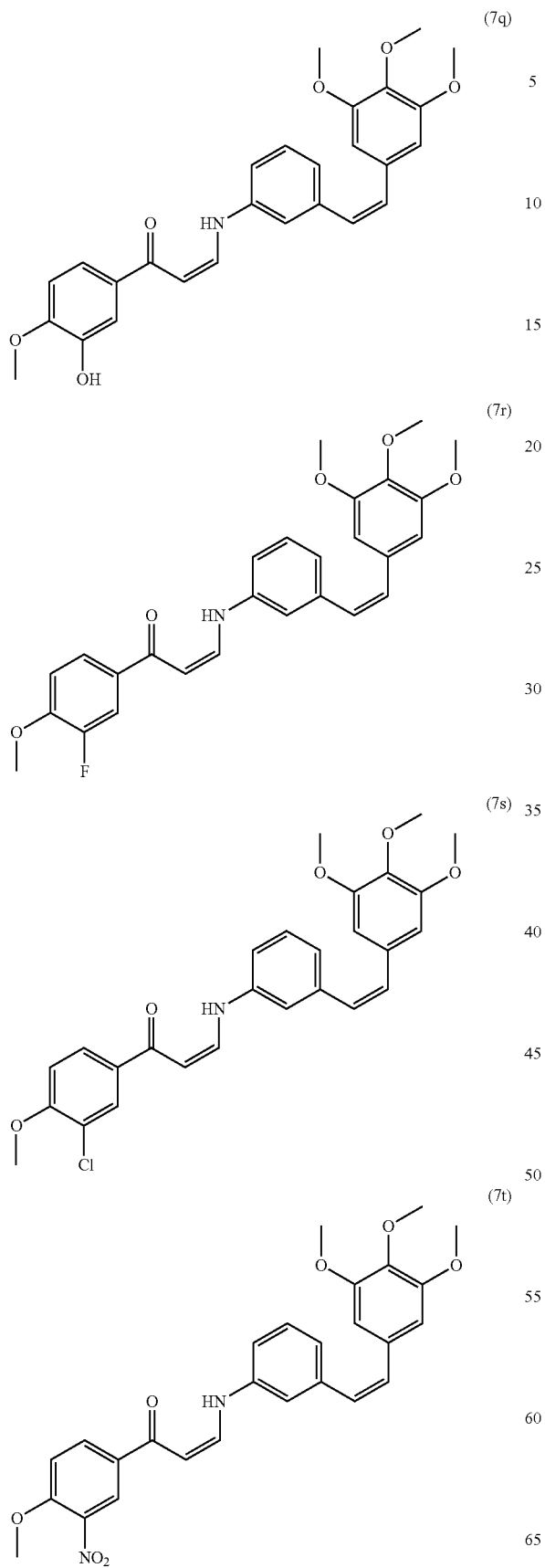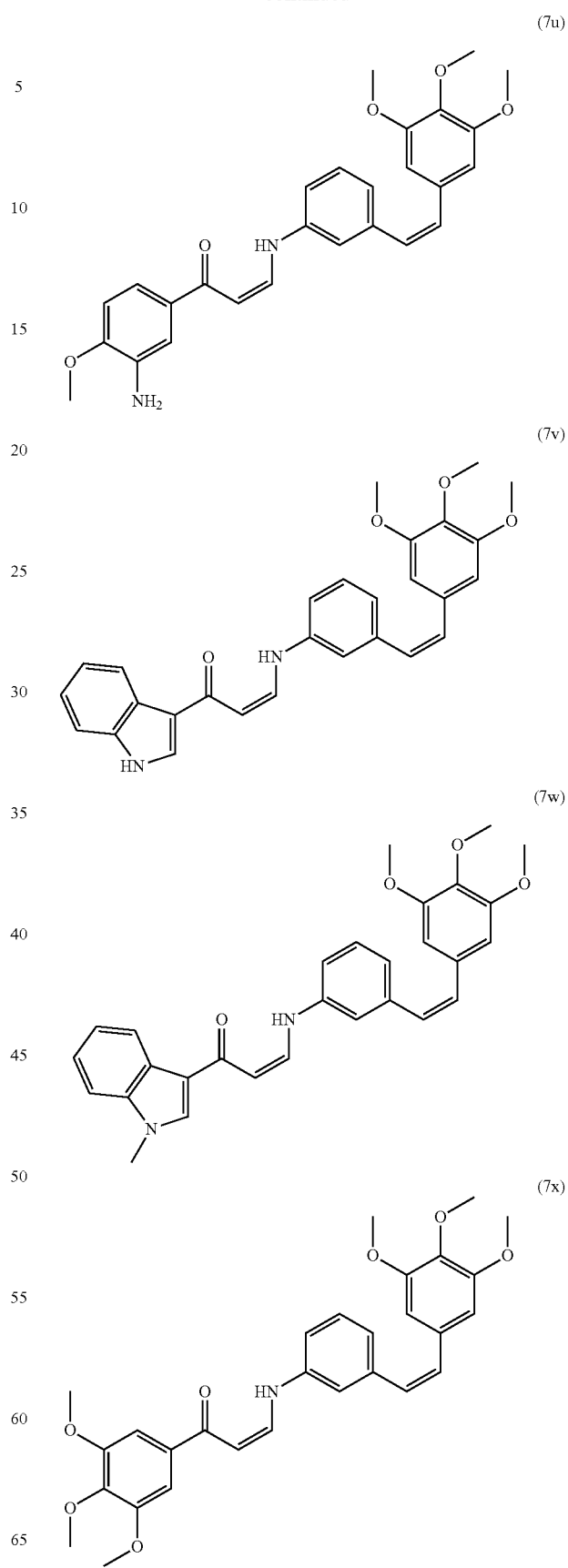

(7y)
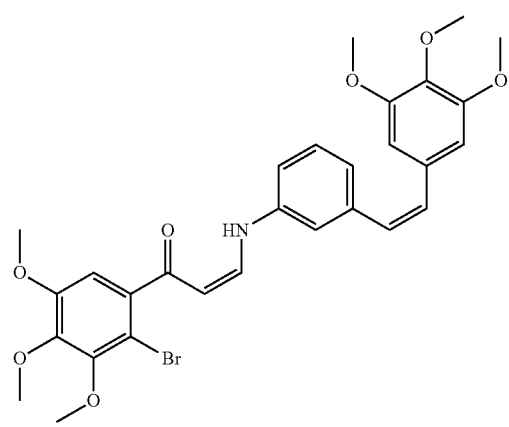
(8a)
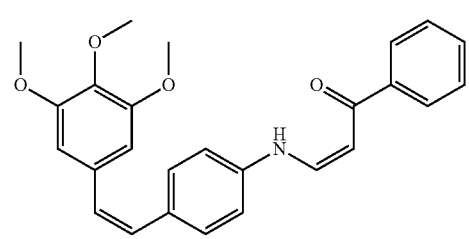
(8b)
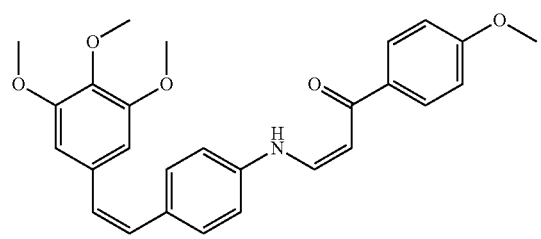
(8c)
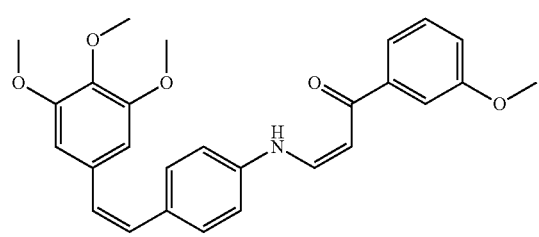
(8d)
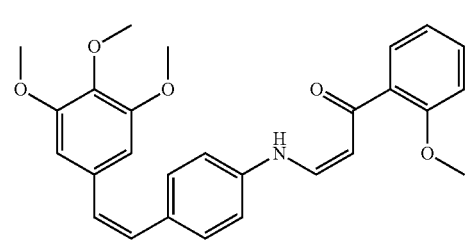
(8e)
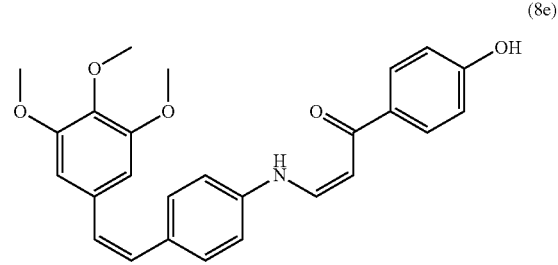
(8f)
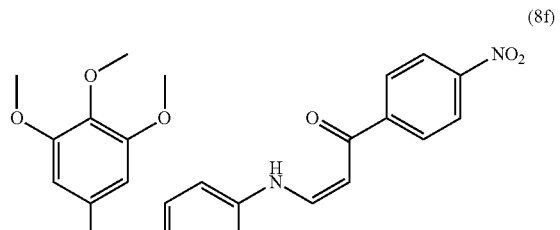
(8g)
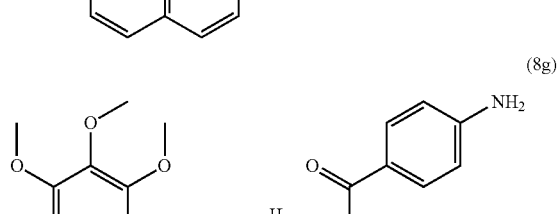
(8h)
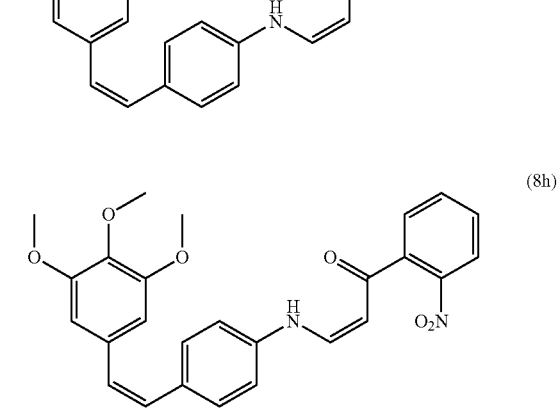
(8i)
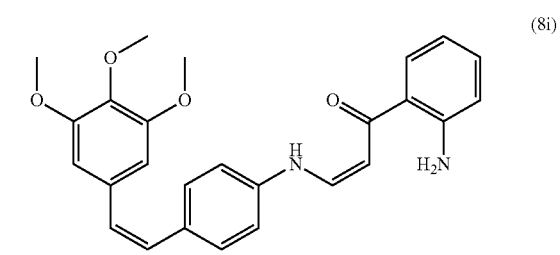
(8j)
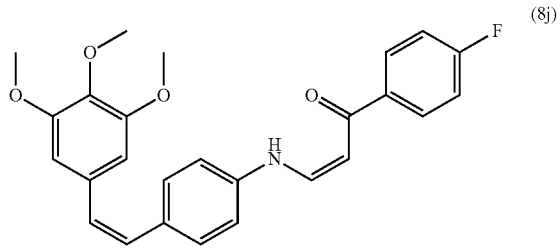

-continued
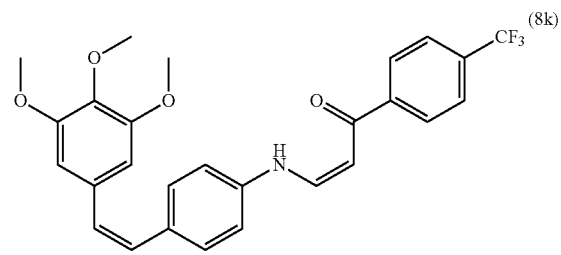
(8k)
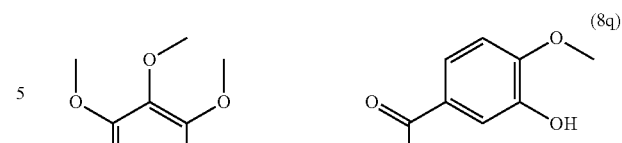
(8q)
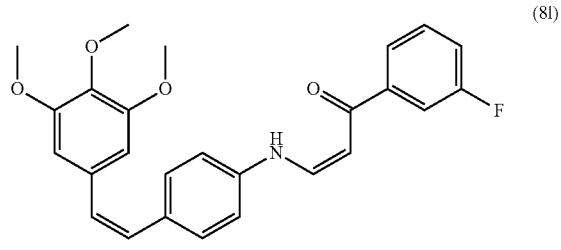
(8l)
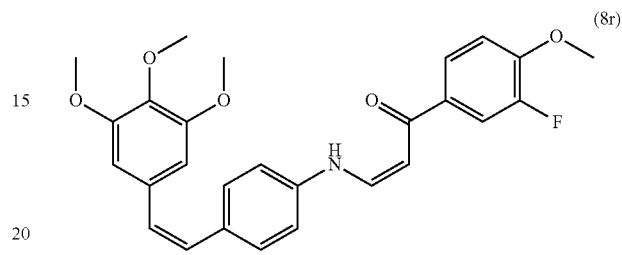
(8r)
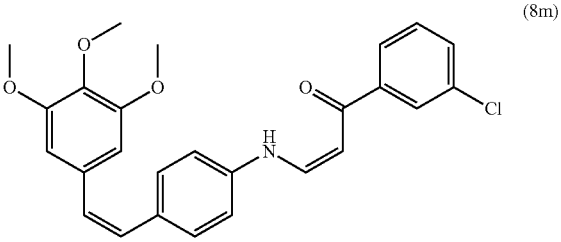
(8m)
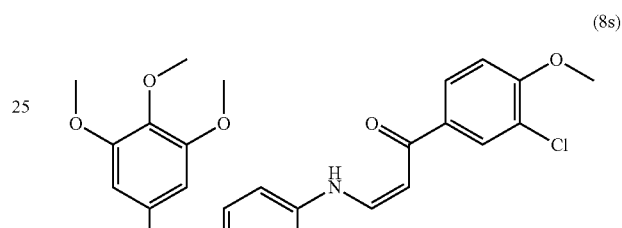
(8s)
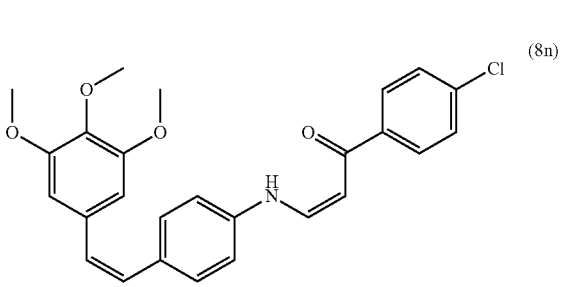
(8n)
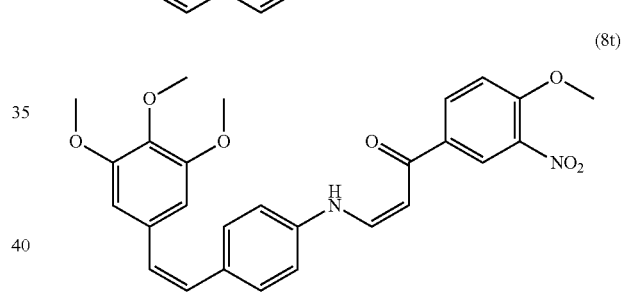
(8t)
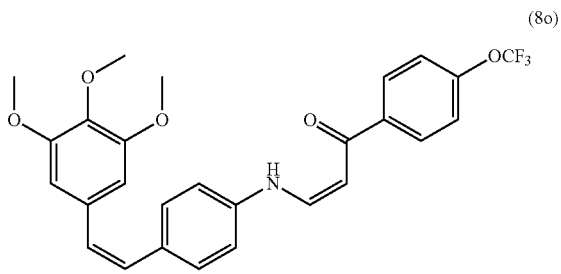
(8o)
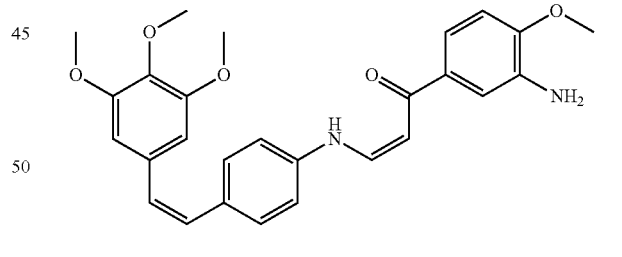
(8u)
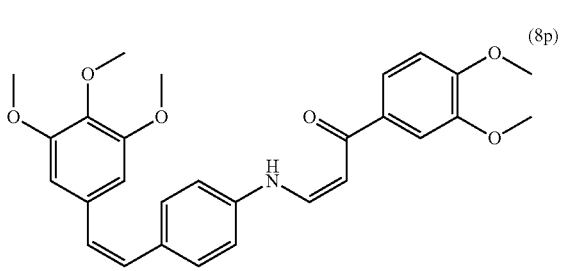
(8p)
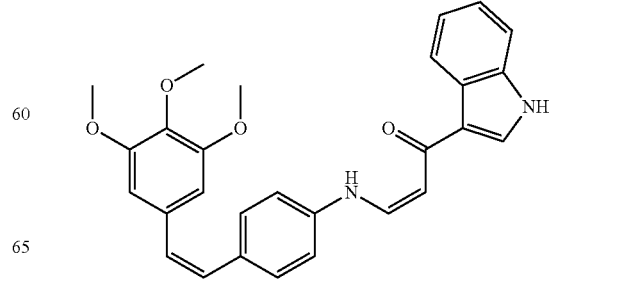
(8v)

(8w)
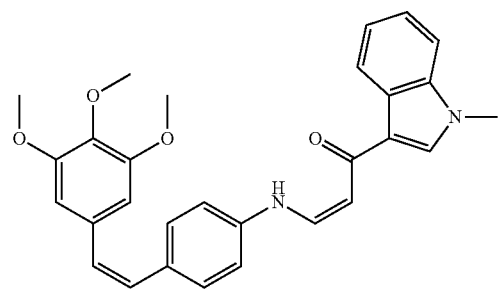
(8x)
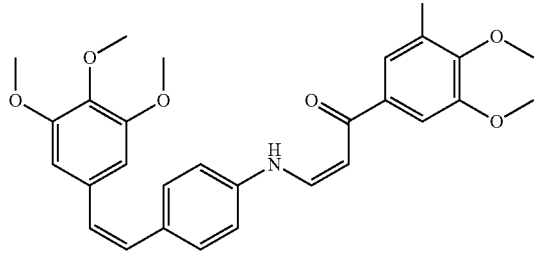
(8y)
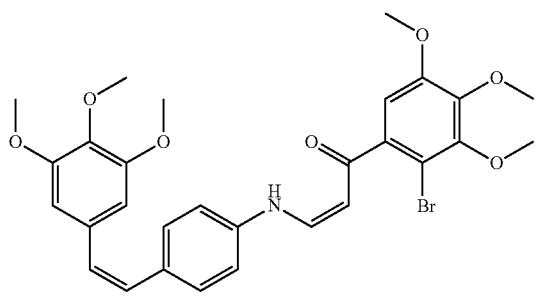
(9a)
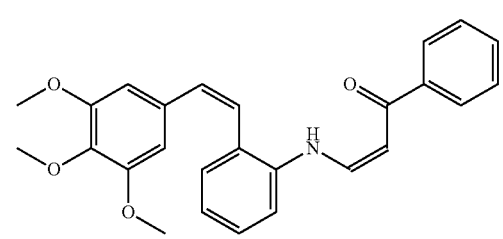
(9b)
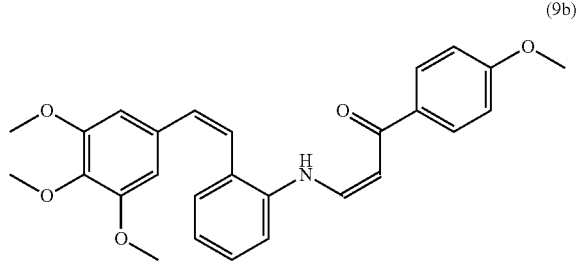
(9c)
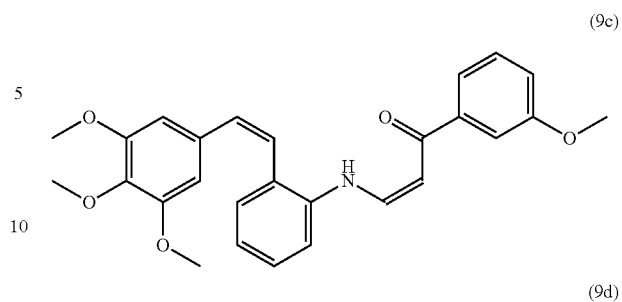
(9d)
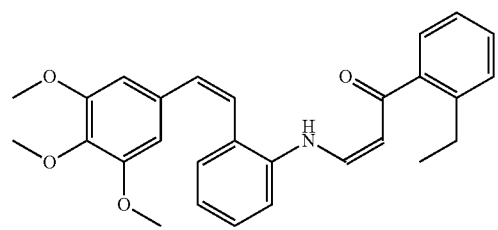
(9e)
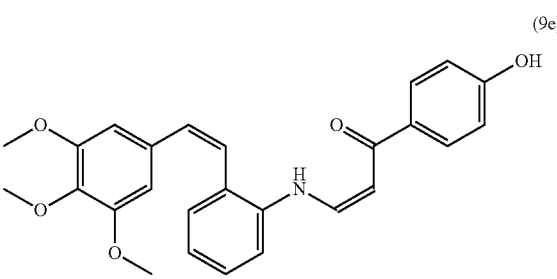
(9f)
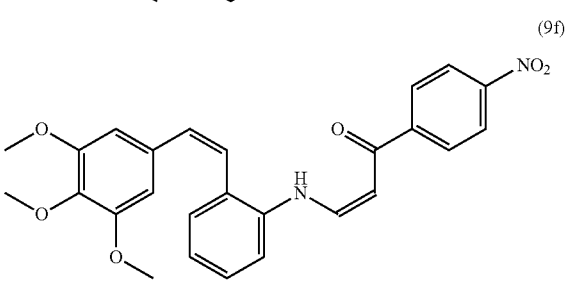
(9g)
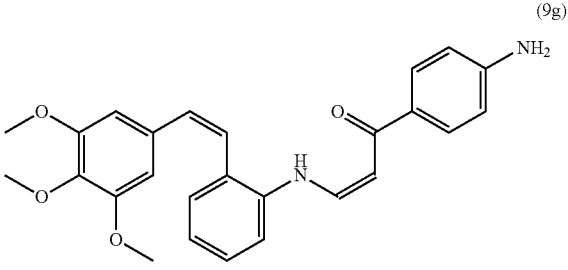
(9h)
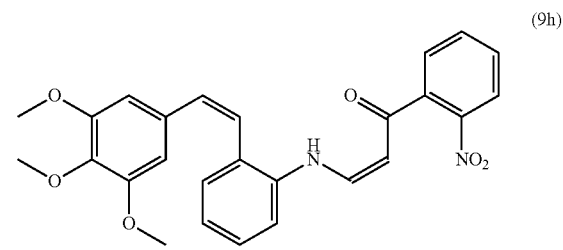

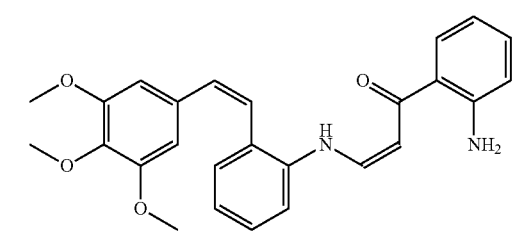
(9i)
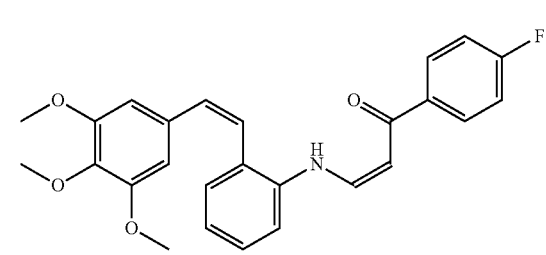
(9j)
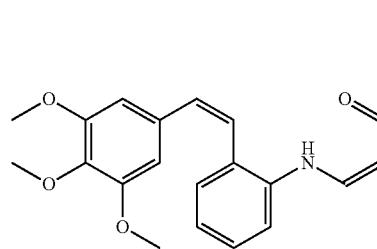
(9k)
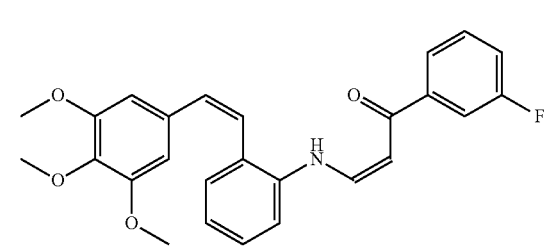
(9l)
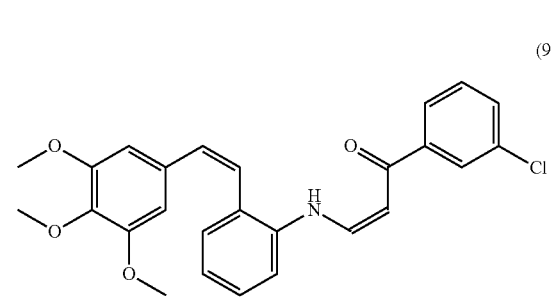
(9m)
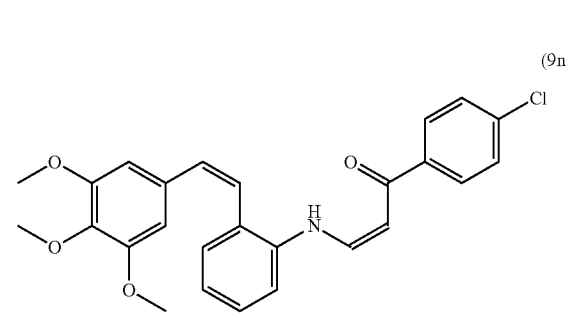
(9n)
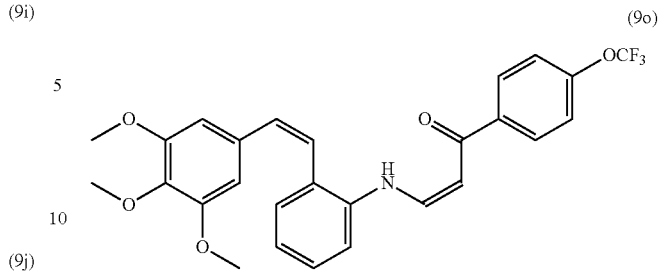
(9o)
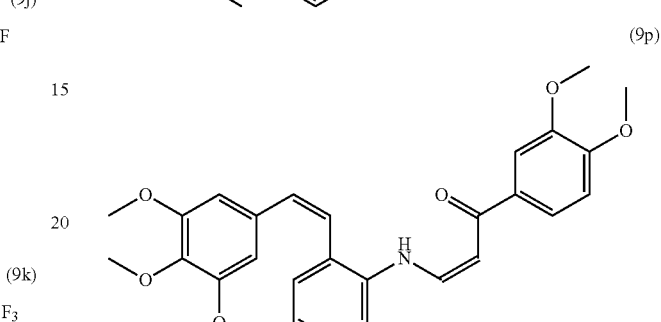
(9p)
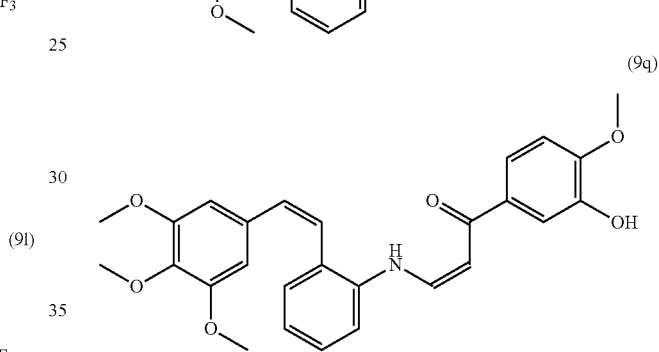
(9q)
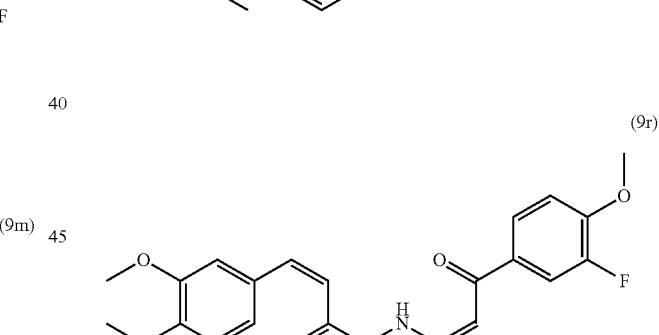
(9r)
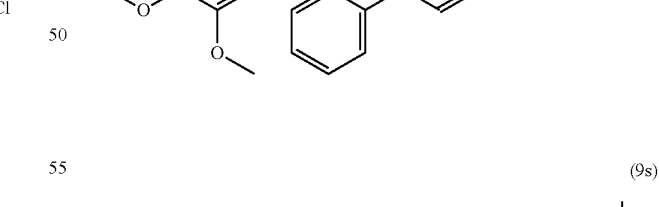
(9s)

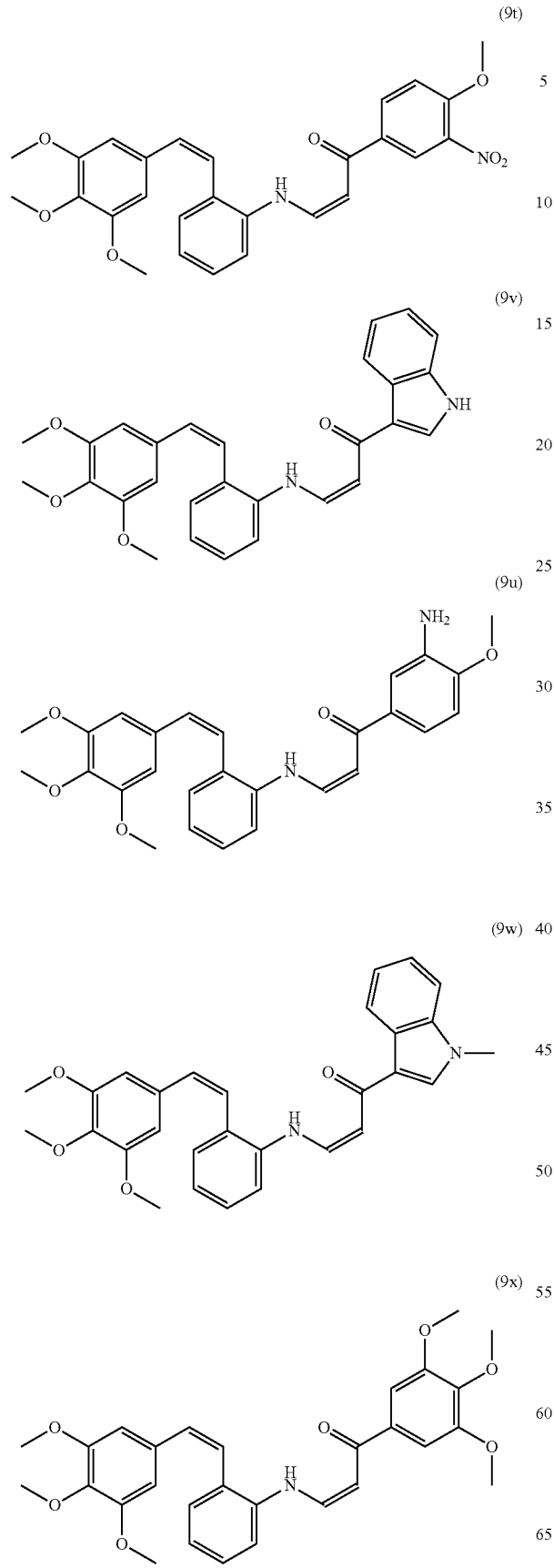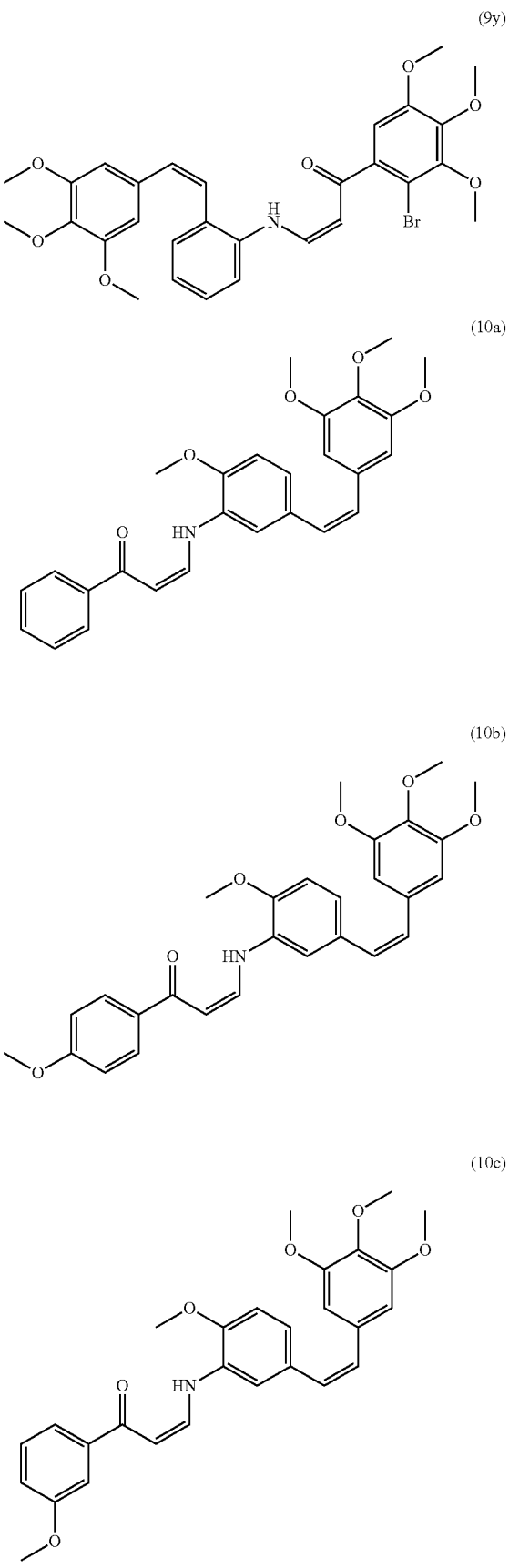

(10d)
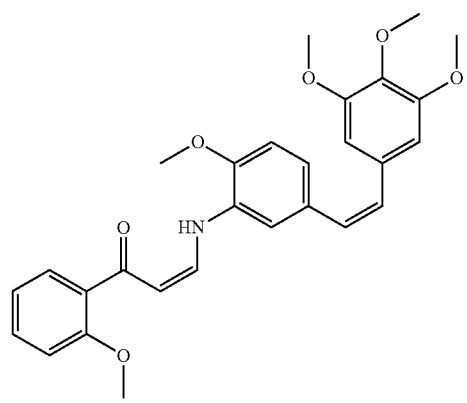
(10e)
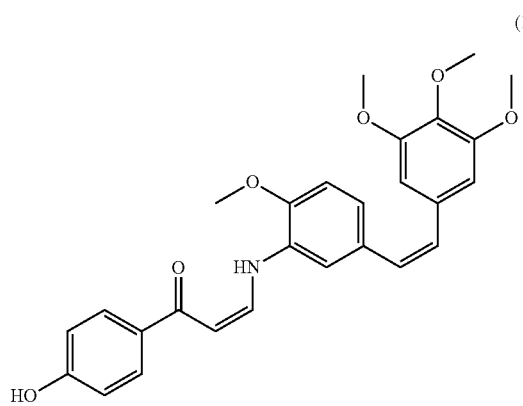
(10f)
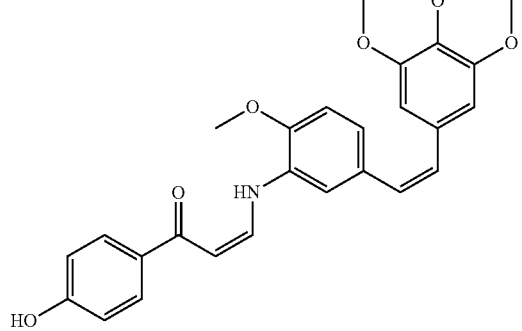
(10g)
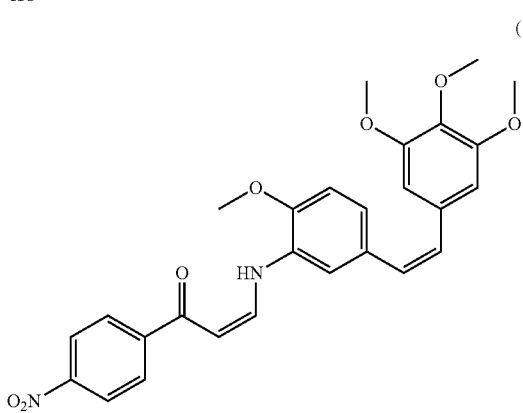
(10h)
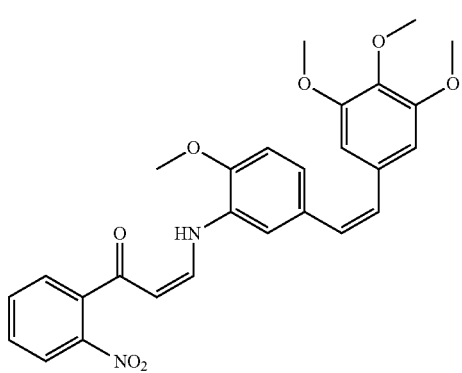
(10i)
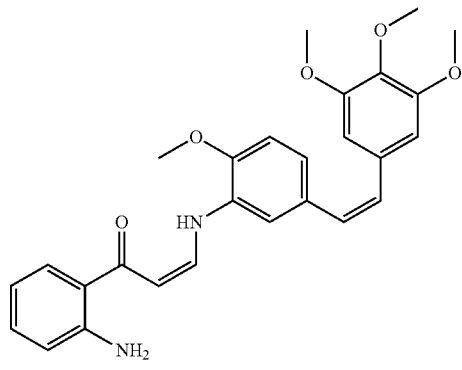
(10j)
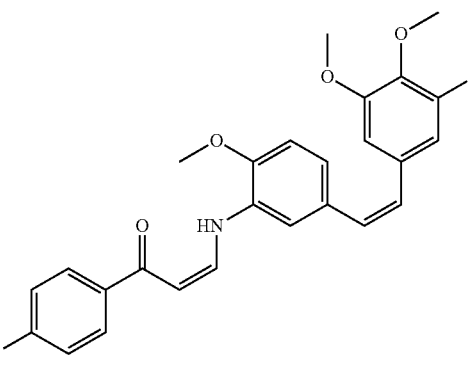
(10k)
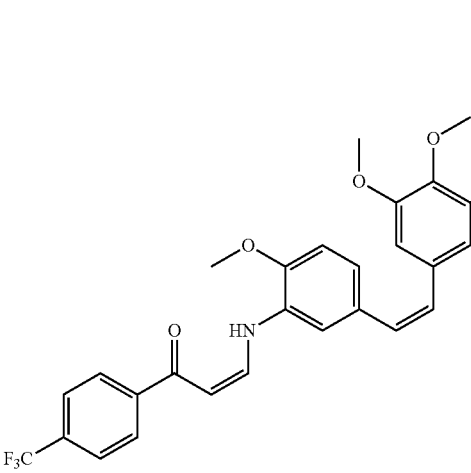

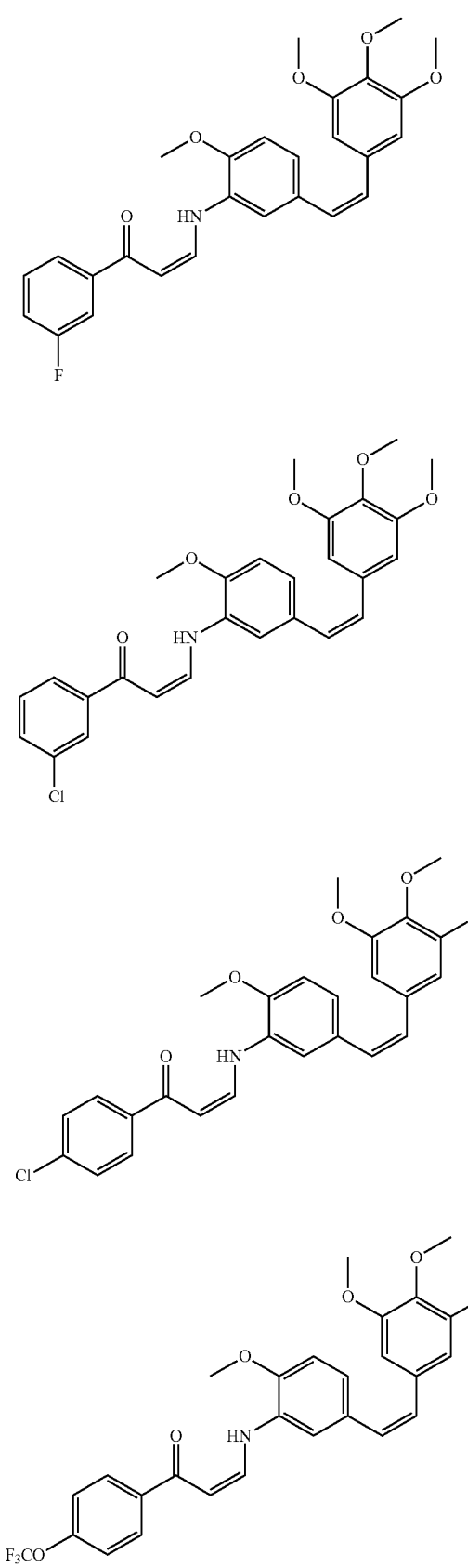
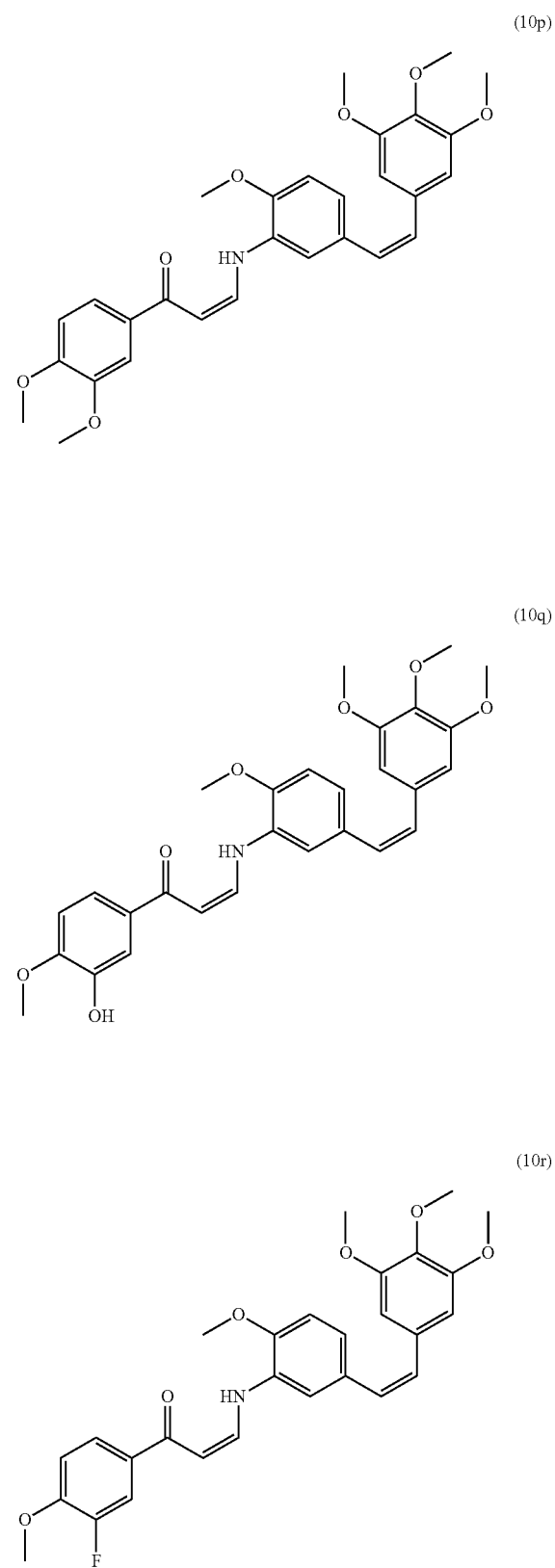

(10s)
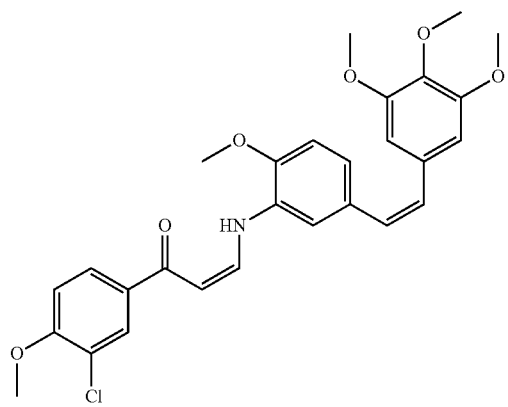
(10t)
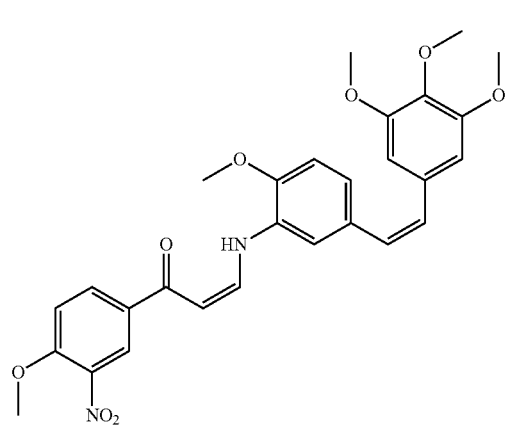
(10u)
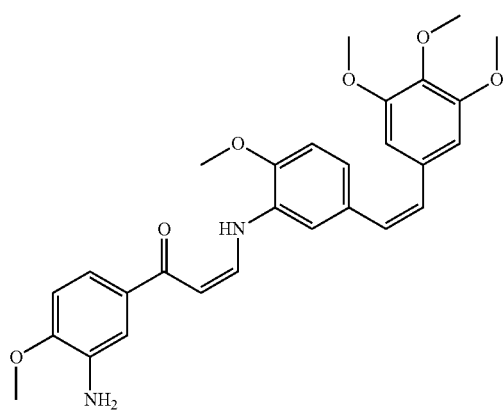
(10v)
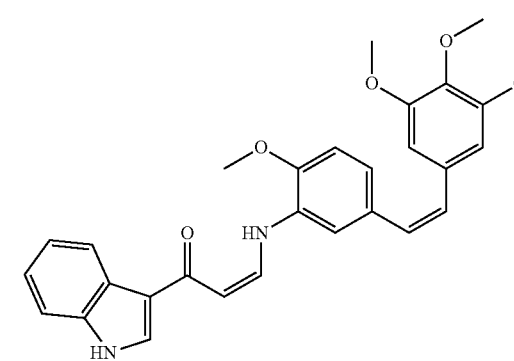
(10w)
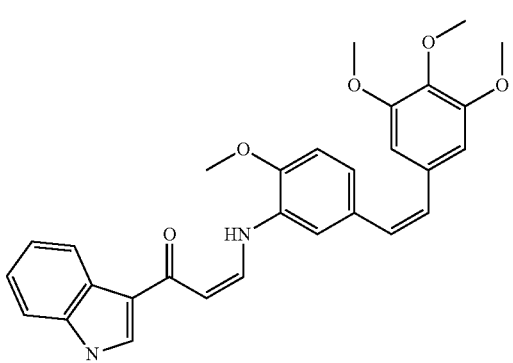
(10x)
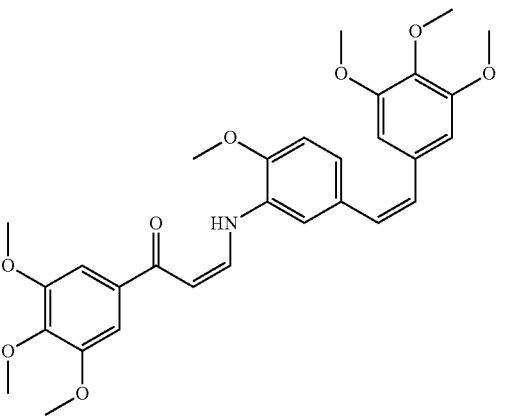
(10y)
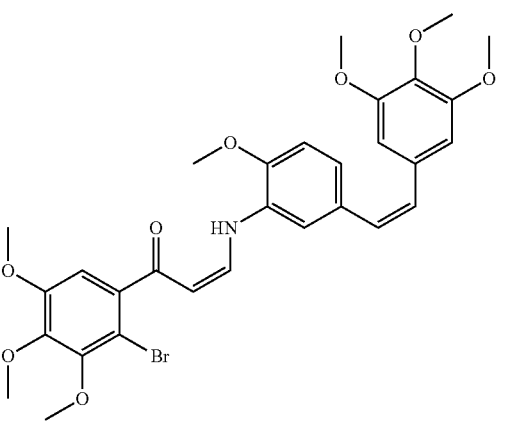
(11a)
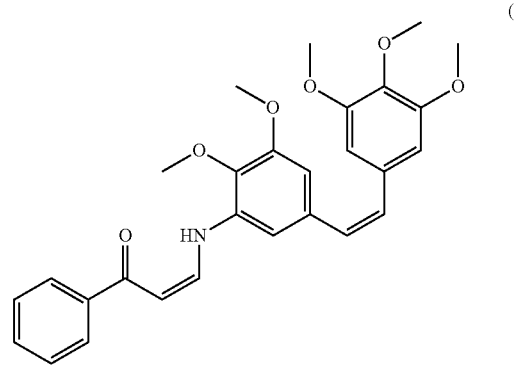

-continued
(11b)
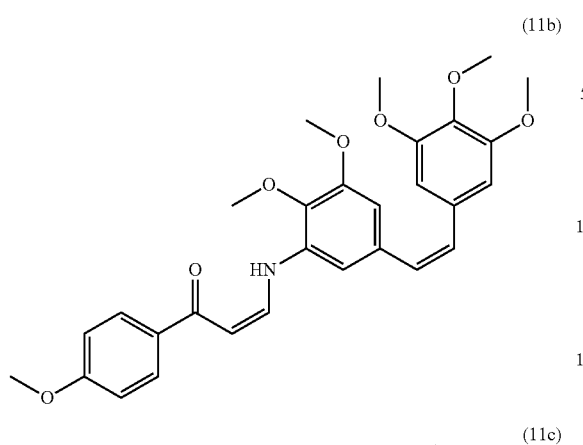
(11c)
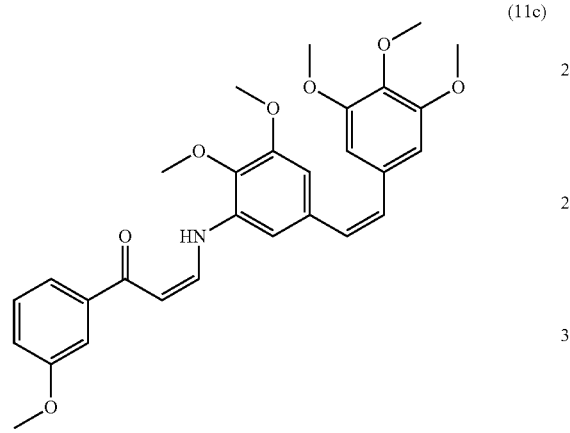
(11d)
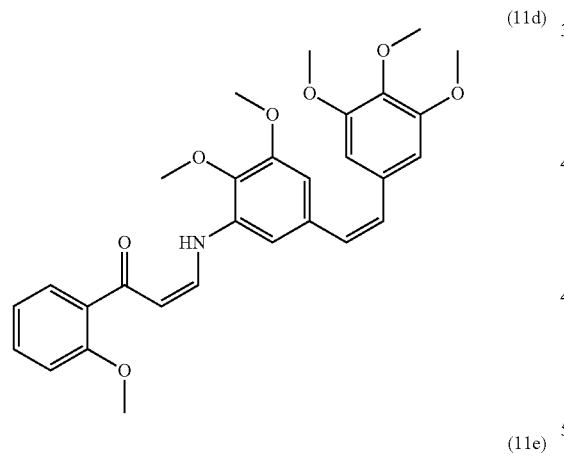
(11e)
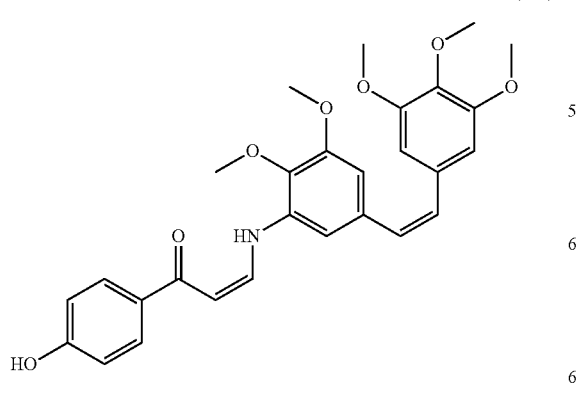
(11f)
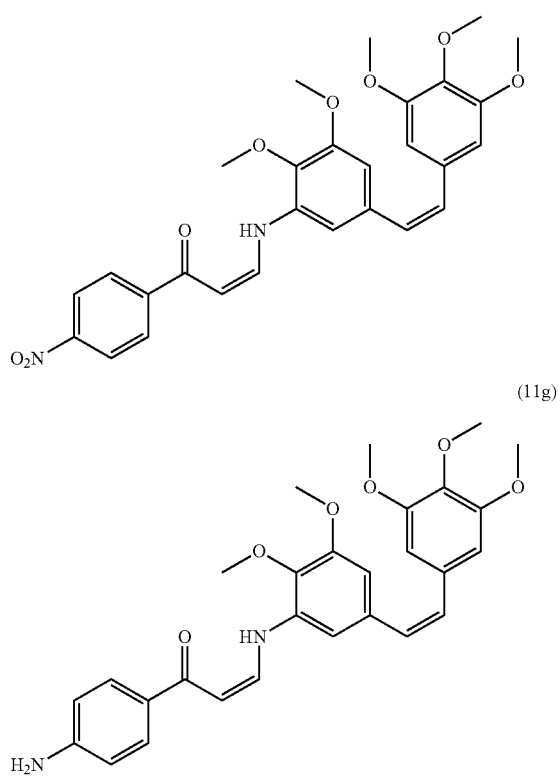
(11g)
(11h)
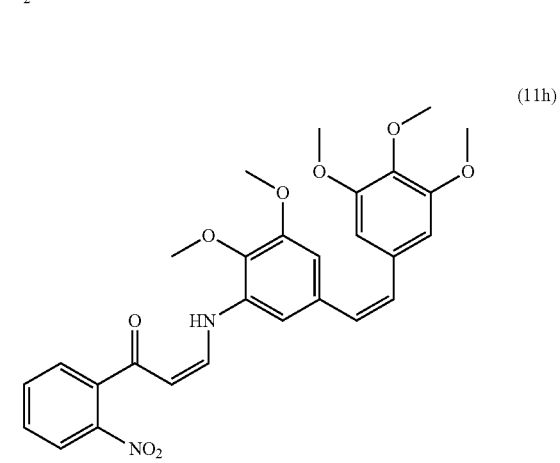
(11i)
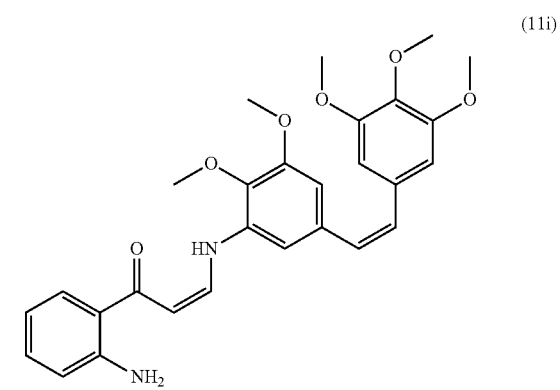

(11j) 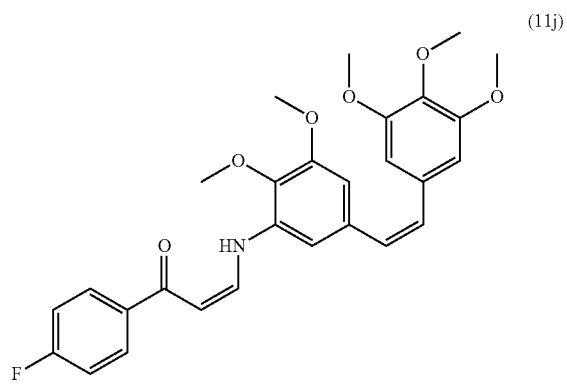
(11k) 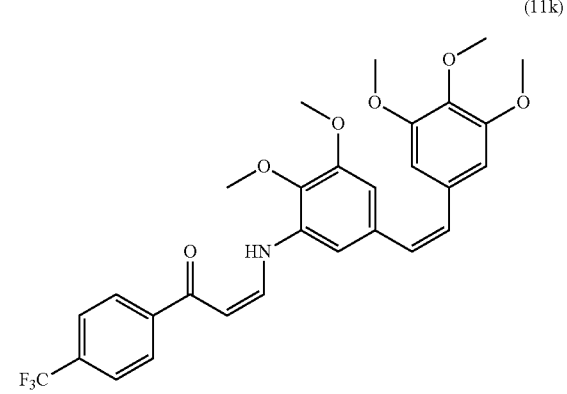
(11l) 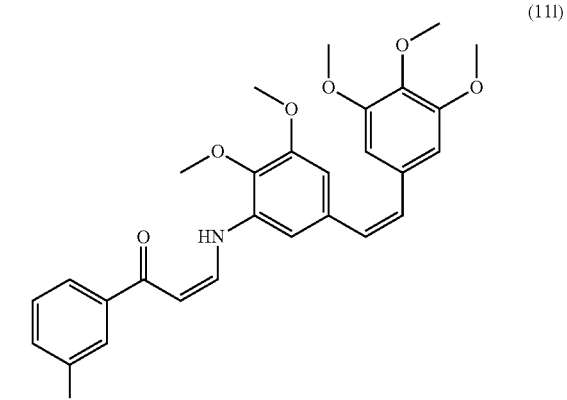
(11m) 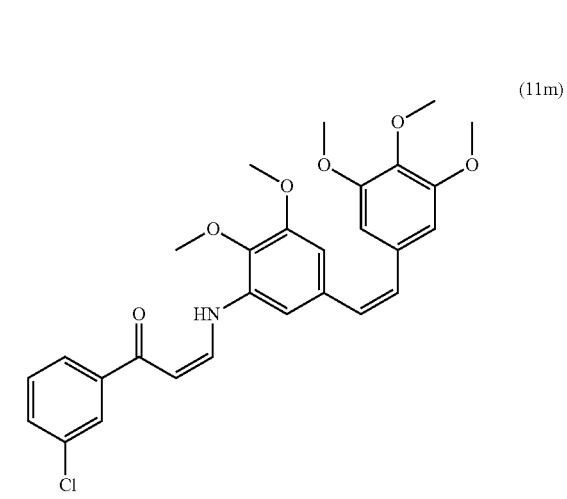
(11n) 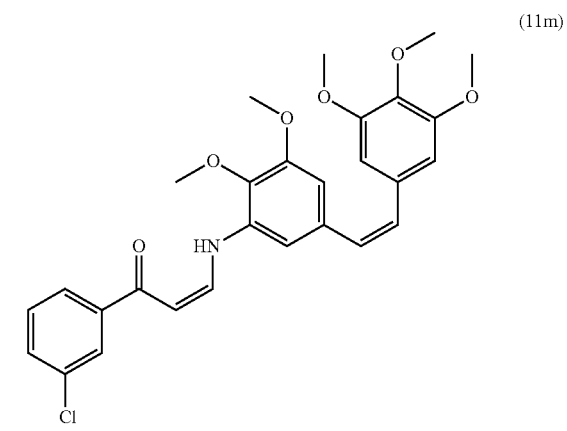
(11o) 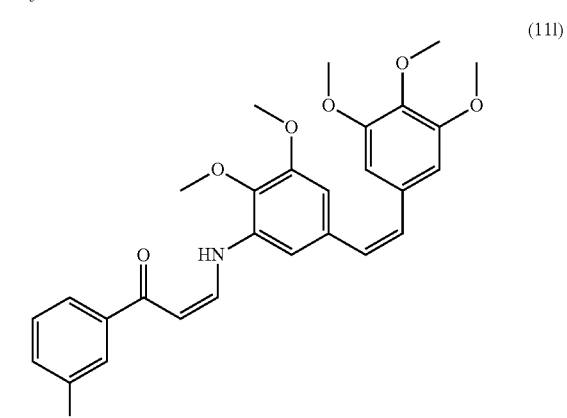
(11p) 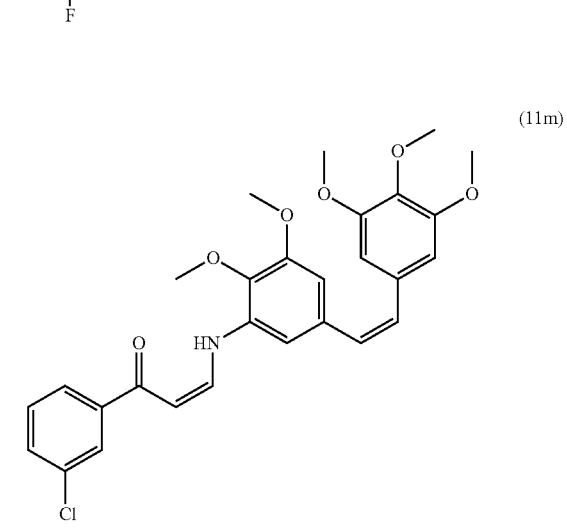
(11q) 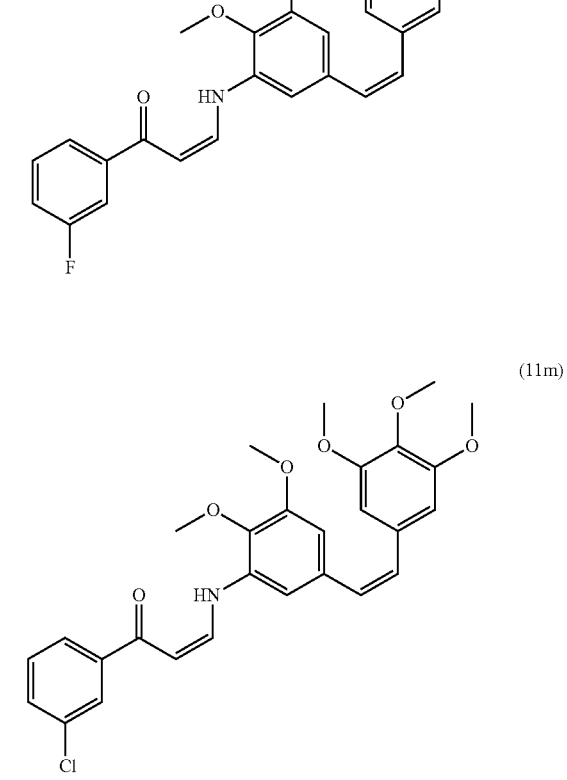

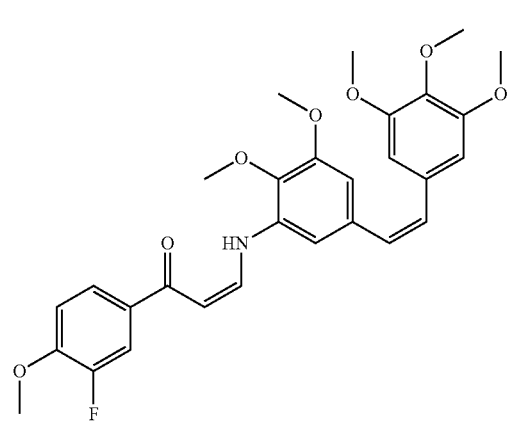 (11r)
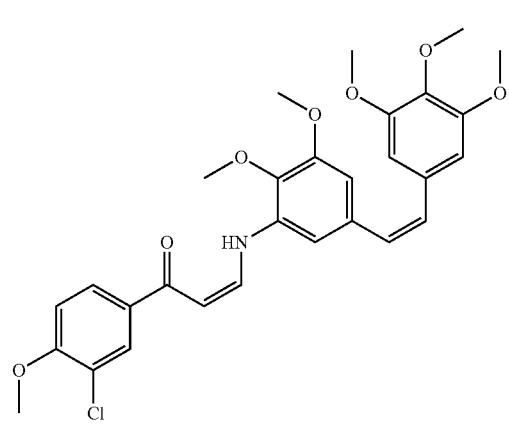 (11s)
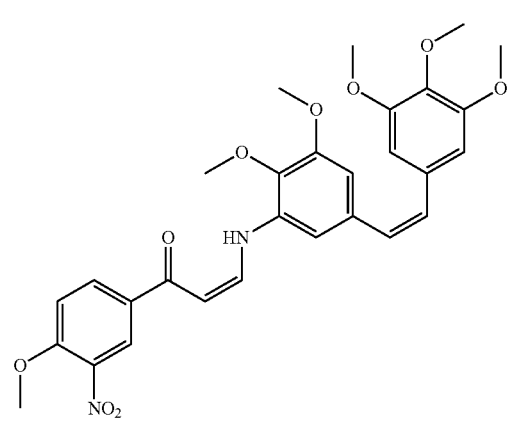 (11t)
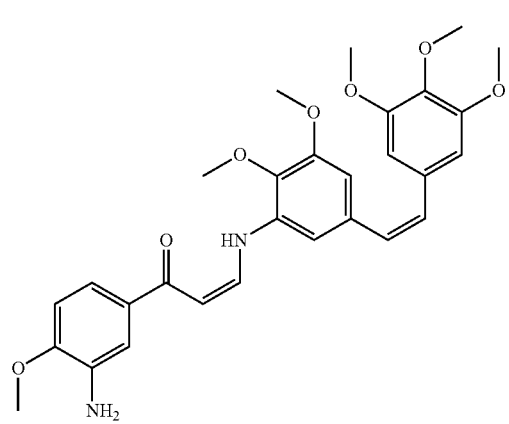 (11u)
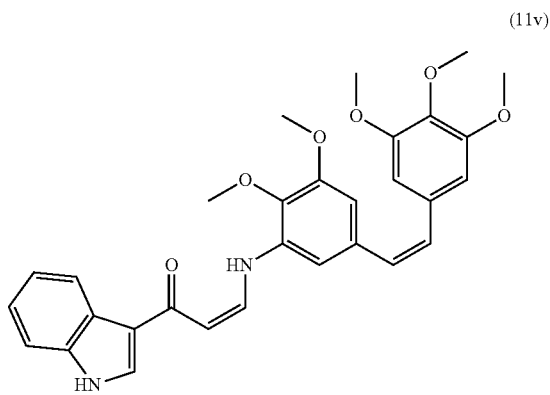 (11v)
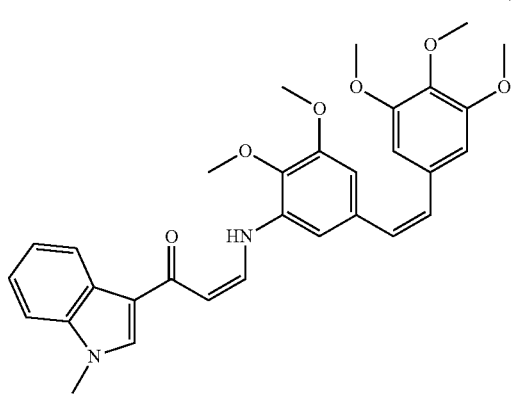 (11w)
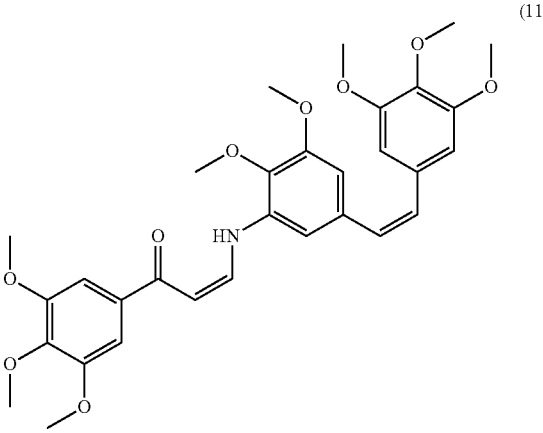 (11x)
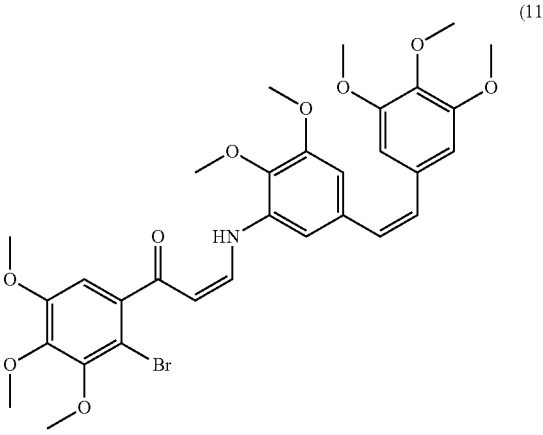 (11y)

(12a)
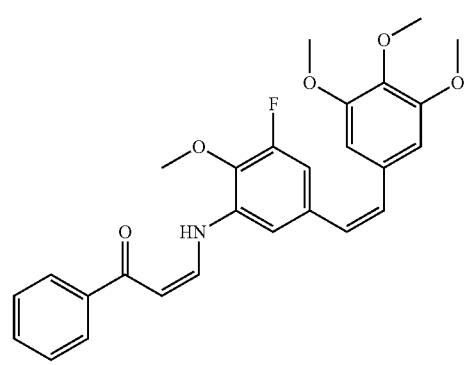
(12b)
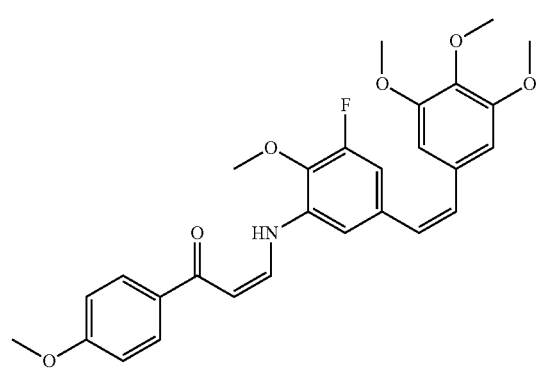
(12c)
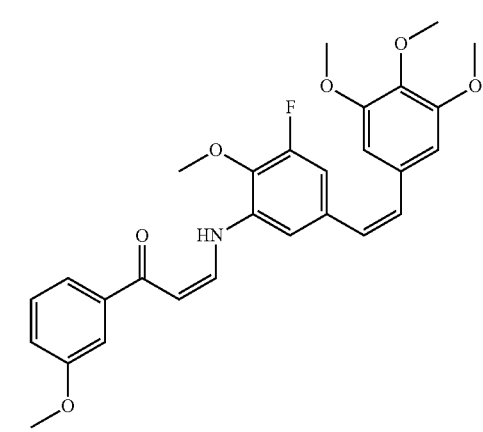
(12d)
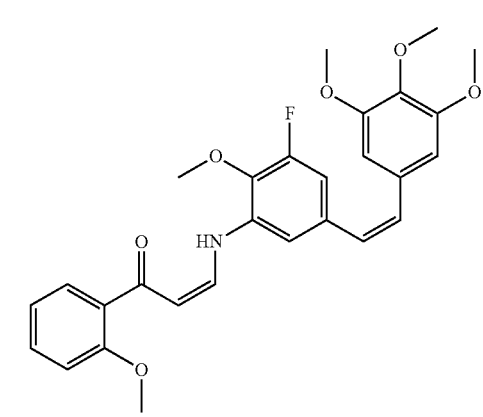
(12e)
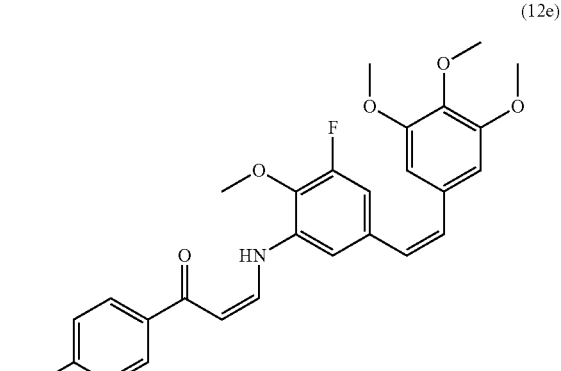
(12f)
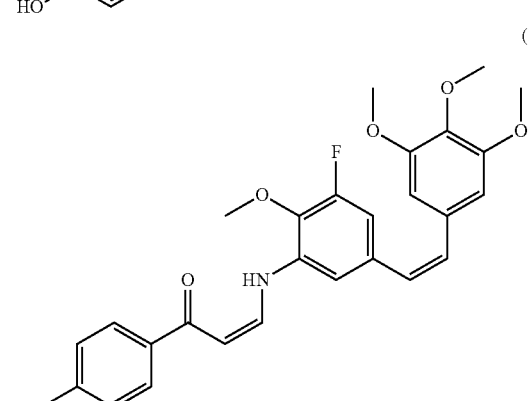
(12g)
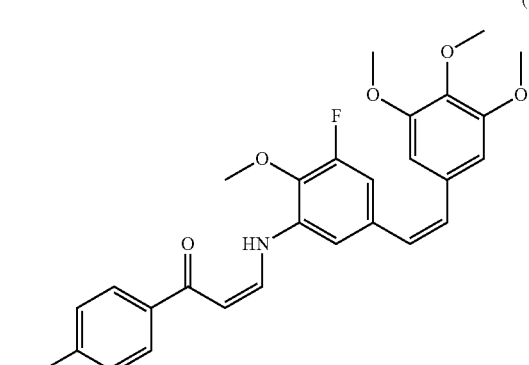
(12h)

(12i)
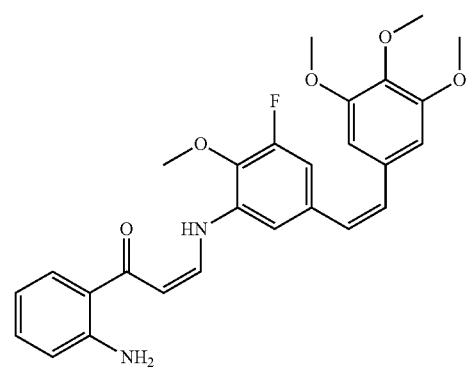
(12j)
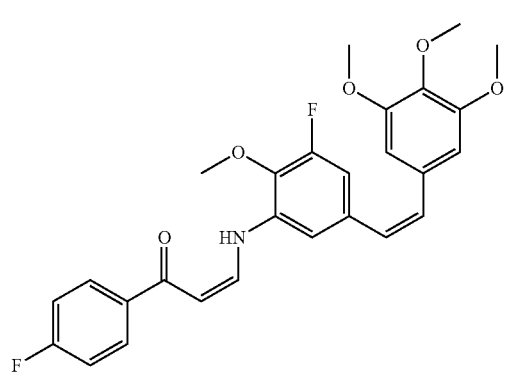
(12k)
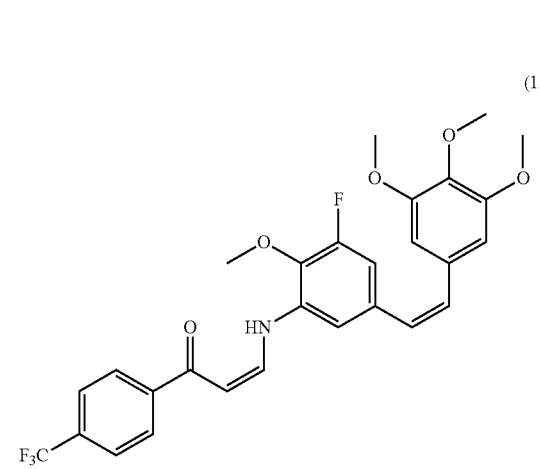
(12l)
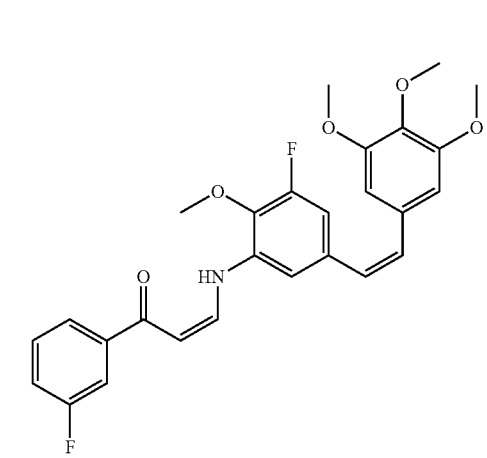
(12m)
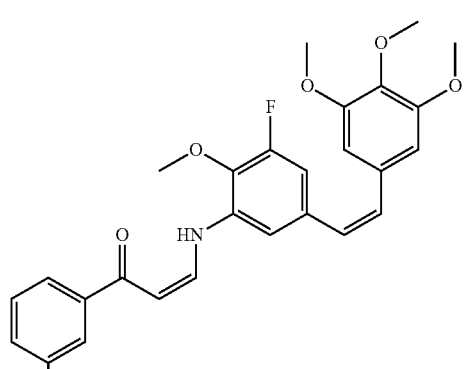
(12n)
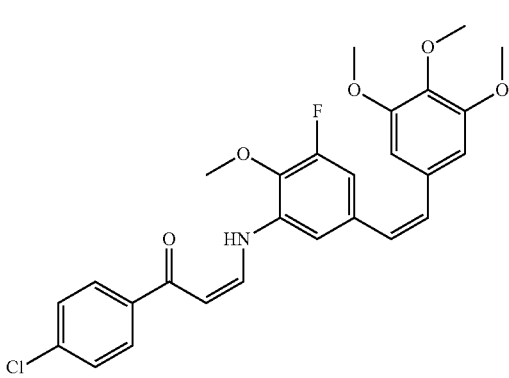
(12o)
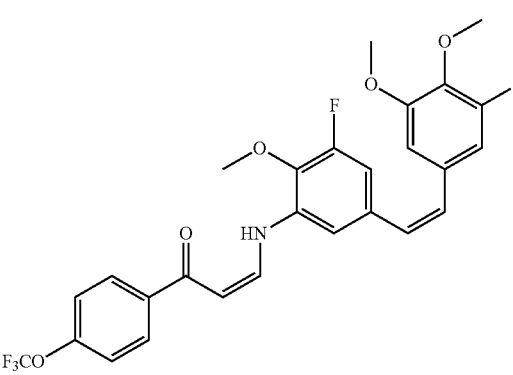
(12p)
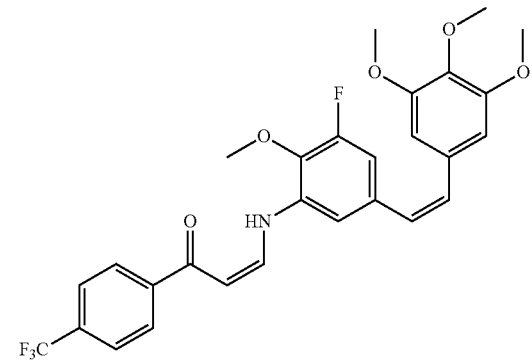

(12q) 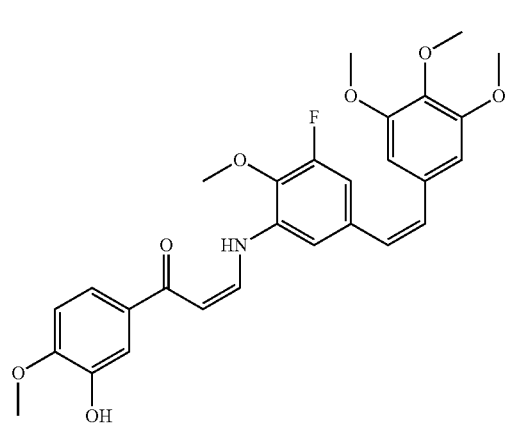
(12r) 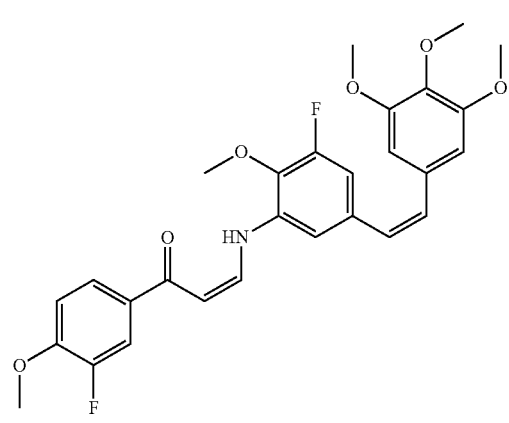
(12s) 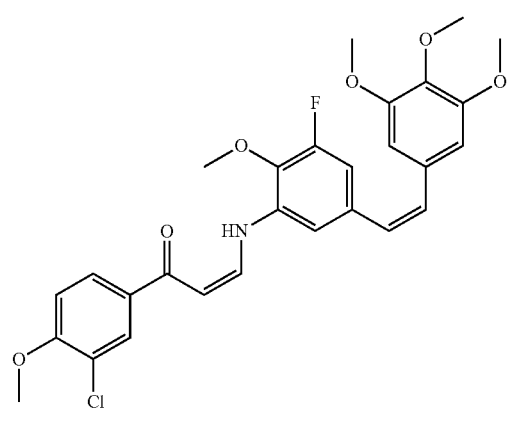
(12t) 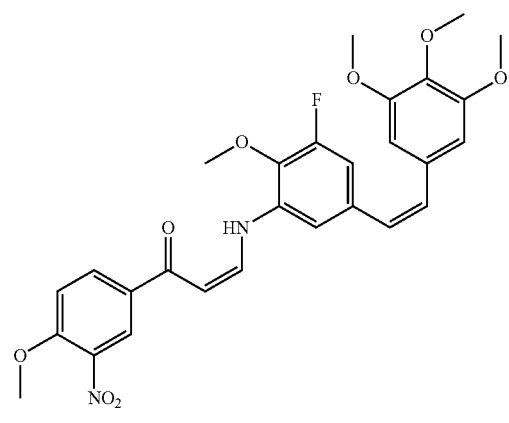
(12u) 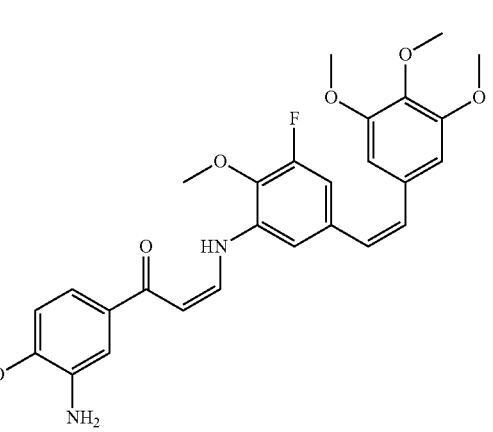
(12v) 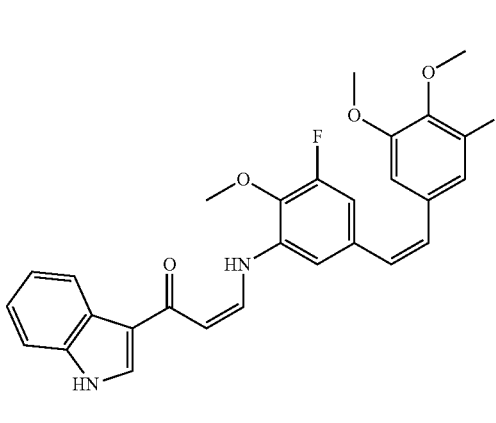
(12w) 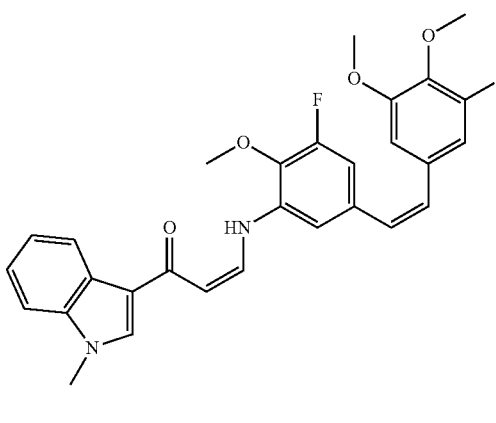
(12x) 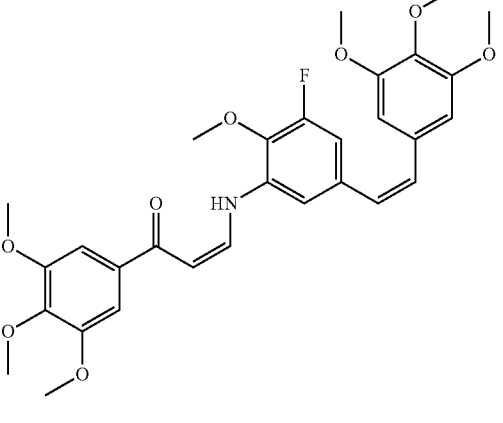

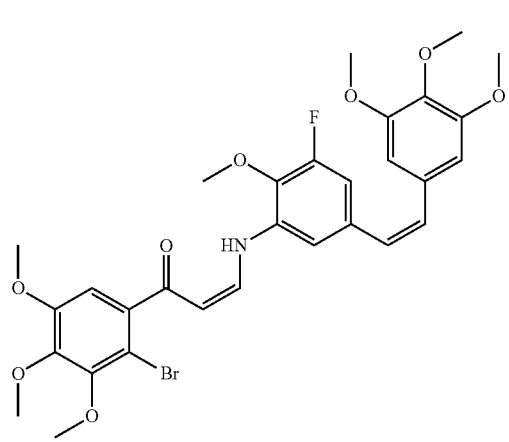
(12y)
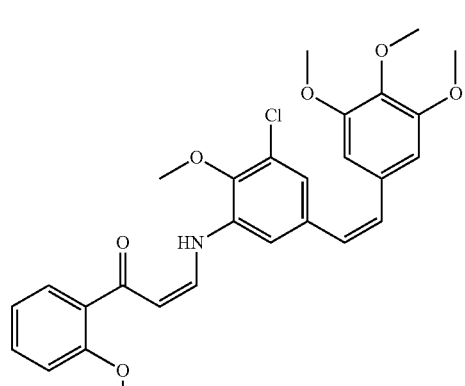
(13d)
(13a)
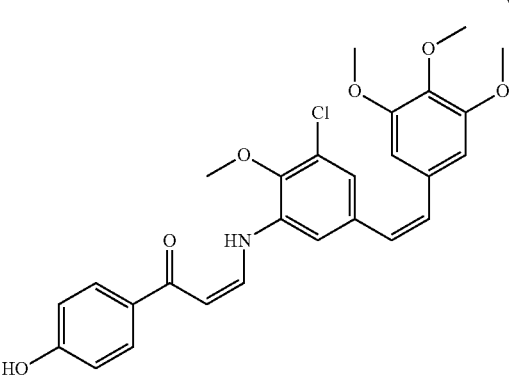
(13e)
(13b)
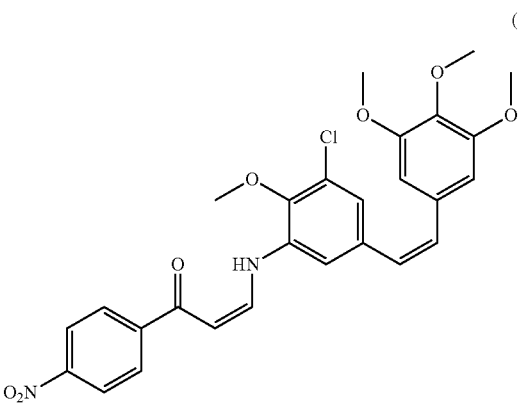
(13f)
(13c)
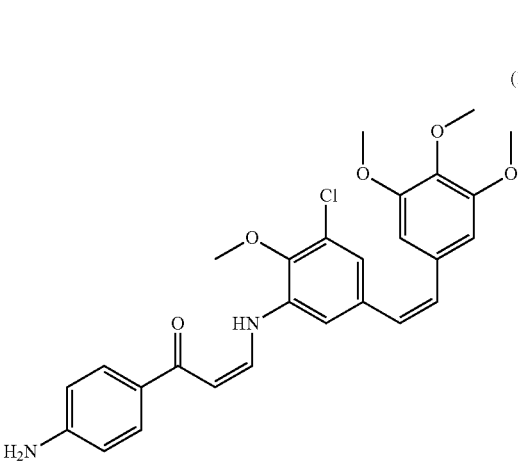
(13g)

(13h)
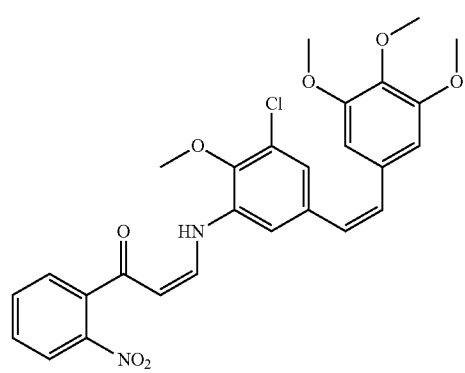
(13i)
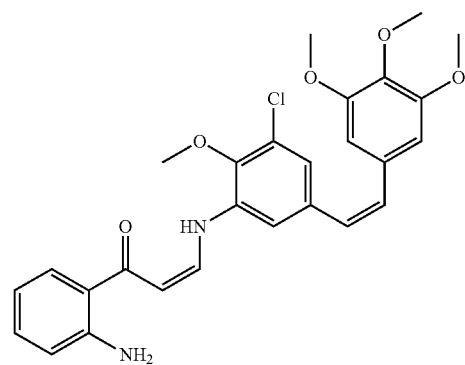
(13j)
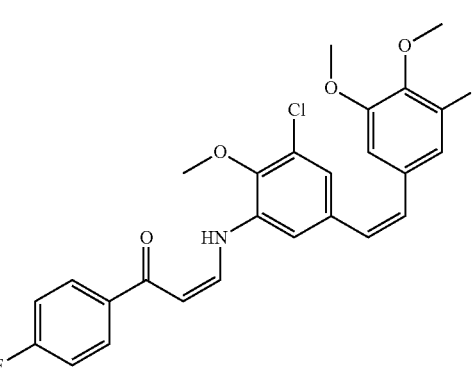
(13k)
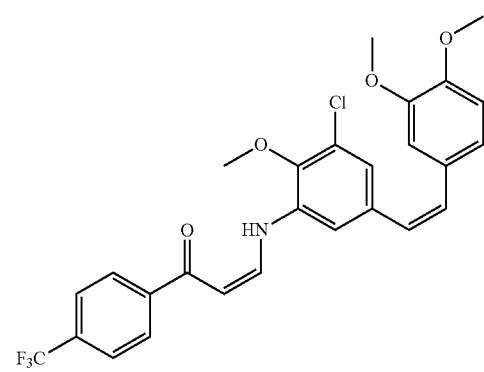
(13l)
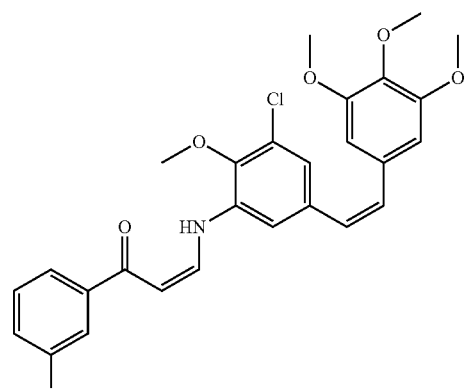
(13m)
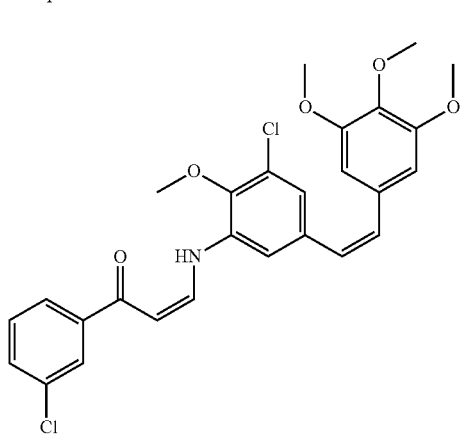
(13n)
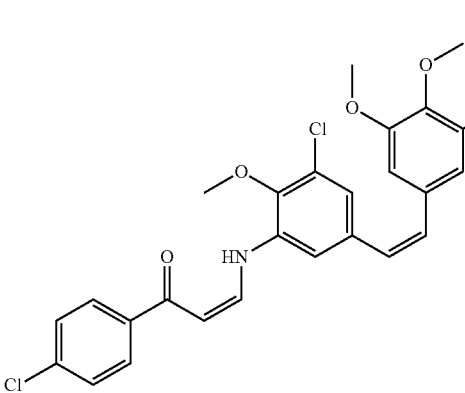
(13o)
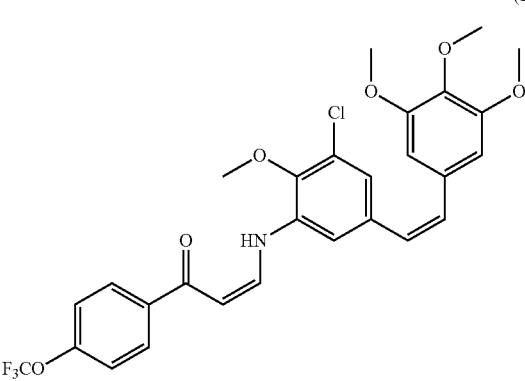

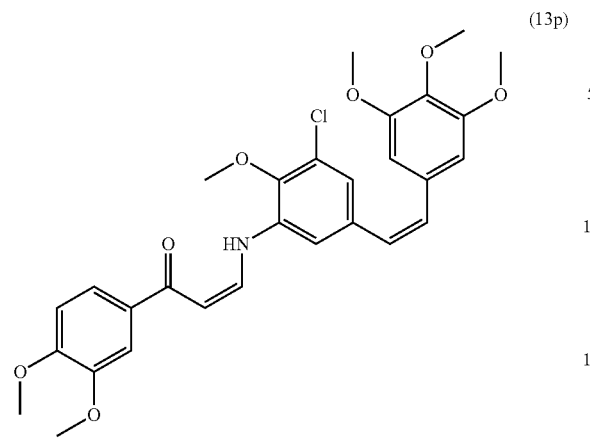
(13p)
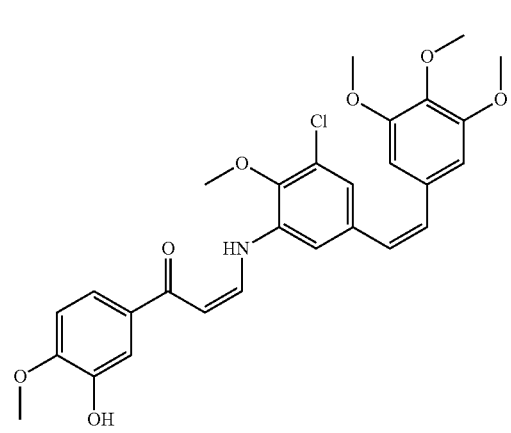
(13q)
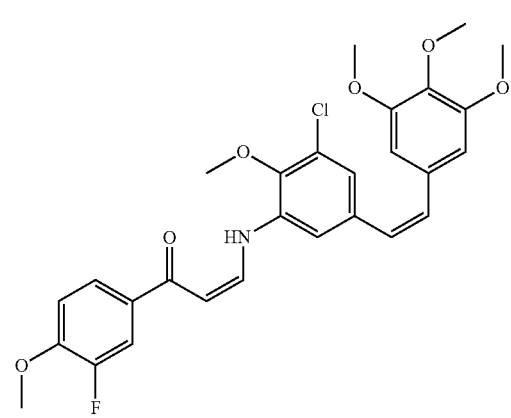
(13r)
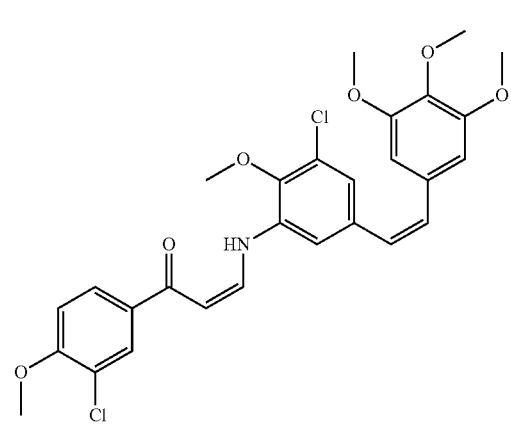
(13s)
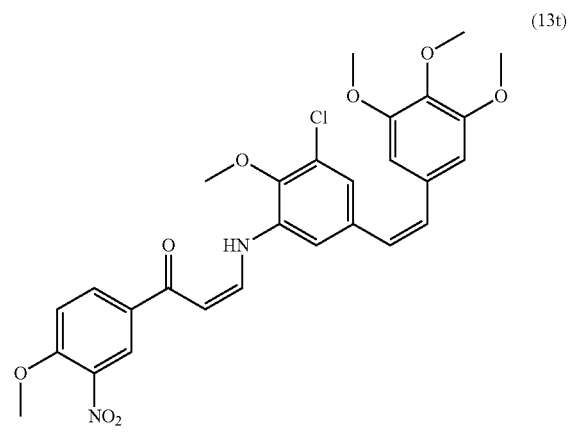
(13t)
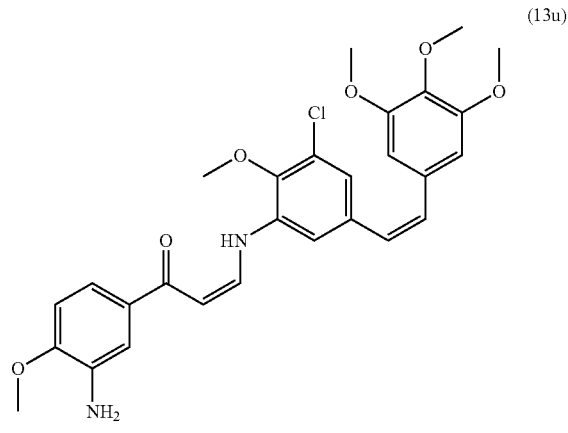
(13u)
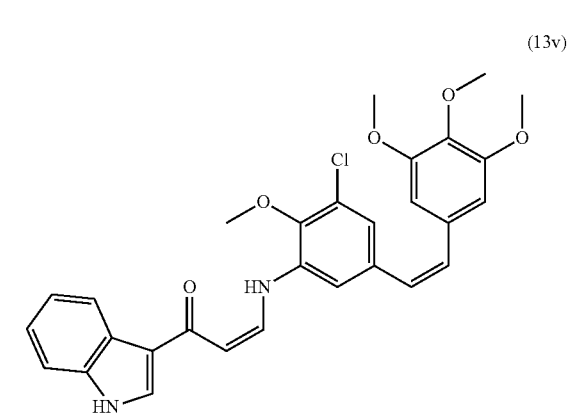
(13v)
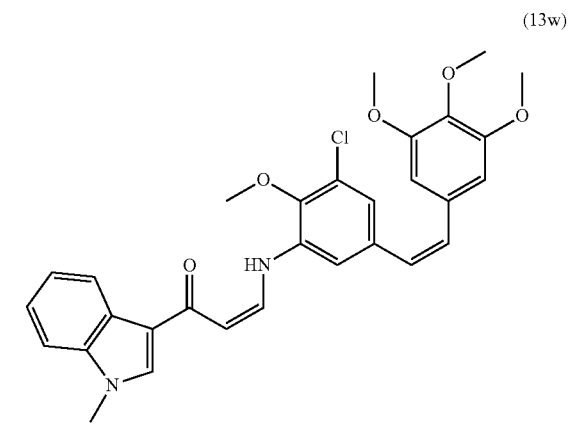
(13w)

(13x)
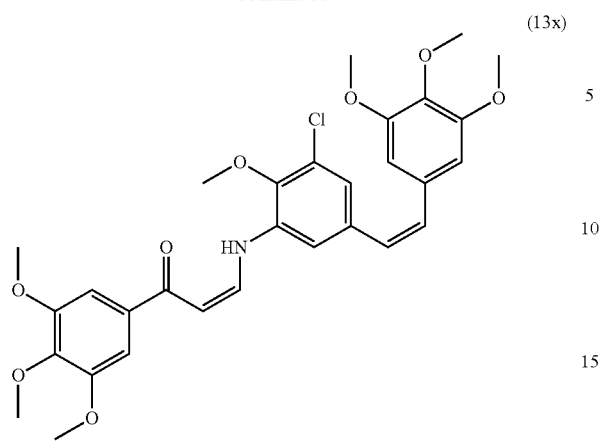
(13y)
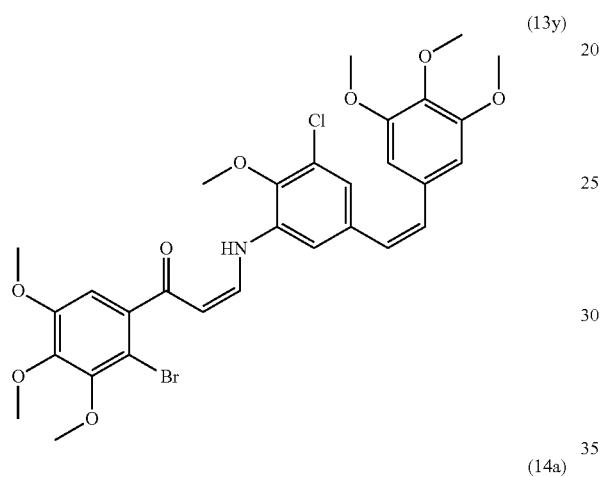
(14a)
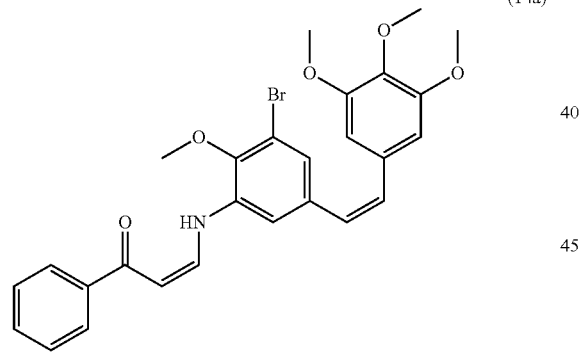
(14b)
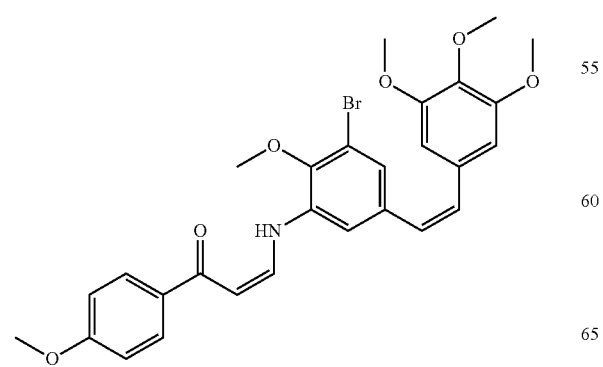
(14c)
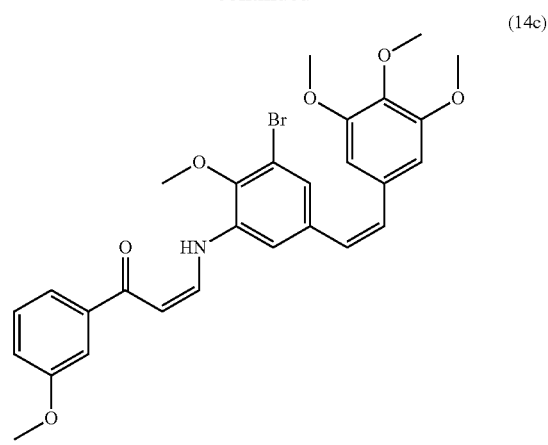
(14d)
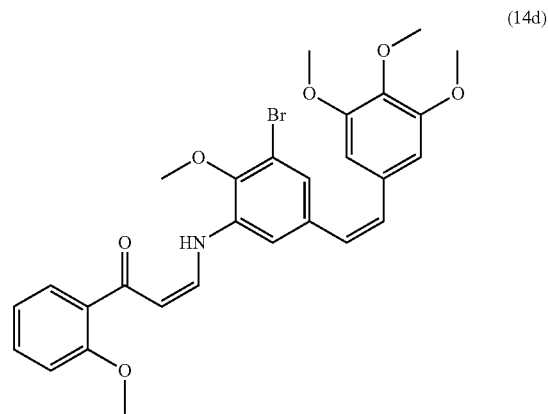
(14e)
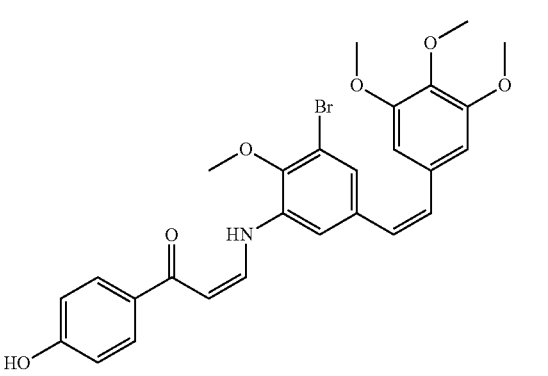
(14f)
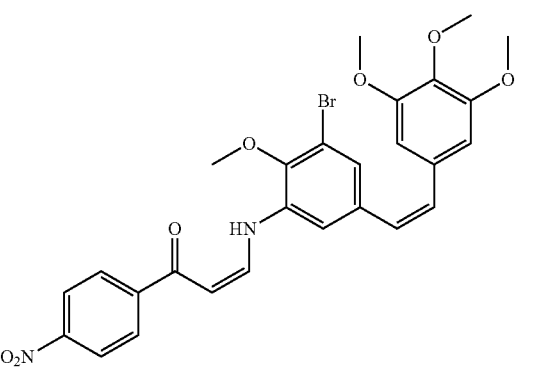

-continued
(14g)
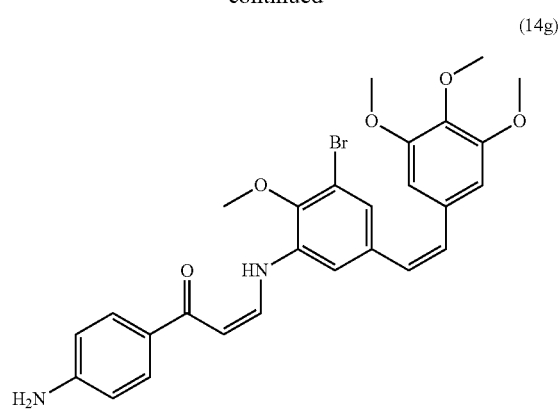
(14h)
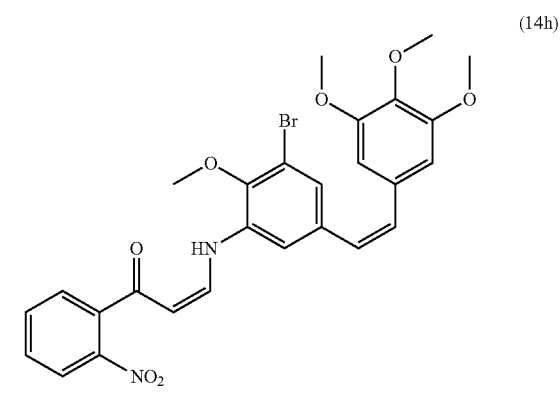
(14i)
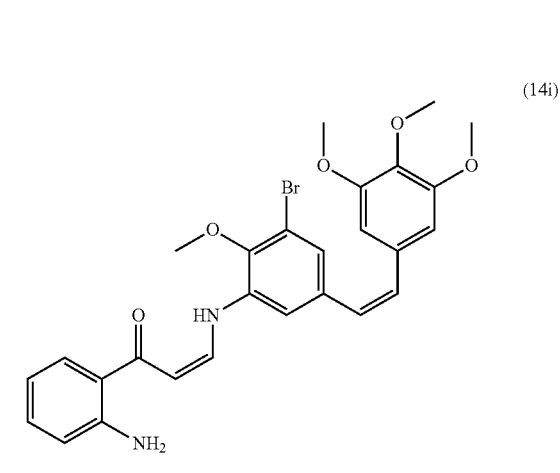
(14j)
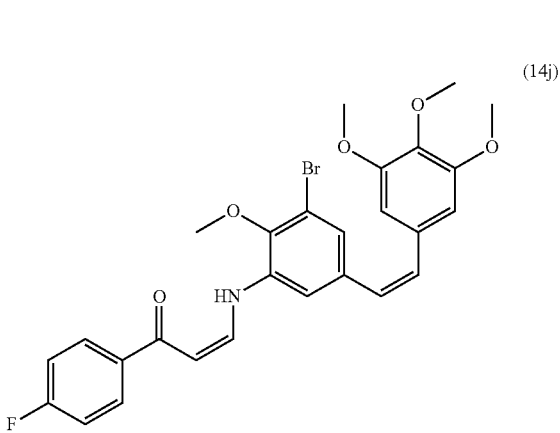
-continued
(14k)
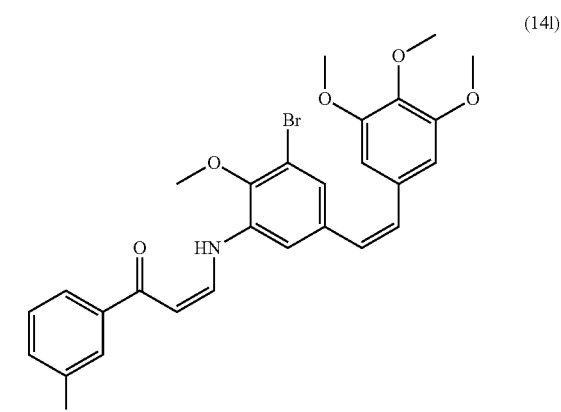
(14l)
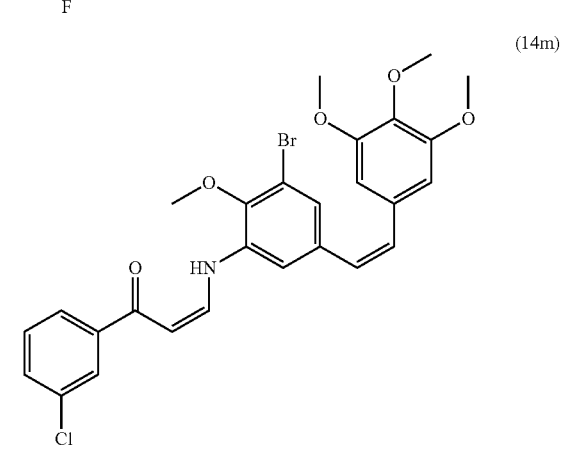
(14m)
(14n)
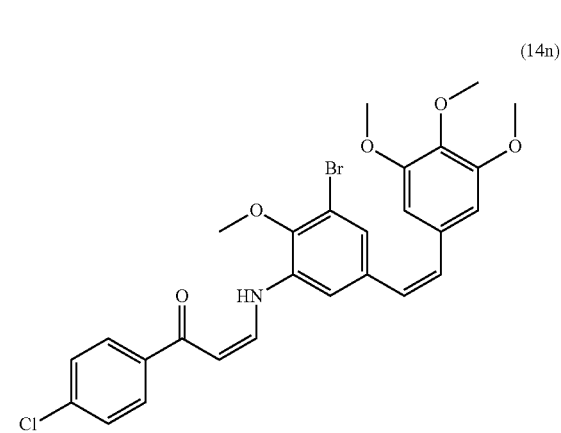

-continued
(14o)
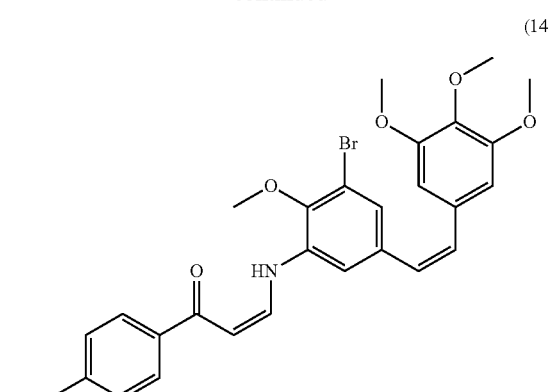
(14p)
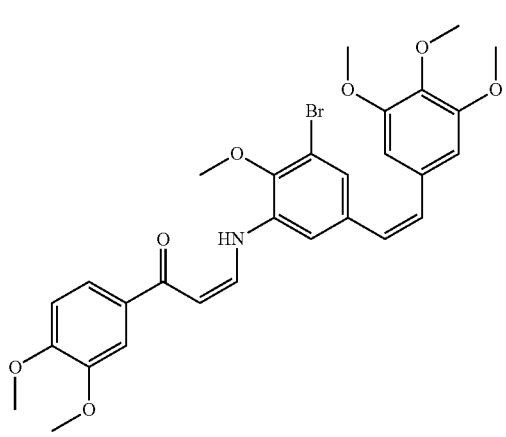
(14q)
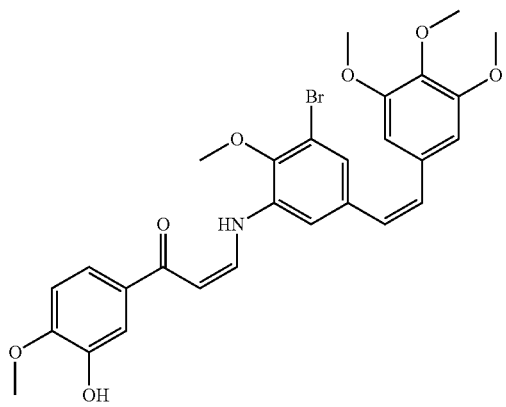
(14r)
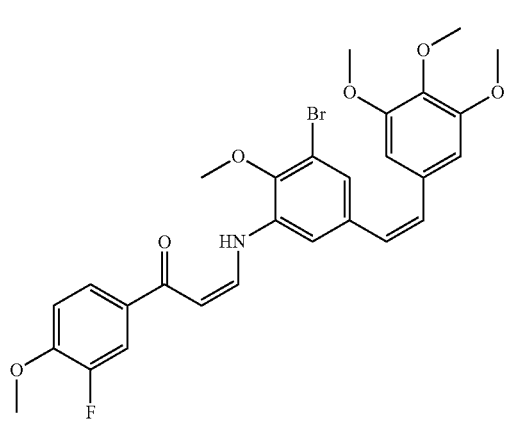
-continued
(14s)
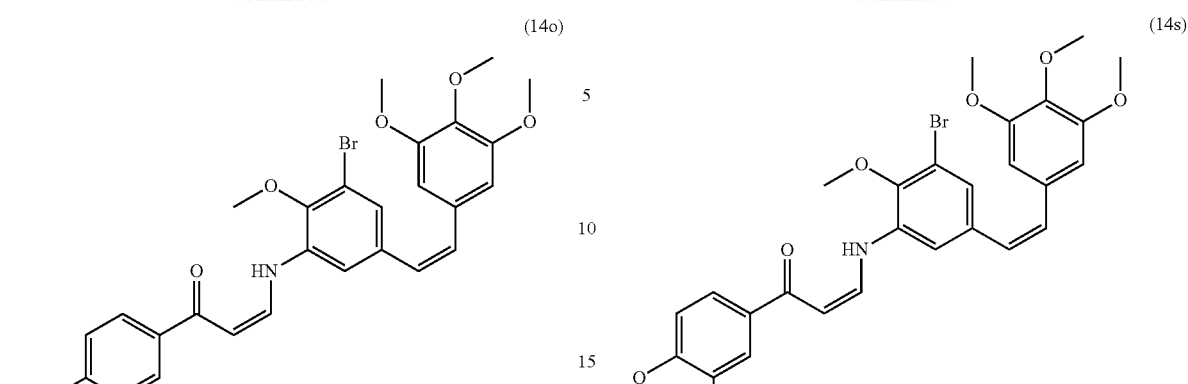
(14t)
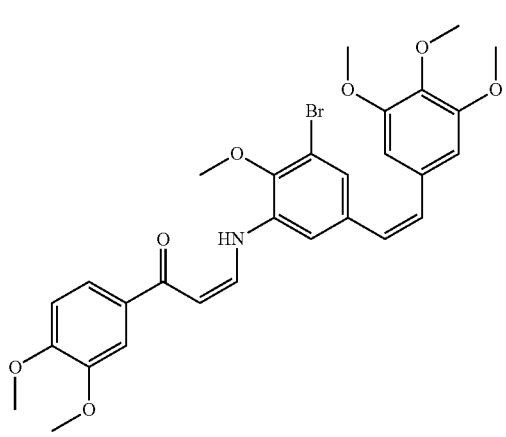
(14u)
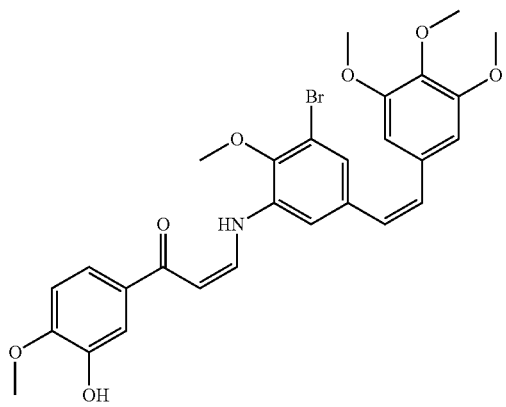
(14v)
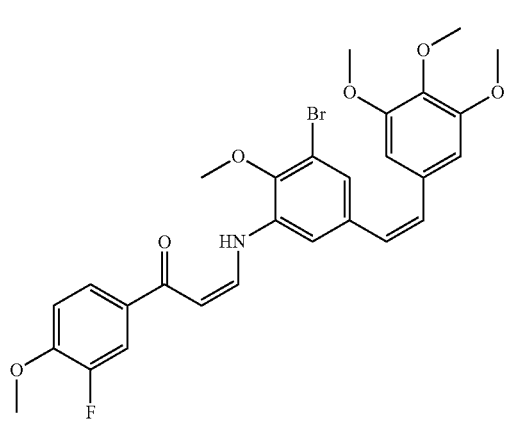

-continued
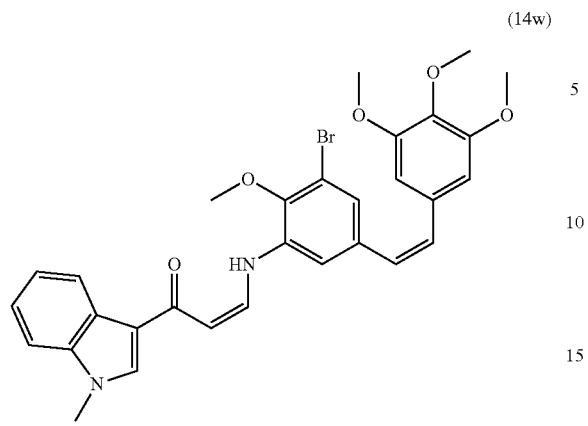
(14w)
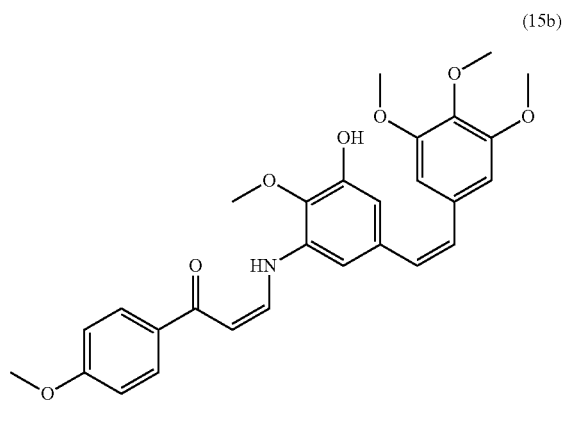
(15b)
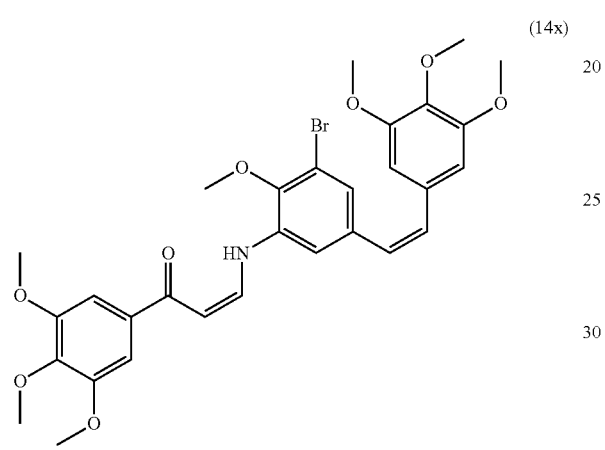
(14x)
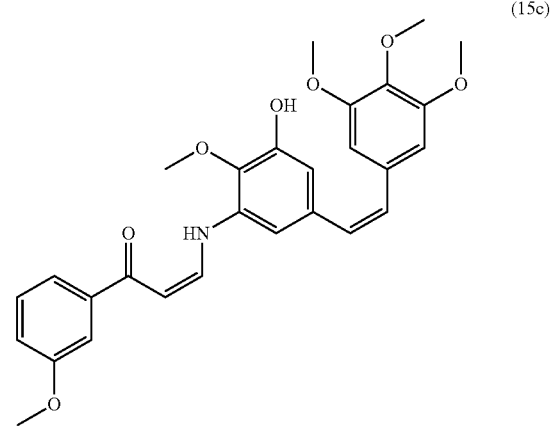
(15c)
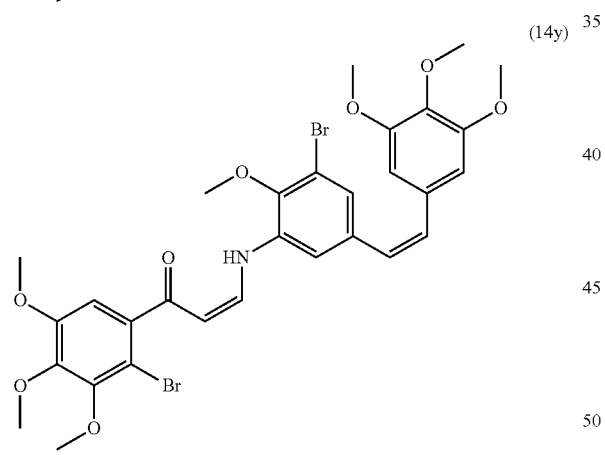
(14y)
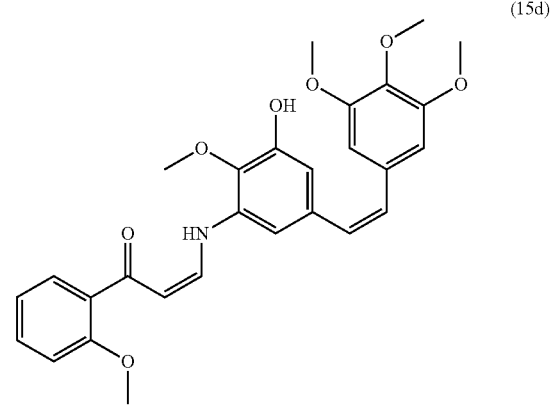
(15d)
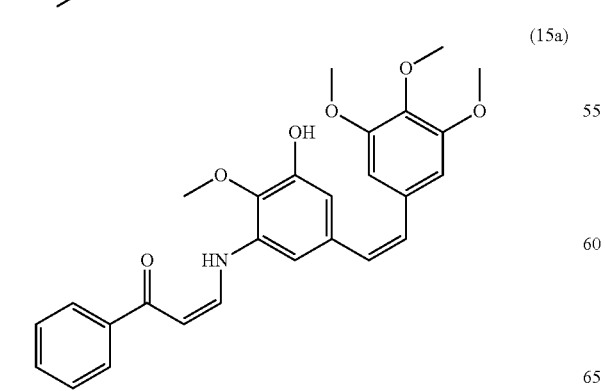
(15a)
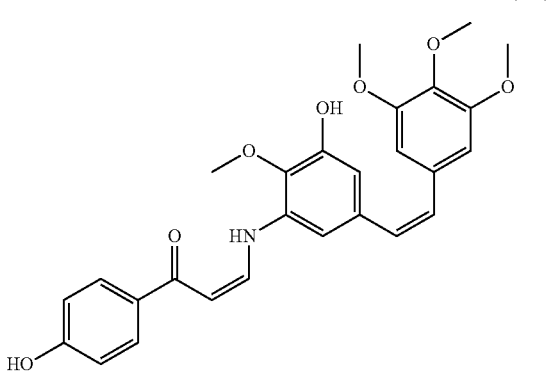
(15e)

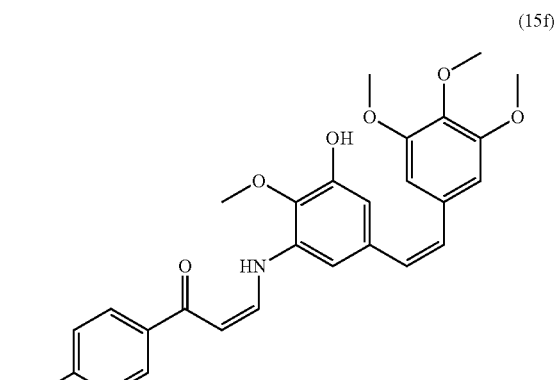 (15f)
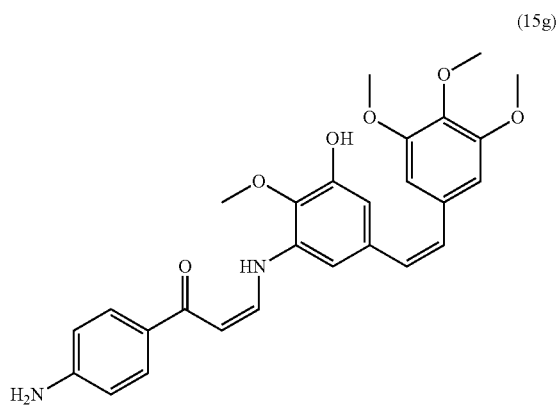 (15g)
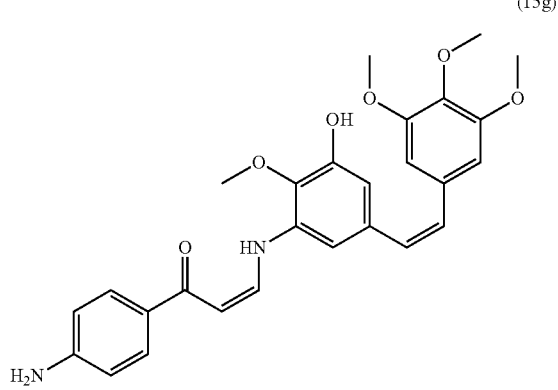 (15h)
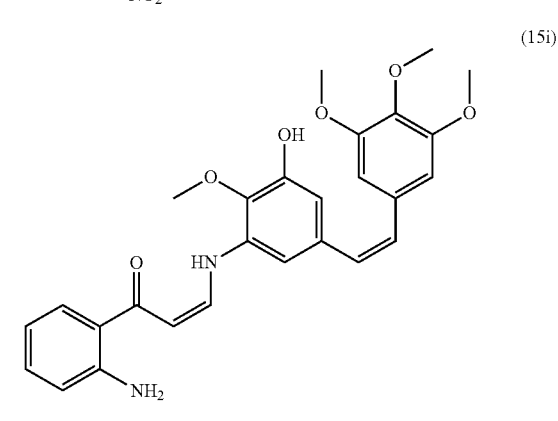 (15i)
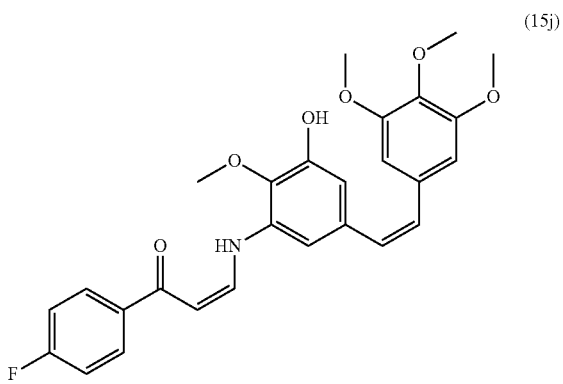 (15j)
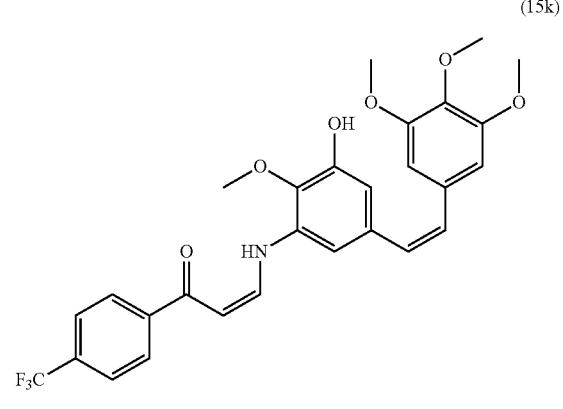 (15k)
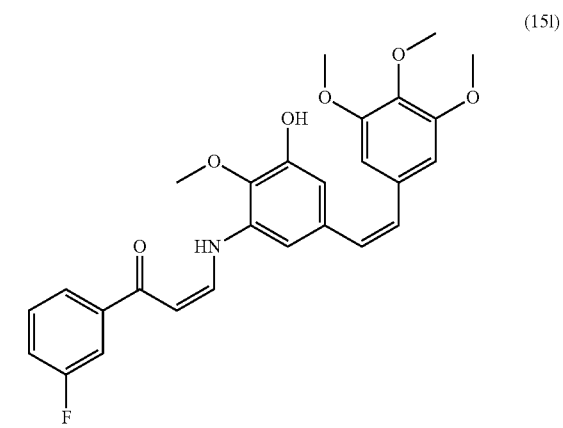 (15l)
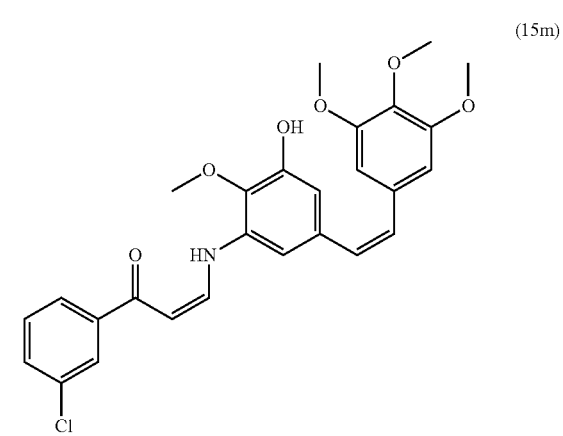 (15m)

-continued
(15n)
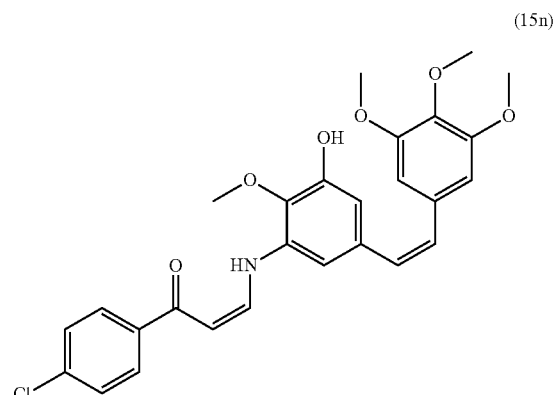
(15o)
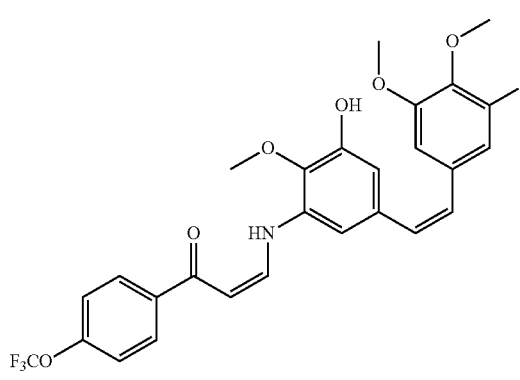
(15p)
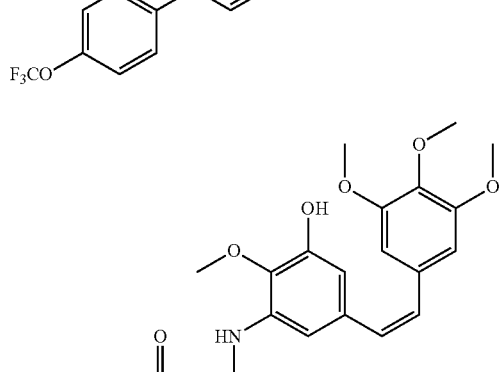
(15q)
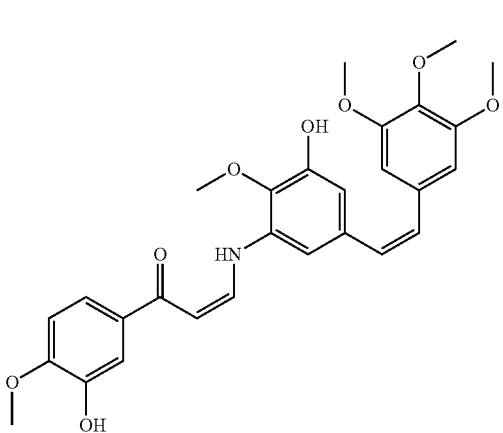
(15r)
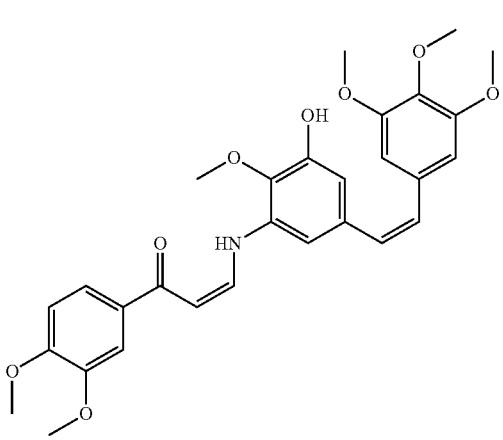
(15s)
(15t)
(15u)

(15v)
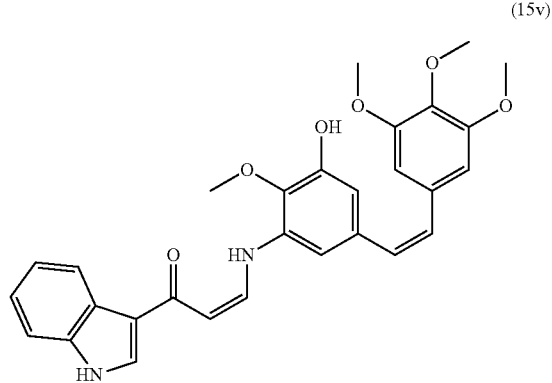
(15w)
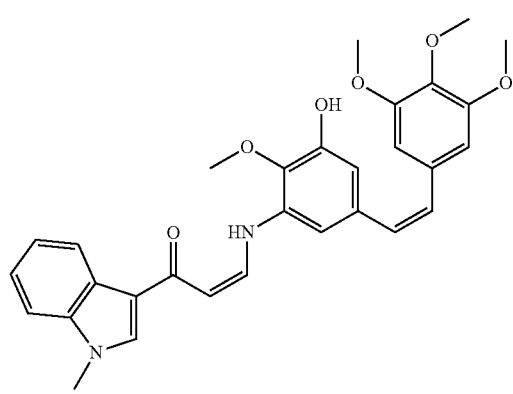
(15x)
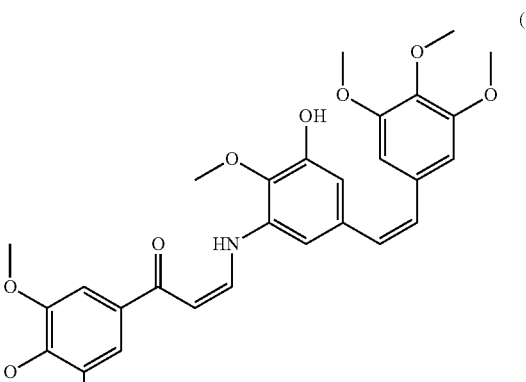
(15y)
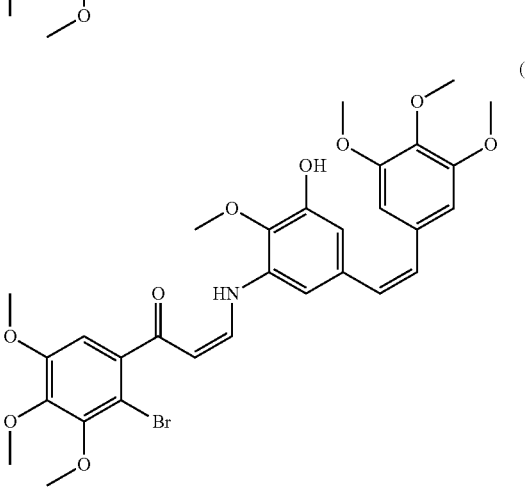
(16a)
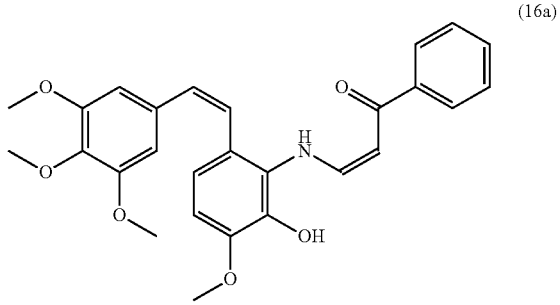
(16b)
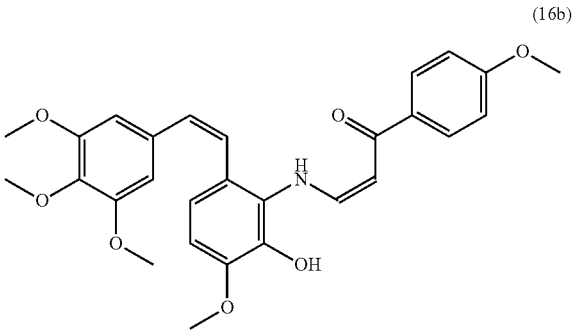
(16c)
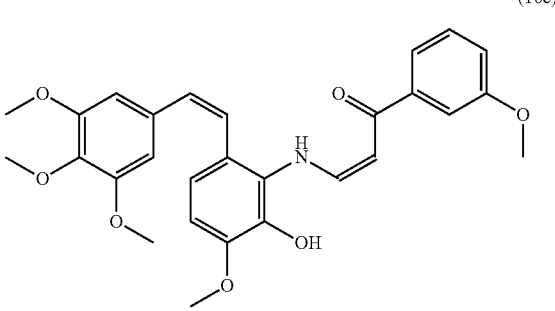
(16d)
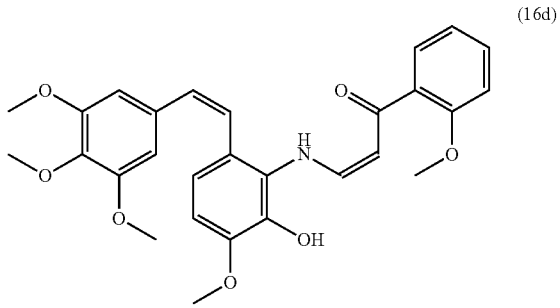
(16e)
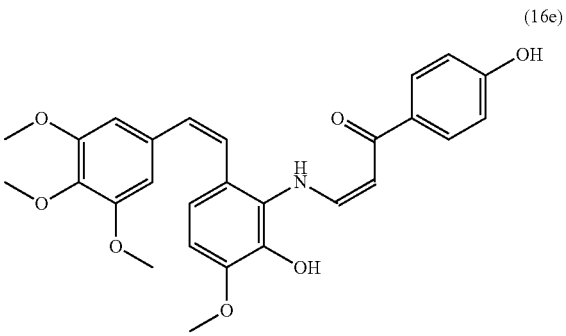

-continued
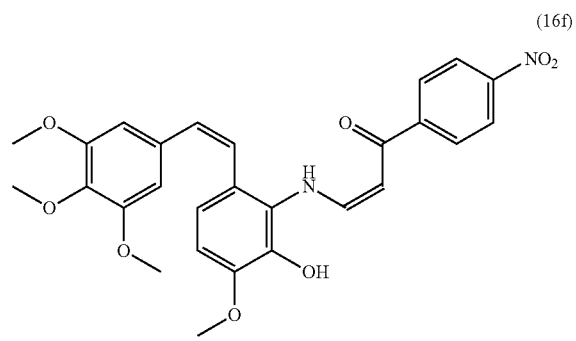
(16f)
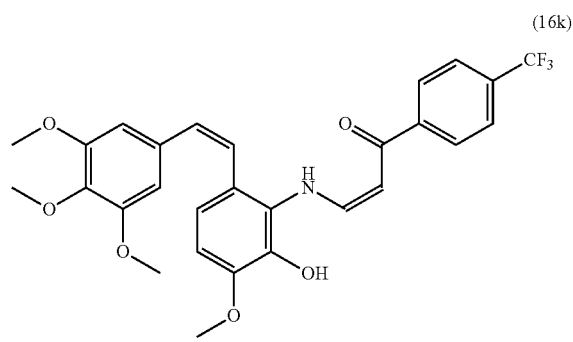
(16k)
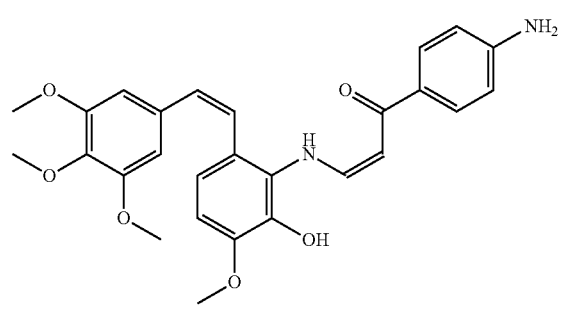
(16g)
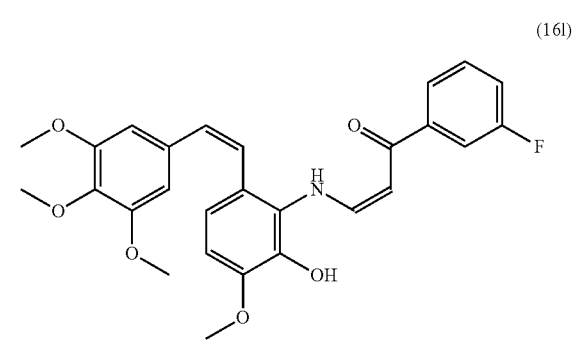
(16l)
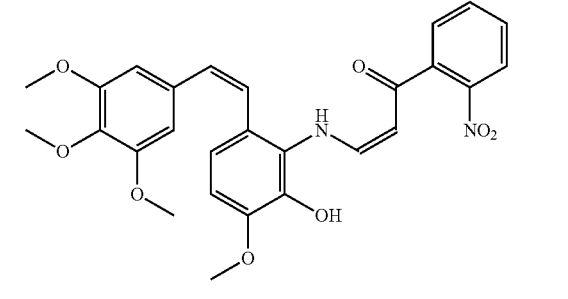
(16h)
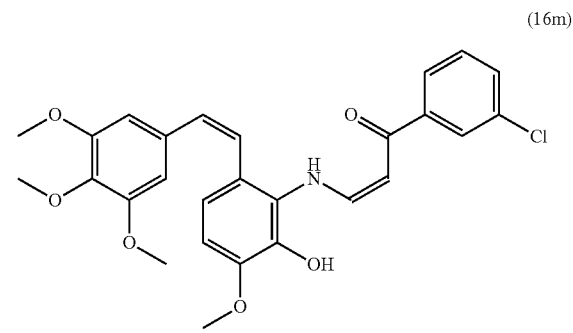
(16m)
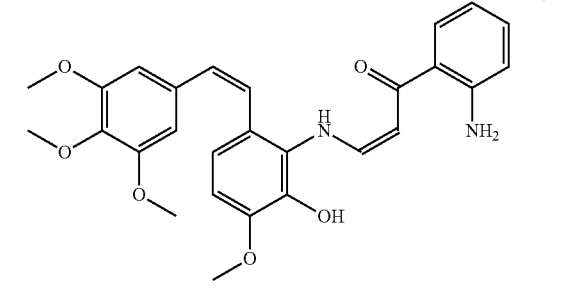
(16i)
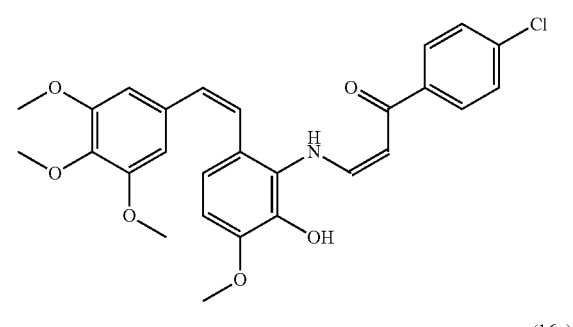
(16n)
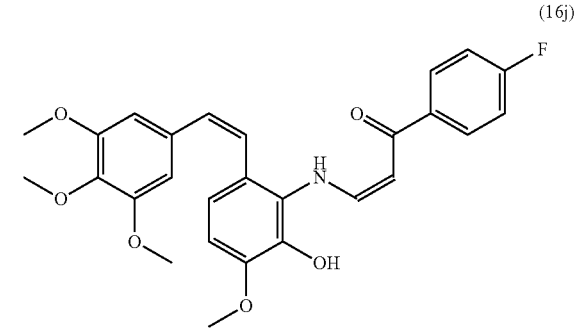
(16j)
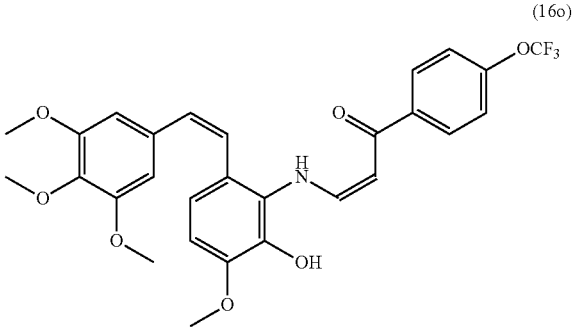
(16o)

(16p)
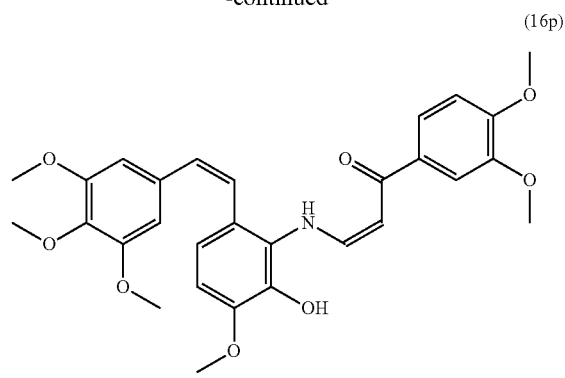
(16t)
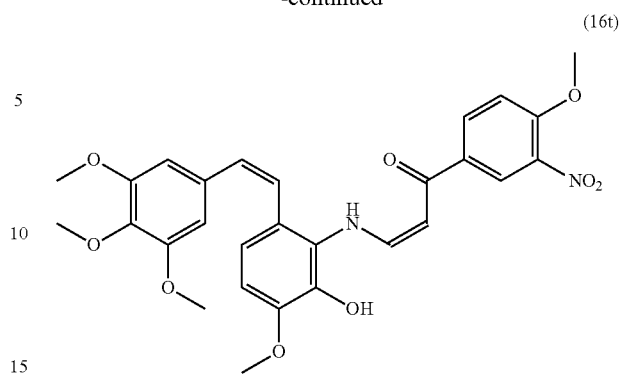
(16q)
(16u)
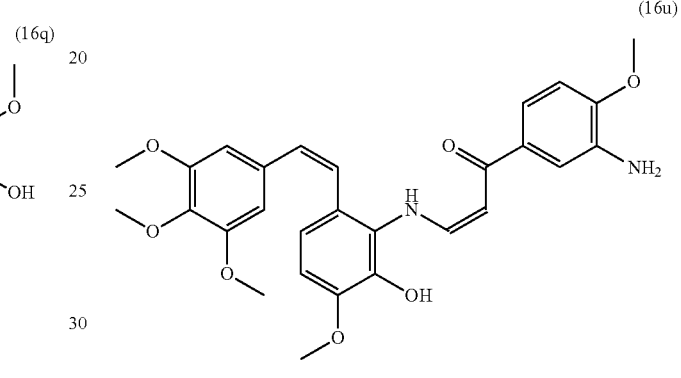
(16r)
(16v)
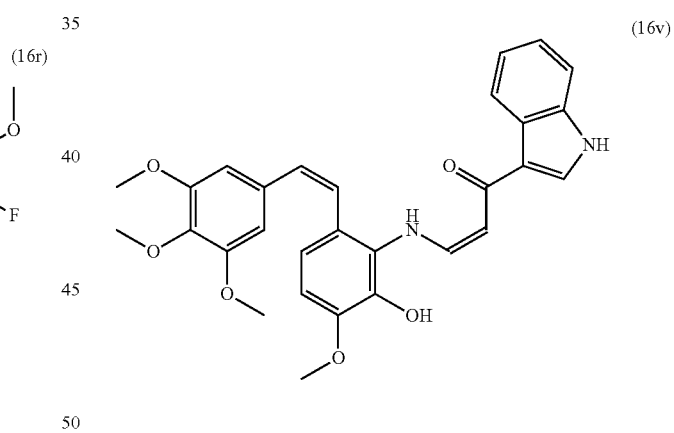
(16s)
(16w)
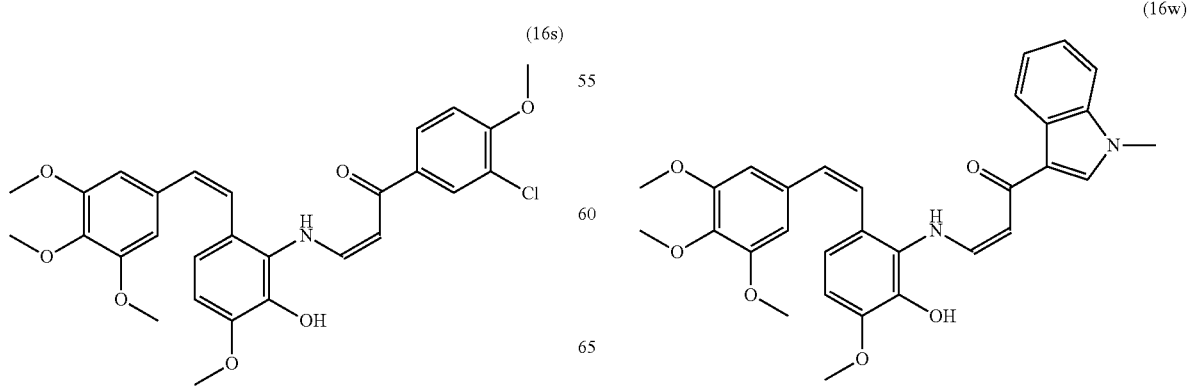

(16x)
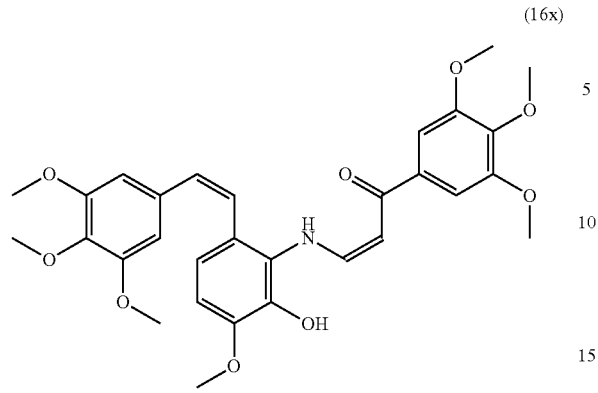
(16y)
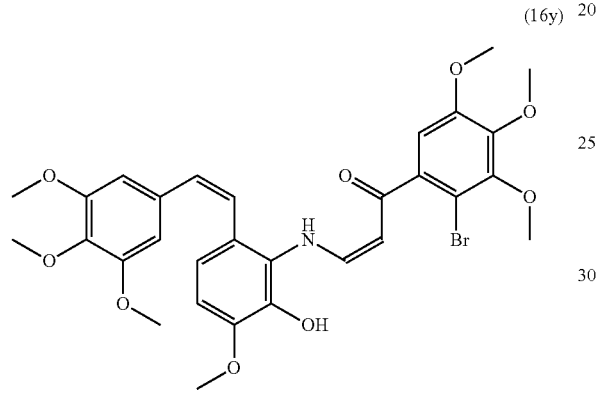
(17a)
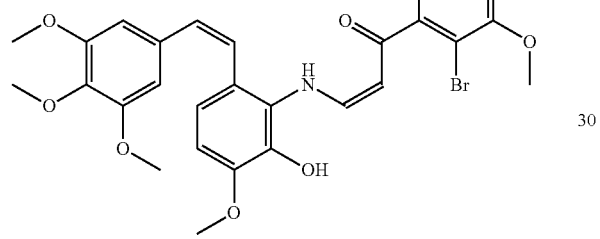
(17b)
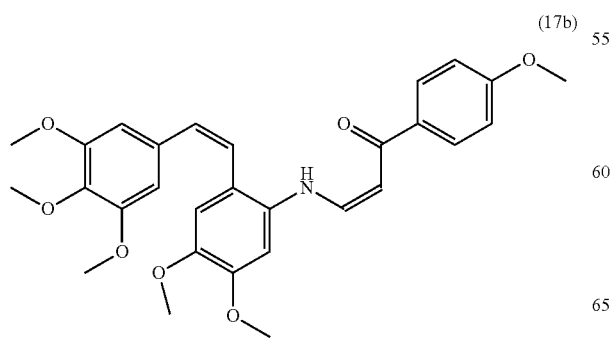
(17c)
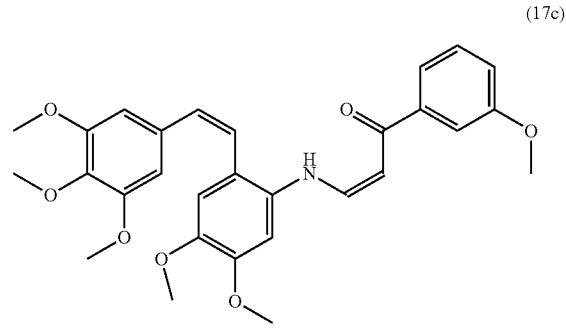
(17d)
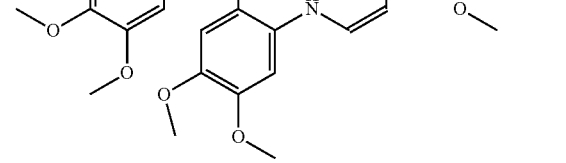
(17e)
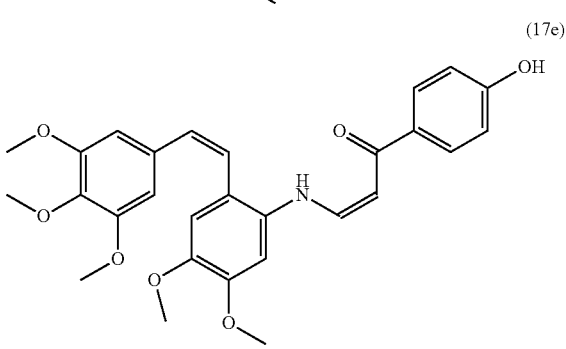
(17f)
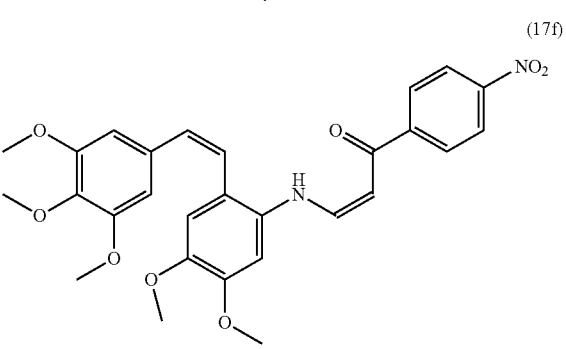
(17g)
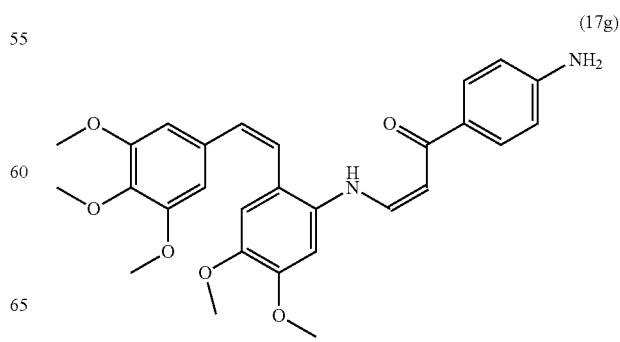

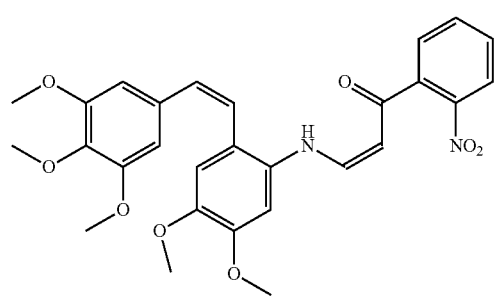
(17h)
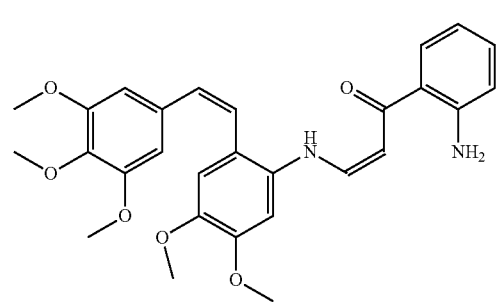
(17i)
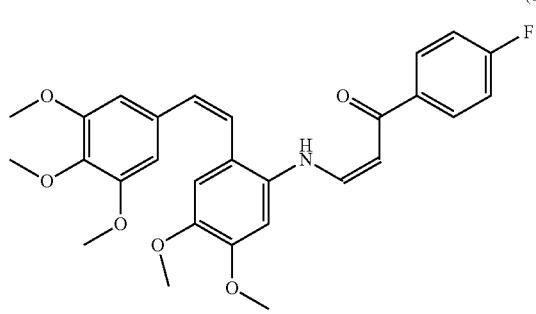
(17j)
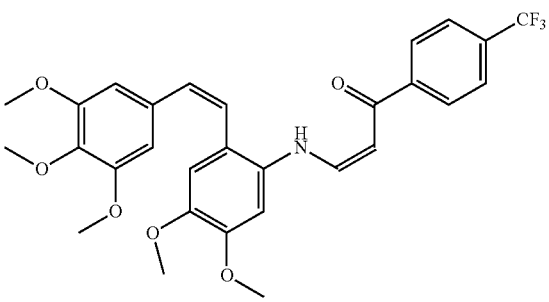
(17k)
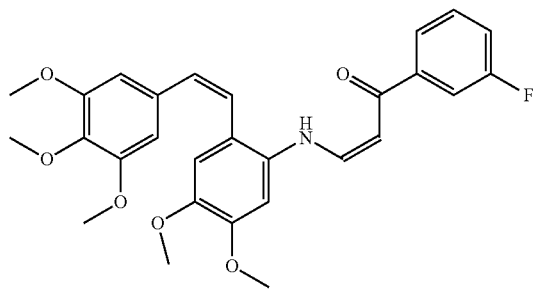
(17l)
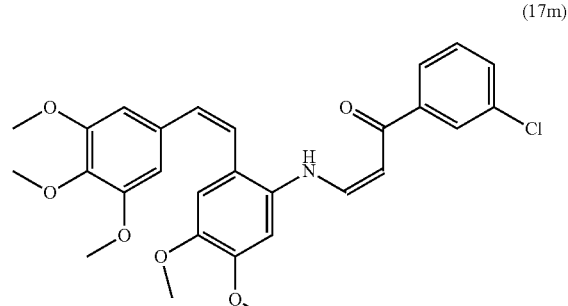
(17m)
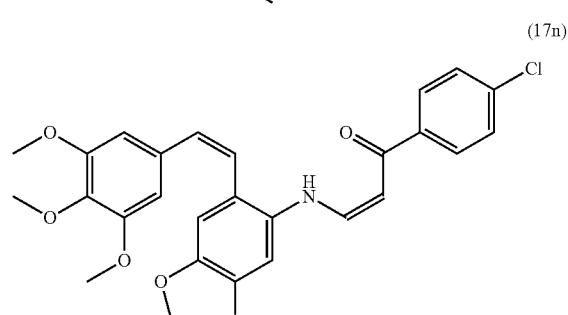
(17n)
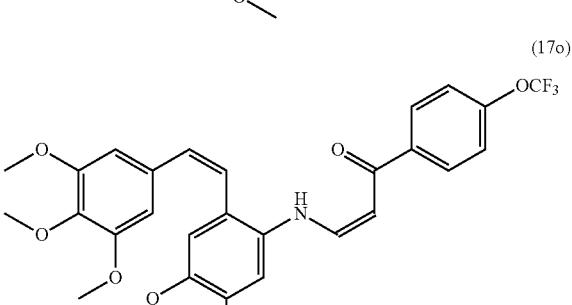
(17o)
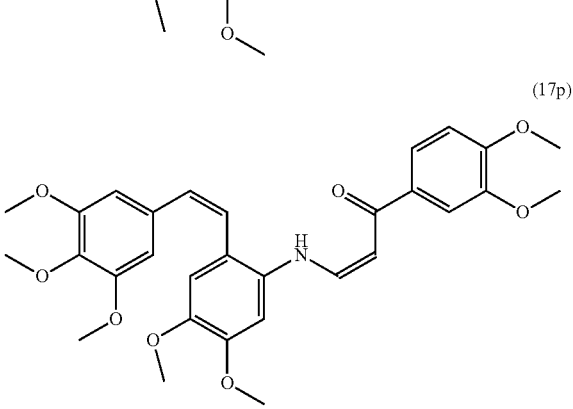
(17p)
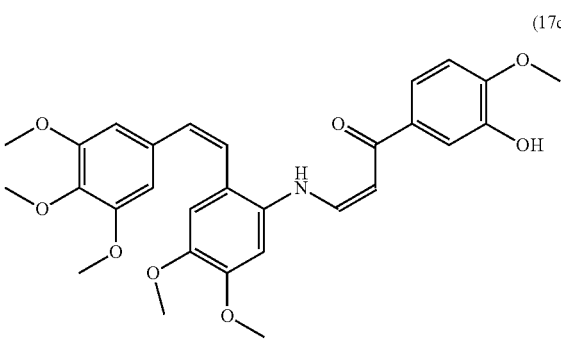
(17q)

-continued
(17r)
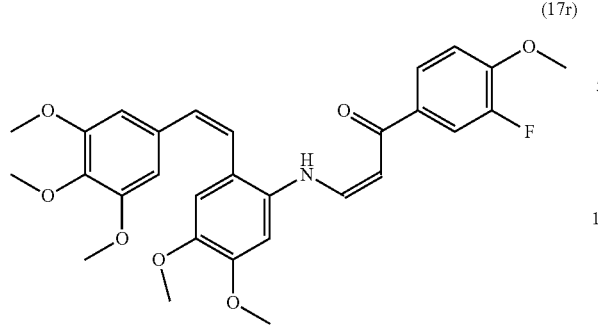
(17s)
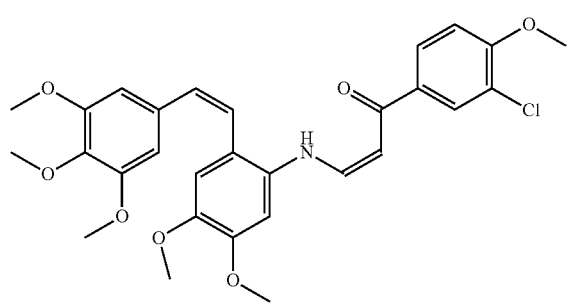
(17t)
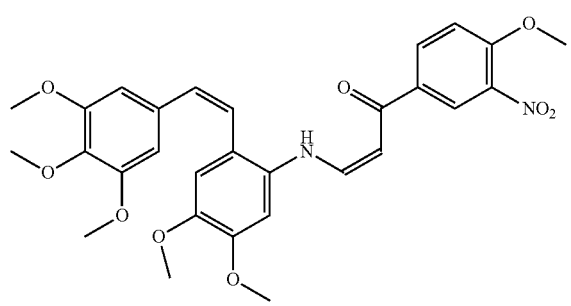
(17u)
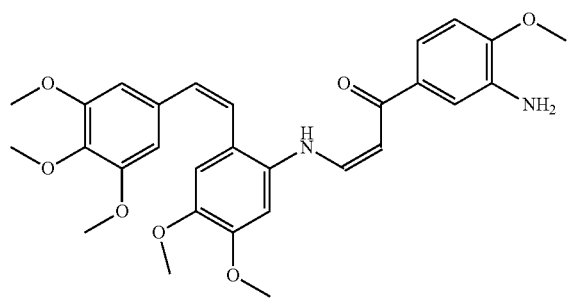
(17v)
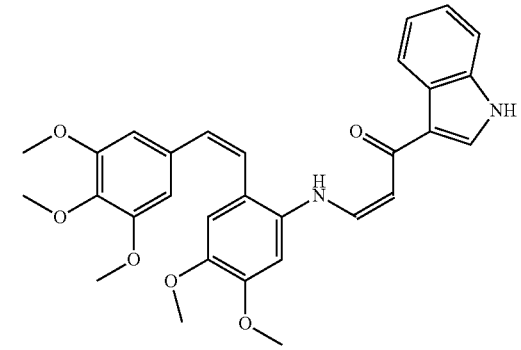
-continued
(17w)
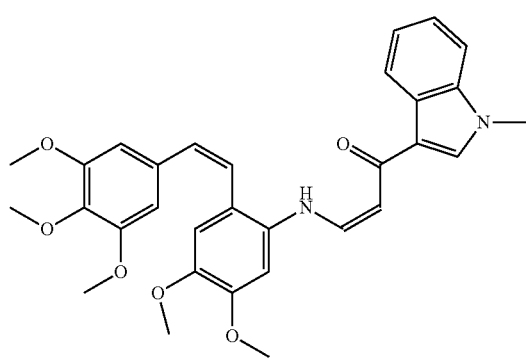
(17x)
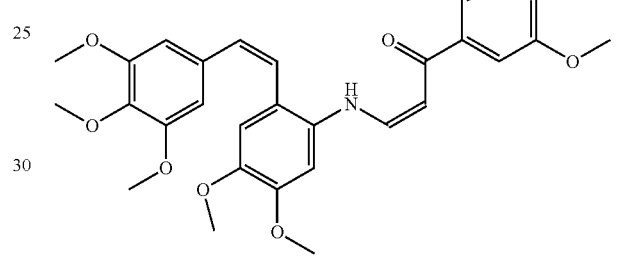
(17y)
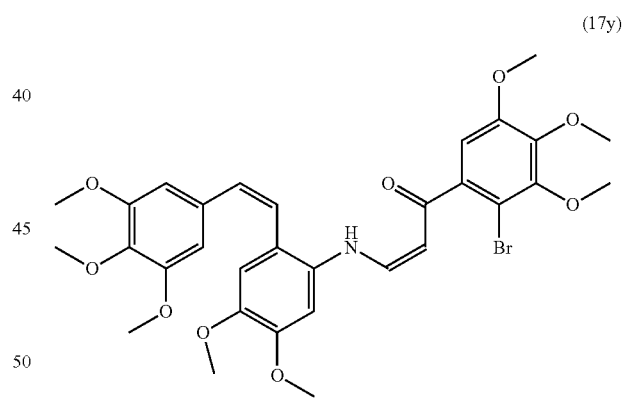
(18a)
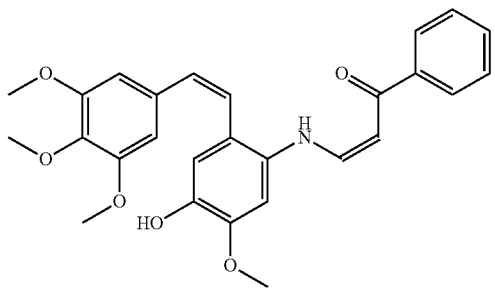

-continued
(18b)
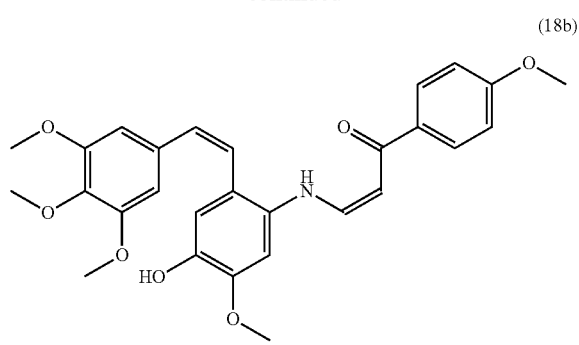
(18c)
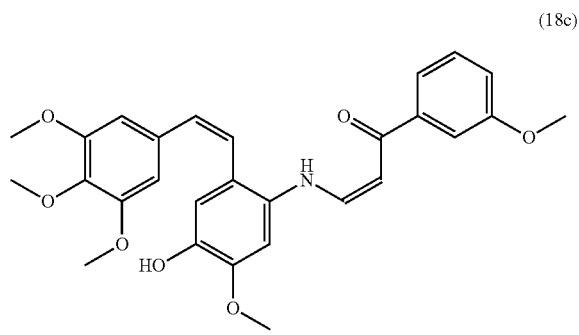
(18d)
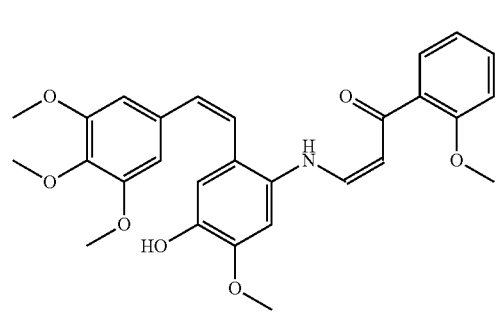
(18e)
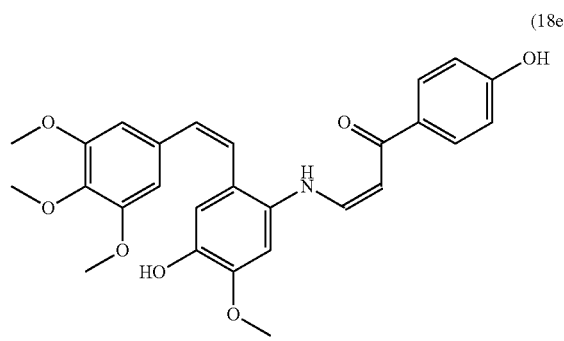
(18f)
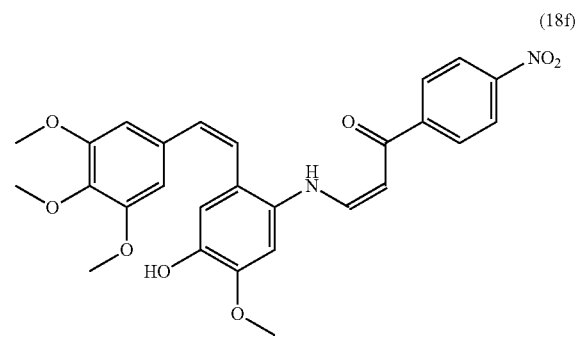
-continued
(18g)
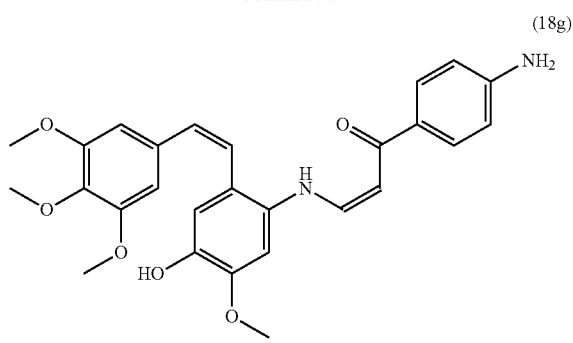
(18h)
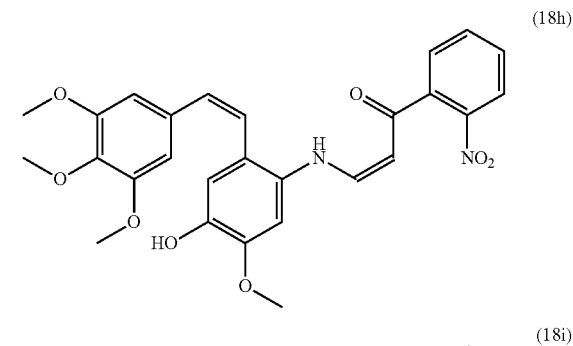
(18i)
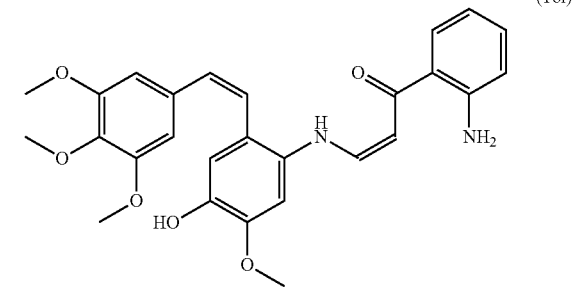
(18j)
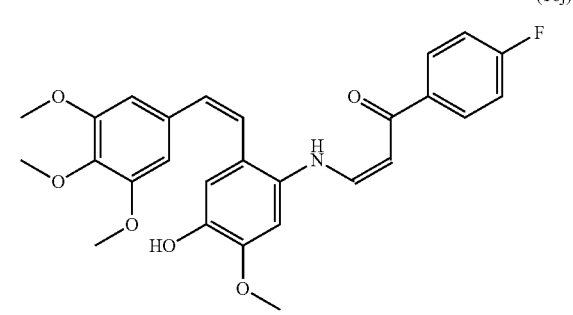
(18k)
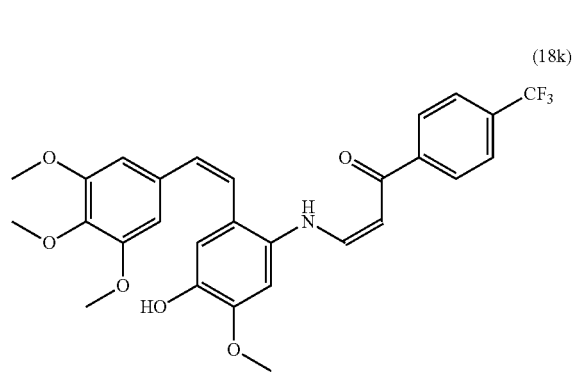

-continued
(18l)
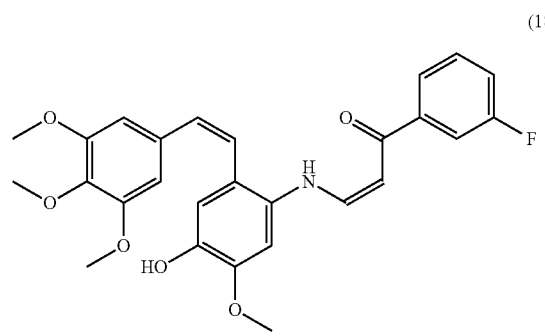
(18m)
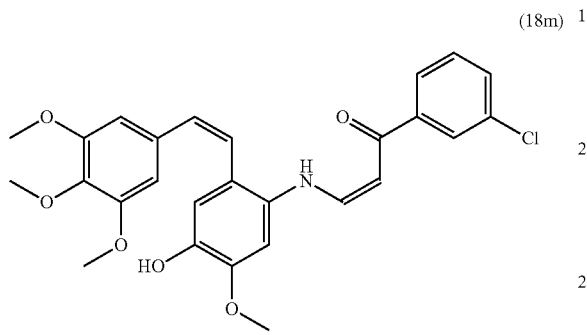
(18n)
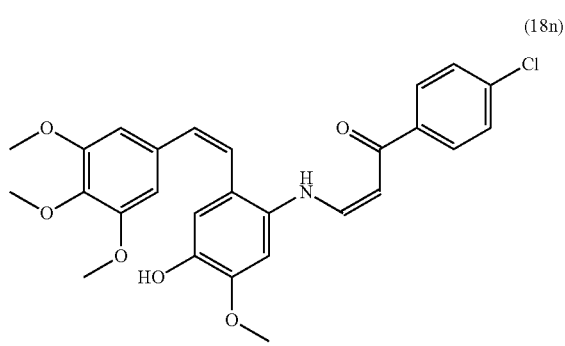
(18o)
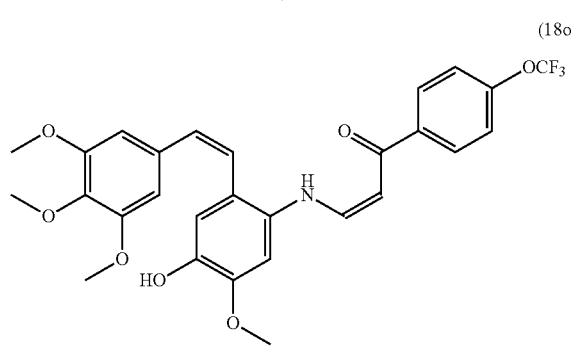
(18p)
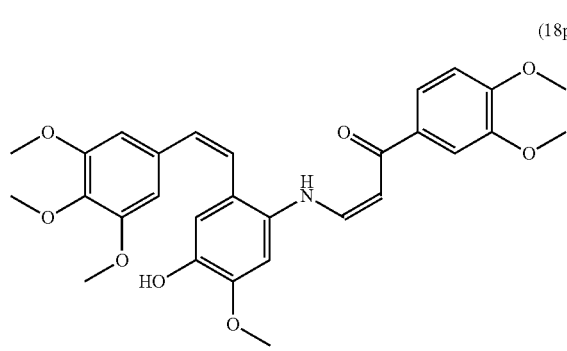
(18q)
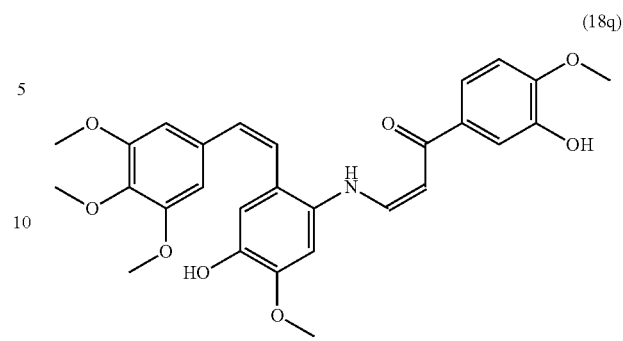
(18r)
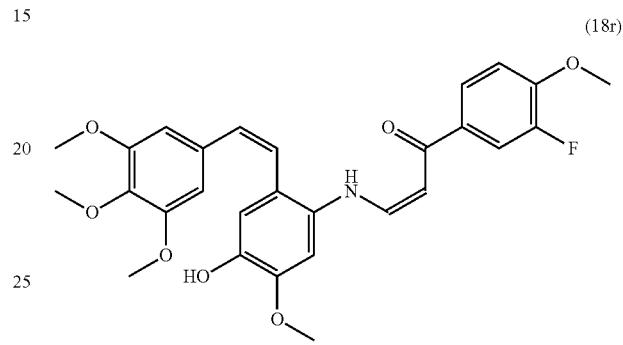
(18s)
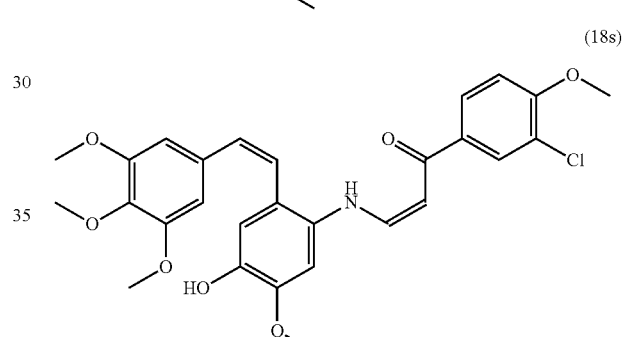
(18t)
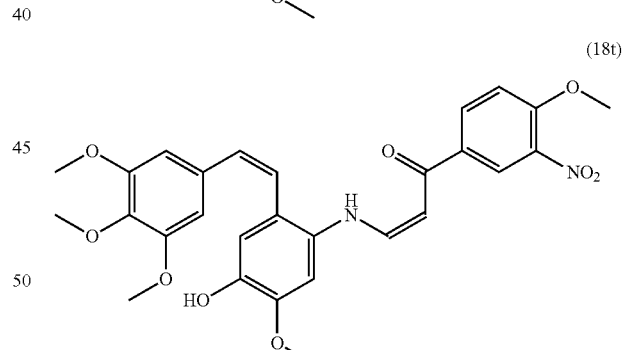
(18u)
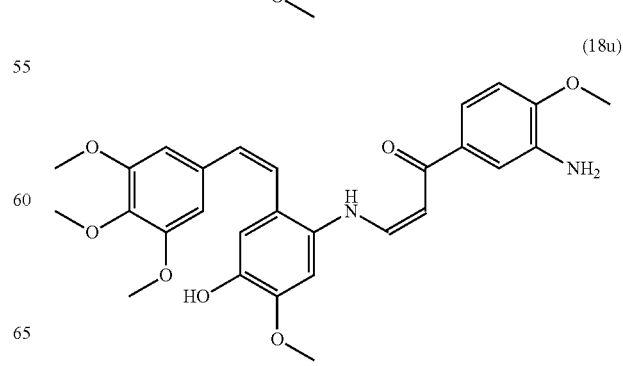

(18v)
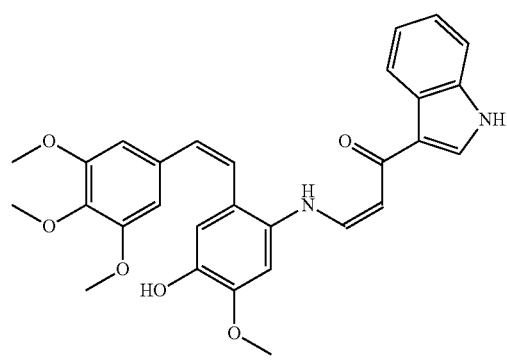
(18w)
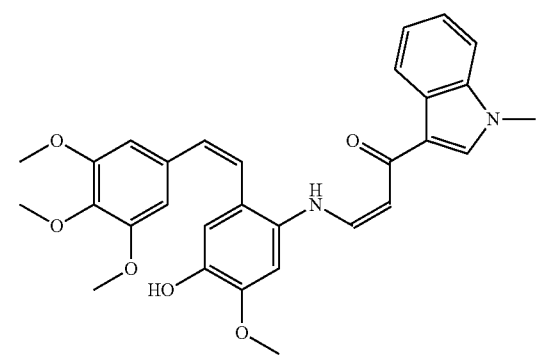
(18x)
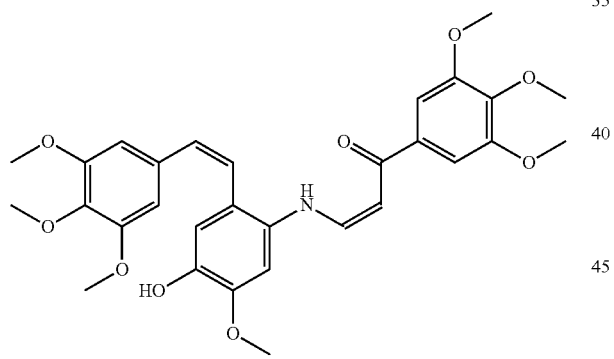
(18y)
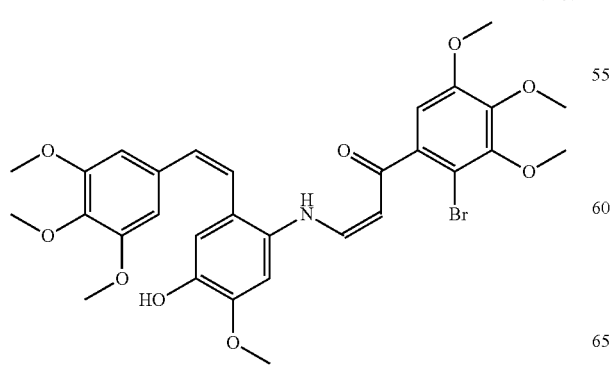
(19a)
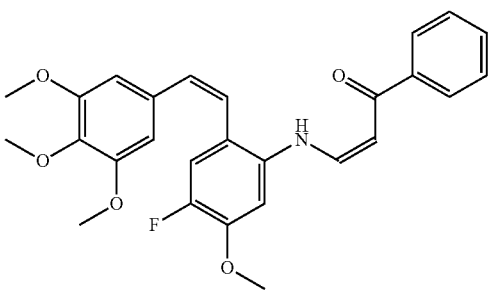
(19b)
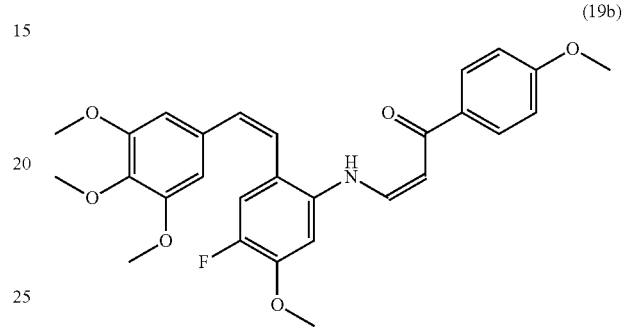
(19c)
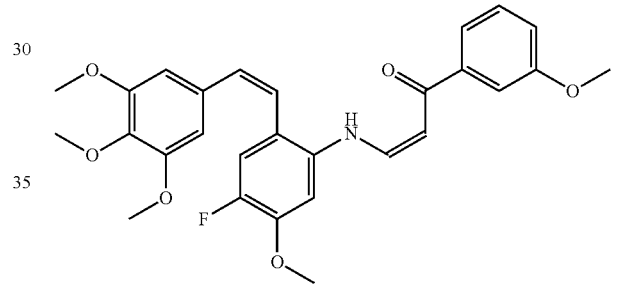
(19d)
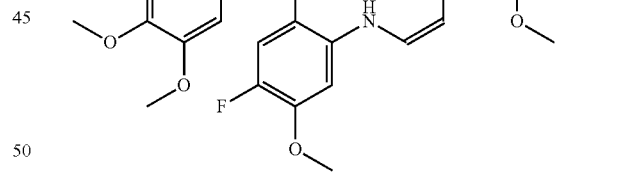
(19e)
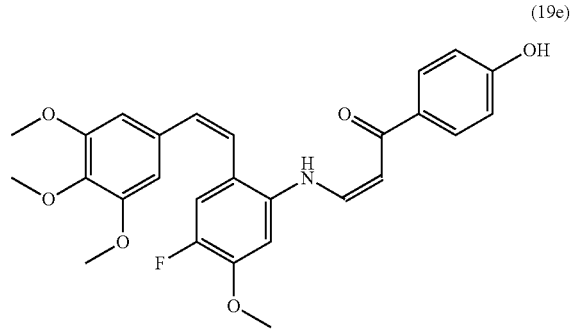

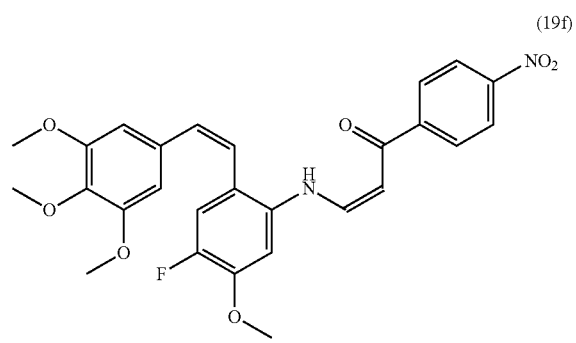
(19f)
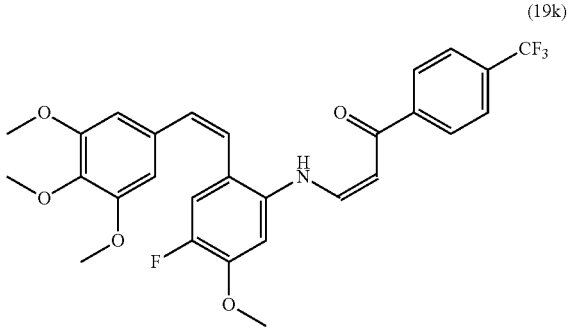
(19k)
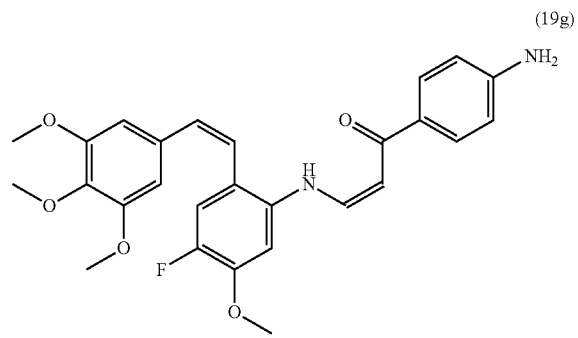
(19g)
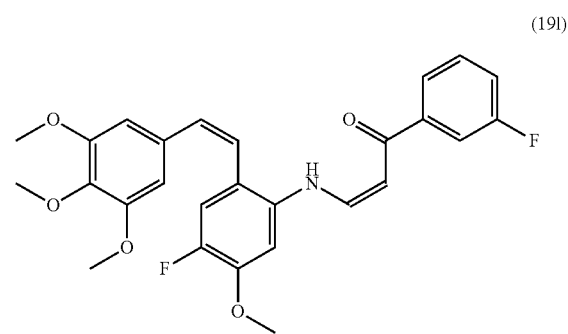
(19l)
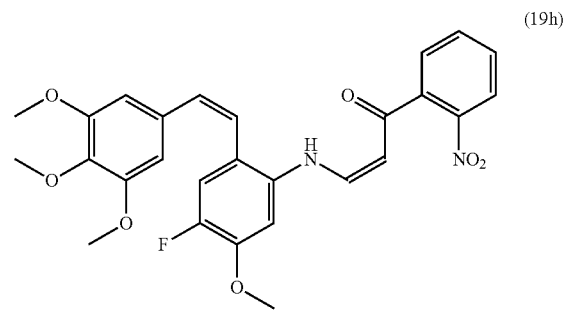
(19h)
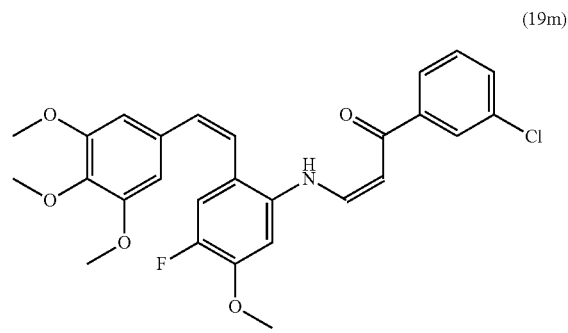
(19m)
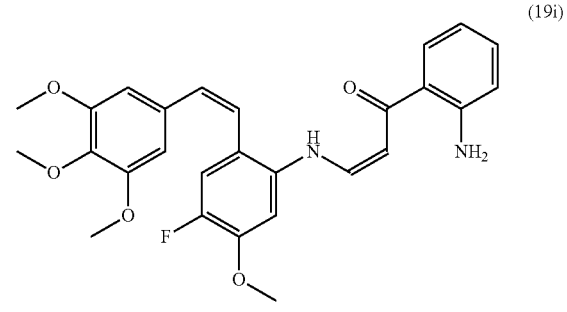
(19i)
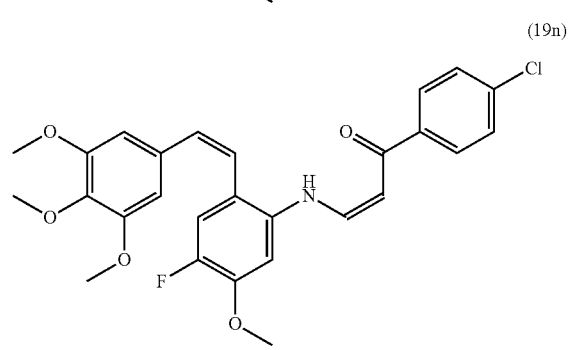
(19n)
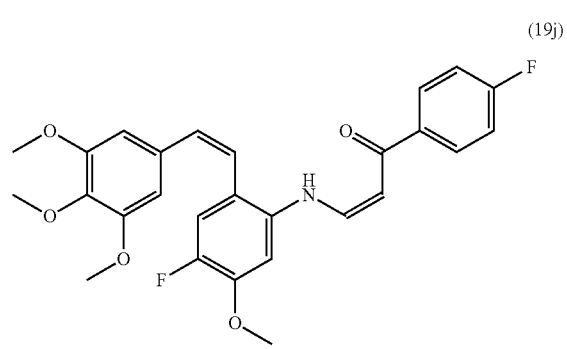
(19j)
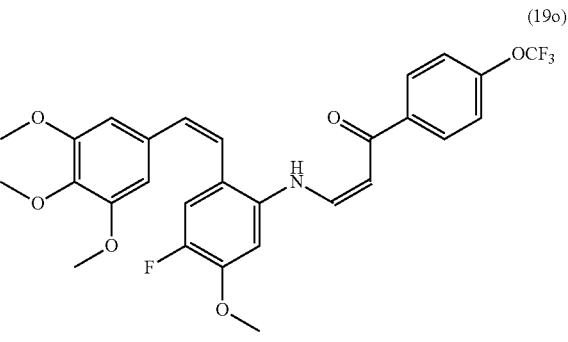
(19o)

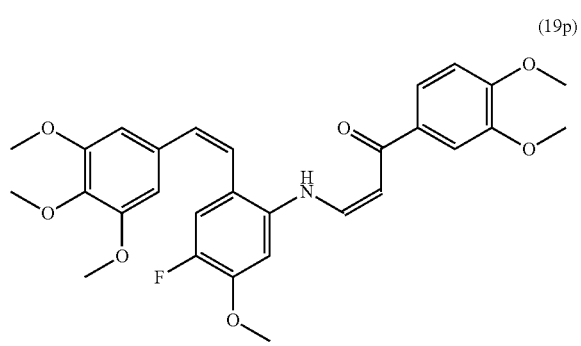
(19p)
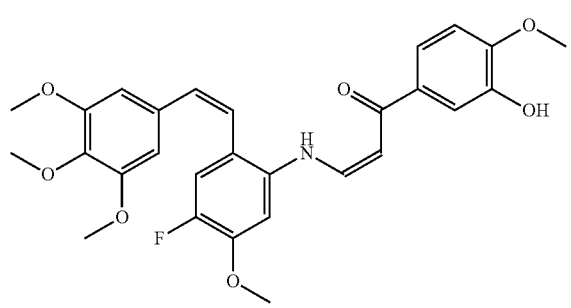
(19q)
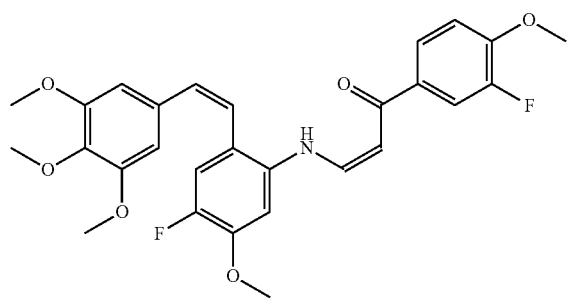
(19r)
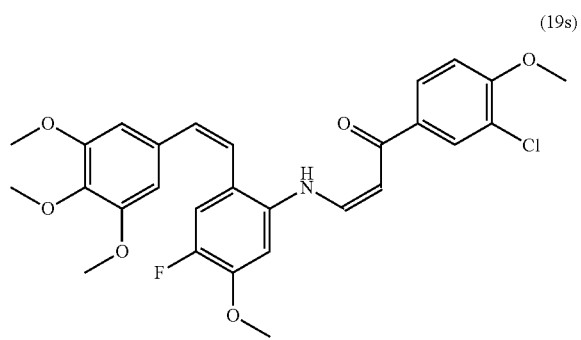
(19s)
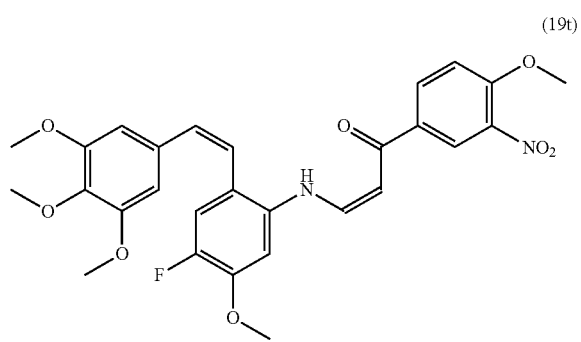
(19t)
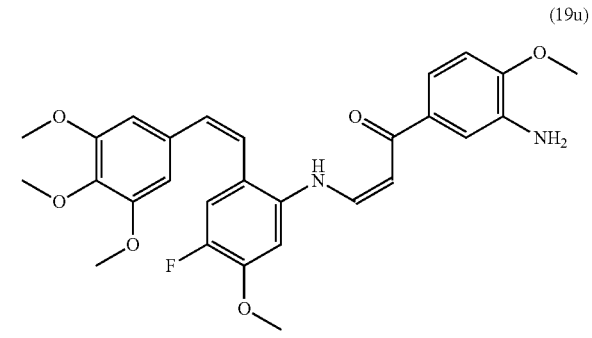
(19u)
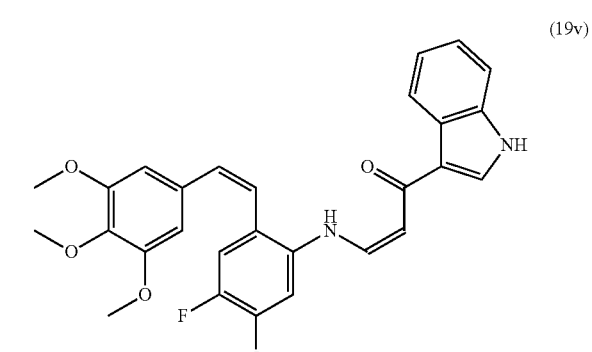
(19v)
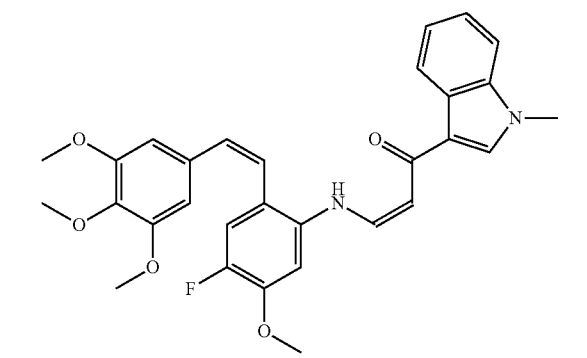
(19w)
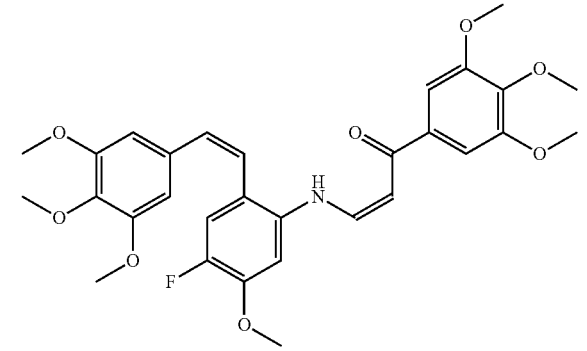
(19x)

(19y)
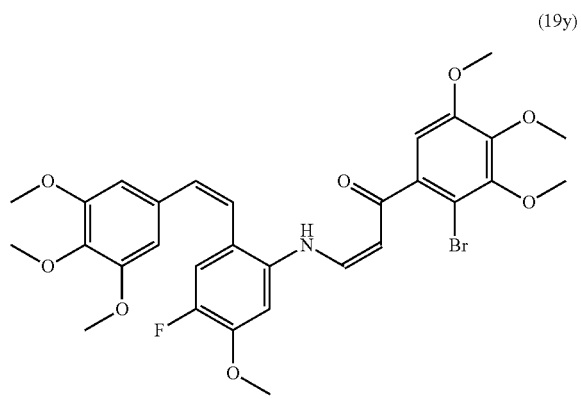
(20a)
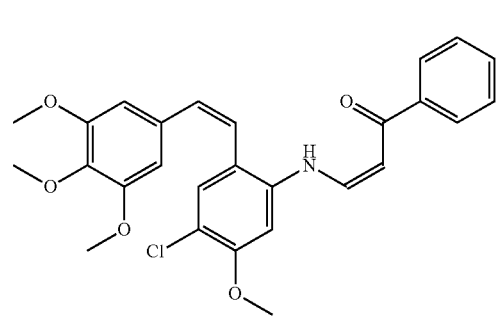
(20b)
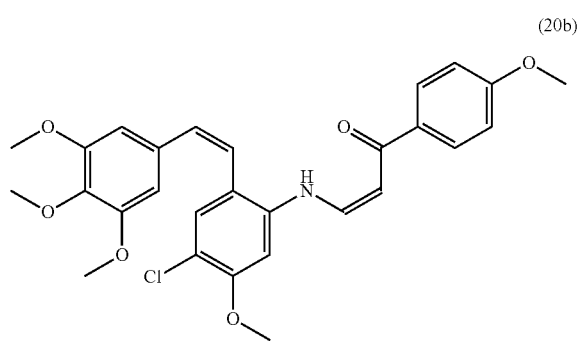
(20c)
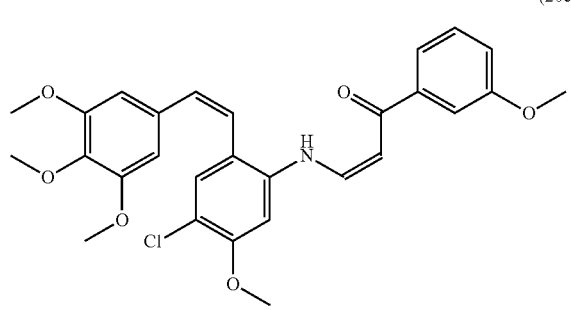
(20d)
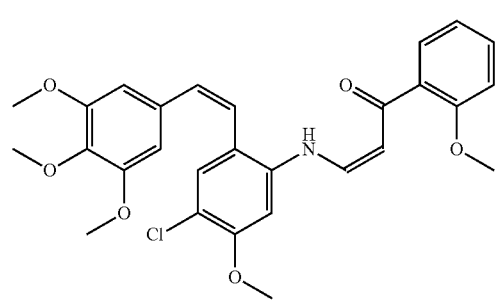
(20e)
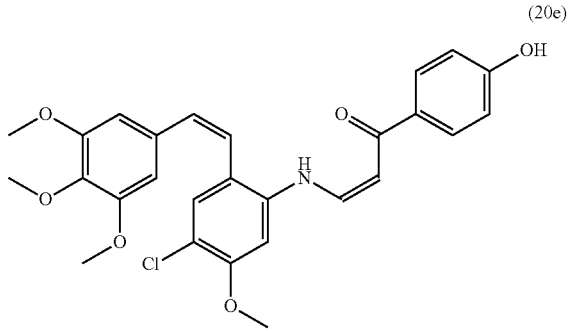
(20f)
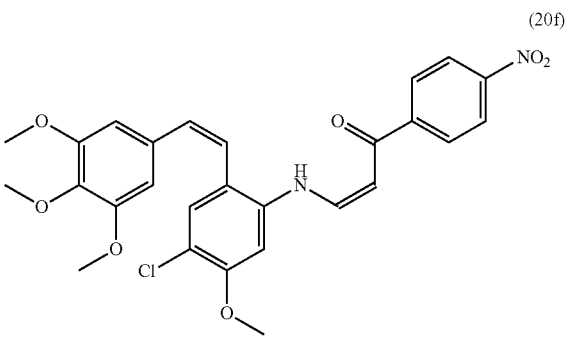
(20g)
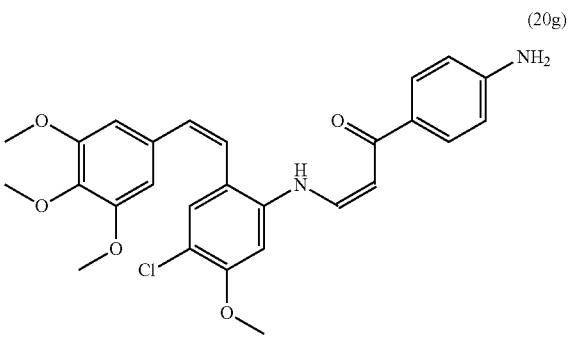
(20h)
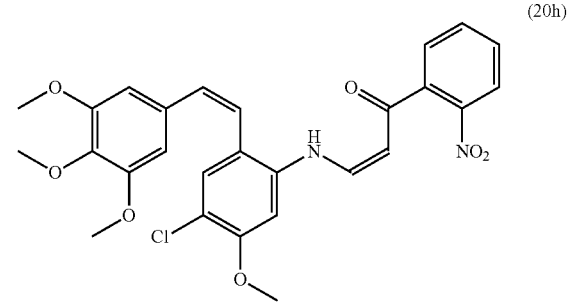
(20i)
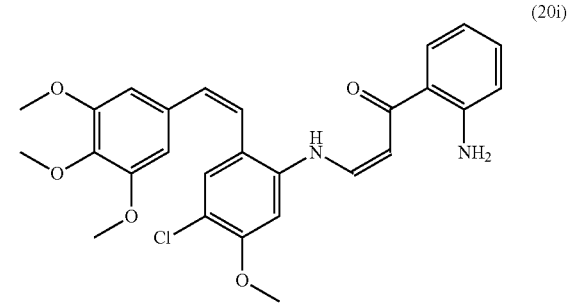

(20j)
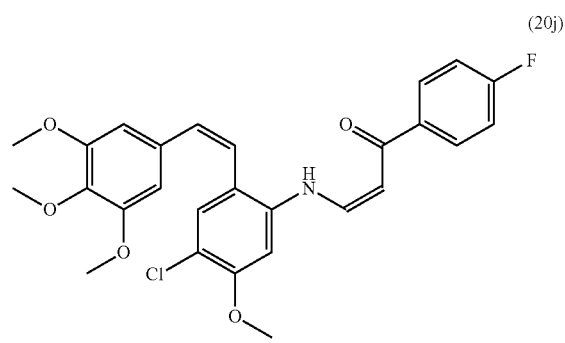
(20k)
(20l)
(20m)
(20n)
(20o)
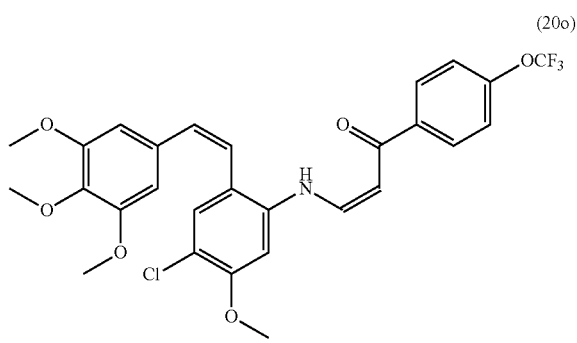
(20p)
(20q)
(20r)
(20s)

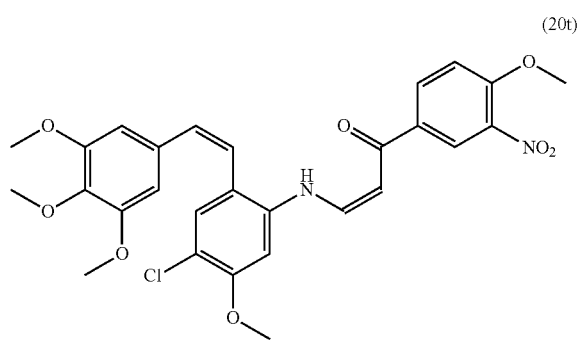 (20t)
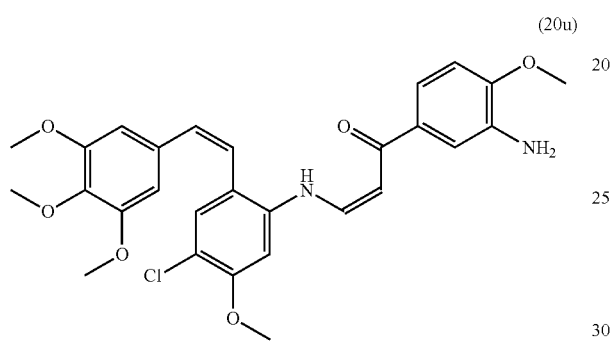 (20u)
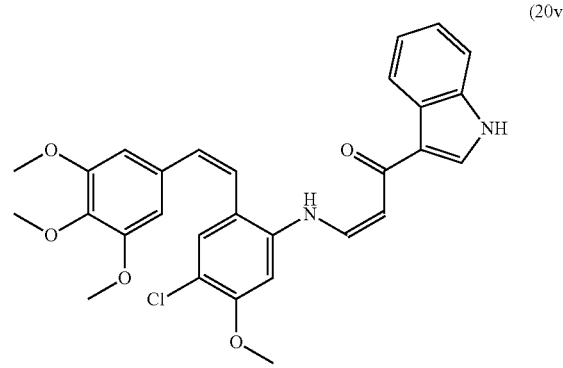 (20v)
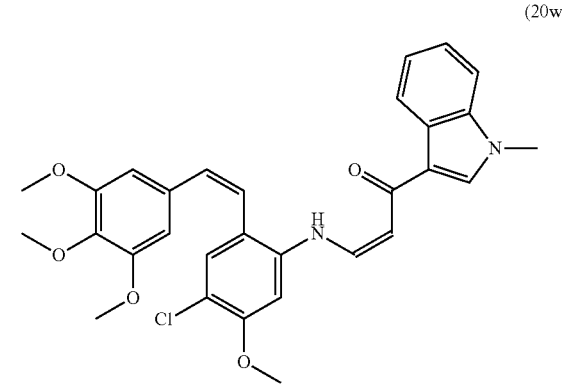 (20w)
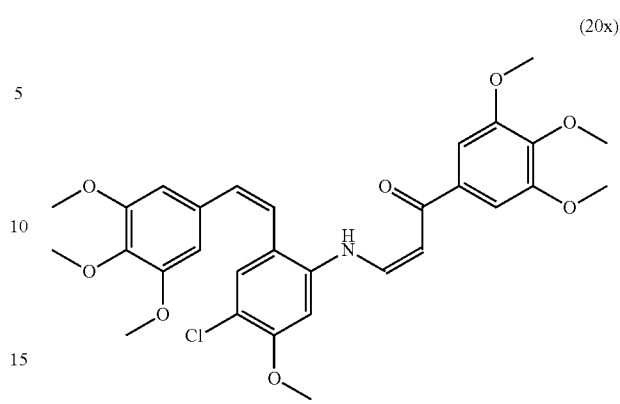 (20x)
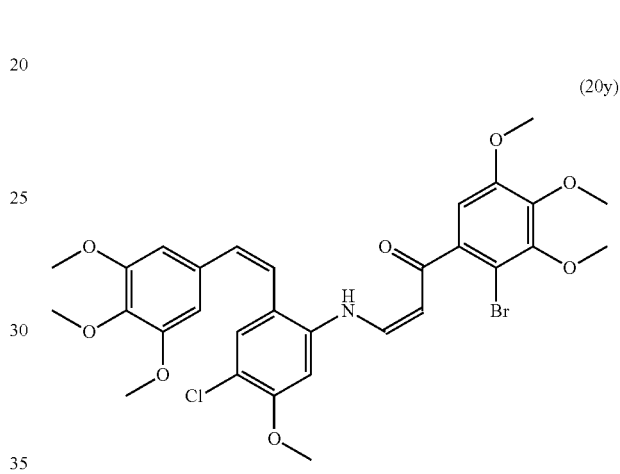 (20y)
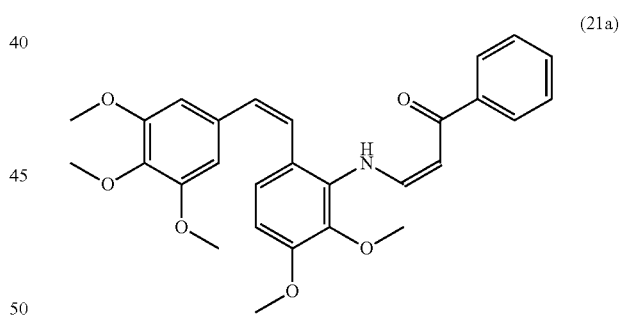 (21a)
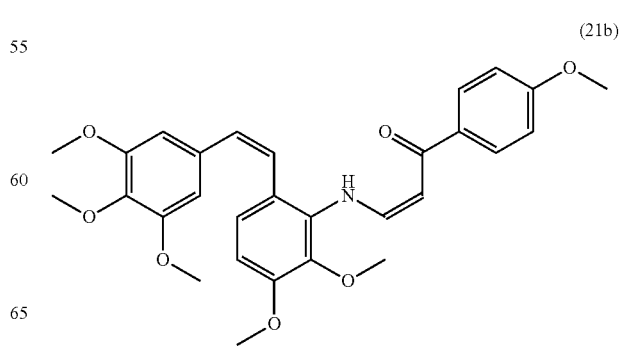 (21b)

(21c)
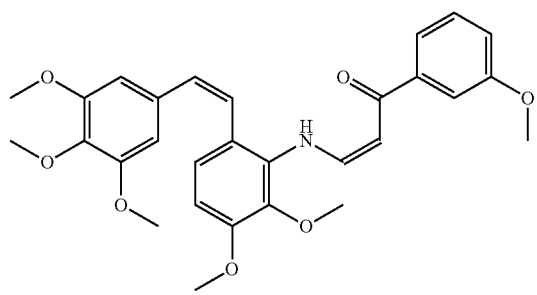
(21d)
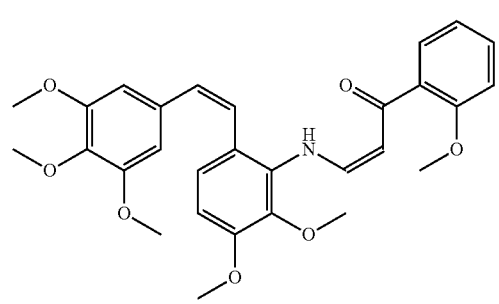
(21e)
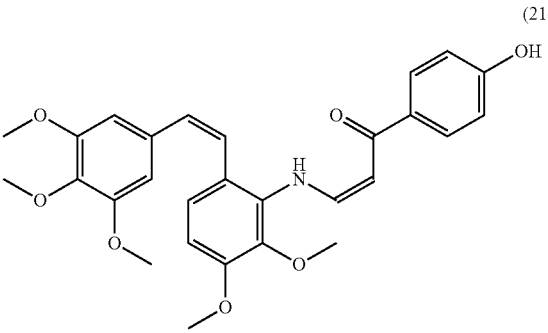
(21f)
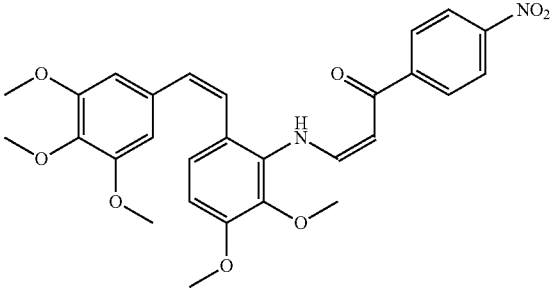
(21g)
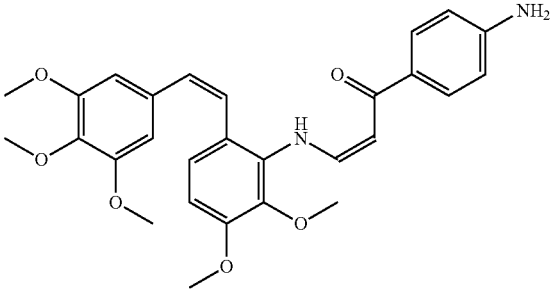
(21h)
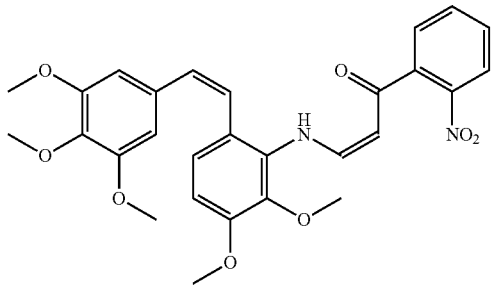
(21i)
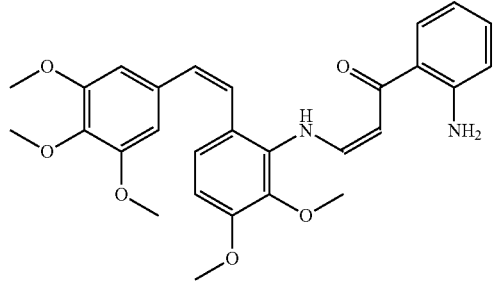
(21j)
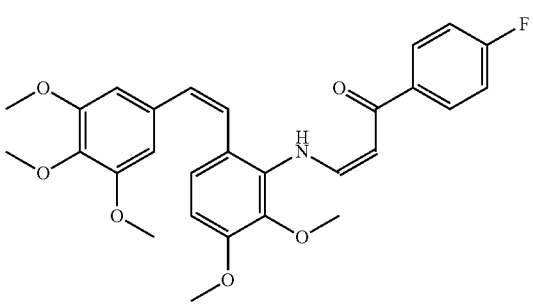
(21k)
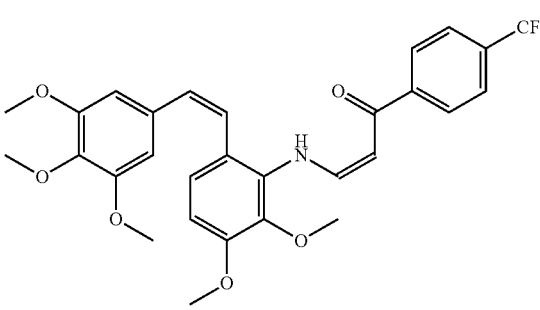
(21l)
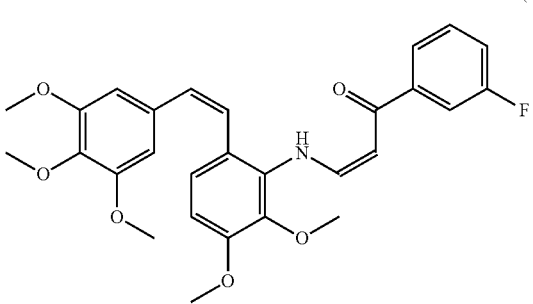

(21m)
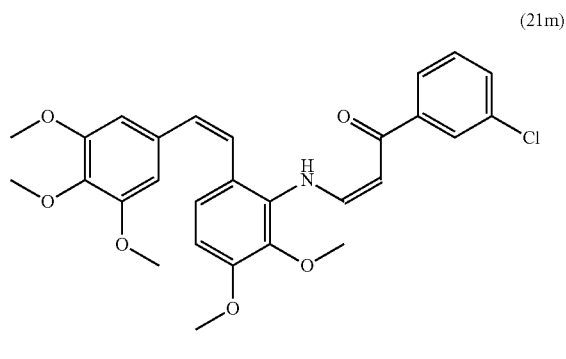
(21n)
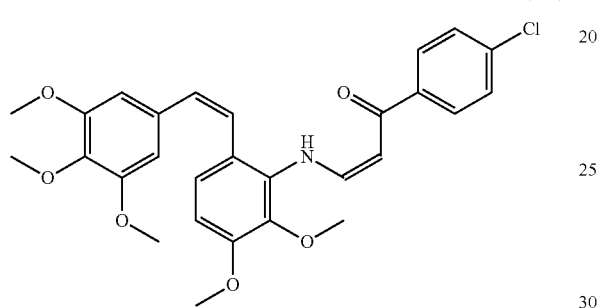
(21o)
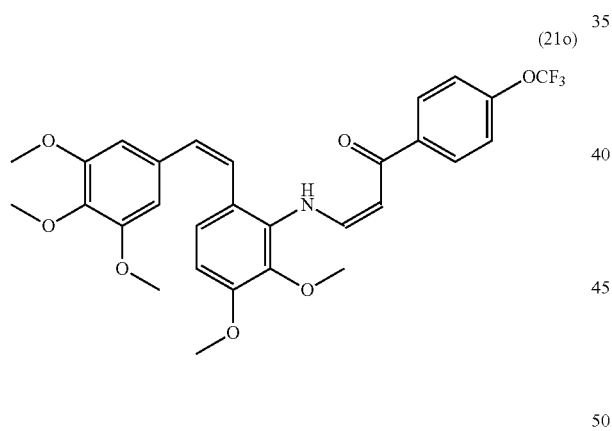
(21p)
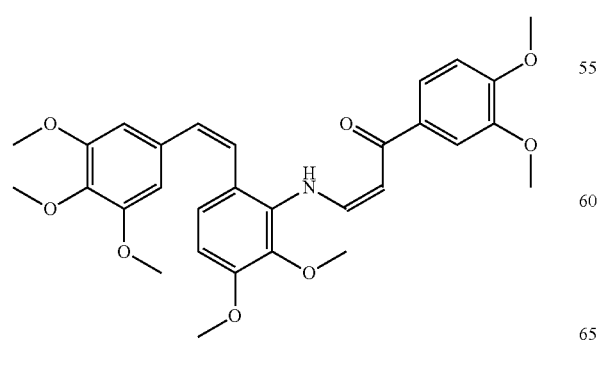
(21q)
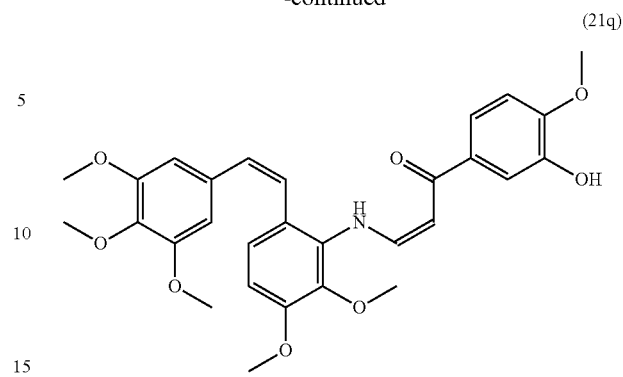
(21r)
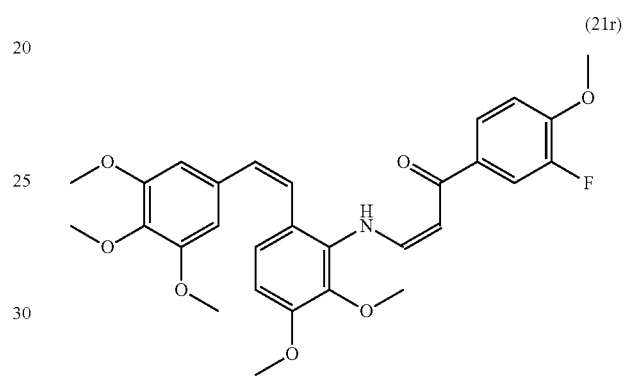
(21s)
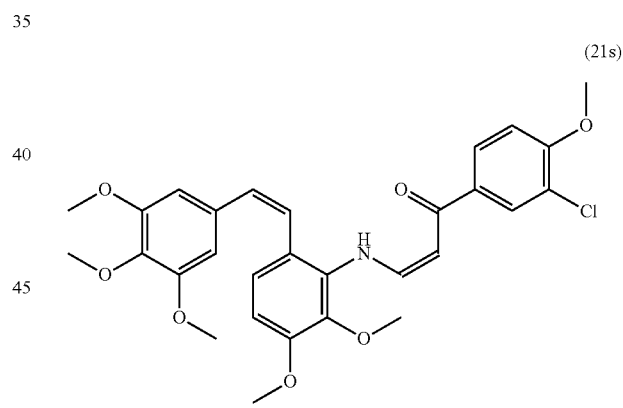
(21t)
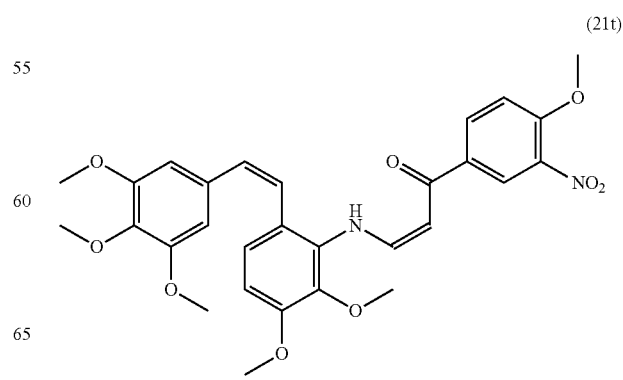

(21u)
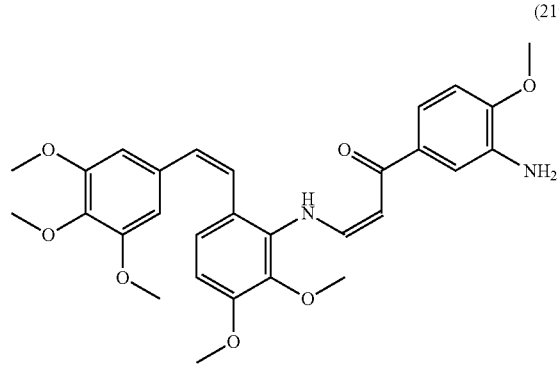

(21v)
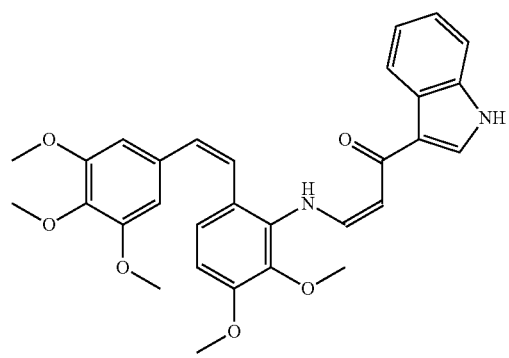

(21w)

(21x)
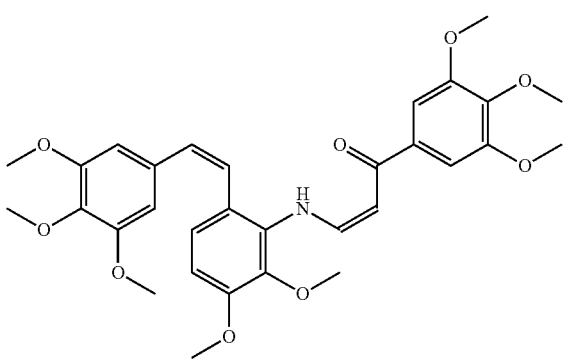

(21y)
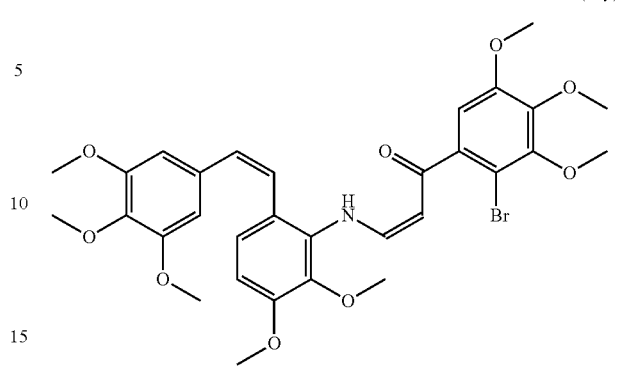

5. Novel 3,4,5-trimethoxystyrylarylaminopropenones of general formulae A as claimed in claim 1 wherein said compounds are useful as antitumor agents.

6. Novel 3,4,5-trimethoxystyrylarylaminopropenones of general formulae A as claimed in claim 1 wherein said compounds have antitumour activity against cell lines selected from the group consisting of non-small cell lung cancer, colon cancer, cervical carcinoma and breast cancer.

7. A process for the preparation of a compound of formula A wherein said process comprises reacting a compound of formula 5 with a compound of formula 6 in ethanol/methanol at a temperature ranging between 25-35° C. for a period ranging between 3-4 h;

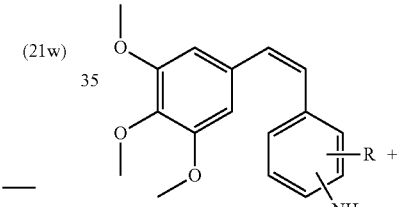

5

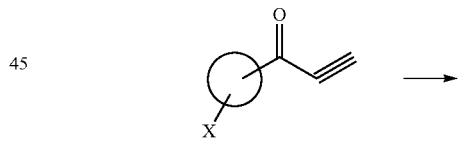

6

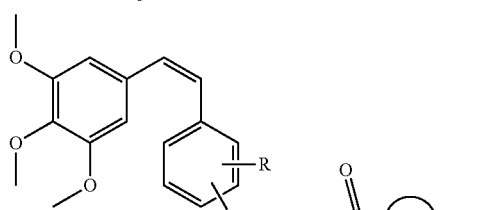

A wherein R is H, OMe, OH, Cl, F or Me; X is aryl or heteroaryl; and wherein the product of formula A is 7a-7y, 8a-8y, 9a-9y, 10a-10y, 11a-11y, 12a-12y, 13a-13y, 14a-14y, 15a-15y, 16a-16y, 17a-17y, 18a-18y, 19a-19y, 20a-20y or 21a-21y:

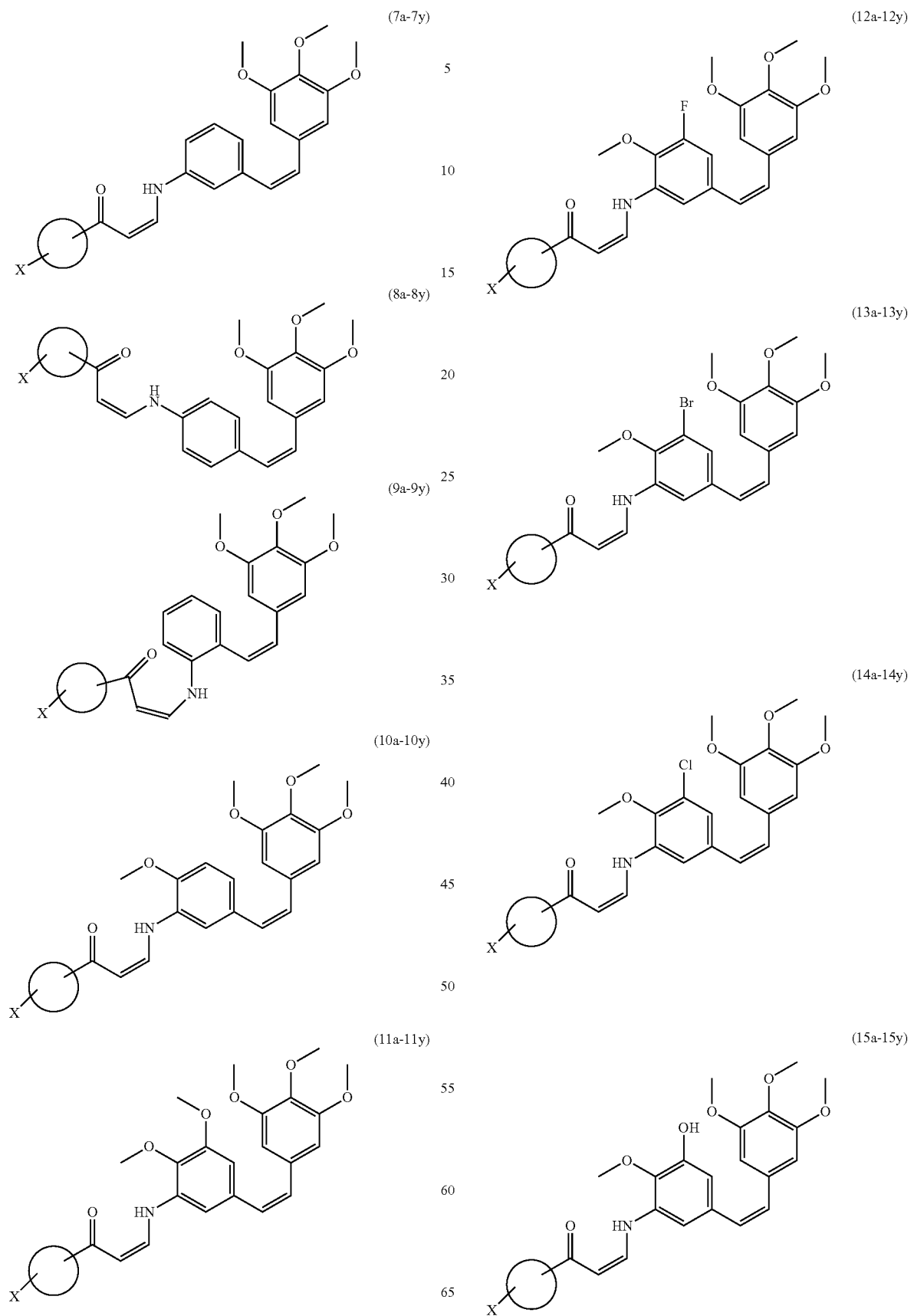

(16a-16y)
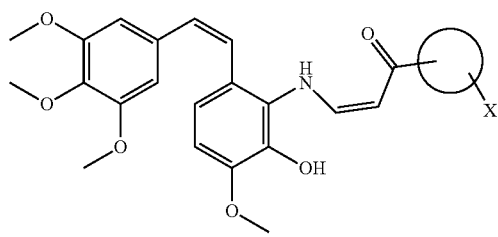
(17a-17y)
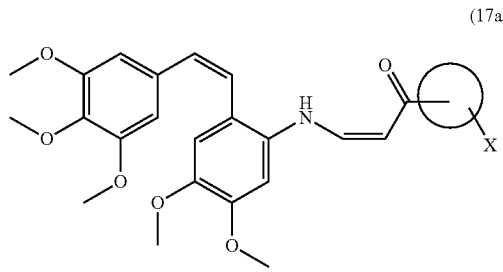
(18a-18y)
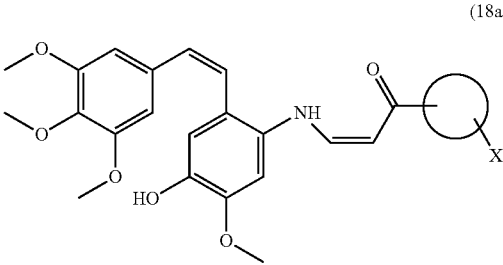
(19a-19y)
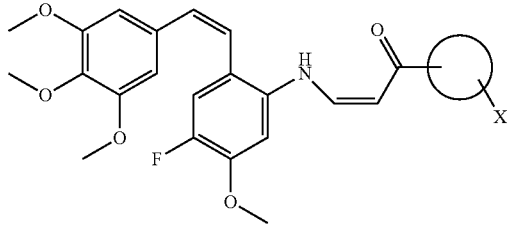
(20a-20y)
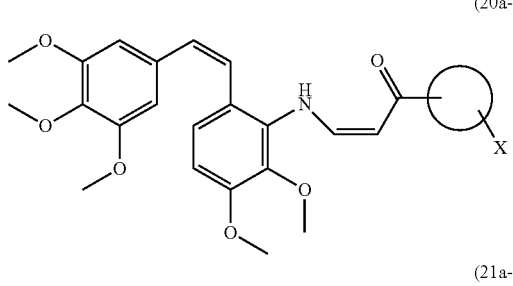
(21a-21y)
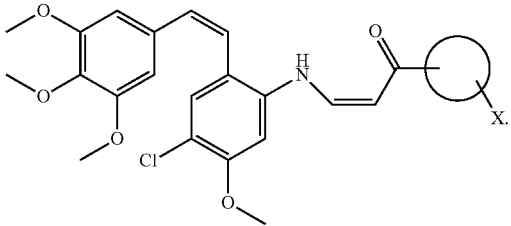
* * * * *